US011421287B2

(12) United States Patent
Bianchi et al.

(10) Patent No.: US 11,421,287 B2
(45) Date of Patent: Aug. 23, 2022

(54) METHODS FOR ASSESSING THE PRESENCE OR ABSENCE OF REPLICATION COMPETENT VIRUS

(71) Applicant: Juno Therapeutics, Inc., Seattle, WA (US)

(72) Inventors: Allison Adin Bianchi, Seattle, WA (US); Ruth Berry, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 431 days.

(21) Appl. No.: 16/320,076

(22) PCT Filed: Jul. 28, 2017

(86) PCT No.: PCT/US2017/044550
§ 371 (c)(1),
(2) Date: Jan. 23, 2019

(87) PCT Pub. No.: WO2018/023094
PCT Pub. Date: Feb. 1, 2018

(65) Prior Publication Data

US 2020/0056249 A1 Feb. 20, 2020

Related U.S. Application Data

(60) Provisional application No. 62/448,954, filed on Jan. 20, 2017, provisional application No. 62/369,024, filed on Jul. 29, 2016.

(51) Int. Cl.
*C12Q 1/70* (2006.01)

(52) U.S. Cl.
CPC .................................... *C12Q 1/702* (2013.01)

(58) Field of Classification Search
None
See application file for complete search history.

(56) References Cited

U.S. PATENT DOCUMENTS

| | | | |
|---|---|---|---|
| 4,452,773 | A | 6/1984 | Molday |
| 4,683,202 | A | 7/1987 | Mullis |
| 4,795,698 | A | 1/1989 | Owen et al. |
| 4,996,143 | A | 2/1991 | Heller et al. |
| 5,168,062 | A | 12/1992 | Stinski |
| 5,200,084 | A | 4/1993 | Liberti et al. |
| 5,210,015 | A | 5/1993 | Gelfand et al. |
| 5,385,839 | A | 1/1995 | Stinski |
| 5,510,474 | A | 4/1996 | Quail et al. |
| 5,538,848 | A | 7/1996 | Livak et al. |
| 5,565,322 | A | 10/1996 | Hell |
| 5,686,279 | A | 11/1997 | Finer et al. |
| 5,849,489 | A | 12/1998 | Heller |
| 5,925,517 | A | 7/1999 | Tyagi et al. |
| 5,928,906 | A | 7/1999 | Koster et al. |
| 5,994,056 | A | 11/1999 | Higuchi |
| 5,994,136 | A | 11/1999 | Naldini et al. |
| 6,013,516 | A | 1/2000 | Verma et al. |
| 6,162,603 | A | 12/2000 | Heller |
| 6,165,782 | A | 12/2000 | Naldini et al. |
| 6,171,785 | B1 | 1/2001 | Higuchi |
| 6,174,670 | B1 | 1/2001 | Wittwer et al. |
| 6,207,455 | B1 | 3/2001 | Chang |
| 6,326,145 | B1 | 12/2001 | Whitcombe et al. |
| 6,329,144 | B1 | 12/2001 | Kubista et al. |
| 6,410,319 | B1 | 6/2002 | Raubitschek et al. |
| 6,451,995 | B1 | 9/2002 | Cheung et al. |
| 6,635,427 | B2 | 10/2003 | Wittwer et al. |
| 6,712,612 | B1 | 3/2004 | Tung et al. |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen et al. |
| 7,446,190 | B2 | 11/2008 | Sadelain et al. |
| 7,446,191 | B2 | 11/2008 | Jensen |
| 7,510,687 | B2 | 3/2009 | Mazzeo et al. |
| 7,741,467 | B2 | 6/2010 | Will |
| 8,324,353 | B2 | 12/2012 | Jensen |
| 8,389,282 | B2 | 3/2013 | Sadelain et al. |

(Continued)

FOREIGN PATENT DOCUMENTS

| | | | |
|---|---|---|---|
| CN | 102 154 368 | | 8/2011 |
| CN | 102154368 | * | 1/2015 |

(Continued)

OTHER PUBLICATIONS

US 8,252,592 B2, 08/2012, Sadelain (withdrawn)
Bruhn et al. Journal of Virological Methods. vol. 123, No. 2, February , pp. 179-186 (Year: 2005).*
Uchida et al. (Biologicals 32 (2004) 139-146) (Year: 2004).*
Weijtens et al. (Gene Therapy (1998) 5, 1995-1203) (Year: 1998).*
Humeau et al. 2004. Molecular Therapry vol. 9, No. 6, Jun. 2004, pp. 902-913 (Year: 2004).*
Sastry et al. 2003. Molecular Therapy 8, 830-839 (Year: 2003).*
Alm et al. (PLoS Negi Trap Dis 8(12): e3416. doi:10.1371/journal.pntd.0003416, 10 pages) (Year: 2014).*
Lizee et al. (Human Gene Therapy 14:497-507 (2003)) (Year: 2003).*

(Continued)

*Primary Examiner* — Juliet C Switzer
(74) *Attorney, Agent, or Firm* — Morrison & Foerster LLP

(57) ABSTRACT

Provided are methods of detecting replication competent retrovirus in a sample containing a cell transduced with a viral vector particle encoding a recombinant and/or heterologous molecule, e.g., heterologous gene product. The methods may include assessing transcription of one or more target genes, such as viral genes, that are expressed in a retrovirus but not expressed in the viral vector particle. Replication competent retrovirus may be determined to be present if the levels of RNA of the one or more target genes is higher than a reference value, which can be measured directly or indirectly, including from a positive control sample containing RNA from the respective target gene at a known level and/or at or above the limit of detection of the assay.

35 Claims, No Drawings

Specification includes a Sequence Listing.

(56) References Cited

U.S. PATENT DOCUMENTS

| | | | |
|---|---|---|---|
| 8,399,645 | B2 | 3/2013 | Campana et al. |
| 8,497,118 | B2 | 7/2013 | Jensen |
| 9,572,836 | B2 | 2/2017 | June et al. |
| 2002/0131960 | A1 | 9/2002 | Sadelain et al. |
| 2009/0028836 | A1 | 1/2009 | Von Kalle et al. |
| 2011/0003380 | A1 | 1/2011 | Miltenyi et al. |
| 2013/0149337 | A1 | 6/2013 | Cooper et al. |
| 2013/0287748 | A1 | 10/2013 | June et al. |
| 2021/0164062 | A1 | 6/2021 | Berry et al. |

FOREIGN PATENT DOCUMENTS

| | | | |
|---|---|---|---|
| EP | 0452342 | 10/1991 | |
| EP | 2537416 | 12/2012 | |
| WO | WO 1994/19491 | 9/1994 | |
| WO | WO 1997/046707 | 12/1997 | |
| WO | WO 1997/046712 | 12/1997 | |
| WO | WO 1997/046714 | 12/1997 | |
| WO | WO 1998/032869 | 7/1998 | |
| WO | WO 2000/014257 | 3/2000 | |
| WO | WO 2001/04360 | 1/2001 | |
| WO | WO 2002/090587 | 11/2002 | |
| WO | WO-2007008309 A2 * | 1/2007 | ........... C12N 5/0634 |
| WO | WO 2009/072003 | 6/2009 | |
| WO | WO 2009/076524 | 6/2009 | |
| WO | WO 2010/033140 | 3/2010 | |
| WO | WO 2012/129514 | 9/2012 | |
| WO | WO 2013/071154 | 5/2013 | |
| WO | WO 2013/123061 | 8/2013 | |
| WO | WO 2013/126726 | 8/2013 | |
| WO | WO 2013/166321 | 11/2013 | |
| WO | WO 2014/011996 | 1/2014 | |
| WO | WO 2014/031687 | 2/2014 | |
| WO | WO 2014/055668 | 4/2014 | |
| WO | WO 2015/013681 | 1/2015 | |
| WO | WO 2015/104376 | 7/2015 | |
| WO | WO 2019/152747 | 8/2019 | |

OTHER PUBLICATIONS

Adra et al., "Cloning and expression of the mouse pgk-1 gene and the nucleotide sequence of its promoter," Gene (1987) 60(1):65-74.

Aloia et al., "A reporter system for replication-competent gammaretroviruses: the inGluc-MLV-DERSE assay," Gene Therapy (2013) 20(2): 169-176.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2:e93.

Anton et al., "Sensitive and reproducible quantitation of mucosal HIV-1 RNA and DNA viral burden in patients with detectable and undetechtable plasma viral HIV-1 RNA using endoscopic biopsies," J Virol Methods (2001) 95(102):65-79.

Bailey et al., "Quality and Risk Management in ensuring the virus safety of biopharmaceutical: Subramanian: Biophtech 2V 0-BK," Biopharmaceutical Production Technology: Subramanian: Biophtech 2V 0-BK (2012) p. 585-612.

Bear et al., "Replication-competent retroviruses in gene-modified T cells used in clinical trials: is it time to revise the testing requirements?" Molecular Therapy (2012) 20 (2): 246-249.

Bianchi et al., "Developing A Predictive, Pcr-Based Replication Competent Retrovirus (Rcr) Detection Method to Enhance Patient Safety For Engineered T Cell Products" ECI Conference abstract. Dated Nov. 18, 2016.

Bieche et al., "Quantitation of MYC gene expression in sporadic breast tumors with a real-time reverse transcription-PCR assay," Cancer Res (1999) 59(12):2759-2765.

Boshart et al., "A very strong enhancer is located upstream of an immediate early gene of human cytomegalovirus," Cell (1985) 41(2):521-530.

Brown et al., "Structure-Based Mutagenesis of the Human Immunodeficiency Virus Type 1 DNA Attachment Site: Effects on Integration and cDNA Synthesis," J Virol (1999) 73:9011.

Bruhn et al., "Application of RT-PCR for the detection of avian reovirus contamination in avian viral vaccines," J Virol Methods (2005) 123(2):179-186.

Carlens et al., "Ex vivo T lymphocyte expansion for retroviral transduction: influence of serum-free media on variations in cell expansion rates and lymphocyte subset distribution," Exp Hematol (2000) 28(10):1137-46.

Cavalieri et al., "Human T lymphocytes transduced by lentiviral vectors in the absence of TCR activation maintain an intact immune competence," Blood (2003) 102(2):497-505.

Chen et al., "Safety testing for replication-competent retrovirus associated with gibbon ape leukemia virus-pseudotyped retroviral vectors," Hum Gene Ther. (2001) 12(1): 61-70.

CHEN et al., "Packaging cell line DNA contamination of vector supernatants: Implication for Laboratory and Clinical Research," Virology (2001) 282 : 186-197.

Cho et al., "Human mammalian cell sorting using a highly integrated micro-fabricated fluorescence-activated cell sorter (microFACS)," Lab Chip (2010) 10: 1567-1573.

Cohen et al., "Recognition of fresh human tumor by human peripheral blood lymphocytes transduced with a bicistronic retr oviral vector encoding a murine anti-p53 TCR," J Immunol. (2005) 175:5799-5808.

Committee for medicainal products and manufacture of lentiviral vectors (CHMTP), "Guidelines on development and manufacture of lentiviral vectors," Dated May 26, 2005, p. 1-8. Retrieved on http://www.ema.europa.eu/docs/en_GB/documentlibrary/Regulatory_and_procedural_guideliFie/2009/10/WC500004075.pdf.

Cooper et al., "T-cell clones can be rendered specific for CD19: toward the selective augmentation of the graft-versus-B-lineage leukemia effect," Blood (2003) 101 (4):1637-1644.

Cornetta et al., "Absence of Replication-Competent Lentivirus in the Clinic: Analysis of Infused T-cell Products," Molecular Therapy: The Journal of the American Society of Gene Therapy (2017) 26(1):280-288.

Cornetta et al., "Replication-competent lentivirus analysis of clinical grade vector products," Molecular Therapy (2011) 19(3): 557-566.

Corre et al., "RCL-Pooling Assay: A Simplified Method for the Detection of Replication-Competent Lentiviruses in Vector Batches Using Sequential Pooling," Human Gene Therapy (2016) 27(2): 202-210.

Davila et al., "CD19 CAR-targeted T cells induce long-term remission and B Cell Aplasia in an immunocompetent mouse model of B cell acute lymphoblastic leukemia," PLoS ONE (2013) 8(4):e61338.

Dobson et al., "Conservation of high efficiency promoter sequences in *Saccharomyces cerevisiae*," Nucleic Acids Research (1982) 10(8):2625-2637.

Dull et al., "A third-generation lentivirus vector with a conditional packaging system", J Virol., Nov. 1998; 72(11):8463-71.

Ebeling et al., "Human primary T lymphocytes have a low capacity to amplily MLV-based amphotropic RCR and the virions produced are largely noninfectious," Gene Therapy (2003), 10: 1800-1806.

Engelman et al., "Multiple effects of mutations in human immunodeficiency virus type 1 integrase on viral replication," J Virol (1995) 69(5):2729-2736.

FDA website "Guidance for industry: Supplemental Guidance on Testing for Replication Competent Retrovirus in Retroviral Vector Based Gene Therapy Products and During Follow-up of Patients in clinical Trials Using Retroviral Vectors," Oct. 2006. http://www.fda.gov/BiologicsBloodVaccines/GuidanceComplianceRegulatoruInformation/Guidances/CellularandGeneTherapy/ucm072961.htm.

Fedorov et al., "PD-1- and CTLA-4-based inhibitory chimeric antigen receptors (iCARs) divert off-target immunotherapy responses," Sci. Transl. Medicine (2013) 5(215):215ra172.

Gibson et al., "A novel method for real time quantitative RT-PCR," Genome Res (1996) 6:995-1001.

(56) References Cited

OTHER PUBLICATIONS

Godin et al., "Microfluidics and photonics for Bio-System-on-a-Chip: a review of advancements in technology towards a microfluidic flow cytometry chip," J Biophoton. (2008) 1(5):355-376.
Gossen et al., "Tight control of gene expression in mammalian cells by tetracycline-responsive promoters," Proc Natl Acad Sci U S A. Jun. 15, 1992;89(12):5547-51.
Gunning et al., "A human beta-actin expression vector system directs high-level accumulation of antisense transcripts," Proc Natl Acad Sci USA (1987) 84(14):4831-4835.
Hudecek et al., "Receptor affinity and extracellular domain modifications affect tumor recognition by ROR1-specific chimeric antigen receptor T cells," Clin Cancer Res (2013) 19(12):3153-3164.
Kim et al., "Development of enzyme-linked immunosorbent assay for detecting antibodies to replication-competent murine leukemia virus," J Virol Methods. (2004) 118(1):1-7.
Klebanoff et al., "Sorting through subsets: which T-cell populations mediate highly effective adoptive immunotherapy?" J Immunother. (2012) 35(9):651-660.
Koste et al., "T-cell receptor transfer into human T cells with ecotropic retroviral vectors," Gene Therapy (2014) 21:533-538.
Lamers et al., "Gibbon ape leukemia virus poorly replicates in primary human T lymphocytes: implications for safety testing of primary human T lymphocytes transduced with GALV-pseudotyped vectors," J. Immunother (2009) 32(3):272-279.
Li et al., "Directed evolution of human T-cell receptors with picomolar affinities by phage display," Nat Biotechnol. (2005) 23:349-354.
Lindemann et al., "Versatile lelovirus vector systems for regulated gene expression in vitro and in vivo," Mol Med. Jul. 1997;3(7):466-76.
Macejak et al., "Internal initiation of translation mediated by the 5' leader of a cellular mRNA," Nature, (1991); 353:90-94.
Marcucci et al., "Retroviral and Lentiviral Safety Analysis of Gene Modified T cell products and Infused HIV and Oncology Patients," Molecular Therapy: the Journal of the American Society of Gene Therapy. (2018) 26(1): 269-279.
Martineau et al., "Evaluation of PCR and ELISA assays for screening clinical trial subjects for replication-competent retrovirus," Hum. Gene. Ther. (1997) 8(10): 1231-1241.
McWilliams et al., "Mutations in the 5' End of the Human Immunodeficiency Virus Type 1 Polypurine Tract Affect RNase H Cleavage Specificity and Virus Titer," J Virol (2003) 77:11150.
Miskin et al., "Assays for the quality control of lentiviral vectors," Concepts in Genetic Medicine (2008):289-297.
Miyoshi et al., "Development of a self-inactivating lentivirus vector," J Virol (1998) 72(10):8150-8157.
Murphy et al., "Design of a titering assay for lentiviral vectorsutilizing direct extraction of DNA from transduced cells in microtiter plates," Molecular Therapy: Methods and clinical Develop (2016)3:16005.
Naldini et al., Efficient transfer, integration, and sustained long-term expression of the transgene in adult rat brains injected with a lentiviral vector, Proc Natl Acad Sci U S A. Oct. 15, 1996;93(21):11382-8.
Naldini et al., "In vivo gene delivery and stable transduction of nondividing cells by a lentiviral vector," Science. Apr. 12, 1996;272(5259):263-7.
Naldini et al., "Lentiviruses as gene transfer agents for delivery to non-dividing cells", Curr Opin Biotechnol., Oct. 9, 1998; 5:457-63.
Nowrousian, "Next-generation sequencing techniques for eukaryotic microorganisms sequencing-based solutions to biological problems," Eukaryot Cell (2010) 9(9):1300-1310.
Ory et al., "A stable human-derived packaging cell line for production of high titer retrovirus/vesicular stomatitis virus G pseudotypes," Proc Natl Acad Sci U S A. Oct. 15, 1996;93(21):11400-6.
Paar et al., "Influence of vector design and host cell on the mechanism of recombination and emergence of mutant subpopulations of replicating retroviral vectors," BMC Mol. Biol. (2009) 10:8 doi: 10.1186/1471-2199-10-8.
Park et al., "Treating cancer with genetically engineered T cells," Trends Biotechnol. (2011) 29(11):550-557.
Parkhurst et al., "Characterization of genetically modified T-cell receptors that recognize the CEA:691-699 peptide in the context of HLA-A2.1 on human colorectal cancer cells," Clin Cancer Res. (2009) 15:169-180.
Pelletier et al., "Internal initiation of translation of eukaryotic mRNA directed by a sequence derived from poliovirus RNA," Nature. Jul. 28, 1998; 334(6180):320-5.
Pfeifer et al., "Gene therapy: promises and problems," Annu Rev Genomics Hum Genet (2001) 2:177-211.
Philpott et al., "Use of nonintegraling lentiviral vectors for gene therapy," Human Gene Therapy (2007) 18:483.
Powell et al., "Sequence and Structural Determinants Required for Priming of Plus-Strand DNA Synthesis by the Human Immunodeficiency Virus Type 1 Polypurine Tract," J Virol (1996) 70(8):5288-5296.
Sadelain et al., "The basic principles of chimeric antigen receptor design," Cancer Discov. (2013) 3(4):388-398.
Sastry et al., "Detection of replication competent retrovirus and lentivirus," Methods in Molecular Biology, Methods and Protocols (2009) vol. 506 : 243-263.
Sastry et al., "Product-enhanced reverse transcriptase assay for replication-competent retroviruses and lentivirus detection," Hum Gene Ther. (2005), 16(10):1227-1236.
Segura et al., "New developments in lentiviral vector design, production and purification," Expert Opinion on Biological Therapy (2013) 13(7):987-1011.
Shendure et al., "Advanced sequencing technologies: methods and goals," Nat Rev Genet (2004) 5(5):335-344.
Shockett et al., "A modified tetracycline-regulated system provides autoregulatory, inducible gene expression in cultured cells and transgenic mice," Proc Natl Acad Sci USA (1995) 92:6522-6526.
Singer-Sam et al., "Sequence of the promoter region of the gene for human X-linked 3-phosphoglycerate kinase," Gene (1984) 32(3):409-417.
Skrdlant et al., "Detection of Replication Competent Lentivirus using a qPCR Assay for VSV-G," Molecular Therapy-Methods and Clinical Develop (2017) 8:1-7.
Terakura et al., "Generation of CD19-chimeric antigen receptor modified CD8+ T cells derived from virus-specific central memory T cells," Blood (2012) 1:72-82.
Thomsen et al., "Promoter-regulatory region of the major immediate early gene of human cytomegalovirus," PNAS (1984) 81:659.
Turtle et al., "Engineered T cells for anti-cancer therapy," Curr. Opin. Immunol. (2012) 24(5):633-39.
Uchida et al., "An improved method for detection of replication-competent retrovirus in retrovirus vector products," Biologicals (2004), 32(3):139-146.
Varela-Rohena et al., "Control of HIV-1 immune escape by CD8 T cells expressing enhanced T-cell receptor," Nat Med. (2008) 14:1390-1395.
Verhoeyen et al., "Lentiviral vector gene transfer into human T cells," Methods Mol Biol (2009) 506:97-114.
Wang et al., "Phenotypic and functional attributes of lentivirus-modified CD19-specific human CD8+ central memory T cells manufactured at clinical scale," J Immunother. (2012) 35(9):689-701.
Wu et al., "Adoptive T-cell therapy using autologous tumor-infiltrating lymphocytes for metastatic melanoma: current status and future outlook," Cancer (2012) 18(2):160-75.
Zufferey et al., "Multiply attenuated lentiviral vector achieves efficient gene delivery in vivo," Nat Biotechnol. Sep. 15, 1997(9):871-5.
Zufferey et al., "Self-inactivating lentivirus vector for safe and efficient in vivo gene delivery," J Virol (1998) 72(12):9873-9880.
Aerts et al., "Selection of appropriate control genes to assess expression of tumor antigens using real-time RT-PCR," Biotechniques (2004) 36(1):84-86.

* cited by examiner

SEQUENCE LISTING

<160> NUMBER OF SEQ ID NOS: 41

<210> SEQ ID NO 1
<211> LENGTH: 20
<212> TYPE: DNA
<213> ORGANISM: Artificial Sequence
<220> FEATURE:
<223> OTHER INFORMATION: Actin forward primer

<400> SEQUENCE: 1
gcgagaagat gacccagatc 20

<210> SEQ ID NO 2
<211> LENGTH: 19
<212> TYPE: DNA
<213> ORGANISM: Artificial Sequence
<220> FEATURE:
<223> OTHER INFORMATION: Actin reverse primer

<400> SEQUENCE: 2
ccagtggtac ggccagagg 19

<210> SEQ ID NO 3
<211> LENGTH: 26
<212> TYPE: DNA
<213> ORGANISM: Artificial Sequence
<220> FEATURE:
<223> OTHER INFORMATION: VIC-labeled actin probe

<400> SEQUENCE: 3
ccagccatgt acgttgctat ccaggc 26

<210> SEQ ID NO 4

<211> LENGTH: 22
<212> TYPE: DNA
<213> ORGANISM: Artificial Sequence
<220> FEATURE:
<223> OTHER INFORMATION: GaLV env forward primer

<400> SEQUENCE: 4
tctgggatac aaaggcagtc ca 22

<210> SEQ ID NO 5
<211> LENGTH: 22
<212> TYPE: DNA
<213> ORGANISM: Artificial Sequence
<220> FEATURE:
<223> OTHER INFORMATION: GaLV env reverse primer

<400> SEQUENCE: 5
gccaaggcac atacatcagg tt 22

<210> SEQ ID NO 6
<211> LENGTH: 24
<212> TYPE: DNA
<213> ORGANISM: Artificial Sequence
<220> FEATURE:
<223> OTHER INFORMATION: FAM-labeled GaLV env probe

<400> SEQUENCE: 6
cccttggact tggtggccca cact 24

<210> SEQ ID NO 7
<211> LENGTH: 26
<212> TYPE: DNA
<213> ORGANISM: Artificial Sequence
<220> FEATURE:
<223> OTHER INFORMATION: Beta Actin probe

<400> SEQUENCE: 7
ccagccatgt acgttgctat ccaggc 26

<210> SEQ ID NO 8
<211> LENGTH: 19
<212> TYPE: DNA
<213> ORGANISM: Artificial Sequence
<220> FEATURE:
<223> OTHER INFORMATION: Actin reverse primer

<400> SEQUENCE: 8
ccagtggtac ggccagacc 19

<210> SEQ ID NO 9
<211> LENGTH: 26
<212> TYPE: DNA
<213> ORGANISM: Artificial Sequence
<220> FEATURE:
<223> OTHER INFORMATION: Vic-labeled Actin hydrolysis probe

<400> SEQUENCE: 9
ccagccatgt acgttgctat ccaggc 26

<210> SEQ ID NO 10
<211> LENGTH: 18
<212> TYPE: DNA
<213> ORGANISM: Artificial Sequence
<220> FEATURE:
<223> OTHER INFORMATION: Actin forward primer

<400> SEQUENCE: 10

```
aaggccaacc gcgagaag                                                  18


<210> SEQ ID NO 11
<211> LENGTH: 22
<212> TYPE: DNA
<213> ORGANISM: Artificial Sequence
<220> FEATURE:
<223> OTHER INFORMATION: Actin reverse primer

<400> SEQUENCE: 11

acagcctgga tagcaacgta ca                                             22


<210> SEQ ID NO 12
<211> LENGTH: 17
<212> TYPE: DNA
<213> ORGANISM: Artificial Sequence
<220> FEATURE:
<223> OTHER INFORMATION: HEX-labeled Actin hydrolysis probe

<400> SEQUENCE: 12

tgacccagat catgttt                                                   17


<210> SEQ ID NO 13
<211> LENGTH: 19
<212> TYPE: DNA
<213> ORGANISM: Artificial Sequence
<220> FEATURE:
<223> OTHER INFORMATION: Actin forward primer

<400> SEQUENCE: 13

ttctacaatg agctgcgtg                                                 19


<210> SEQ ID NO 14
<211> LENGTH: 21
<212> TYPE: DNA
<213> ORGANISM: Artificial Sequence
<220> FEATURE:
<223> OTHER INFORMATION: Actin reverse primer

<400> SEQUENCE: 14

cctggatagc aacgtacatg g                                              21


<210> SEQ ID NO 15
<211> LENGTH: 20
<212> TYPE: DNA
<213> ORGANISM: Artificial Sequence
<220> FEATURE:
<223> OTHER INFORMATION: HEX-labeled Actin hydrolysis probe

<400> SEQUENCE: 15

ctgaacccca aggccaaccg                                                20


<210> SEQ ID NO 16
<211> LENGTH: 21
<212> TYPE: DNA
<213> ORGANISM: Artificial Sequence
<220> FEATURE:
<223> OTHER INFORMATION: MMLV gag forward primer

<400> SEQUENCE: 16

actccactac ctcgcaggca t                                              21


<210> SEQ ID NO 17
<211> LENGTH: 21
<212> TYPE: DNA
```

<213> ORGANISM: Artificial Sequence
<220> FEATURE:
<223> OTHER INFORMATION: MMLV gag reverse primer

<400> SEQUENCE: 17
agaggagaac ggccagtatt g 21

<210> SEQ ID NO 18
<211> LENGTH: 21
<212> TYPE: DNA
<213> ORGANISM: Artificial Sequence
<220> FEATURE:
<223> OTHER INFORMATION: Fam-labeled MMLV gag hydrolysis probe

<400> SEQUENCE: 18
ccgcgcagga ggaaacggac a 21

<210> SEQ ID NO 19
<211> LENGTH: 20
<212> TYPE: DNA
<213> ORGANISM: Artificial Sequence
<220> FEATURE:
<223> OTHER INFORMATION: MMLV gag forward primer

<400> SEQUENCE: 19
ctccttctct aggcgccaaa 20

<210> SEQ ID NO 20
<211> LENGTH: 15
<212> TYPE: DNA
<213> ORGANISM: Artificial Sequence
<220> FEATURE:
<223> OTHER INFORMATION: MMLV gag reverse primer

<400> SEQUENCE: 20
gcggcccccc actgt 15

<210> SEQ ID NO 21
<211> LENGTH: 19
<212> TYPE: DNA
<213> ORGANISM: Artificial Sequence
<220> FEATURE:
<223> OTHER INFORMATION: Fam-labeled MMLV gag hydrolysis probe

<400> SEQUENCE: 21
ctaaacctca agttctttc 19

<210> SEQ ID NO 22
<211> LENGTH: 22
<212> TYPE: DNA
<213> ORGANISM: Artificial Sequence
<220> FEATURE:
<223> OTHER INFORMATION: MMLV gag forward primer

<400> SEQUENCE: 22
ggacagaaac aggatagaca gg 22

<210> SEQ ID NO 23
<211> LENGTH: 21
<212> TYPE: DNA
<213> ORGANISM: Artificial Sequence
<220> FEATURE:
<223> OTHER INFORMATION: MMLV gag reverse primer

<400> SEQUENCE: 23
tcgtggtttc ttgggacaat c 21

```
<210> SEQ ID NO 24
<211> LENGTH: 23
<212> TYPE: DNA
<213> ORGANISM: Artificial Sequence
<220> FEATURE:
<223> OTHER INFORMATION: Fam-labeled MMLV gag hydrolysis probe

<400> SEQUENCE: 24

ccagtgcccc ttttctttgc agt                                            23


<210> SEQ ID NO 25
<211> LENGTH: 2058
<212> TYPE: DNA
<213> ORGANISM: Gibbon ape leukemia virus
<220> FEATURE:
<223> OTHER INFORMATION: GaLV env
<300> PUBLICATION INFORMATION:
<308> DATABASE ACCESSION NUMBER: NC_001885.2
<309> DATABASE ENTRY DATE: 2007-05-24

<400> SEQUENCE: 25

atggtattgc tgcctgggtc catgcttctc acctcaaacc tgcaccacct tcggcaccag      60

atgagtcctg ggagctggaa aagactgatc atcctcttaa gctgcgtatt cggcggcggc     120

gggacgagtc tgcaaaataa gaacccccac cagcccatga ccctcacttg gcaggtactg     180

tcccaaactg gagacgttgt ctgggataca aaggcagtcc agccccttg gacttggtgg      240

cccacactta aacctgatgt atgtgccttg gcggctagtc ttgagtcctg ggatatcccg     300

ggaaccgatg tctcgtcctc taaacgagtc agacctccgg actcagacta tactgccgct     360

tataagcaaa tcacctgggg agccataggg tgcagctacc ctcgggctag gactagaatg     420

gcaagctcta ccttctacgt atgtccccgg gatggccgga ccctttcaga agctagaagg     480

tgcggggggc tagaatccct atactgtaaa gaatgggatt gtgagaccac ggggaccggt     540

tattggctat ctaaatcctc aaaagacctc ataactgtaa aatgggacca aaatagcgaa     600

tggactcaaa aatttcaaca gtgtcaccag accggctggt gtaaccccct taaaatagat     660

ttcacagaca aaggaaaatt atccaaggac tggataacgg gaaaaacctg ggggattaga     720

ttctatgtgt ctggacatcc aggcgtacag ttcaccattc gcttaaaaat caccaacatg     780

ccagctgtgg cagtaggtcc tgacctcgtc cttgtggaac aaggacctcc tagaacgtcc     840

ctcgctctcc cacctcctct tcccccaagg gaagcgccac cgccatctct ccccgactct     900

aactccacag ccctggcgac tagtgcacaa actcccacgg tgagaaaaac aattgttacc     960

ctaaacactc cgcctcccac cacaggcgac agactttttg atcttgtgca gggggccttc    1020

ctaaccttaa atgctaccaa cccaggggcc actgagtctt gctggctttg tttggccatg    1080

ggcccccctt attatgaagc aatagcctca tcaggagagg tcgcctactc caccgacctt    1140

gaccggtgcc gctgggggac ccaaggaaag ctcaccctca ctgaggtctc aggacacggg    1200

ttgtgcatag gaaaggtgcc ctttacccat cagcatctct gcaatcagac cctatccatc    1260

aattcctccg gagaccatca gtatctgctc ccctccaacc atagctggtg ggcttgcagc    1320

actggcctca ccccttgcct ctccacctca gtttttaatc agactagaga tttctgtatc    1380

caggtccagc tgattcctcg catctattac tatcctgaag aagttttgtt acaggcctat    1440

gacaattctc accccaggac taaaagagag gctgtctcac ttaccctagc tgttttactg    1500

gggttgggaa tcacggcggg aataggtact ggttcaactg ccttaattaa aggacctata    1560

gacctccagc aaggcctgac aagcctccag atcgccatag atgctgacct ccgggccctc    1620
```

```
caagactcag tcagcaagtt agaggactca ctgacttccc tgtccgaggt agtgctccaa   1680

aataggagag gccttgactt gctgtttcta aaagaaggtg gcctctgtgc ggccctaaag   1740

gaagagtgct gtttttacat agaccactca ggtgcagtac gggactccat gaaaaaactc   1800

aaagaaaaac tggataaaag acagttagag cgccagaaaa gccaaaactg gtatgaagga   1860

tggttcaata actccccttg gttcactacc ctgctatcaa ccatcgctgg gccccctatta   1920

ctcctccttc tgttgctcat cctcgggcca tgcatcatca ataagttagt tcaattcatc   1980

aatgatagga taagtgcagt taaaattctg gtccttagac agaaatatca ggccctagag   2040

aacgaaggta acctttaa                                                 2058
```

```
<210> SEQ ID NO 26
<211> LENGTH: 1665
<212> TYPE: DNA
<213> ORGANISM: Vesicular stomatitis virus
<220> FEATURE:
<223> OTHER INFORMATION: VSVG env
<300> PUBLICATION INFORMATION:
<308> DATABASE ACCESSION NUMBER: gi:9627229:3
<309> DATABASE ENTRY DATE: 2005-12-05

<400> SEQUENCE: 26

aacagagatc gatctgtttc cttgacacta tgaagtgcct tttgtactta gcctttttat     60

tcattggggt gaattgcaag ttcaccatag tttttccaca caaccaaaaa ggaaactgga    120

aaaatgttcc ttctaattac cattattgcc cgtcaagctc agatttaaat tggcataatg    180

acttaatagg cacagccata caagtcaaaa tgcccaagag tcacaaggct attcaagcag    240

acggttggat gtgtcatgct tccaaatggg tcactacttg tgatttccgc tggtatggac    300

cgaagtatat aacacagtcc atccgatcct tcactccatc tgtagaacaa tgcaaggaaa    360

gcattgaaca aacgaaacaa ggaacttggc tgaatccagg cttccctcct caaagttgtg    420

gatatgcaac tgtgacggat gccgaagcag tgattgtcca ggtgactcct caccatgtgc    480

tggttgatga atacacagga gaatgggttg attcacagtt catcaacgga aaatgcagca    540

attacatatg ccccactgtc cataactcta caacctggca ttctgactat aaggtcaaag    600

ggctatgtga ttctaacctc atttccatgg acatcacctt cttctcagag gacggagagc    660

tatcatccct gggaaaggag ggcacagggt tcagaagtaa ctactttgct tatgaaactg    720

gaggcaaggc ctgcaaaatg caatactgca agcattgggg agtcagactc ccatcaggtg    780

tctggttcga gatggctgat aaggatctct ttgctgcagc cagattccct gaatgcccag    840

aagggtcaag tatctctgct ccatctcaga cctcagtgga tgtaagtcta attcaggacg    900

ttgagaggat cttggattat tccctctgcc aagaaacctg gagcaaaatc agagcgggtc    960

ttccaatctc tccagtggat ctcagctatc ttgctcctaa aaacccagga accggtcctg   1020

ctttcaccat aatcaatggt accctaaaat actttgagac cagatacatc agagtcgata   1080

ttgctgctcc aatcctctca agaatggtcg gaatgatcag tggaactacc acagaaaggg   1140

aactgtggga tgactgggca ccatatgaag acgtggaaat tggacccaat ggagttctga   1200

ggaccagttc aggatataag tttcctttat acatgattgg acatggtatg ttggactccg   1260

atcttcatct tagctcaaag gctcaggtgt tcgaacatcc tcacattcaa gacgctgctt   1320

cgcaacttcc tgatgatgag agtttatttt ttggtgatac tgggctatcc aaaaatccaa   1380

tcgagcttgt agaaggttgg ttcagtagtt ggaaaagctc tattgcctct tttttcttta   1440

tcatagggtt aatcattgga ctattcttgg ttctccgagt tggtatccat ctttgcatta   1500
```

aattaaagca caccaagaaa agacagattt atacagacat agagatgaac cgacttggaa 1560
agtaactcaa atcctgcaca acagattctt catgtttgga ccaaatcaac ttgtgatacc 1620
atgctcaaag aggcctcaat tatatttgag tttttaattt ttatg 1665

<210> SEQ ID NO 27
<211> LENGTH: 1617
<212> TYPE: DNA
<213> ORGANISM: Moloney murine leukemia virus
<220> FEATURE:
<223> OTHER INFORMATION: MMLV gag
<300> PUBLICATION INFORMATION:
<308> DATABASE ACCESSION NUMBER: NC_001501.1
<309> DATABASE ENTRY DATE: 2000-08-01

<400> SEQUENCE: 27
atgggccaga ctgttaccac tcccttaagt ttgaccttag gtcactggaa agatgtcgag 60
cggatcgctc acaaccagtc ggtagatgtc aagaagagac gttgggttac cttctgctct 120
gcagaatggc caacctttaa cgtcggatgg ccgcgagacg gcacctttaa ccgagacctc 180
atcacccagg ttaagatcaa ggtcttttca cctggcccgc atggacaccc agaccaggtc 240
ccctacatcg tgacctggga agccttggct tttgaccccc ctccctgggt caagcccttt 300
gtacacccta agcctccgcc tcctcttcct ccatccgccc cgtctctccc ccttgaacct 360
cctcgttcga ccccgcctcg atcctccctt tatccagccc tcactccttc tctaggcgcc 420
aaacctaaac ctcaagttct ttctgacagt gggggggccgc tcatcgacct acttacagaa 480
gaccccccgc cttataggga cccaagacca cccccttccg acagggacgg aaatggtgga 540
gaagcgaccc ctgcgggaga ggcaccggac ccctccccaa tggcatctcg cctacgtggg 600
agacgggagc cccctgtggc cgactccact acctcgcagg cattcccccct ccgcgcagga 660 ggaaacggac agcttcaata ctggccgttc tcctcttctg acctttacaa ctggaaaaat 720
aataaccctt ctttttctga agatccaggt aaactgacag ctctgatcga gtctgttctc 780
atcacccatc agcccacctg ggacgactgt cagcagctgt tggggactct gctgaccgga 840
gaagaaaaac aacgggtgct cttagaggct agaaaggcgg tgcggggcga tgatgggcgc 900
cccactcaac tgcccaatga agtcgatgcc gcttttcccc tcgagcgccc agactgggat 960
tacaccaccc aggcaggtag gaaccaccta gtccactatc gccagttgct cctagcgggt 1020
ctccaaaacg cgggcagaag ccccaccaat ttggccaagg taaaaggaat aacacaaggg 1080
cccaatgagt ctccctcggc cttcctagag agacttaagg aagcctatcg caggtacact 1140
ccttatgacc ctgaggaccc agggcaagaa actaatgtgt ctatgtcttt catttggcag 1200
tctgccccag acattgggag aaagttagag aggttagaag atttaaaaaa caagacgctt 1260
ggagatttgg ttagagaggc agaaaagatc tttaataaac gagaaacccc ggaagaaaga 1320
gaggaacgta tcaggagaga aacagaggaa aaagaagaac gccgtaggac agaggatgag 1380
cagaaagaga aagaaagaga tcgtaggaga catagagaga tgagcaagct attggccact 1440
gtcgttagtg gacagaaaca ggatagacag ggaggagaac gaaggaggtc ccaactcgat 1500
cgcgaccagt gtgcctactg caaagaaaag gggcactggg ctaaagattg tcccaagaaa 1560
ccacgaggac ctcggggacc aagaccccag acctccctcc tgaccctaga tgactag 1617

<210> SEQ ID NO 28
<211> LENGTH: 3454
<212> TYPE: DNA
<213> ORGANISM: Homo sapiens
<220> FEATURE:
<223> OTHER INFORMATION: Beta actin

<400> SEQUENCE: 28

```
accgccgaga ccgcgtccgc cccgcgagca cagagcctcg cctttgccga tccgccgccc     60
gtccacaccc gccgccaggt aagcccggcc agccgaccgg ggcaggcggc tcacggcccg    120
gccgcaggcg gccgcggccc cttcgcccgt gcagagccgc cgtctgggcc gcagcggggg    180
gcgcatgggg ggggaaccgg accgccgtgg ggggcgcggg agaagcccct gggcctccgg    240
agatggggga cacccccacgc cagttcggag gcgcgaggcc gcgctcggga ggcgcgctcc    300
gggggtgccg ctctcggggc gggggcaacc ggcggggtct ttgtctgagc cgggctcttg    360
ccaatgggga tcgcagggtg ggcgcggcgg agcccccgcc aggcccggtg gggctgggg    420
cgccattgcg cgtgcgcgct ggtcctttgg gcgctaactg cgtgcgcgct gggaattggc    480
gctaattgcg cgtgcgcgct gggactcaag gcgctaactg cgcgtgcgtt ctggggcccg    540
gggtgccgcg gcctgggctg gggcgaaggc gggctcggcc ggaaggggtg gggtcgccgc    600
ggctcccggg cgcttgcgcg cacttcctgc ccgagccgct ggccgcccga gggtgtggcc    660
gctgcgtgcg cgcgcgccga cccggcgctg tttgaaccgg gcggaggcgg ggctggcgcc    720
cggttgggag gggggttgggg cctggcttcc tgccgcgcgc cgcggggacg cctccgacca    780
gtgtttgcct tttatggtaa taacgcggcc ggcccggctt cctttgtccc caatctgggc    840
gcgcgccggc gccccctggc ggcctaagga ctcggcgcgc cggaagtggc cagggcgggg    900
gcgacctcgg ctcacagcgc gcccggctat tctcgcagct caccatggat gatgatatcg    960
ccgcgctcgt cgtcgacaac ggctccggca tgtgcaaggc cggcttcgcg ggcgacgatg   1020
ccccccgggc cgtcttcccc tccatcgtgg ggcgccccag gcaccaggta ggggagctgg   1080
ctgggtgggg cagccccggg agcgggcggg aggcaagggc gctttctctg cacaggagcc   1140
tcccggtttc cggggtgggg gctgcgcccg tgctcagggc ttcttgtcct ttccttccca   1200
gggcgtgatg gtgggcatgg gtcagaagga ttcctatgtg ggcgacgagg cccagagcaa   1260
gagaggcatc ctcaccctga agtaccccat cgagcacggc atcgtcacca actgggacga   1320
catggagaaa atctggcacc acaccttcta caatgagctg cgtgtggctc ccgaggagca   1380
ccccgtgctg ctgaccgagg cccccctgaa ccccaaggcc aaccgcgaga agatgaccca   1440
ggtgagtggc ccgctacctc ttctggtggc cgcctccctc cttcctggcc tcccggagct   1500
gcgccctttc tcactggttc tctcttctgc cgttttccgt aggactctct tctctgacct   1560
gagtctcctt tggaactctg caggttctat ttgcttttc ccagatgagc tctttttctg   1620
gtgtttgtct ctctgactag gtgtctaaga cagtgttgtg ggtgtaggta ctaacactgg   1680
ctcgtgtgac aaggccatga ggctggtgta aagcggcctt ggagtgtgta ttaagtaggt   1740
gcacagtagg tctgaacaga ctccccatcc caagacccca gcacacttag ccgtgttctt   1800
tgcactttct gcatgtcccc cgtctggcct ggctgtcccc agtggcttcc ccagtgtgac   1860
atggtgtatc tctgccttac agatcatgtt tgagaccttc aacaccccag ccatgtacgt   1920
tgctatccag gctgtgctat ccctgtacgc ctctggccgt accactggca tcgtgatgga   1980
ctccggtgac ggggtcaccc acactgtgcc catctacgag gggtatgccc tcccccatgc   2040
catcctgcgt ctggacctgg ctggccggga cctgactgac tacctcatga agatcctcac   2100
cgagcgcggc tacagcttca ccaccacggc cgagcgggaa atcgtgcgtg acattaagga   2160
gaagctgtgc tacgtcgccc tggacttcga gcaagagatg gccacggctg cttccagctc   2220
```

```
ctccctggag aagagctacg agctgcctga cggccaggtc atcaccattg gcaatgagcg   2280
gttccgctgc cctgaggcac tcttccagcc ttccttcctg ggtgagtgga gactgtctcc   2340
cggctctgcc tgacatgagg gttacccctc ggggctgtgc tgtggaagct aagtcctgcc   2400
ctcatttccc tctcaggcat ggagtcctgt ggcatccacg aaactacctt caactccatc   2460
atgaagtgtg acgtggacat ccgcaaagac ctgtacgcca acacagtgct gtctggcggc   2520
accaccatgt accctggcat tgccgacagg atgcagaagg agatcactgc cctggcaccc   2580
agcacaatga agatcaaggt gggtgtcttt cctgcctgag ctgacctggg caggtcggct   2640
gtggggtcct gtggtgtgtg gggagctgtc acatccaggg tcctcactgc ctgtcccctt   2700
ccctcctcag atcattgctc ctcctgagcg caagtactcc gtgtggatcg gcggctccat   2760
cctggcctcg ctgtccacct tccagcagat gtggatcagc aagcaggagt atgacgagtc   2820
cggcccctcc atcgtccacc gcaaatgctt ctaggcggac tatgacttag ttgcgttaca   2880
ccctttcttg acaaaaccta acttgcgcag aaaacaagat gagattggca tggctttatt   2940
tgtttttttt gttttgtttt ggtttttttt tttttttgg cttgactcag gatttaaaaa   3000
ctggaacggt gaaggtgaca gcagtcggtt ggagcgagca tcccccaaag ttcacaatgt   3060
ggccgaggac tttgattgca cattgttgtt tttttaatag tcattccaaa tatgagatgc   3120
gttgttacag gaagtccctt gccatcctaa aagccacccc acttctctct aaggagaatg   3180
gcccagtcct ctcccaagtc cacacagggg aggtgatagc attgctttcg tgtaaattat   3240
gtaatgcaaa attttttaa tcttcgcctt aatacttttt tattttgttt tattttgaat   3300
gatgagcctt cgtgcccccc cttcccctt ttttgtcccc caacttgaga tgtatgaagg   3360
cttttggtct ccctgggagt gggtggaggc agccagggct tacctgtaca ctgacttgag   3420
accagttgaa taaaagtgca caccttaaaa atga                              3454
```

```
<210> SEQ ID NO 29
<211> LENGTH: 3604
<212> TYPE: DNA
<213> ORGANISM: Murine leukemia virus
<220> FEATURE:
<223> OTHER INFORMATION: MLV pol
<300> PUBLICATION INFORMATION:
<308> DATABASE ACCESSION NUMBER: NC_001501.1
<309> DATABASE ENTRY DATE: 2000-08-01

<400> SEQUENCE: 29

ctagggaggt cagggtcagg agcccccccc tgaacccagg ataaccctca aagtcggggg     60
gcaacccgtc accttcctgg tagatactgg ggcccaacac tccgtgctga cccaaaatcc    120
tggaccccta agtgataagt ctgcctgggt ccaaggggct actggaggaa agcggtatcg    180
ctggaccacg gatcgcaaag tacatctagc taccggtaag gtcacccact ctttcctcca    240
tgtaccagac tgtccctatc ctctgttagg aagagatttg ctgactaaac taaaagccca    300
aatccacttt gagggatcag gagctcaggt tatgggacca atggggcagc ccctgcaagt    360
gttgacccta aatatagaag atgagcatcg gctacatgag acctcaaaag agccagatgt    420
ttctctaggg tccacatggc tgtctgattt tcctcaggcc tgggcggaaa ccgggggcat    480
gggactggca gttcgccaag ctcctctgat catacctctg aaagcaacct ctacccccgt    540
gtccataaaa caataccccca tgtcacaaga agccagactg gggatcaagc cccacataca    600
gagactgttg gaccagggaa tactggtacc ctgccagtcc ccctggaaca cgcccctgct    660
acccgttaag aaaccaggga ctaatgatta taggcctgtc caggatctga gagaagtcaa    720
```

```
caagcgggtg gaagacatcc accccaccgt gcccaaccct tacaacctct tgagcgggct    780
cccaccgtcc caccagtggt acactgtgct tgatttaaag gatgcctttt tctgcctgag    840
actccacccc accagtcagc ctctcttcgc ctttgagtgg agagatccag agatgggaat    900
ctcaggacaa ttgacctgga ccagactccc acagggtttc aaaaacagtc ccaccctgtt    960
tgatgaggca ctgcacagag acctagcaga cttccggatc cagcacccag acttgatcct   1020
gctacagtac gtggatgact tactgctggc cgccacttct gagctagact gccaacaagg   1080
tactcgggcc ctgttacaaa ccctagggaa cctcgggtat cgggcctcgg ccaagaaagc   1140
ccaaatttgc cagaaacagg tcaagtatct ggggtatctt ctaaaagagg gtcagagatg   1200
gctgactgag gccagaaaag agactgtgat ggggcagcct actccgaaga cccctcgaca   1260
actaagggag ttcctaggga cggcaggctt ctgtcgcctc tggatccctg ggtttgcaga   1320
aatggcagcc cccttgtacc ctctcaccaa aacggggact ctgtttaatt ggggcccaga   1380
ccaacaaaag gcctatcaag aaatcaagca agctcttcta actgccccag ccctggggtt   1440
gccagatttg actaagccct ttgaactctt tgtcgacgag aagcagggct acgccaaagg   1500
tgtcctaacg caaaaactgg gaccttggcg tcggccggtg gcctacctgt ccaaaaagct   1560
agacccagta gcagctgggt ggcccccttg cctacggatg gtagcagcca ttgccgtact   1620
gacaaaggat gcaggcaagc taaccatggg acagccacta gtcattctgg ccccccatgc   1680
agtagaggca ctagtcaaac aaccccccga ccgctggctt tccaacgccc ggatgactca   1740
ctatcaggcc ttgcttttgg acacggaccg ggtccagttc ggaccggtgg tagccctgaa   1800
cccggctacg ctgctcccac tgcctgagga agggctgcaa cacaactgcc ttgatatcct   1860
ggccgaagcc cacggaaccc gacccgacct aacggaccag ccgctcccag acgccgacca   1920
cacctggtac acggatggaa gcagtctctt acaagaggga cagcgtaagg cgggagctgc   1980
ggtgaccacc gagaccgagg taatctgggc taaagccctg ccagccggga catccgctca   2040
gcgggctgaa ctgatagcac tcacccaggc cctaaagatg gcagaaggta agaagctaaa   2100
tgtttatact gatagccgtt atgcttttgc tactgcccat atccatggag aaatatacag   2160
aaggcgtggg ttgctcacat cagaaggcaa agagatcaaa aataaagacg agatcttggc   2220
cctactaaaa gccctctttc tgcccaaaag acttagcata atccattgtc caggacatca   2280
aaagggacac agcgccgagg ctagaggcaa ccggatggct gaccaagcgg cccgaaaggc   2340
agccatcaca gagactccag acacctctac cctcctcata gaaaattcat caccctacac   2400
ctcagaacat tttcattaca cagtgactga tataaaggac ctaaccaagt tgggggccat   2460
ttatgataaa acaaagaagt attgggtcta ccaaggaaaa cctgtgatgc ctgaccagtt   2520
tacttttgaa ttattagact ttcttcatca gctgactcac ctcagcttct caaaaatgaa   2580
ggctctccta gagagaagcc acagtcccta ctacatgctg aaccgggatc gaacactcaa   2640
aaatatcact gagacctgca aagcttgtgc acaagtcaac gccagcaagt ctgccgttaa   2700
acagggaact agggtccgcg ggcatcggcc cggcactcat tgggagatcg atttcaccga   2760
gataaagccc ggattgtatg gctataaata tcttctagtt tttatagata ccttttctgg   2820
ctggatagaa gccttcccaa ccaagaaaga aaccgccaag gtcgtaacca agaagctact   2880
agaggagatc ttccccaggt tcggcatgcc tcaggtattg ggaactgaca atgggcctgc   2940
cttcgtctcc aaggtgagtc agacagtggc cgatctgttg gggattgatt ggaaattaca   3000
ttgtgcatac agaccccaaa gctcaggcca ggtagaaaga atgaatagaa ccatcaagga   3060
gactttaact aaattaacgc ttgcaactgg ctctagagac tgggtgctcc tactcccctt   3120
```

```
agccctgtac cgagcccgca acacgccggg cccccatggc ctcaccccat atgagatctt   3180

atatggggca cccccgcccc ttgtaaactt ccctgaccct gacatgacaa gagttactaa   3240

cagcccctct ctccaagctc acttacaggc tctctactta gtccagcacg aagtctggag   3300

acctctggcg gcagcctacc aagaacaact ggaccgaccg gtggtacctc acccttaccg   3360

agtcggcgac acagtgtggg tccgccgaca ccagactaag aacctagaac ctcgctggaa   3420

aggaccttac acagtcctgc tgaccacccc caccgccctc aaagtagacg gcatcgcagc   3480

ttggatacac gccgcccacg tgaaggctgc cgaccccggg ggtggaccat cctctagact   3540

gacatggcgc gttcaacgct ctcaaaaccc cttaaaaata aggttaaccc gcgaggcccc   3600

ctaa                                                                3604
```

<210> SEQ ID NO 30
<211> LENGTH: 4617
<212> TYPE: DNA
<213> ORGANISM: Artificial Sequence
<220> FEATURE:
<223> OTHER INFORMATION: pActin-MMLVgag

<400> SEQUENCE: 30

```
tcgacatggg ccagactgtt accactccct taagtttgac cttaggtcac tggaaagatg     60

tcgagcggat cgctcacaac cagtcggtag atgtcaagaa gagacgttgg gttaccttct    120

gctctgcaga atggccaacc tttaacgtcg gatggccgcg agacggcacc tttaaccgag    180

acctcatcac ccaggttaag atcaaggtct tttcacctgg cccgcatgga cacccagacc    240

aggtccccta catcgtgacc tgggaagcct tggcttttga ccccccctccc tgggtcaagc    300

cctttgtaca ccctaagcct ccgcctcctc ttcctccatc cgccccgtct ctcccccttg    360

aacctcctcg ttcgaccccg cctcgatcct ccctttatcc agccctcact ccttctctag    420

gcgccaaacc taaacctcaa gttctttctg acagtggggg gccgctcatc gacctactta    480

cagaagaccc cccgccttat agggacccaa gaccaccccc ttccgacagg gacggaaatg    540

gtggagaagc gacccctgcg ggagaggcac cggacccctc cccaatggca tctcgcctac    600

gtgggagacg ggagcccccct gtggccgact ccactacctc gcaggcattc cccctccgcg    660

caggaggaaa cggacagctt caatactggc cgttctcctc ttctgacctt tacaactgga    720

aaaataataa cccttctttt tctgaagatc caggtaaact gacagctctg atcgagtctg    780

ttctcatcac ccatcagccc acctgggacg actgtcagca gctgttgggg actctgctga    840

ccggagaaga aaaacaacgg gtgctcttag aggctagaaa ggcggtgcgg ggcgatgatg    900

ggcgccccac tcaactgccc aatgaagtcg atgccgcttt tccccctcgag cgcccagact    960

gggattacac cacccaggca ggtaggaacc acctagtcca ctatcgccag ttgctcctag   1020

cgggtctcca aaacgcgggc agaagcccca ccaatttggc caaggtaaaa ggaataacac   1080

aagggcccaa tgagtctccc tcggccttcc tagagagact taaggaagcc tatcgcaggt   1140

acactcctta tgaccctgag gacccagggc aagaaactaa tgtgtctatg tctttcattt   1200

ggcagtctgc cccagacatt gggagaaagt tagagaggtt agaagattta aaaaacaaga   1260

cgcttggaga tttggttaga gaggcagaaa agatctttaa taaacgagaa accccggaag   1320

aaagagagga acgtatcagg agagaaacag aggaaaaaga agaacgccgt aggacagagg   1380

atgagcagaa agagaaagaa agagatcgta ggagacatag agagatgagc aagctattgg   1440

ccactgtcgt tagtggacag aaacaggata gacagggagg agaacgaagg aggtcccaac   1500
```

-continued

```
tcgatcgcga ccagtgtgcc tactgcaaag aaaaggggca ctgggctaaa gattgtccca   1560
agaaaccacg aggacctcgg ggaccaagac cccagacctc cctcctgacc ctagatgact   1620
agaagcttat cagttctgga ccagcgagct gtgctgcgac tcgtggcgta atcatggtca   1680
tagctgtttc ctgtgtgaaa ttgttatccg ctcacaattc cacacaacat acgagccgga   1740
agcataaagt gtaaagcctg gggtgcctaa tgagtgagct aactcacatt aattgcgttg   1800
cgctcactgc ccgctttcca gtcgggaaac ctgtcgtgcc agctgcatta atgaatcggc   1860
caacgcgcgg ggagaggcgg tttgcgtatt gggcgctctt ccgcttcctc gctcactgac   1920
tcgctgcgct cggtcgttcg gctgcggcga gcggtatcag ctcactcaaa ggcggtaata   1980
cggttatcca cagaatcagg ggataacgca ggaaagaaca tgtgagcaaa aggccagcaa   2040
aaggccagga accgtaaaaa ggccgcgttg ctggcgtttt tccataggct ccgcccccct   2100
gacgagcatc acaaaaatcg acgctcaagt cagaggtggc gaaacccgac aggactataa   2160
agataccagg cgtttccccc tggaagctcc ctcgtgcgct ctcctgttcc gaccctgtcg   2220
cttaccggat acctgtccgc ctttctccct tcgggaagcg tggcgctttc tcatagctca   2280
cgctgtaggt atctcagttc ggtgtaggtc gttcgctcca agctgggctg tgtgcacgaa   2340
ccccccgttc agcccgaccg ctgcgcctta tccggtaact atcgtcttga gtccaacccg   2400
gtaagacacg acttatcgcc actggcagca gccactggta acaggattag cagagcgagg   2460
tatgtaggcg gtgctacaga gttcttgaag tggtggccta actacggcta cactagaaga   2520
acagtatttg gtatctgcgc tctgctgaag ccagttacct tcggaaaaag agttggtagc   2580
tcttgatccg gcaaacaaac caccgctggt agcggtggtt tttttgtttg caagcagcag   2640
attacgcgca gaaaaaaagg atctcaagaa gatcctttga tcttttctac ggggtctgac   2700
gctcagtgga acgaaaactc acgttaaggg attttggtca tgagattatc aaaaaggatc   2760
ttcacctaga tccttttaaa ttaaaaatga agttttaaat caatctaaag tatatatgag   2820
taaacttggt ctgacagtta ccaatgctta atcagtgagg cacctatctc agcgatctgt   2880
ctatttcgtt catccatagt tgcctgactc cccgtcgtgt agataactac gatacgggag   2940
ggcttaccat ctggccccag tgctgcaatg ataccgcgag acccacgctc accggctcca   3000
gatttatcag caataaacca gccagccgga agggccgagc gcagaagtgg tcctgcaact   3060
ttatccgcct ccatccagtc tattaattgt tgccgggaag ctagagtaag tagttcgcca   3120
gttaatagtt tgcgcaacgt tgttgccatt gctacaggca tcgtggtgtc acgctcgtcg   3180
tttggtatgg cttcattcag ctccggttcc caacgatcaa ggcgagttac atgatccccc   3240
atgttgtgca aaaaagcggt tagctccttc ggtcctccga tcgttgtcag aagtaagttg   3300
gccgcagtgt tatcactcat ggttatggca gcactgcata attctcttac tgtcatgcca   3360
tccgtaagat gcttttctgt gactggtgag tactcaacca agtcattctg agaatagtgt   3420
atgcggcgac cgagttgctc ttgcccggcg tcaatacggg ataataccgc gccacatagc   3480
agaactttaa aagtgctcat cattggaaaa cgttcttcgg ggcgaaaact ctcaaggatc   3540
ttaccgctgt tgagatccag ttcgatgtaa cccactcgtg cacccaactg atcttcagca   3600
tcttttactt tcaccagcgt ttctgggtga gcaaaaacag gaaggcaaaa tgccgcaaaa   3660
aagggaataa gggcgacacg gaaatgttga atactcatac tcttcctttt tcaatattat   3720
tgaagcattt atcagggtta ttgtctcatg agcggataca tatttgaatg tatttagaaa   3780
aataaacaaa taggggttcc gcgcacattt ccccgaaaag tgccacctga cgtctaagaa   3840
accattatta tcatgacatt aacctataaa aataggcgta tcacgaggcc ctttcgtctc   3900
```

```
gcgcgtttcg gtgatgacgg tgaaaacctc tgacacatgc agctcccgga gacggtcaca   3960
gcttgtctgt aagcggatgc cgggagcaga caagcccgtc agggcgcgtc agcgggtgtt   4020
ggcgggtgtc ggggctggct taactatgcg gcatcagagc agattgtact gagagtgcac   4080
caaatgcggt gtgaaatacc gcacagatgc gtaaggagaa aataccgcat caggcgccat   4140
tcgccattca ggctgcgcaa ctgttgggaa gggcgatcgg tgcgggcctc atcgctatta   4200
cgccagctgg cgaaaggggg atgtgctgca aggcgattaa gttgggtaac gccagggttt   4260
tcccagtcac gacgttgtaa aacgacggcc agtgcaacgc gatgacgatg gatagcgatt   4320
catcgatgag ctgacccgat cgccgccgcc ggagggttgc gtttgagacg ggcgacagat   4380
gaattccttc tacaatgagc tgcgtgtggc tcccgaggag caccccgtgc tgctgaccga   4440
ggcccccctg aaccccaagg ccaaccgcga gaagatgacc cagatcatgt ttgagacctt   4500
caacacccca gccatgtacg ttgctatcca ggctgtgcta tccctgtacg cctctggccg   4560
taccactggc atcgtgatgg actccggtga cggggtcacc cacactgtgc ccatctg      4617
```

<210> SEQ ID NO 31
<211> LENGTH: 1503
<212> TYPE: DNA
<213> ORGANISM: Human immunodeficiency virus
<220> FEATURE:
<223> OTHER INFORMATION: HIV Gag

<400> SEQUENCE: 31

```
atgggagcac gggctagtgt tctttctgga ggtgagcttg acaggtggga gaagatcaga     60
ctgcgccccg gcggcaaaaa gaagtacaag ctgaagcaca tcgtgtgggc ctctcgcgaa    120
ttggagaggt ttgccgtgaa ccccgggctc ctggagacaa gcgaggggtg ccggcagatc    180
ctcggccaat tgcagcccag tttgcaaacc ggcagcgagg agttgcggag cctgtacaac    240
accgtggcca cattgtactg cgtccaccag cgcatcgaaa tcaaggatac aaaagaggcc    300
ctggataaaa tcgaagagga acagaataag agcaaaaaga aggcccaaca agccgccgct    360
gataccggcc attctaacca agtgtctcag aactatccca tcgtccaaaa tattcaaggc    420
cagatggtcc accaagctat cagcccccgg accctgaacg cctgggtgaa ggtggtggag    480
gaaaaagcct ttctcccga ggtcatccct atgttcagcg ccctgagcga gggcgctaca    540
ccccaggacc tgaatacaat gttgaatacc gtcggcggcc accaggccgc tatgcagatg    600
ctgaaggaaa caattaacga agaggccgcc gagtgggacc gggtccaccc cgtccaggct    660
ggccccatcg cacccgggca aatgcgggag ccgagaggct ccgatatcgc cggcaccacc    720
tccacattgc aagagcagat cggctggatg accaacaatc cccaattcc cgtgggcgag    780
atctacaagc ggtggatcat tctcggcctg aacaagatcg tgcggatgta ctctcccaca    840
tctatcctcg atatccggca gggccccaaa gagcctttcc gggattacgt ggatagattt    900
tacaagacct tgcgggctga acaggccagc caagaagtga agaactggat gacggagaca    960
ctcctcgtgc agaacgccaa tcccgactgc aaaaccatcc tgaaggcctt gggcccagcc   1020
gccaccttgg aggagatgat gaccgcctgc caaggcgtgg gaggccctgg gcacaaagcc   1080
cgggtgctcg ccgaggccat gtctcaggtg accaacagcg ccacaatcat gatgcaacgg   1140
gggaacttcc gcaatcagcg gaaaatcgtg aaatgcttta actgtggcaa agaagggcac   1200
acagcccgca actgcagggc ccctaggaaa aagggctgtt ggaaatgtgg aaaggaagga   1260
caccaaatga aagattgtac tgagagacag gctaattttt tagggaagat ctggccttcc   1320
```

```
cacaagggaa ggccagggaa ttttcttcag agcagaccag agccaacagc cccaccagaa   1380

gagagcttca ggtttgggga agagacaaca actccctctc agaagcagga gccgatagac   1440

aaggaactgt atcctttagc ttccctcaga tcactctttg gcagcgaccc ctcgtcacaa   1500

taa                                                                 1503
```

<210> SEQ ID NO 32
<211> LENGTH: 2739
<212> TYPE: DNA
<213> ORGANISM: Human immunodeficiency virus
<220> FEATURE:
<223> OTHER INFORMATION: HIV Pol

<400> SEQUENCE: 32

```
atgtcactcc ctggtcggtg gaagcctaag atgattggtg gtataggggg cttcattaag     60

gtgcggcaat acgaccaaat cttgatcgag atttgcggcc acaaggccat cggcaccgtg    120

ctggtgggcc ccaccccegt gaatatcatc ggccggaacc tcctcaccca aatcggctgt    180

accctgaact tccctatctc tcccatcgaa accgtgcccg tgaagctgaa acccggcatg    240

gacgggccca aggtgaagca gtggcccctc accgaggaga agatcaaggc cctggtggag    300

atctgcaccg aaatggagaa agagggcaag atcagcaaga tcggccccga gaacccctat    360

aacacccccg tgttcgctat caaaaagaag gattccacca agtggcggaa gctggtggac    420

tttcgggagt tgaacaaacg gacccaggat tttgggaggt tgcagctggg catcccccac    480

cctgccggcc tgaagaaaaa gaagagcgtg accgtgctcg acgtcggcga cgcctacttc    540

agcgtgcctc tggacgagga ttttcgcaaa tacaccgcct tcacaatccc ctccatcaat    600

aacgaaaccc ccggcatccg gtaccaatat aacgtcttgc cccaaggctg gaagggcagc    660

cccgccatct ttcagtcctc tatgaccaag attctggaac ccttccggaa gcagaacccc    720

gatatcgtga tttaccagta tatggacgac ctctacgtgg gcagcgatct ggagatcggc    780

caacaccgga ccaagatcga agaactccgg cagcacctcc tccgctgggg cttgacaacc    840

cccgataaga agcaccaaaa ggagcctccc tttttgtgga tgggctacga gttgcacccc    900

gacaagtgga ccgtgcaacc catcgtcctc cccgagaagg attcttggac cgtgaacgat    960

atccaaaaac tggtcggcaa gctcaactgg gcctccccaaa tctatcccgg catcaaggtg   1020

cgccagctgt gcaagttgtt gcggggcaca aaggcgttga ccgaggtgat ccccttgacc   1080

gaggaggccg aattggagct cgccgagaat cgggaaatct tgaaggagcc cgtgcacggc   1140

gtctactacg atcccagcaa ggatctgatc gccgagatcc aaaaacaagg ccaggggcag   1200

tggacctacc agatctacca ggaacccttc aagaacctca agaccggcaa gtacgcccgg   1260

atgagaggcg cccataccaa cgacgtgaag cagctgaccg aagccgtcca gaagatcaca   1320

accgagtcta tcgtgatctg gggcaaaacc cccaagttca agctccctat ccagaaggaa   1380

acgtgggaaa cctggtggac cgaatactgg caggctacat ggattcccga atgggagttc   1440

gtgaacacac cccctctggt caagctgtgg tatcaactgg aaaaggagcc tatcgtgggc   1500

gccgagacat tttacgtgga cggcgctgcc aatcgcgaaa ccaagctggg caaggccggc   1560

tacgtgacca atcggggccg ccagaaggtg gtgacattga ccgataccac caaccagaaa   1620

accgaactgc aggccatcta cttggccctc caagacagcg gcctggaggt gaatatcgtg   1680

accgatagcc agtacgccct gggcattatc caggcccagc ccgaccagtc cgagagcgaa   1740

ctggtgaacc agatcatcga acaactgatc aagaaagaga aagtgtacct cgcctgggtg   1800

cccgcccata aggggatcgg cggcaacgag caggtggaca agctggtgtc cgccggcatt   1860
```

```
cgcaaggtgt tgttcctgga cggcatcgac aaagctcagg acgagcacga aaagtaccat   1920

tccaactggc gggccatggc ctccgacttc aatttgccac ccgtggtggc caaggagatc   1980

gtggcttctt gcgacaagtg ccaattgaag ggcgaggcta tgcacggcca ggtggattgc   2040

tcccccggca tctggcagtt ggactgcacc cacctggagg gcaaggtgat tctcgtggcc   2100

gtgcacgtgg cttccggcta catcgaggct gaggtgatcc cggccgaaac cggccaagag   2160

actgcctact tcttgctgaa gctggccggc aggtggcccg taaagaccat ccacaccgat   2220

aacgggtcta actttacatc cgccaccgtg aaagctgctt gctggtgggc aggcattaaa   2280

caagagttcg gcatccctta taaccctcag tcccagggcg tggtggagag catgaacaag   2340

gagctgaaaa agatcatcgg ccaagtgcgg gaccaagccg agcacttgaa aaccgccgtg   2400

cagatggccg tgtttattca taacttcaag cggaagggcg gcatcggcgg ctattccgcc   2460

ggtgagcgga tcgtggatat catcgccacc gatatccaga ccaaggagct gcagaagcag   2520

atcaccaaga tccagaactt cagagtgtac tatcgcgatt ctcggaaccc cttgtggaag   2580

gggccagcca aattgttgtg gaagggggag ggcgccgtgg tgatccagga caactccgat   2640

atcaaggtgg tcccgcggag gaaggccaaa attatccgcg actacggcaa gcaaatggcc   2700

ggcgacgact gcgtcgcctc ccggcaagac gaggactga                          2739
```

<210> SEQ ID NO 33
<211> LENGTH: 1095
<212> TYPE: DNA
<213> ORGANISM: Human immunodeficiency virus
<220> FEATURE:
<223> OTHER INFORMATION: HIV Rev

<400> SEQUENCE: 33

```
gtcgagggat ctccataaga gaagagggac agctatgact gggagtagtc aggagaggag     60

gaaaaatctg gctagtaaaa catgtaagga aaattttagg gatgttaaag aaaaaaataa    120

cacaaaacaa aatataaaaa aaatctaacc tcaagtcaag gcttttctat ggaataagga    180

atggacagca gggggctgtt tcatatactg atgacctctt tatagccaac ctttgttcat    240

ggcagccagc atatgggcat atgttgccaa actctaaacc aaatactcat tctgatgttt    300

taaatgattt gccctcccat atgtccttcc gagtgagaga cacaaaaaat tccaacacac    360

tattgcaatg aaaataaatt tcctttatta gccagaagtc agatgctcaa ggggcttcat    420

gatgtcccca taatttttgg cagagggaaa aagatctgct agctatagtt ctagaggtac    480

cggttgtttc gagcttatag caaaatcctt tccaagccct gtcttattct tctaggtatg    540

tggcgaatag ctctacaagc tccttgtact acttctataa ccctatctgt cccctcagct    600

actgctatgg ctgtggcatt gagcaagcta acagcactat tctttagctc ctgactccaa    660

tattgtagga gattccacca atatttgagg gcttcccacc ccctgcgtcc cagaagttcc    720

acaatcctcg ttacaatcaa gagtaagtct ctcaagcggt ggtagctgaa gaggcacagg    780

ctccgcagat cgtcccagat aagtgccaag gatccgttca ctaatcgaat ggatctgtct    840

ctgtctctct ctccaccttc ttcttctatt ccttcgggcc tgtcgggtcc cctcggggtt    900

gggaggtggg tctgaaacga taatggtgaa tatccctgcc taactctatt cactatagaa    960

agtacagcaa aaactattct taaacctacc aagcctccta ctatcattat gaataatttt   1020

atataccaca gccaatttgt tatgttaaac caattccaca aacttgccca tttatctaat   1080

tccaataatt cttgt                                                    1095
```

<210> SEQ ID NO 34
<211> LENGTH: 5066
<212> TYPE: DNA
<213> ORGANISM: Artificial Sequence
<220> FEATURE:
<223> OTHER INFORMATION: pActin-GaLV

<400> SEQUENCE: 34

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accaaatgcg gtgtgaaata ccgcacagat gcgtaaggag aaaataccgc atcaggcgcc    240
attcgccatt caggctgcgc aactgttggg aagggcgatc ggtgcgggcc tcatcgctat    300
tacgccagct ggcgaaaggg ggatgtgctg caaggcgatt aagttgggta acgccagggt    360
tttcccagtc acgacgttgt aaaacgacgg ccagtgcaac gcgatgacga tggatagcga    420
ttcatcgatg agctgacccg atcgccgccg ccggagggtt gcgtttgaga cgggcgacag    480
atgaattcct tctacaatga gctgcgtgtg gctcccgagg agcacccccgt gctgctgacc    540
gaggcccccc tgaaccccaa ggccaaccgc gagaagatga cccagatcat gtttgagacc    600
ttcaacaccc cagccatgta cgttgctatc caggctgtgc tatccctgta cgcctctggc    660
cgtaccactg gcatcgtgat ggactccggt gacggggtca cccacactgt gcccatctgt    720
cgacgcggcc gcatggtatt gctgcctggg tccatgcttc tcacctcaaa cctgcaccac    780
cttcggcacc agatgagtcc tgggagctgg aaaagactga tcatcctctt aagctgcgta    840
ttcggcggcg gcgggacgag tctgcaaaat aagaaccccc accagcccat gaccctcact    900
tggcaggtac tgtcccaaac tggagacgtt gtctgggata caaaggcagt ccagcccccct    960
tggacttggt ggcccacact taaacctgat gtatgtgcct tggcggctag tcttgagtcc   1020
tgggatatcc cgggaaccga tgtctcgtcc tctaaacgag tcagacctcc ggactcagac   1080
tatactgccg cttataagca aatcacctgg ggagccatag ggtgcagcta ccctcgggct   1140
aggactagaa tggcaagctc taccttctac gtatgtcccc gggatggccg gaccctttca   1200
gaagctagaa ggtgcggggg gctagaatcc ctatactgta aagaatggga ttgtgagacc   1260
acggggaccg gttattggct atctaaatcc tcaaaagacc tcataactgt aaaatgggac   1320
caaaatagcg aatggactca aaaatttcaa cagtgtcacc agaccggctg gtgtaacccc   1380
cttaaaatag atttcacaga caaaggaaaa ttatccaagg actggataac gggaaaaacc   1440
tggggattaa gattctatgt gtctggacat ccaggcgtac agttcaccat tcgcttaaaa   1500
atcaccaaca tgccagctgt ggcagtaggt cctgacctcg tccttgtgga acaaggacct   1560
cctagaacgt ccctcgctct cccacctcct cttcccccaa gggaagcgcc accgccatct   1620
ctccccgact ctaactccac agccctggcg actagtgcac aaactcccac ggtgagaaaa   1680
acaattgtta ccctaaacac tccgcctccc accacaggcg acagactttt tgatcttgtg   1740
cagggggcct tcctaacctt aaatgctacc aacccagggg ccactgagtc ttgctggctt   1800
tgtttggcca tgggcccccc ttattatgaa gcaatagcct catcaggaga ggtcgcctac   1860
tccaccgacc ttgaccggtg ccgctggggg acccaaggaa agctcaccct cactgaggtc   1920
tcaggacacg ggttgtgcat aggaaaggtg ccctttaccc atcagcatct ctgcaatcag   1980
accctatcca tcaattcctc cggagaccat cagtatctgc tcccctccaa ccatagctgg   2040
tgggcttgca gcactggcct caccccttgc ctctccacct cagtttttaa tcagactaga   2100
```

```
gatttctgta tccaggtcca gctgattcct cgcatctatt actatcctga agaagttttg   2160
ttacaggcct atgacaattc tcaccccagg actaaaagag aggctgtctc acttacccta   2220
gctgttttac tggggttggg aatcacggcg ggaataggta ctggttcaac tgccttaatt   2280
aaaggaccta tagacctcca gcaaggcctg acaagcctcc agatcgccat agatgctgac   2340
ctccgggccc tccaagactc agtcagcaag ttagaggact cactgacttc cctgtccgag   2400
gtagtgctcc aaaataggag aggccttgac ttgctgtttc taaaagaagg tggcctctgt   2460
gcggccctaa aggaagagtg ctgtttttac atagaccact caggtgcagt acgggactcc   2520
atgaaaaaac tcaaagaaaa actggataaa agacagttag agcgccagaa aagccaaaac   2580
tggtatgaag gatggttcaa taactcccct tggttcacta ccctgctatc aaccatcgct   2640
gggcccctat tactcctcct tctgttgctc atcctcgggc catgcatcat caataagtta   2700
gttcaattca tcaatgatag gataagtgca gttaaaattc tggtccttag acagaaatat   2760
caggccctag agaacgaagg taacctttaa aagcttatca gttctggacc agcgagctgt   2820
gctgcgactc gtggcgtaat catggtcata gctgtttcct gtgtgaaatt gttatccgct   2880
cacaattcca cacaacatac gagccggaag cataaagtgt aaagcctggg gtgcctaatg   2940
agtgagctaa ctcacattaa ttgcgttgcg ctcactgccc gctttccagt cgggaaacct   3000
gtcgtgccag ctgcattaat gaatcggcca acgcgcgggg agaggcggtt tgcgtattgg   3060
gcgctcttcc gcttcctcgc tcactgactc gctgcgctcg gtcgttcggc tgcggcgagc   3120
ggtatcagct cactcaaagg cggtaatacg gttatccaca gaatcagggg ataacgcagg   3180
aaagaacatg tgagcaaaag gccagcaaaa ggccaggaac cgtaaaaagg ccgcgttgct   3240
ggcgtttttc cataggctcc gcccccctga cgagcatcac aaaaatcgac gctcaagtca   3300
gaggtggcga aacccgacag gactataaag ataccaggcg tttccccctg gaagctccct   3360
cgtgcgctct cctgttccga ccctgtcgct taccggatac ctgtccgcct ttctcccttc   3420
gggaagcgtg gcgctttctc atagctcacg ctgtaggtat ctcagttcgg tgtaggtcgt   3480
tcgctccaag ctgggctgtg tgcacgaacc ccccgttcag cccgaccgct gcgccttatc   3540
cggtaactat cgtcttgagt ccaacccggt aagacacgac ttatcgccac tggcagcagc   3600
cactggtaac aggattagca gagcgaggta tgtaggcggt gctacagagt tcttgaagtg   3660
gtggcctaac tacggctaca ctagaagaac agtatttggt atctgcgctc tgctgaagcc   3720
agttaccttc ggaaaaagag ttggtagctc ttgatccggc aaacaaacca ccgctggtag   3780
cggtggtttt tttgtttgca agcagcagat tacgcgcaga aaaaaaggat ctcaagaaga   3840
tcctttgatc ttttctacgg ggtctgacgc tcagtggaac gaaaactcac gttaagggat   3900
tttggtcatg agattatcaa aaaggatctt cacctagatc cttttaaatt aaaaatgaag   3960
ttttaaatca atctaaagta tatatgagta aacttggtct gacagttacc aatgcttaat   4020
cagtgaggca cctatctcag cgatctgtct atttcgttca tccatagttg cctgactccc   4080
cgtcgtgtag ataactacga tacgggaggg cttaccatct ggccccagtg ctgcaatgat   4140
accgcgagac ccacgctcac cggctccaga tttatcagca ataaaccagc cagccggaag   4200
ggccgagcgc agaagtggtc ctgcaacttt atccgcctcc atccagtcta ttaattgttg   4260
ccgggaagct agagtaagta gttcgccagt taatagtttg cgcaacgttg ttgccattgc   4320
tacaggcatc gtggtgtcac gctcgtcgtt tggtatggct tcattcagct ccggttccca   4380
acgatcaagg cgagttacat gatcccccat gttgtgcaaa aaagcggtta gctccttcgg   4440
```

```
tcctccgatc gttgtcagaa gtaagttggc cgcagtgtta tcactcatgg ttatggcagc   4500

actgcataat tctcttactg tcatgccatc cgtaagatgc ttttctgtga ctggtgagta   4560

ctcaaccaag tcattctgag aatagtgtat gcggcgaccg agttgctctt gcccggcgtc   4620

aatacgggat aataccgcgc cacatagcag aactttaaaa gtgctcatca ttggaaaacg   4680

ttcttcgggg cgaaaactct caaggatctt accgctgttg agatccagtt cgatgtaacc   4740

cactcgtgca cccaactgat cttcagcatc ttttactttc accagcgttt ctgggtgagc   4800

aaaaacagga aggcaaaatg ccgcaaaaaa gggaataagg gcgacacgga aatgttgaat   4860

actcatactc ttcctttttc aatattattg aagcatttat cagggttatt gtctcatgag   4920

cggatacata tttgaatgta tttagaaaaa taaacaaata ggggttccgc gcacatttcc   4980

ccgaaaagtg ccacctgacg tctaagaaac cattattatc atgacattaa cctataaaaa   5040

taggcgtatc acgaggccct ttcgtc                                        5066
```

<210> SEQ ID NO 35
<211> LENGTH: 20
<212> TYPE: DNA
<213> ORGANISM: Artificial Sequence
<220> FEATURE:
<223> OTHER INFORMATION: VSV-G Forward Primer

<400> SEQUENCE: 35

```
attgcccgtc aagctcagat                                                 20
```

<210> SEQ ID NO 36
<211> LENGTH: 23
<212> TYPE: DNA
<213> ORGANISM: Artificial Sequence
<220> FEATURE:
<223> OTHER INFORMATION: VSV-G Reverse Primer

<400> SEQUENCE: 36

```
gtgactcttg ggcattttga ctt                                             23
```

<210> SEQ ID NO 37
<211> LENGTH: 30
<212> TYPE: DNA
<213> ORGANISM: Artificial Sequence
<220> FEATURE:
<223> OTHER INFORMATION: VSV-G Probe

<400> SEQUENCE: 37

```
tggcataatg acttaatagg cacagcctta                                      30
```

<210> SEQ ID NO 38
<211> LENGTH: 21
<212> TYPE: DNA
<213> ORGANISM: Artificial Sequence
<220> FEATURE:
<223> OTHER INFORMATION: rev Forward Primer

<400> SEQUENCE: 38

```
agcgacgaag acctcctcaa g                                               21
```

<210> SEQ ID NO 39
<211> LENGTH: 27
<212> TYPE: DNA
<213> ORGANISM: Artificial Sequence
<220> FEATURE:
<223> OTHER INFORMATION: rev Reverse Primer

<400> SEQUENCE: 39

```
ctctccacct tcttcttcta ttccttc                                          27


<210> SEQ ID NO 40
<211> LENGTH: 30
<212> TYPE: DNA
<213> ORGANISM: Artificial Sequence
<220> FEATURE:
<223> OTHER INFORMATION: rev Probe

<400> SEQUENCE: 40

caagtttctc tatcaaagca acccacctcc                                       30


<210> SEQ ID NO 41
<211> LENGTH: 21
<212> TYPE: DNA
<213> ORGANISM: Artificial Sequence
<220> FEATURE:
<223> OTHER INFORMATION: ACTB Forward Primer

<400> SEQUENCE: 41

gcgagaagat gacccagatc a                                                21
```

METHODS FOR ASSESSING THE PRESENCE OR ABSENCE OF REPLICATION COMPETENT VIRUS

CROSS-REFERENCE TO RELATED APPLICATIONS

This application is a U.S. National Stage of International Application No. PCT/US2017/044550 filed Jul. 28, 2017, which claims priority from U.S. provisional application No. 62/369,024 filed Jul. 29, 2016, entitled "Methods for Assessing the Presence or Absence of Replication Competent Virus," and from U.S. provisional application No. 62/448,954 filed on Jan. 20, 2017, entitled "Methods for Assessing the Presence or Absence of Replication Competent Virus," the contents of which are incorporated by reference in their entirety.

INCORPORATION BY REFERENCE OF SEQUENCE LISTING

The present application is being filed with a Sequence Listing in electronic format. The Sequence Listing is provided as a filed entitled 735042005600SeqList.txt, created on Jan. 22, 2019, which is 40,511 bytes in size. The information in the electronic format of the Sequence Listing is incorporated by reference in its entirety.

FIELD

The present disclosure relates to methods of detecting or confirming the absence of replication competent retrovirus. The methods may include assessing RNA levels of one or more target genes, such as viral genes, e.g. structural or packaging genes, from which gene products are expressed in certain cells infected with a replication-competent retrovirus, such as a gammaretrovirus or lentivirus, but not present in a viral vector used to transduce cells with a heterologous nucleic acid and not, or not expected to be, present and/or expressed in cells not containing replication-competent retrovirus. Replication competent retrovirus may be determined to be present if RNA levels of the one or more target genes is higher than a reference value, which can be measured directly or indirectly, e.g. from a positive control sample containing the target gene.

BACKGROUND

Retroviral vector particles, such as gammaretroviral and lentiviral vector particles, are used in various clinical applications, including for the introduction of therapeutic genes into cells and/or subjects. Such viral vector particles are engineered to be replication defective, however, in many instances it may be desirable or even necessary to verify the absence of replication competent virus (e.g., as replication competent retrovirus (RCR) or replication competent lentivirus (RCL)) in a sample or composition, such as a therapeutic or pharmaceutical composition formulated for administration. For example, in certain applications, methods are used to verify or confirm that no RCR has resulted during generation or processing steps, such as through homologous or non-homologous recombination between the transfer vector, packaging components, and/or endogenous viral elements in the cells used for production of the viral vector particles. Various methods are available for such confirmation and verification, such as to verify the absence of replication competent virus, for example during or after generation and processing, in formulated therapeutic compositions and/or drug products for administration, such as engineered cells and/or in samples from subjects, e.g., those having received therapies containing cells transduced with viral vector particles. However, existing methods can be overly time consuming and/or carry a risk of false positive results. There is a need for improved methods are needed for detecting RCR.

SUMMARY

Provided herein are methods including: a) determining a level of a parameter in a test sample, wherein the parameter or level indicates or correlates (optionally positively or inversely) with a presence, absence, or amount or concentration of a viral RNA in a biological sample, the biological sample including at least one cell that contains a heterologous nucleic acid and/or a nucleic acid encoding a heterologous protein, wherein: the presence, absence or amount or concentration of the viral RNA in the biological sample indicates a presence or absence of, or risk of, a replication competent virus in the biological sample, or a sample from which the biological sample is derived; and/or the viral RNA is required for, or encodes a gene product or specifically identifiable portion thereof that is required for, replication competency of a replication competent virus.

In some embodiments, the method further includes determining the presence, absence, concentration, or amount of the viral RNA in the biological sample or risk thereof, based on said level so-determined. In some embodiments, the method further includes the steps of: b) comparing the level of the parameter, determined in (a), to a first reference value for the parameter. In some embodiments, the comparison indicates the presence, absence, concentration or amount of the viral RNA in the biological sample or sample derived therefrom, or risk of any of the foregoing.

In some embodiments, the method further includes determining the presence, absence, or amount or concentration of the viral RNA, or risk of any of the foregoing, in the biological sample or portion thereof; and/or determining whether replication competent virus is (or is potentially or is likely to be) present or at risk for being present in the biological sample, or a portion thereof.

In some embodiments, the biological sample is deemed to have, to potentially have, or to be at risk for, presence of the replication competent virus, and/or to have the presence or at least a threshold amount of the viral RNA, if, and optionally only if, the level of the parameter determined in (a) is at or is above the first reference value, optionally wherein the level of the parameter positively correlates with the amount of the RNA in the biological sample; and/or the biological sample is deemed to have, or to be at risk for, the presence of the replication competent virus, and/or to have the presence or at least a threshold amount of the viral RNA, if, and optionally only if, the level of the parameter determined in (a) is at or below the first reference value, optionally wherein the level of the parameter inversely correlates with the amount of viral RNA in the biological sample; the biological sample, and/or one or more of the at least one cell, is deemed RCR negative, or is deemed to not have, to not be at risk for, or to not potentially contain the presence of replication competent virus, if, and optionally only if, the level of the parameter determined in (a) is below the first reference value, optionally wherein the level of the parameter positively correlates with the amount of the RNA in the biological sample; and/or the biological sample and/or one or more of the at least one cell is deemed not to have or not to be at risk for the presence of the replication competent virus, and/or not to have the presence or at least a threshold amount of the viral RNA, if, and optionally only if, the level of the parameter determined in (a) is above the first reference value, optionally wherein the level of the parameter inversely correlates with the amount of viral RNA in the biological sample.

In some embodiments, the biological sample is so-deemed negative, not to have, or not to be at risk, even if another replication competent-required viral RNA is determined to be present in the biological sample; the biological sample is so-deemed negative, not to have, or not to be at risk, even if a level, at or above a second reference value, of a second parameter that is positively correlated with an amount of another replication competent-required viral RNA in the biological sample, is or has been detected in the test sample or a second test sample derived from or containing nucleic acid from the biological sample; and/or the biological sample is so-deemed negative, not to have, or not to be at risk, even if a level, at or below a second reference value, of a second parameter negatively correlated with an amount of another replication competent-required viral RNA, is or has been detected in the test sample or another test sample derived from or containing nucleic acid from the biological sample.

In some embodiments, the biological sample is deemed to have, to potentially have, or to be at risk for the presence of the replication competent virus, if (and optionally only if) the presence of the viral RNA in the biological sample is determined, and/or if (and optionally only if) an amount, which optionally is at or above a threshold amount, of the viral RNA is determined to be in the biological sample; the biological sample is deemed to potentially have or to be at risk for the presence of the replication competent virus if (and optionally only if) the presence of the viral RNA in the biological sample is determined, and/or if (and optionally only if) an amount, which optionally is at or above a threshold amount, of the viral RNA is determined to be in the biological sample, but is not deemed to contain the presence of the replication competent virus without further indication of risk and/or without assessing another parameter indicative of another viral RNA; and/or the biological sample is deemed not to have, not to potentially have, and/or not to be at risk for the presence of the replication competent virus, if the absence of the viral RNA in the biological sample is determined, and/or if an amount (or no more than the amount), which amount optionally is at or below a threshold amount, of the viral RNA is determined to be in the biological sample, optionally even if the presence of another RNA required for replication competency of the virus is determined to be present in the biological sample; and/or the biological sample is deemed replication competent virus negative if the parameter and/or the viral RNA is undetectable or is not detected in the test sample and/or is not determined to be present in the biological sample.

In some embodiments, the first reference value is a value at or approximately at or just above a threshold level or a minimum detectable level or readout corresponding thereto; the first reference value is a value of the parameter detected in, and/or a value of a parameter indicative of an amount of RNA in, a positive control sample; and/or the level of the parameter indicates the presence or the absence of the viral RNA in the biological sample; and/or the viral RNA includes a nucleic acid encoding a first viral gene; and/or the heterologous nucleic acid encodes a heterologous gene product.

In some embodiments, the parameter assessed in the test sample is or includes an amount or relative amount of the viral RNA, or a product expressed therefrom or from a viral gene corresponding to the RNA, which optionally is a relative copy number, or a relative weight, or is or includes a concentration, or relative concentration, of the viral RNA, or of a product expressed therefrom or from a viral gene corresponding to the RNA. In some embodiments, the amount is an absolute or relative amount. In some embodiments, the parameter and/or level is or includes a surrogate or relative value, which optionally is a cycle threshold (Ct) value.

In some embodiments, the viral RNA or the expression thereof is determined to be present or at risk of being present in the biological sample or in the test sample, if the CT value for the test sample is below a first reference value, which is a reference Ct score. In some embodiments, wherein the test sample is or is derived from the biological sample or a portion thereof.

Also provided herein are methods including a) determining or assessing a first level of a first parameter in a test sample, wherein said first level or first parameter correlates (optionally positively or inversely) with a presence, absence, amount or concentration, in a biological sample, of a first viral RNA and/or a first nucleic acid encoding a first viral gene that encodes the first viral RNA; b) determining or assessing a second level of a second parameter in a test sample, which optionally is the same or a different test sample, wherein said second level or second parameter correlates (optionally positively or inversely) with a presence, absence, amount or concentration, in the biological sample, of a second viral RNA distinct from the first viral RNA and/or a second nucleic acid encoding a second and distinct viral gene encoding said second viral RNA; wherein at least one cell that contains a heterologous nucleic acid, a heterologous gene product, and/or a nucleic acid encoding a heterologous protein and/or has been transduced with a viral vector; wherein: the presence, absence or amount or concentration of the first viral RNA or gene or the second viral RNA or gene, and/or the presence, absence, or amount or concentration of both the first and the second viral RNA or gene, in the biological sample indicates a presence or absence of, or risk of, a replication competent virus in the biological sample, or a sample from which the biological sample is derived; and/or the first viral RNA, the second viral RNA, and/or both the first and the second viral RNA, is required for, or encodes a gene product or specifically identifiable portion thereof that is required for, replication competency of a replication competent virus.

In some embodiments, the method further includes determining the presence, absence, concentration, or amount of the first and/or the second viral RNA or gene product in the biological sample, or risk thereof, based on said level(s) so-determined. In some embodiments, the method further includes c) comparing the level of the first and/or the second parameter determined in (a) and/or (b) to a first and/or a second reference value, wherein the comparison optionally indicates the presence, absence, concentration or amount of the viral RNA in the biological sample or sample derived therefrom, or risk of any of the foregoing.

In some embodiments, the method further includes c) determining the presence, absence, or amount or concentration of the first viral RNA or expression, or risk of any of the foregoing, in the biological sample or portion thereof, and/or determining the presence, absence, or amount or concentration of the second viral RNA or expression, or risk of any of the foregoing, in the biological sample or portion thereof; and/or d) determining whether a replication competent virus is (or is potentially or is likely to be) present or at risk for being present in the biological sample or a portion thereof, optionally based on the determination in c).

In some embodiments, the viral RNA is from and/or the first viral RNA is from and/or the first viral gene is env, gag, pol, or rev; and/or the viral RNA is from and/or the second viral RNA is from, and/or the second viral gene is, env, gag, pol, or rev.

Also provided herein are methods including a) assessing a level of a first parameter in a test sample, which is indicative of or correlates (optionally positively or inversely) with of an amount or presence or absence of a first viral RNA in a biological sample, wherein the first viral RNA is from a first viral gene that is an env gene, and assessing a level of a second parameter in a test sample, which optionally is the same or a different test sample, wherein the second viral parameter is indicative of or correlates (optionally positively or inversely) with a presence, absence or amount of a second viral RNA in the biological sample, wherein the second viral RNA is from a gene selected from a gag, pol, and rev gene, wherein the biological sample includes a cell transduced with a viral vector particle, optionally including a heterologous gene product and/or includes a cell with a heterologous gene product; wherein at least one cell that contains a heterologous nucleic acid, a heterologous gene product, and/or a nucleic acid encoding a heterologous protein and/or has been transduced with a viral vector; wherein: the presence, absence or amount or concentration of the first viral RNA or gene or the second viral RNA or gene, and/or the presence, absence, or amount or concentration of both the first and the second viral RNA or gene, in the biological sample indicates a presence or absence of, or risk of, a replication competent virus in the biological sample, or a sample from which the biological sample is derived; and/or the first viral RNA, the second viral RNA, and/or both the first and the second viral RNA, is required for, or encodes a gene product or specifically identifiable portion thereof that is required for, replication competency of a replication competent virus.

In some embodiments, parameter is a presence or absence of viral RNA. In some embodiments, the reference value, the first reference value and/or the second reference value is or corresponds to a threshold level or a minimum detectable level. In some embodiments, the reference value, the first reference value and/or the second reference value is a value corresponding to or for the parameter in a positive control test sample, which optionally contains a known amount or concentration of the viral RNA, the second viral RNA and/or the first viral RNA.

In some embodiments, the biological sample is deemed to contain or to be at risk for containing or to potentially contain a replication competent virus if the method determines the presence or an amount above a threshold amount of the first and the second viral RNA in the biological sample, and optionally not if the method determines the presence or an amount above a threshold amount for one but not both the first and second RNAs; and/or the biological sample is deemed negative for or not to contain or to not be at risk for containing or not potentially containing a replication competent virus, if the method determines the absence of, the absence of a detectable amount of, or an amount below a threshold amount of, the first viral RNA, or the second viral RNA, and/or both the first and the second viral RNA, in the biological sample.

In some embodiments, the biological sample is deemed replication competent virus negative if the level of viral RNA encoding the first and second viral genes is undetectable in the test sample and/or is not determined to be present or present above a threshold level in the biological sample.

In some embodiments, the method further includes a step of isolating RNA from the biological sample or a portion therefrom or a sample or portion thereof derived from the biological sample, prior to step a), wherein the RNA contains RNA from one or more of the at least one cell.

In some embodiments, the replication competent virus is or includes a retrovirus, and/or wherein the viral RNA or the first and/or the second viral RNA is expressed by a retrovirus. In some embodiments, the retrovirus is a gammaretrovirus. In some embodiments, the retrovirus is a lentivirus.

In some embodiments, the biological sample is from a human or mammal and/or the one or more cell is a primary cell, which is optionally a human or mammalian cell. In some embodiments, the one or more cell and/or biological sample is from a master cell bank (MCB), a working cell bank (WCB), or a cell line, or a sample thereof. In some embodiments, the at least one cell or biological sample is or is from a cryopreserved material (CMAT), a cryopreserved drug product (CDP), or a formulated drug product (FDP) for autologous cell therapy, or a sample thereof. In some embodiments, the at least one cell or biological sample is or is from a cell that is undergoing expansion, such as ex-vivo expansion, after transduction.

In some embodiments, the heterologous nucleic acid or heterologous gene product is or encodes a recombinant receptor, a chimeric receptor, optionally a chimeric antigen receptor, or a transgenic T cell receptor.

In some embodiments, the determining or assessing is carried out using one or more oligonucleotide primers specific for a sequence of the viral RNA, the first viral RNA and/or the second viral RNA. In some embodiments, the level of viral RNA encoding the second viral gene is assessed using one or more oligonucleotide primers specific for a sequence of the second viral gene. In some embodiments, the level of viral RNA is assessed by real-time polymerase chain reaction (PCR). In some embodiments, the determining or assessing includes carrying out reverse transcriptase quantitative PCR (RT-qPCR).

In some embodiments, the viral RNA and/or the first and/or second viral RNA and/or viral RNA and/or gene is from a retrovirus. In some embodiments, the viral RNA, the first viral RNA and/or second viral RNA (or gene encoding any of the foregoing) is or is encoded by a gene involved in virion replication and/or packaging. In some embodiments, the viral RNA and/or the first viral RNA and/or the second viral RNA (or gene encoding one or more of the foregoing) is not a gene encoded by a transfer vector that has been used to transduce the transduced cell. In some embodiments, the viral RNA, the first viral RNA and/or the second viral RNA encodes a viral surface protein, an envelope protein, a group-specific antigen, a virally-derived polymerase, a virally-derived reverse transcriptase, a virally-derived regulatory element, a transactivator of transcription, or a response element.

In some embodiments, the gag gene is selected from the group consisting of murine leukemia virus (MMLV) gag and Human Immunodeficiency Virus (HIV) gag. In some embodiments, the env gene is selected from GaLV env and VSVG. In some embodiments, the one or more oligonucleotide primers specific for a sequence of the first viral gene include one or more sequences set forth in SEQ ID NOs: 4-5. In some embodiments, the one or more oligonucleotide primers specific for a sequence of the first viral gene include one or more sequences set forth in SEQ ID NOs: 16-24. In some embodiments, the one or more oligonucleotide primers specific for a sequence of the second viral gene include one or more sequences set forth in SEQ ID NOs: 4-5. In some embodiments, the one or more oligonucleotide primers specific for a sequence of the second viral gene include one or more sequences set forth in SEQ ID NOs: 16-24.

In some embodiments, the assessing or determining includes use of a hydrolysis probe specific for a sequence of the viral RNA, the viral gene, the first viral RNA or the first viral gene, or the second viral RNA or second viral gene. In some embodiments, the hydrolysis probe specific for a sequence of the first viral gene includes a sequence set forth in SEQ ID NO: 6. In some embodiments, the hydrolysis probe specific for a sequence of the first viral gene includes a sequence set forth in SEQ ID NO: 18, 21, or 24.

In some embodiments, the assessing, determining or detecting includes using a hydrolysis probe specific for a sequence of one or more of the viral RNA, second viral RNA, first viral RNA, and/or second viral gene. In some embodiments, the hydrolysis probe includes a sequence set forth in SEQ ID NO: 6. In some embodiments, the hydrolysis probe specific for a sequence of the first viral gene includes a sequence set forth in SEQ ID NO: 18, 21, or 24.

In some embodiments, the method further includes assessing in the test sample a level of, or a level of a parameter indicative of or correlative with, an RNA encoding a control gene in the test or biological sample, optionally wherein the control gene is or includes β-actin and/or optionally wherein the level of the parameter or control gene is assessed using one or more oligonucleotide primers specific to a sequence of the control gene, which individually optionally include one or more sequences set forth in SEQ ID NO: 1 or 2 or one of 8-15, optionally wherein the level is assessed using a hydrolysis probe specific for a sequence of the control gene, which optionally includes a sequence set forth in SEQ ID NO: 3, 9, 12, or 15.

In some embodiments, the assessment or determining includes carrying out a multiplex reaction, wherein optionally the level, the first level, and/or the second level; and optionally the level or parameter indicative or correlative with the control gene, is assessed in the multiplex reaction.

In some embodiments, the parameter, the first parameter, and/or the second parameter, individually, is or includes an amount or relative amount of the viral RNA (or first or second viral RNA), or a product expressed therefrom or from a viral gene corresponding to the RNA, which optionally is a relative copy number, or a relative weight, or is or includes a concentration, or relative concentration, of the viral RNA (or first or second viral RNA) or of a product expressed therefrom or from a viral gene corresponding to the RNA (or first or viral RNA).

In some embodiments, the amount is an absolute or relative amount. In some embodiments, the parameter and/or level is or includes a cycle threshold (Ct) value. In some embodiments, the viral RNA or the expression thereof is determined to be present or at risk of being present in the biological sample or in the test sample, if the CT value for the test sample is below a first reference value, which is a reference Ct score.

In some embodiments, the biological sample and/or the one or more cells is or are from a subject. In some embodiments, said at least one cell includes a plurality of cells, and wherein: said plurality of cells and/or said biological sample includes suspension cells; said plurality of cells and/or said biological sample includes white blood cells; and/or said plurality of cells and/or said biological sample includes T cells or NK cells.

In some embodiments, one or both of the first test sample and the second test sample, individually is derived from or contains RNA derived from the biological sample or a portion thereof. In some embodiments, the test sample assessed for the first viral RNA and the test sample assessed for the second RNA are the same or are portions of the same sample or composition. In some embodiments, said plurality of cells includes unfractionated T cells, isolated CD8+ T cells, or isolated CD4+ T cells. In some embodiments, said at least one cell is a human cell. In some embodiments, the test sample is or is a portion of the biological sample.

In some embodiments, acceptance criteria are set to assess validity of the real-time PCR. In some embodiments, the acceptance criteria include a percent efficiency of between or between about 90% and 110%. In some embodiments, the acceptance criteria include an R2 value of about or greater than at or about 0.95, 0.96, 0.97, 0.98, or 0.99. In some embodiments, the methods further include assessing the purity, integrity, and/or concentration of the RNA.

Also provided are primers including an oligonucleotide including a sequence set forth in any of SEQ ID NOs: 1-24. In some embodiments, the primer includes a fluorescent moiety or label.

Also provided are kits including one or more primers according. In some embodiments, the kit further includes one or more of nuclease-free water, a reverse transcriptase, a polymerase, deoxynucleotide triphosphates, a buffer, and a DNase.

In some embodiments, the method is capable of detecting the viral RNA or the first and/or the second viral RNA in a test sample in which at least 5 or at least 10 or at least 20 or at least 50 or at least 100 cells in the sample, or per 10 million cells in the test sample or biological sample; and/or wherein the method is capable of detecting an amount of target RNA that is no more than at or about 1.5 pg, 1 pg, or 0.75 pg or less of the viral target, in the test sample and/or the biological sample.

DETAILED DESCRIPTION

Provided herein are methods and compositions for detecting the presence, absence, amount, and/or concentration of viral RNA from a replication competent retrovirus in a sample or composition, such as a therapeutic cell composition containing transduced cells. In particular embodiments, the methods include one or more steps of measuring or determining the level or amount of a parameter that indicates or correlates with the presence, absence, amount and/or concentration of the viral RNA. In some embodiments, the presence, absence, amount, and/or concentration of the viral RNA in the biological sample indicates the presence or absence of, or a risk associated with the presence or absence of, a replication competent retrovirus. In some embodiments, the viral RNA is required for, or encodes a gene product or specifically identifiable portion thereof that is required for, replication competency of a replication competent virus.

Viral production processes, including retroviral production process, include the use of viral packaging elements. For certain exemplary gammaretroviral based virues, a combination of Moloney murine leukemia virus (MMLV) gag and pol, along with Gibbon ape leukemia virus envelope (GaLV env) are all encoded on separate plasmids with minimal homolgosu sequence and heterologous promoters and enhancers, which reduces the risk of recombination. Use of a human parental cell line for viral production, in some aspects, further reduces the risk of recombination by eliminating the presence of endogenous, homologous retroviral sequences. Nevertheless, RCR testing is generally employed at multiple points during the viral manufacturing process to ensure the absence of RCR.

There are two main categories of assays currently used to detect RCR. The first is a rapid, PCR based assay targeting a DNA of a gene specific to the viral vector (e.g., GaLV env). The second is a cell-based, co-culture assay where cells or harvest supernatant are first co-cultured with a permissive cell line for a few weeks to allow for amplification of any existing replicating virus, followed by incubation with an indicator cell line to detect any active virus present. While the cell-based RCR co-culture is widely used, the assay is lengthy and costly, and in some cases, the results from the RCR co-culture assay may not be available until after the desired time to administer a product has passed. Conversely, while current PCR-based testing is faster, this technique is prone to false positives.

The provided compositions and methods in some embodiments provide a fast and accurate assay capable of detecting contaminating RCR with high sensitivity. For example, in some embodiments, the compositions and methods provided herein rapidly and accurately measure parameters of a sample, e.g., a test sample and/or a biological sample that may be used to indicate the presence or amount of viral RNA from an RCR. The provided compositions and methods are able to rapidly measure such parameters without previous amplification in cell culture. Furthermore, the provided compositions and methods provide a higher degree of sensitivity than existing DNA-based PCR methods.

Viral vectors, such retroviral vectors including lentiviral and gammaretroviral vectors, are currently utilized for the development of therapies to address a wide range of unmet medical needs. Replication deficient retroviruses are generated to serve as gene delivery systems that allow for a controlled delivery of the gene of interest. Such viral vectors may be used to deliver genes directly, such as in gene therapy, or to deliver genes into cells for the production of a cell therapy such as CAR-T cell therapy. However, in rare cases, it is hypothesized that replication competent virus may emerge during the gene delivery process due to events such as site-specific recombination. While such events are considered to be extremely rare and/or improbable, it is advantageous to develop tests or other safe guards to detect the presence and/or risk of replication competent virus in a sample, for example a therapy such as a gene therapy or CAR-T cell therapy, to confirm that no replication competent viruses are present in the sample.

The methods and compositions provided herein are useful for the sensitive and accurate detection of potential replication competent viruses that may arise during the production of viral vectors for gene delivery. In some embodiments, the methods provided herein are used to determine if a replication competent virus has contaminated, originated, developed, or has been inadvertently produced from the plasmids and viral vectors used for transduction. In certain embodiments, the methods of the present invention are tailored and/or utilized to test for the replication competent virus that may have or would have derived from the same viral vectors that were used for gene delivery. Thus, in some embodiments, the methods provided herein are utilized to detect the replication competent form of the virus that has been used for the transduction and/or gene delivery. In particular embodiments, the methods provided herein are especially useful for the detection of viral genes that are present and/or required for the replication competent version of the virus. In some embodiments, the viral genes are present in the plasmids used for the production of replication deficient virus.

In some embodiments, the provided methods include one or more steps of measuring or detecting one or more parameters that are associated with viral RNA, as opposed to viral DNA. Particular embodiments contemplate that the detection of parameters that are associated with or correlate to levels or amounts of viral RNA reduces or prevents instances of false positives. For example, without being bound by theory, false positives may occur in DNA-based PCR techniques as a result from residual viral producer line DNA that remains present in the viral vector stocks used for transduction. In some aspects, the detection of parameters associated with and/or correlated to viral RNA minimizes or prevents the detection of the residual DNA and thus minimizes or prevents a false positive.

In some aspects, the provided methods include one or more steps of measuring or detecting parameters that are associated with a level or amount viral RNA encoding specific genes. In certain embodiments, the specific genes that are assessed or detected by measuring these parameters have little similarity to normally endogenous human RNA sequences, and thus allow for sensitive and/or accurate detection of the viral genes. For example, in some embodiments, the viral gene is from the Gibbon Ape Leukemia Virus (GaLV).

In some embodiments, the methods provided herein are useful for indicating the presence of RCR and/or viral RNA of RCR in a sample with at least the same or greater sensitivity than alternative methods. In some embodiments, the provided methods can indicate a presence or amount of RCR and/or viral RNA of the RCR when the RCR or RNA is below a threshold for detection of other methods and/or is detectable at an earlier timepoint in a process. For example, in some embodiments, the methods provided herein are useful for detecting the RCR or its viral RNA at an amount or level in a sample that is below the threshold level of detection of a DNA-based PCR assay. In certain embodiments, the methods provided herein are useful for detecting RCR or its viral RNA at an amount or level in a sample that is assessed at an earlier time compared with a cell culture based RCR assay protocol. For example, in certain embodiments, the methods provided herein are useful for detecting RCR and/or viral RNA in a sample assayed without passaging, amplification, or expansion via co-culture with a permissive cell line between sample collection and RCR assessment.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are described herein for clarity and/or for ready reference, and the inclusion of such descriptions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section heading used herein are for organizational purposes only and are not to be construed as limiting the subject matter described.

I. DETECTION OF REPLICATION COMPETENT VIRUS

Provided herein are methods of detecting the presence, absence, or level of replication competent virus in a sample. In some embodiments, the methods provided herein include measuring, determining, assessing, and/or quantifying the value, amount, or level of a parameter. In some embodiments, the amount, value, and/or level of the parameter indicates or correlates with a presence, absence, and/or amount or concentration of a viral RNA. In particular embodiments, the presence, absence or amount or concentration of the viral RNA in the biological sample indicates a presence or absence of, or risk of, a replication competent virus. In certain embodiments, the viral RNA is required for, or encodes a gene product or specifically identifiable portion thereof that is required for, replication competency of a replication competent virus.

In some aspects, the provided methods involve measuring or assessing parameters to determine if a replication competent retrovirus is present in a sample containing or derived from one or more cells transduced with a viral vector particle. Thus, in some cases, the viral vector particle has been used or can be used to transduce the cells that are subsequently assessed by the provided methods to either insure that the virus used for transduction is not present in a replication competent form.

In some embodiments, the parameter is measured in a sample. In particular embodiments, the sample is a test sample and/or a biological sample. In certain embodiments, the test sample is the biological sample. In some embodiments, the test sample is derived from the biological sample. In particular embodiments, the test sample is a portion of a biological sample. In some embodiments, the test sample originates, is derived, and/or is taken from the biological sample and/or the same source as the biological sample. In particular embodiments, the amount, level, concentration, and/or value of the one or more parameters in the test sample reflects, correlates, and/or is associated with the amount, level, concentration, and/or value of the one or more parameters in the biological sample. In some embodiments, the amount, level, concentration, and/or value of the one or more parameters in the test sample reflects, correlates, and/or is associated with the presence, absence, amount, level, concentration, and/or value of viral RNA in the biological sample. In particular embodiments, the amount, level, concentration, and/or value of the one or more parameters in the test sample reflects, correlates, and/or is associated with the presence, absence, amount, level, and/or concentration of virus, e.g., replication competent retrovirus, in the biological sample. In particular embodiments, the amount, level, concentration, and/or value of the one or more parameters in the test sample reflects, correlates, and/or is associated with a risk of the presence of viral RNA and/or virus, e.g., replication competent retrovirus, in the biological sample.

In some embodiments, the methods include assessing, measuring, and/or detecting one or more parameters of the sample that indicate and/or correlate to an amount, level, and/or expression of one or more target genes, e.g., viral genes. In particular embodiments, the one or more parameters indicate and/or correlate to the presence, absence, amount, and/or level of a replication competent virus, such as a replication competent retrovirus. In some embodiments, the one or more target genes serve as a marker for the detection of potential replication competent virus.

In certain embodiments, the methods provided herein include one or more steps of comparing the measurement, assessment, detection, and/or quantification of the parameter to a corresponding reference value. In some embodiments, the reference value is a known value of the parameter. In some embodiments, the parameter positively correlates to the amount, level, and/or concentration of viral RNA, viral RNA encoding target genes, and/or replication competent virus, and the replication competent virus is detected as present if the value of the parameter is above the reference value. In particular aspects, the parameter negatively or inversely correlates to the amount, level, and/or concentration of viral RNA, viral RNA encoding target genes, and/or replication competent virus, and the replication competent virus is considered not to be present if the value of the parameter is below the reference value.

In particular embodiments, the value or measurement of the parameter indicates the presence or absence, and/or is correlated and/or associated with the presence or absence, of the target gene, e.g., a viral gene, a viral RNA, and/or a viral RNA gene. In certain embodiments, the value or measurement of the parameter is correlated, e.g., negatively or positively, to the presence or absence of the target gene. In particular embodiments, the value or measurement of the parameter is correlated, e.g., negatively or positively, to the level or amount of the target gene.

In some embodiments, the parameter is a gene and/or a gene expression product. Thus, in some embodiments, measuring, assessing, detecting, and/or quantifying a parameter is or includes measuring, assessing, detecting, and/or quantifying the level or amount of a gene or gene expression product. In particular embodiments, the gene is a viral gene. In some embodiments, the parameter is a cDNA that is generated and/or derived from viral RNA, e.g., viral RNA encoding one or more genes. In particular embodiments, the gene is a target gene. In certain embodiments, the parameter is a protein, and the measuring, assessing, detecting, and/or quantifying a parameter is or includes measuring, assessing, detecting, and/or quantifying the level or amount of the protein. In some embodiments, the protein is a viral protein. In certain embodiments, the protein is encoded by a viral gene, e.g., a viral RNA gene. In some embodiments, the protein is encoded by the target gene. In certain embodiments, the parameter is a protein or polynucleotide that is present and/or expressed when the target gene is present. In some embodiments, the parameter is a protein and/or a polynucleotide that is present, expressed, modified, increased, or decreased as a result of the presence of the target gene. For example, in some embodiments, the parameter is protein that is expressed by a cell in response to presence or stimulus of the target gene.

In some embodiments, the presence, absence, level, concentration and/or amount of viral RNA is measured, assessed, detected, and/or quantified to determine the presence, absence, level, concentration and/or amount of a virus. In some embodiments, the virus is a replication competent virus, for example, that is in a sample. In certain embodiments, the presence, absence, level, concentration and/or amount of viral RNA is measured, assessed, detected, and/or quantified by measuring, assessing, detecting, and/or quantifying one or more parameters, e.g., one or more parameters of the test sample. In some embodiments, the presence or absence of a replication competent virus in a biological sample is determined from the level, amount, and/or concentration of the viral RNA.

In some aspects, the method includes comparing the nucleic acid levels of the target gene in the sample to a corresponding reference value, such as a known level of nucleic acids of the target gene and/or a nucleic acid level of the target gene at a limit of detection of the assay used to assess gene nucleic acid levels. In some embodiments, replication competent virus is detected as present in the test sample if the nucleic acid level of the target gene is above a reference value for the target gene. In some aspects, replication competent virus is considered to not be present in the test sample if nucleic acid level of the target gene is below the reference value.

In some embodiments, the viral nucleic acids do not comprise or are not DNA. In some embodiments, the viral nucleic acids are or comprise RNA. In some embodiments, the RNA is viral RNA. In some embodiments, the methods include reverse transcribing the RNA into DNA for amplification and/or detection.

In some embodiments, the replication competent virus is a replication competent retrovirus (RCR). In some embodiments, the replication competent retrovirus is a replication competent gammaretrovirus. In some embodiments, the replication competent virus is a replication competent lentivirus (RCL).

In some embodiments, the levels of viral RNA indicate the level of expression of a particular viral sequence or viral gene. In some embodiments, expression comprises the production of RNA. In some embodiments, expression does not necessarily include the translation of a particular sequence or gene into protein. In some embodiments, the levels of viral RNA indicate the level of transcription of a particular viral sequence or viral gene. In some embodiments, transcription of viral RNA indicates a level of transcription of an integrated proviral DNA into RNA during viral replication. In some embodiments, the viral RNA is translated into viral proteins. In some embodiments, the viral RNA is a viral genome that is packaged into new viral particles during replication. In aspects of the provided methods, the test sample contains RNA isolated or obtained from a biological sample, such as from a cell or population of cells. In some embodiments, the test sample comprises RNA from a cell used to produce viral vector particles. In some embodiments, the cell is from a viral packaging cell line. In some embodiments, the cell is a packaging cell or host cell used to transiently produce viral vector particles. In some embodiments, the test sample comprises RNA from a cell or population of cells genetically engineered with a viral vector particle. In some cases, the cell or population of cells is derived from a patient. In some embodiments, the cell is derived from the blood, bone marrow, lymph, or lymphoid organs, is a cell of the immune system, such as a cell of the innate or adaptive immunity, e.g., myeloid or lymphoid cell, including a lymphocyte, typically a T cell and/or NK cell. In some cases, the test sample comprises RNA from a cell from a patient who was or is being treated with adoptive cell therapy.

In some cases, the cell or population of cells is or has been transduced with a viral vector particle, such as one encoding a recombinant and/or heterologous molecule. In some embodiments, the viral vector particle comprises a genome containing a nucleic acid encoding a recombinant or heterologous molecule, such as a recombinant receptor, e.g., an antigen receptor, such as a chimeric antigen receptor or transgenic T cell receptor, whereby transduction of cells can generate recombinant receptor (e.g. CAR)-expressing cells. By heterologous in this context refers to a protein that is not normally expressed from a virus and/or not encoded by a viral genome. In some cases, the viral vector particle is or has been used to transduce the cells, such as T cells. In some embodiments, the resulting cells and compositions comprising such cells can be used in methods of adoptive immunotherapy. Exemplary viral vector particles and cells are described below.

In some embodiments, the provided methods are used to assess the presence, absence, or level of replication competent virus in the biological sample. In some embodiments, the biological sample is or includes cells into which has been or will be engineered with a viral vector particle encoding a heterologous nucleic acid, such as at any stage of the manufacturing process of producing genetically engineered cells. In some aspects, replication competent virus is detected by assessing RNA levels of one or more target genes, such as viral genes, e.g., a first, second, and/or subsequent viral gene, expressed in the retrovirus used to produce the viral vector particle, but not expressed in the viral vector particle itself, which in some cases is or has been engineered to be replication defective.

In certain embodiments, the parameter is viral RNA of or encoding the target gene. In some embodiments, RNA levels of the target gene, e.g., first and/or second viral gene, is assessed using a real-time polymerase chain reaction (qPCR) assay. In some cases, reverse transcriptase PCR (RT-PCR) is performed either as part of the same assay as qPCR (e.g., in a RT-qPCR assay) or is performed prior to the qPCR assay. Thus, in some cases, RNA comprised in the test sample, e.g., RNA that is or has been extracted from a sample comprising transduced cells, is used as a template for synthesis of cDNA by RT-PCR.

In some embodiments, the amount of RNA in the samples is determined from a surrogate readout, e.g., a parameter or surrogate parameter, which is indicative of or indicates the degree, level or amount of RNA in the sample. In some embodiments, the surrogate readout is a cycle threshold (CT) value obtained by the provided RT-PCR methods, which is a readout for the number of cycles it took to detect a signal from the sample. The CT value inversely correlates to the amount of nucleic acid, e.g. RNA, in the sample, whereby a lower CT value indicates higher amounts of a target RNA while a higher CT value indicates lower amounts of a target RNA.

In certain embodiments, the parameter is a surrogate readout. In some embodiments, the parameter is a cycle threshold (CT) value obtained by the provided RT-PCR methods. In particular embodiments, the parameter is a CT value.

In the provided methods, the presence, level or amount of one or more target viral RNA is assessed. In some embodiments, the one or more target RNAs are selected because of their ability to discriminate between samples containing or at risk of containing RCR and samples that do not contain RCR. For example, in some embodiments one or more target RNAs are present in samples containing or at risk of containing RCR and absent or substantially absent in samples that do not contain RCR. In some embodiments, the levels or amounts or concentrations of target RNAs are higher in samples containing or at risk of containing RCR than in samples that do not contain RCR. In some embodiments, the one or more target RNAs yield high signal to noise ratios and/or low background levels or noise when used in the methods described herein. In some embodiments, the target viral RNA is GaLV. In some embodiments, the target viral RNA is MMLV. In some embodiments, the target viral RNA is GaLV and MMLV.

In some aspects, in addition to the target gene, a control gene, e.g., actin, is assessed as a control for the assay. Assessment of the control gene may take place in the same reaction, e.g., well, as assessment of one or more of the target genes, e.g., in a multiplex reaction. For instance, the control gene and a first viral gene may be assessed in the same reaction. In other cases, the control gene and a second viral gene may be assessed in the same reaction. In some aspects, the first and second viral genes may be assessed in a multiplex reaction. In some cases, 3 or more target genes may be assessed in a multiplex reaction. In some instances, the control gene may be assessed in a multiplex reaction with both the first and second gene and/or with three or more target genes.

In some instances, the target gene, e.g. first and/or second viral gene, and/or the control gene is assessed using oligonucleotide primers specific for a sequence of the target gene or control gene, respectively. In some embodiments, viral RNA levels of the target gene and/or the control gene is assessed using a hydrolysis probe specific to the target gene or control gene, respectively. Exemplary oligonucleotide primers and hydrolysis probes are discussed below.

In some embodiments, one or more control samples are assessed in addition to the test sample. For example, a plasmid standard control may be used as a control for the amplification portion of the assay. In some aspects, a no template control may be used to provide information about the contamination state of the PCR reagents. In some cases, a no reverse transcriptase control may be used to evaluate the purity of the RNA template and/or to detect contaminating DNA. In some instances, a negative control that does not contain copies of the target gene, e.g., RNA from a cell line that does not express the target gene, is used. In some embodiments, an in-process control containing RNA from patient-matched material that has not been transduced with the viral vector particle encoding a recombinant and/or heterologous molecule is used as a control, such as for background signal, e.g. due to possible contamination during the RNA isolation procedure.

Degree of amplification detected in a RT-negative condition in an RT-PCR can be indicative of contaminating DNA. In some embodiments, RNA isolation is carried out to minimize contaminating DNA, for example, by selecting RNA isolation or preparation methods that have been observed to result in relatively lower signal in RT-negative samples. In some embodiments, a lower degree of amplification in the no-RT condition, and/or a lower degree of presence of any contaminating DNA, is observed in samples containing RNA isolated using a particular method (in some aspects, an RNeasy Plus Kit). In some aspects, an RNeasy Kit with on column DNase digestion is used.

In some embodiments, a positive control may be used that contains a known level of the target gene. The known RNA level of the target gene may be at or slightly above the limit of detection of the target gene by the assay. In some embodiments of the provided methods, a test sample containing RNA derived from transduced cells is spiked with the positive control RNA. As described further below, in some embodiments, RNA levels of the target gene in the positive control sample in some aspects sets a reference value to which the RNA level of the target gene in the test sample is compared.

In some embodiments, where the RNA level of the target gene in the test sample is higher than the reference value, the test sample may be deemed to have present one or more RNA that is from, and generally that is required for or believed to be required for, replication competent virus or replication competency of a virus. In some embodiments, a sample deemed to have an RNA that is from, that is required for, that is believed to be required for, or that is generally associated with, replication competent virus, is deemed positive in the assay, and/or is deemed to be at risk of containing replication competent virus, is deemed to contain one or more RNA required for retroviral replication and/or required for replication competent virus; is deemed to contain putative replication competent virus, and/or is deemed to potentially contain replication competent virus. In some embodiments, a sample is not deemed positive for or potentially positive for or at risk for RCR unless it is deemed positive with respect to a plurality of viral target RNAs or a plurality of RNAs required for replication competency of the virus.

In some embodiments, a sample that is deemed by the assay (i) to contain the presence of the target RNA (and/or two or more of the plurality of target RNAs), (ii) to contain a level of a surrogate readout generally inversely indicative of an amount of the RNA such as a CT value that is at or below a reference level, such as a reference CT value, and/or (iii) to contain an amount, or surrogate readout thereof, of the RNA that is at or higher than a reference value, in each case optionally for each of two or more of a plurality of target viral RNAs, is deemed positive.

In some embodiments, a sample deemed (i) to contain the presence of the target RNA (and/or two or more of the plurality of target RNAs), (ii) to contain a level of a surrogate readout generally inversely indicative of an amount of the RNA such as a CT value that is at or below a reference level, such as a reference CT value, (iii) to contain an amount, or surrogate readout thereof, of the RNA that is at or higher than a reference value, in each case optionally for each of two or more of a plurality of target viral RNAs, and/or (iv) that is or has been deemed positive by the assay, is (a) deemed to be at risk of containing replication competent virus, (b) deemed to contain an RNA (or optionally multiple RNAs and/or the RNAs) required for retroviral replication and/or required for replication competent virus; (c) deemed to contain putative replication competent virus, and/or (d) deemed to potentially contain replication competent virus.

In some aspects, the sample is deemed, or is only deemed to be at risk of containing replication competent virus and/or to contain putative replication competent virus, and/or to potentially contain replication competent virus, and/or to be positive in the assay, if it has been deemed to contain the respective readout in any of (i)-(iii) or (i)-(iv) for at least two viral RNAs, such as at least the first and the second viral RNA.

In some embodiments, a sample that is deemed in the assay (1) to not contain the presence of, or to contain the absence of, the target RNA (and/or to not contain two or more of the plurality of target RNAs), (2) to contain a level of a surrogate readout generally inversely indicative of an amount of the RNA such as a CT value, that is at or above a reference level, such as a reference CT value, and/or (3) to contain an amount, or surrogate readout thereof, of the RNA that is at or below a reference value, in each case optionally for at least two of a plurality of viral RNAs, is deemed negative.

In some embodiments, a sample deemed (1) to not contain the presence of the target RNA (and/or two or more of the plurality of target RNAs), (2) to contain a level of a surrogate readout generally inversely indicative of an amount of the RNA such as a CT value that is at or above a reference level, such as a reference CT value, (3) to contain an amount, or surrogate readout thereof, of the RNA that is at or below than a reference value, and/or (4) that is or has been deemed negative by the assay, is (a) deemed not to be at risk of containing replication competent virus, (b) deemed not to contain an RNA required for retroviral replication and/or required for replication competent virus; (c) is deemed not to contain putative replication competent virus, and/or (d) deemed not to contain replication competent virus.

In some aspects, the sample is deemed to be not at risk for, to be negative for, or to not contain the presence of, replication competent virus, if it has been deemed to contain the respective readout in any of (1)-(4) for a target viral RNA, such as any one or more target viral RNA that is or is believed to be required for replication competent virus or replication competency of a virus, such as one or more of the first and the second viral RNA.

In some cases, where the RNA level of the target gene is lower than the reference value, the test sample is considered to not be positive for the assay, the presence of, risk of, or presence of putative, replication competent virus. In some such cases, the sample and/or cells derived therefrom, e.g., the transduced cells, are released, such as on to further processing or formulation and/or for use or administration in therapy, such as adoptive cell therapy. In some such cases, a patient, which optionally is a human subject, from which the biological sample was derived is considered to be free of replication competent virus.

In some aspects, the provided methods can be used to provide or assess a presence or absence of, or risk of, a replication competent virus in an engineered cell product sample containing cells that have been subjected to retroviral transduction and cultured. Retroviral vector particles, such as gammaretroviral and lentiviral vector particles, have been used in various clinical gene transfer applications to introduce therapeutic genes into cells, including in connection with preparing cell products. Retroviral vector particles are generally derived from the retrovirus family, Retroviridae. In some embodiments, the virion particles contain a genomic RNA. Upon entry into a host cell, the genomic RNA is reverse transcribed into DNA. In some embodiments, the DNA integrates into the host cell's chromosomal DNA, in some cases using an integrase enzyme, at which point the retroviral DNA may be referred to as a provirus. In some embodiments, the host cell treats the proviral DNA as part of its own genome, translating and transcribing the integrated genes along with the host cell's own genes, thereby producing proteins encoded by the viral genomic nucleic acid. In some cases, these proteins are required to assemble new copies of the virus, wherein optionally the virus is replication-competent and/or infectious.

Retroviruses may be classified as "simple" and "complex" retroviruses. The genomes of simple retroviruses encode only the gag, pro, pol, and env genes. Examples of simple retroviruses include alpharetroviruses, betaretroviruses, and gammaretroviruses. In contrast, the genomes of complex retroviruses include the gag, pro, pot, and env genes, as well as an array of regulatory or accessory genes with a variety of functions. Examples of complex retroviruses include deltaretroviruses, epsilonretroviruses, lentiviruses, and spumaviruses. Examples of accessory genes include vif, vpr, vpu, rev, vpx, and nef.

In some embodiments, genomes or portions thereof of recombinant retroviruses, such as gammaretroviruses and lentiviruses, are able to stably integrate into a host genome. In some cases, such retroviruses contain a reverse transcriptase and/or integrase that allows for such integration. In some cases, viral vector particles containing components of such a retrovirus, such as such as a human immunodeficiency virus (HIV), for example HIV-1, a Gibbon ape leukemia virus (GaLV) or a Moloney murine leukemia virus (MMLV), have been used in various clinical gene transfer applications to introduce therapeutic genes into cells. In some cases, a retroviral vector is an oncoretroviral vector, for example Moloney murine leukemia virus (MoMLV)-derived vectors. In some embodiments, the viral vector is a second or third-generation lentiviral vector.

Viral vector particles intended for use in gene therapy or transduction of cells, including cells ultimately intended for implantation or administration to a subject, in some embodiments are derived from such viruses and may be engineered to be replication defective. In some embodiments, this engineering involves separating nucleic acids encoding viral proteins and heterologous proteins into separate nucleic acid sequences. In some embodiments, these separate sequences may be referred to as the vector sequence, in some embodiments called the transfer vector and/or transfer plasmid, comprising the heterologous gene and one or more helper sequences comprising the genes necessary for packaging of the vector into an infectious viral particle. For example, in some embodiments, one nucleic acid sequence may comprise gag/pol, another sequence may comprise env, and another sequence may comprise the heterologous nucleic acid. In some embodiments, methods are desirable that would be capable of detecting any replication competent virus that had been generated during generation or processing steps, such as through homologous or non-homologous recombination, e.g., between the vector and helper sequences. In some embodiments, such methods are capable of confirming that such events have not occurred prior to administration of a therapeutic composition.

Generally, replication defective viral vectors lack genes encoding packaging, structural, regulatory, and/or enzymatic components. Such components include the gag, pro, pol, and env genes.

Although not likely, recombination may occur between the transfer vector (such as one containing a sequence encoding a recombinant and/or heterologous molecule), and packaging, structural, regulatory, or enzymatic components (such as env, gag, pol, or rev), encoded by plasmids introduced into the packaging cell. The occurrence of such a recombination event could theoretically produce replication competent virus (e.g., RCR). The provided methods can be used to confirm that recombination has not occurred between the transfer vector, packaging or regulatory components, and endogenous or introduced viral elements, in a sample, such as in cells used for production of viral vector particles. In some aspects, the provided method can be used to confirm or verify the absence of RCR in certain samples such as therapeutic compositions and intermediate products generated during production.

In some aspects, samples comprising transduced cells are assayed for the presence or absence of replication competent virus or an indicator thereof, e.g., at various or certain steps during manufacturing, formulation, packaging, and/or prior to or following administration to patients, such as in methods of adoptive cell therapy. In some aspects, engineering of cells for cell therapy can include transducing cells with the viral vector particles and culturing the cells for up to 14 days, generally at 37° C., prior to cryopreservation and/or formulation. In some aspects, test samples obtained from cells obtained at any time after transduction, such as typically after culture for at least or greater than 1, 2, 3, 4, 5, 6, 7, 8, 9, 10, 11, 12, 13, 14 or more days after transduction, can be assessed in accord with the provided methods. In some aspects, test samples obtained from cells transduced and cultured (e.g. for expansion) that have been cryopreserved and/or formulated for administration to a subject also can be assessed by the provided methods, typically prior to administration to the subject.

In some aspects, the provided methods offer advantages to existing methods for detecting RCR in a sample. Some available methods for RCR testing, such as approved such methods, include cell culture based assays. In such assays, supernatant is obtained from a cell sample co-cultured with a permissive cell line, such as HEK293 cell line, after an amplification phase in which the cells are cultured for several weeks, generally 3 to 6 weeks, in order to amplify the viral particles for detection. Culture supernatant collected during the amplification, e.g. during a 3-week or 6-week amplification phase, can be placed on an indicator cell line and RCR is indicated when a transformation occurs, typically observed by plaque formation. One exemplary assay is the S+/L− assay, which generally involves detection of (or verification of the absence of) RCR using an indicator cells line, such as the PG-4 cell line, which contain the murine sarcoma virus genome (S+) but lacks the murine leukemia virus genome (L−). Typically, in such an assay, a transformed phenotype is only produced by the cells when both the murine sarcoma virus and the murine leukemia virus are expressed.

Other cell culture based assays include marker rescue assays, in which a permissive cell line may be used, which contains a retroviral vector with a marker, such as a marker transgene, that can be identified in the supernatant after an amplification, such as a 3-week or 6-week amplification, of any potential RCR. Generally, if RCR were present, the RCR genome would be packaged and the marker transgene would be rescued and thus expressed when transduced into a naïve cell line.

In some aspects, certain cell culture based assays may not be entirely optimal, such as because they are time consuming and/or labor intensive and/or require a high volume or amount of sample for testing and/or result in false positive RCR results for compositions not actually containing RCR, and/or may not provide information in a timeframe that is sufficient for certain particular purposes. Certain cell culture based assays may also result in false negative results for compositions actually containing RCR. False negative results may occur more frequently in samples assessed using certain cell culture assays at time points shortly after vector exposure, and thus limit the use of such assays to provide rapid results. Certain common cell culture assays typically take up to six weeks or more to complete. Certain methods may be inappropriate for use with cells that cannot be cryopreserved prior to use or during a time period in which the method is being completed.

An exemplary alternative to certain cell culture based assays may include assays involving polymerase chain reaction (PCR) assay. Limitations of such PCR assays can include that DNA template-based PCR assays, while sensitive, can be prone to producing false-positives, for example, due to residual DNA not associated with actual RCR, e.g., due to presence of vector producer line DNA and/or other residual DNA, which may be detected under permissive DNA-based PCR conditions. Such false positive results may occur more frequently in samples assessed at time points shortly after vector exposure and thus limit the use of such assays to provide rapid results.

In some embodiments, the provided methods, compositions, and systems are advantageous in various respects. The provided methods exhibit similar or improved sensitivity, specificity and/or accuracy compared to existing methods. Yet, the provided methods are carried out and/or are able to detect the presence or absence of replication competent virus in a sample rapidly, such as over the course of days or hours, as opposed to the cell culture assays that involve weeks of culture. In some aspects, such as in connection with adoptive cell therapy methods in which autologous or allogeneic cells are engineered by transduction methods, the ability to obtain results more efficiently is ideal.

In some aspects, the provided methods are more sensitive, such that the assay can be run on test samples obtained at an earlier time point after transduction and/or from less total sample compared to existing methods, in particular co-culture methods.

In some embodiments, the methods and systems are advantageous in that they produce fewer false positive results than certain available PCR-based methods, e.g., in testing of the same composition or sample, which may be limited by their detection of contamination, such as from producer cell or plasmid DNA. In some aspects, advantages of the present methods as compared to certain available cell culture based and PCR methods relates to the use (or detection of the presence or absence or level) of RNA (such as RNA from a test sample as opposed to a supernatant from a sample in a cell culture-based method), by the present methods, as opposed to DNA templated PCR. In some such aspects, the provided embodiments are advantageous in their ability to detect, in the event of sample subjected to the methods that did contain RCR, that the sampled cells are actively transcribing viral genes. Thus, presence of replication competent virus detected by the current methods in test samples comprising RNA may be a more specific indicator of replication competent virus as compared to certain PCR assays using DNA template and/or may be less prone to false positives, while maintaining a high level of sensitivity and reliability. In some aspects, the provided methods may be more sensitive and reliable than certain available cell culture based methods, thereby allowing for the reduction of false negative results.

In some embodiments, the performance of the assays disclosed herein are compared against other assays as a benchmark. In some embodiments, in general, the assays disclosed herein are at least as sensitive as the S+/L− assay, the marker rescue assay, and/or the template-based RCR PCR assays, such as those described herein. For example, in some embodiments, the assays disclosed herein can be used to detect RCR at earlier time points, in samples containing lower numbers of RCR, using smaller samples, using fewer cells, or using lower volumes other assays. In some embodiments, the assays disclosed herein can be performed more quickly than the S+/L− assay while retaining the same or greater sensitivity. For example, in some embodiments the assays can be performed within hours or days of generating the test sample. In some embodiments, the assays disclosed herein have a lower false positive rate than other assays, including, for example the S+/L− assay, the marker rescue assay, and/or the template-based RCR/RCL PCR assays. In some embodiments, provided assays disclosed herein may have a low false negative rate, such as one that is lower than a given reference assay. In some embodiments, the provided assays disclosed herein can be run in parallel to simultaneously detect RCR from a greater number of samples, conditions, or controls than other reference assays.

The provided sections describe exemplary aspects of the provided methods.

II. METHODS FOR DETECTING REPLICATION COMPETENT RETROVIRUS IN A TEST SAMPLE

Provided herein are methods of detecting the presence, absence, or level of, such as confirming the absence of, replication competent virus, in a sample, such as a test sample containing RNA from a sample, e.g., a biological sample, that could potentially contain, or in which it is desired and/or required to conclusively confirm the absence of, a replication competent virus. In some embodiments, the test sample is obtained from a sample, e.g., a biological sample and/or the source of the biological sample, that comprises a cell that has been transduced with nucleic acid using a replication defective viral vector particle encoding a recombinant and/or heterologous molecule. In some aspects it is theoretically possible, prior to verification or assaying, that a replication competent virus could have been generated, such as by recombination, and such sample is verified as not containing a replication competent virus, such as an RCR, e.g., by the provided methods.

In some embodiments, the provided methods are useful for detecting replication competent retrovirus, such as a replication competent gammaretrovirus (RCR) or a replication competent lentivirus (RCL), in a sample, e.g., a test sample or biological sample. In particular embodiments, the provided methods are useful for detecting replication competent retrovirus that originates from and/or was generated from, the viral vector used to transduce cells of the sample, e.g., biological sample. In certain embodiments, provided methods are useful for detecting viral genes and/or viral polynucleotide sequences that are required for replication competency in the viral vector that was used to transduce the cells in the sample.

In some embodiments, the sample comprises a cell transfected with one or more proviral plasmids. In some embodiments, the sample comprises a cell transfected and/or comprising one or more nucleic acids necessary to generate an infectious viral particle. In some embodiments, the methods include assessing viral RNA levels, such as of one or more target genes, e.g., viral genes, in the sample comprising the transduced cell. In some aspects, the methods include comparing the RNA levels of the one or more target genes in the test sample to a respective reference value. In some instances, the presence of replication competent virus is detected in the sample, such as a sample comprising the transduced cells, based on the comparison of each target gene to its reference value. In some embodiments, replication competent virus is present in the sample comprising the transduced cell if the viral RNA levels of the target gene is above its respective reference value. In some embodiments, the replication competent virus is a replication competent retrovirus (RCR). In some embodiments, the replication competent retrovirus is a replication competent gammaretrovirus. In some embodiments, the replication competent virus is a lentivirus (RCL).

A. Target & Control Genes

Provided in some aspects are methods for detecting or verifying or confirming the absence of replication competent virus. Such methods may include assessing viral RNA levels of or encoded by one or more viral sequences or one or more viral target genes, e.g., viral genes. In some embodiments, the one or more target genes comprise a first viral gene. In some cases, the one or more target genes include a first and second viral gene. In some embodiments, the first and second viral genes are not the same. In some embodiments, the one or more target genes comprise three or more viral genes. In some aspects, the one or more target genes are from a retrovirus, such as a gammaretrovirus or a lentivirus. In some embodiments, in addition to assessment of the target gene, RNA levels of a control gene are assessed, e.g., to confirm the validity or sensitivity and/or specificity of the assay.

1. Target Genes

In some embodiments, the methods provide steps for measuring, detecting, assessing, and/or quantifying a parameter that is associated with and/or correlates, either negatively or positively, to the amount, level, and/or concentration of a target gene or a gene expression product of the target gene. In some embodiments, the parameter is a protein that is encoded by the target gene, and the level, amount, or concentration of the protein is positively correlated to the presence or absence, and/or the amount, level, or concentration of the target gene. In certain embodiments, the parameter is a viral RNA that encodes the target gene, and the level, amount, or concentration of the viral RNA is positively correlated to the presence or absence, and/or the amount, level, or concentration of the target gene.

In some embodiments, the parameter is a protein that is negatively regulated by the target gene, and the level, amount, or concentration of the protein is negatively correlated to the presence or absence, and/or the amount, level, or concentration of the target gene. In particular embodiments, the parameter is a polynucleotide that is negatively regulated by the target gene, and the level, amount, or concentration of the polynucleotide is negatively correlated to the presence or absence, and/or the amount, level, or concentration of the target gene.

In some embodiments, the parameter is a viral RNA that encodes the target gene, and/or cDNA derived from the viral RNA that encodes the target gene. In particular embodiments, measuring, detecting, assessing, and/or quantifying the parameter is or includes measuring, detecting, assessing, and/or quantifying the level and/or amount of the viral RNA that encodes the target gene, and/or cDNA derived from the viral RNA that encodes the target gene. In particular embodiments, the control parameter is measured, assessed, detected, and/or quantified with PCR, e.g., RT-PCR Generally, the one or more target genes or sequences are viral genes or sequences that are not encoded by the transfer vector used to produce a viral vector particles used to transduce the cell. In some embodiments, the viral sequences or genes are encoded by wild-type viruses. In some embodiments, the viral sequences or genes are recombinant sequences or genes. In some embodiments, the viral sequences or genes are necessary for viral replication. In some embodiments, the viral sequences or genes encode packaging, structural, regulatory, or enzymatic components of a virus, or portions of sequences thereof.

In particular embodiments, the one or more target genes or sequences are viral genes or sequences that are used to produce a replication deficient viral vector particle. In certain embodiments, the one or more target genes or sequences are used to produce a retroviral vector. In some embodiments, the one or more target genes are used to produce one or more of a viral vector that is described in Section IV. In particular embodiments, the viral vector is used for gene delivery, e.g., a gene encoding a CAR. In certain embodiments, the one or more target genes or sequences are used to produce a retroviral vector, e.g., a replication deficient retrovirus, that is used for gene delivery. In particular embodiments, the retroviral vector is a gammaretroviral vector. In some embodiments, the retroviral vector is a lentiviral vector.

In some embodiments, the one or more target genes are of or are derived from a different virus, e.g., a different viral species or isotype, than the retroviral vector, e.g., a replication deficient retroviral vector used for gene delivery. In certain embodiments, the one or more target genes are of or are derived from a different virus, e.g., a different viral species or isotype, than the retroviral vector, e.g., a replication deficient retroviral vector used for gene delivery.

In some instances, the one or more target genes, e.g., first and/or second viral genes, include an env, gag, pol, or rev gene. Additional target genes may include those that are associated with virulence, e.g., a primary transactivator of HIV and/or are accessory genes. In some embodiments, one or more of the env, gag, pol, or rev genes are used to produce a retroviral vector, e.g., a replication deficient retrovirus, that is used for gene delivery. In particular embodiments, the one or more of the env, gag, pol, or rev genes are used to produce a gammaretroviral vector. In particular embodiments, the one or more of the env, gag, pol, or rev genes are used to produce a lentiviral vector. In some embodiments, the one or more of the env, gag, pol, or rev genes are of or are derived from a different virus, e.g., a different viral species or isotype, than the retroviral vector, e.g., a replication deficient retroviral vector used for gene delivery. In certain embodiments, the one or more of the env, gag, pol, or rev genes are of or are derived from a different virus, e.g., a different viral species or isotype, than the retroviral vector, e.g., a replication deficient retroviral vector used for gene delivery.

In some embodiments, the one or more target genes include a first viral gene and a second viral gene. In particular embodiments, the one or more target genes are or include two, three, four, five, six, seven, eight, nine, and/or ten viral genes. In particular embodiments, the first viral gene is an env, gag, pol, rev, pro, vpr, vif, vpu, nef, vpx, or Tat gene. In some embodiments, the second viral gene is an env, gag, pol, rev, pro, vpr, vif, vpu, nef, vpx, or Tat gene. In particular embodiments, the first and/or second viral gene is env, gag, pol, or rev gene. In some instances, the first viral gene is an env gene. In some embodiments, the second viral gene is a gag, pol, or rev gene. In some instances, the first viral gene is a gag, pol, or rev gene. In some embodiments, the second viral gene is an env gene. In some embodiments the first or second viral gene is a pro, vpr, vif, vpu, nef, vpx, and/or Tat gene.

In certain embodiments, the provided methods are used to determine if a replication competent virus is present in a sample, for example in a test sample, a biological sample, and/or the source of the biological and/or test sample. In some embodiments, the sample contains or is derived from a cell that has been transduced with a viral vector. In some embodiments, the cell has been transduced with a retroviral vector. In some embodiments, the cell has been transduced with a gammaretroviral vector. In particular embodiments, the cell has been transduced with a lentiviral vector.

In some embodiments, the cell was transduced with a viral vector, e.g. a retroviral vector. In particular embodiments, the cell was transduced with a replication deficient viral vector. In certain embodiments, the replication deficient viral vector particles were produced by transient production methods included cotransfection of multiple plasmids that encoded the vector genome and packaging constructs into a host cell, e.g., a cell from a viral packaging cell line (VPC). In some embodiments, the viral vector, e.g., the replication deficient retroviral vector. In some embodiments, the plasmids and/or genes used for the production of and/or incorporated into the viral vector contain genes from more than one virus, e.g., species or isotype of the virus. For example in some embodiments, the retroviral vector contains one or more genes that are not originated from or derived from a retrovirus.

In some embodiments, a retroviral vector contains one or more viral genes and/or polynucleotide sequences that do not originate from and/or are derived from a retrovirus. In particular embodiments, a gammaretroviral vector contains one or more viral genes and/or polynucleotide sequences that do not originate from and/or are derived from a gammaretrovirus. In particular embodiments, a lentiviral vector contains one or more viral genes and/or polynucleotide sequences that do not originate from and/or are derived from lentivirus.

In some embodiments, a replication competent retrovirus contains one or more viral genes and/or polynucleotide sequences that do not originate from and/or are derived from a retrovirus. In particular embodiments, a replication competent gammaretrovirus (e.g., an RCR) contains one or more viral genes and/or polynucleotide sequences that do not originate from and/or are derived from a gammaretrovirus. In particular embodiments, a replication competent lentiviral vector (e.g., an RCL) contains one or more viral genes and/or polynucleotide sequences that do not originate from and/or are derived from lentivirus.

In certain embodiments, the viral vector is pseudotyped, e.g. combined with foreign viral genes and/or proteins, for example to alter host tropism and/or increase or decrease stability of the viral vector. In certain embodiments, detection, assessment, and/or measurement of a replication competent virus, e.g., an RCR or RCL, is or includes the assessment, measurement, and/or detection of a viral gene and/or a parameter associated with or correlated to the viral gene, that does not derived from and/or originate from the virus.

In some embodiments, detection, assessment, and/or measurement of a replication competent virus, e.g., an RCR or RCL, is or includes detection assessment, measurement, and/or detection of a viral gene that was used for the production of the viral vector. In some embodiments, a replication competent retrovirus, lentivirus, and/or gammaretrovirus is detected, measured, or assessed by detecting a viral gene or polynucleotide sequence that is used to pseudotype the viral vector.

In some embodiments, the target gene, e.g., viral gene (such as first, second, or additional viral gene), can be derived from any appropriate virus, such as a retrovirus, e.g., a gammaretrovirus or lentivirus. In some embodiments, the target gene is a retroviral-derived gene from a virus including, but not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). In some embodiments, the target gene may be one from other viruses such as Vesicular stomatitis virus (VSV), hepatitis viruses, or influenza.

In some embodiments, the target gene is from a gibbon ape leukemia virus (GaLV). In some aspects, the target gene, e.g., viral gene (such as first, second, or additional viral gene), is from a Moloney murine leukemia virus (MMLV). In some embodiments, the target gene, e.g., viral gene (such as first, second, or additional viral gene), is from a vesicular stomatitis virus (VSV).

In some embodiments, the target gene is measured, assessed, quantified, and/or determined to assess the presence, absence, amount, level, and/or concentration of a replication competent retrovirus. In particular embodiments, the replication competent retrovirus is a replication competent gammaretrovirus (RCR). In some embodiments, the replication competent gammaretrovirus is detected by measuring a target gene that is derived from and/or originates from a gammaretrovirus. In some embodiments, the target gene is an env, gag, pol, rev, pro, vpr, vif, vpu, nef, vpx, or Tat gene that originates from and/or is derived from a gammaretrovirus. In particular embodiments, the target gene is an env, gag, pol, or rev that originates from and/or is derived from a gammaretrovirus. In some embodiments, the target gene is used for and/or is contained on a plasmid or expressed in a cell that is used for producing a gammaretroviral vector, and originates from and/or is derived from a virus that is not a gammaretrovirus. In some embodiments, the target gene is an env, gag, pol, rev, pro, vpr, vif, vpu, nef, vpx, or Tat gene that is not derived from a gammaretrovirus. In some embodiments, the target gene is a pseudotyping gene. In particular embodiments, the target gene is an env that originates from and/or is derived from a virus that is not a gammaretrovirus, e.g., VSV. Exemplary gammaretroviruses include, but are not limited to, the murine leukemia virus (MLV), Moloney murine leukemia virus (MMLV), the Abelson murine leukemia virus, the feline leukemia virus, the feline sarcoma virus, and the avian reticuloendotheliosis viruses.

In some embodiments, the target gene is a retroviral gag gene. In some embodiments, the gag gene is a Moloney murine leukemia virus (MMLV) gag gene or a human immunodeficiency virus (HIV) gag gene. In some embodiments, the gag gene encodes a viral protein present in replication competent viruses, but the gene is absent from a non-replication competent viral vector particle comprising the recombinant and/or heterologous molecule. In some embodiments, the gag gene encodes a polyprotein comprising viral matrix, capsid and nucleocapsid proteins. Exemplary proteins include p17, p24, p9 and p6. In some embodiments, transduced cells harboring replication competent viruses will transcribe various viral genes not present in the viral vector particle, including the MMLV or HIV gag gene. In some embodiments, the MMLV gag gene comprises the sequence set forth in SEQ ID NO: 27, or a sequence having at least or about 85, 90, 91, 92, 93, 94, 95, 96, 97, 98, or 99% identity with such a sequence. In some embodiments, the HIV gag gene comprises the sequence set forth in SEQ ID NO: 31, or a sequence having at least or about 85, 90, 91, 92, 93, 94, 95, 96, 97, 98, or 99% identity with such a sequence.

In some embodiments, the target gene is a retroviral pol gene. In some embodiments, the pol gene is an MLV pol gene or an HIV pol gene. In some embodiments, the pol gene encodes, among other proteins, protease (PR), reverse transcriptase (RT) and integrase (IN). In some embodiments, the pol gene encodes a viral protein present in replication competent virus, but the gene is absent from a non-replication competent viral vector particle comprising the recombinant and/or heterologous molecule. Generally, transduced cells harboring replication competent virus will transcribe various viral genes not present in the viral vector particle, including the pol gene. In some embodiments, the pol gene comprises the sequence set forth in SEQ ID NO: 29, or a sequence having at least or about 85, 90, 91, 92, 93, 94, 95, 96, 97, 98, or 99% identity with such a sequence. In some embodiments, the pol gene comprises the sequence set forth in SEQ ID NO: 32, or a sequence having at least or about 85, 90, 91, 92, 93, 94, 95, 96, 97, 98, or 99% identity with such a sequence.

In certain embodiments, the target gene is a retroviral env gene. In some cases, the env gene is a gibbon ape leukemia virus (GaLV) env gene. In some embodiments, the GaLV env gene encodes a viral envelope protein present in replication competent retroviruses, but the gene is absent from a non-replication competent viral vector particle encoding the recombinant and/or heterologous molecule. Generally, transduced cells harboring replication competent virus will transcribe various viral genes not present in the viral vector particle, including the GaLV env gene. In some embodiments, the GaLV env gene comprises the sequence set forth in SEQ ID NO: 25, or a sequence having at least or about 85, 90, 91, 92, 93, 94, 95, 96, 97, 98, or 99% identity with such a sequence.

In some embodiments, the target gene is measured, assessed, quantified, and/or determined to assess the presence, absence, amount, level, and/or concentration of a replication competent lentivirus (RCL). In some embodiments, the RCL is detected by measuring a target gene that is derived from and/or originates from a lentivirus. In some embodiments, the target gene is an env, gag, pol, rev, pro, vpr, vif, vpu, nef, vpx, or Tat gene that originates from and/or is derived from a lentivirus. In particular embodiments, the target gene is an env, gag, pol, or rev that originates from and/or is derived from a lentivirus. In some embodiments, the target gene is used for and/or is contained on a plasmid or expressed in a cell that is used for producing a gammaretroviral vector, and originates from and/or is derived from a virus that is not a lentivirus. In some embodiments, the target gene is an env, gag, pol, rev, pro, vpr, vif, vpu, nef, vpx, or Tat gene that is not derived from a lentivirus. In some embodiments, the target gene is a pseudotyping gene. In particular embodiments, the target gene is an env that originates from and/or is derived from a virus that is not a lentivirus, e.g., VSV.

In some embodiments, lentiviruses include members of the bovine lentivirus group, equine lentivirus group, feline lentivirus group, ovinecaprine lentivirus group and primate lentivirus group. The design and use of lentiviral vectors suitable for gene delivery is described, for example, in U.S. Pat. No. 6,207,455, issued Mar. 27, 2001, and U.S. Pat. No. 6,165,782, issued Dec. 26, 2000. Examples of lentiviruses include, but are not limited to, HIV-1, HIV-2, HIV-1/HIV-2 pseudotype, HIV-1/SIV, FIV, caprine arthritis encephalitis virus (CAEV), equine infectious anemia virus and bovine immunodeficiency virus. In some embodiments, the lentiviral vectors include, but are not limited to, one derived from an HIV-1, SIVmnd1, SIVlst, SIVsun, SIVolc or SIVwrc lentivirus In some embodiments, the target gene is a lentiviral rev gene. In some embodiments, the rev gene is a human immunodeficiency virus (HIV) rev gene. In some embodiments, the rev gene encodes a transactivating protein. In some embodiments, the rev gene encodes a viral protein present in replication competent viruses, but the gene is absent from a non-replication competent viral vector particle comprising the recombinant and/or heterologous molecule. Generally, transduced cells harboring replication competent viruses will transcribe various viral genes not present in the viral vector particle, including the rev gene. In some embodiments, the rev gene comprises the sequence set forth in SEQ ID NO: 33, or a sequence having at least or about 85, 90, 91, 92, 93, 94, 95, 96, 97, 98, or 99% identity with such a sequence.

In some embodiments, the target gene is a pseudo-typing gene and/or is an env that originates from and/or is derived from a virus that is not a retrovirus. In some aspects, the env gene is a vesicular stomatitis virus env gene (e.g. VSVG). In some embodiments, the VSV env gene encodes a viral envelope protein present in replication competent viruses, but the gene is absent from a non-replication competent viral vector particle encoding the recombinant and/or heterologous molecule. Generally, transduced cells harboring replication competent viruses will transcribe various viral genes not present in the viral vector particle, including the VSVG env gene. In some embodiments, the VSVG env gene comprises the sequence set forth in SEQ ID NO: 26, or a sequence having at least or about 85, 90, 91, 92, 93, 94, 95, 96, 97, 98, or 99% identity with such a sequence.

In particular embodiments, the methods include one or more steps for the detection of an RCR in a sample, e.g., in a test sample and/or a biological sample. In particular embodiments, the methods provided herein include one or more steps for the detection, measurement, assessment, and/or quantification of one or more target genes that are gammaretroviral genes and/or are genes that were used to generate a gammaretroviral vector, such as a replication deficient gammaretroviral vector used for gene delivery. In particular embodiments the methods include one or more steps for detection, measurement, assessment, and/or quantification of one or more control genes. In some embodiments, the control gene is actin. In particular embodiments, target gene is GaLV env. In certain embodiments target gene is MMLV gag. In some embodiments, the target genes are GaLV env and MMLV gag.

In particular embodiments, the methods include one or more steps for the detection of an RCL in a sample, e.g., in a test sample and/or a biological sample. In particular embodiments, the methods provided herein include one or more steps for the detection, measurement, assessment, and/or quantification of one or more target genes that are lentiviral genes and/or are genes that were used to generate a lentiviral vector, such as a replication deficient lentiviral vector used for gene delivery. In particular embodiments the methods include one or more steps for detection, measurement, assessment, and/or quantification of one or more control genes. In some embodiments, the control gene is actin. In particular embodiments, the target gene is rev, e.g., HIV rev. In certain embodiments target gene is VSV-G. In some embodiments, the target genes are rev and VSV-G.

2. Control Genes

In some embodiments, in addition to measuring, detecting, assessing, and/or quantifying the parameter, the amount, level, and/or concentration of a control parameter is also measured, detected, assessed, and/or quantified. In particular embodiments, the value or measurement of the control parameter is correlated and/or associated with the amount, level, and/or concentration of a control gene or gene expression product. In some embodiments, the parameter and the control parameter are both a gene or a gene expression product, e.g, a protein. In certain embodiments, the parameter and the control parameter are both a gene, an RNA polynucleotide, and/or a DNA polynucleotide derived from an RNA polynucleotide. In certain embodiments, the value or measurement of the control parameter is correlated, e.g., negatively or positively, to the level, concentration, and/or or amount of the control gene or gene expression product. In some embodiments, the gene expression product is an mRNA. In particular embodiments, the control gene expression product is a non-viral RNA, for example a human mRNA.

In some embodiments, the control parameter is an RNA. In particular embodiments, measuring, detecting, assessing, and/or quantifying the control parameter is or includes measuring, detecting, assessing, and/or quantifying the level and/or amount of an RNA. In particular embodiments, the control parameter is measured, assessed, detected, and/or quantified with PCR, e.g., RT-PCR.

In some embodiments, in addition to assessing viral RNA levels of the target gene, RNA levels of a control gene is also assessed. In some instances, the control gene is one whose RNA levels and/or transcription is not thought to be affected by or change with the presence of replication competent viruses. In some embodiments the control gene is a housekeeping gene, for example: beta actin (ACTB; β-actin), beta tubulin (β-tubulin; TUBB), ubiquitin, β-glucuronidase (GUSB), hypoxanthine-guanine phosphoribosyltransferase (HPRT1), ribosomal RNAs (e.g. 28s or 18s) and/or glyceraldehyde 3-phosphate dehydrogenase (GAPDH). In some aspects, assessment of the control gene is multiplexed with the target gene. In some instances, assessment of the control gene controls for RNA quality in the assay. In some embodiments, presence of the control gene in a reaction, e.g., well, confirms that RNA is present and of sufficient quality to be capable of undergoing reverse transcription and PCR amplification.

In some embodiments, the control gene is any of a number of genes or polynucleotides or portions thereof known to be used as a control gene for RT-PCR and/or qPCR assays.

In some embodiments, the control gene is or comprises actin, such as human beta actin (β-actin). In some aspects, the actin gene comprises the sequence set forth in SEQ ID NO: 28, or a sequence having at least or about 85, 90, 91, 92, 93, 94, 95, 96, 97, 98, or 99% identity with such a sequence.

B. Assay Preparation, Protocol, and Analysis

In certain embodiments, one or more assays are performed for detecting, measuring, assessing, and/or quantifying a parameter. In some embodiments, detecting, measuring, assessing, and/or quantifying a parameter is or includes detecting, measuring, assessing, and/or quantifying the level of a polynucleotide, e.g., a viral RNA polynucleotide and/or a DNA polynucleotide derived from an RNA polynucleotide. In certain embodiments, the detecting, measuring, assessing, and/or quantifying a parameter is or includes detecting, measuring, assessing, and/or quantifying the level of a protein, e.g., a viral protein.

In some embodiments, the parameter is or includes a level or amount of a polynucleotide. In particular embodiments, the amount or level of a polynucleotide in a sample may be assessed, measured, determined, and/or quantified by any suitable means. For example, in some embodiments, the amount or level of a polynucleotide can be assessed, measured, determined, and/or quantified by polymerase chain reaction (PCR), including reverse transcriptase (rt) PCR, droplet digital PCR, real-time and quantitative PCR methods (including, e.g., TAQMAN®, molecular beacon, LIGHTUP™, SCORPION™, SIMPLEPROBES®; see, e.g., U.S. Pat. Nos. 5,538,848; 5,925,517; 6,174,670; 6,329,144; 6,326,145 and 6,635,427); northern blotting; Southern blotting, e.g., of reverse transcription products and derivatives; array based methods, including blotted arrays, microarrays, or in situ-synthesized arrays; and sequencing, e.g., sequencing by synthesis, pyrosequencing, dideoxy sequencing, or sequencing by ligation, or any other methods known in the art, such as discussed in Shendure et al., Nat. Rev. Genet. 5:335-44 (2004) or Nowrousian, Eukaryotic Cell 9(9): 1300-1310 (2010), including such specific platforms as HELICOS®, ROCHE® 454, ILLUMINA®/SOLEXA®, ABI SOLiD®, and POLONATOR® sequencing. In particular embodiments, the levels of a polynucleotide are measured by qRT-PCR. In some embodiments, the qRT-PCR uses three nucleic acid sets for each gene, where the three nucleic acids comprise a primer pair together with a probe that binds between the regions of a target nucleic acid where the primers bind.

In some embodiments, the one or more parameters are measured, assessed, detected, and/or quantified by sequencing one or more polynucleotides. In some embodiments, the sequencing is performed by a non-Sanger sequencing method and/or a next generation sequencing (NGS) technique. Examples of Next Generation Sequencing techniques include, but are not limited to Massively Parallel Signature Sequencing (MPSS), Polony sequencing, pyrosequencing, Reversible dye-terminator sequencing, SOLiD sequencing, Ion semiconductor sequencing, DNA nanoball sequencing, Helioscope single molecule sequencing, Single molecule real time (SMRT) sequencing, Single molecule real time (RNAP) sequencing, and Nanopore DNA sequencing. In some embodiments, the NGS technique is RNA sequencing (RNA-Seq). RNA sequencing methods have been adapted for the most common DNA sequencing platforms [HiSeq systems (Illumina), 454 Genome Sequencer FLX System (Roche), Applied Biosystems SOLiD (Life Technologies), IonTorrent (Life Technologies)]. These platforms generally require initial reverse transcription of RNA into cDNA. Conversely, the single molecule sequencer HeliScope (Helicos BioSciences) is able to use RNA as a template for sequencing. A proof of principle for direct RNA sequencing on the PacBio RS platform has also been demonstrated (Pacific Bioscience). In some embodiments, the one or more RNA gene products are assessed, measured, determined, and/or quantified by RNA-seq.

In some embodiments, the parameter is or includes a level or amount of a protein. In some embodiments, one or more proteins are measured, assessed, detected, and/or quantified by suitable means. Suitable methods include, but are not limited to, immunocytochemistry or immunohistochemistry, ELISA (including direct, indirect, sandwich, competitive, multiple and portable ELISAs (see, e.g., U.S. Pat. No. 7,510,687), western blotting (including one, two or higher dimensional blotting or other chromatographic means, optionally including peptide sequencing), RIA (radioimmunoassay), SPR (surface plasmon resonance), nucleic acid-based or protein-based aptamer techniques, HPLC (high precision liquid chromatography), peptide sequencing (such as Edman degradation sequencing or mass spectrometry (such as MS/MS), optionally coupled to HPLC), and microarray adaptations of any of the foregoing (including nucleic acid, antibody or protein-protein (i.e., non-antibody) arrays).

In some embodiments, the parameter is a level or amount of RNA of a target gene. In some embodiments, RNA levels of the target gene, e.g., first or second viral gene, and/or control gene are assessed by reverse transcriptase polymerase chain reaction (RT-PCR) and/or real-time PCR (qPCR). In some aspects, RT-PCR and qPCR are carried out in the same assay, e.g., in a one-step assay (RT-qPCR). In some embodiments, the RNA level of the target gene is assessed using one or more oligonucleotide primers, e.g., forward and reverse primers, specific for one or more sequences of the target gene. In some embodiments, the RNA level of the control gene is assessed using one or more oligonucleotide primers, e.g., forward and reverse primers, specific for one or more sequences of the control gene. In some cases, an oligonucleotide probe specific for a sequence of the target gene or control gene is used to assess the RNA level of the target gene or control gene, respectively.

In some embodiments, the RNA level of the target gene and/or control gene is assessed in the test sample, e.g., in RNA from cells comprising a heterologous nucleic acid. In some cases, the RNA levels of the target and control genes is assessed by determining a relative amount of target and control RNA present in the test sample, respectively.

In some cases, RNA is extracted from the sample, such as from transduced cells. In some embodiments, cells are lysed prior to RNA extraction. Thus, in some instances RNA is extracted from the cell lysate. RNA can be isolated using reagents and methods known to the skilled artisan.

In some embodiments, the RNA level of the target gene and/or control gene is assessed in the test sample, e.g., in RNA from cells comprising a heterologous nucleic acid. In some cases, the RNA levels of the target and control genes is assessed by determining a relative amount of target and control RNA present in the test sample, respectively.

In some cases, RNA is extracted from the sample, such as from transduced cells. In some embodiments, cells are lysed prior to RNA extraction. Thus, in some instances RNA is extracted from the cell lysate. RNA can be isolated using reagents and methods known to the skilled artisan.

In some aspects, the purity, integrity, and/or concentration of the RNA is assessed. In some cases, the RNA is considered to have acceptable purity, e.g., be free from substantial contamination, such as with DNA, if it has an A260/280 value of above 2, such as between 2.000 and 2.100.

In some embodiments, cDNA is synthesized using RNA from the test sample as a template for reverse transcriptase polymerase chain reaction (RT-PCR). Any of a number of known RT-PCR reagents may be used.

In some embodiments, the RNA levels of the one or more target genes are assessed by real-time polymerase chain reaction (qPCR). In some cases, prior to the qPCR assay, cDNA is synthesized by RT-PCR with RNA from the test sample as a template. In some instances, RT-PCR and qPCR are carried out in a one-step reaction (RT-qPCR).

In some embodiments, the control and test samples are assigned to one or more wells of a multi-well format or plate, such as a 96-well plate. In some cases, the control and/or test samples are each assayed in a single well of the multi-well plate. In some instances, the control and/or test samples are run in replicates, such as triplicates.

In some embodiments, the control and/or test sample is mixed with one or more oligonucleotide primers specific for a sequence of the control gene and/or target gene, such as forward and reverse primers, such as any of those described herein. In some instances, a hydrolysis probe specific for the control gene and/or a hydrolysis probe specific for the target gene is mixed with the test and/or control sample. In some cases, the control and/or target sample is mixed with other reagents for performing the RT-PCR and/or real-time PCR assay, such as any reagents known in the art.

In some embodiments, the amount of RNA is determined or estimated based on detection by real-time PCR and calculation of a Ct value. Thus, in some embodiments, presence of the control and/or target gene amplicon is detected by real-time PCR. In some embodiments, a defined signal threshold is determined or calculated for all reactions to be analyzed. In some embodiments, the number of amplification cycles required to reach this signal threshold (threshold cycle, or "Ct") is determined for the target nucleic acid, such as a viral RNA or viral gene, as well as for one or more control genes. The presence or amount, such as absolute or relative amount, of the viral gene or control gene in the test sample can be determined on the basis of the Ct values obtained for the target nucleic acid and the control gene using methods known in the art (Gibson et al., Genome Research 6:995-1001; Bieche et al., Cancer Research 59:2759-2765, 1999; WO 97/46707; WO 97/46712; WO 97/46714).

In some embodiments, the assay is carried out as a multiplex reaction. For example, in some cases, assessing the RNA levels of the target gene and the control gene is carried out in a multiplex reaction. An advantage of assessing the target gene and control gene simultaneously includes that RNA quality in the assay can be confirmed and normalized across wells and assay plates. In some embodiments, presence of the control gene in a reaction, e.g., well, confirms that RNA is present and of sufficient quality to be capable of undergoing reverse transcription and PCR amplification and this may prevent the detection of false negatives due to poor RNA quality or compromised reaction conditions.

In some aspects, two or more target genes, e.g., first, second, or additional viral genes, may be multiplexed in the assay. In some cases, the two or more target genes are multiplexed with the control gene or control genes. In some aspects, an advantage of assessing two or more target genes in a multiplexed reaction includes that RNA levels of the genes will be determined from the same starting material, e.g., the same amount of RNA with the same quality. In some embodiments, assessing one or more control genes in the same well as the target gene can be advantageous in that the presence of or detection of the control gene provides a positive control in the same well undergoing the same reaction conditions as the target gene.

In some embodiments, the provided methods include comparing the level of viral RNA in the test sample to a reference value or level for each of the viral genes having been assessed, and based on the comparison determining whether replication competent virus is present in the test sample. In some embodiments, the test sample and/or reference value can be measured directly or indirectly.

1. Preparation or Samples a. Test Sample

In some embodiments, the test sample contains one or more parameters that are associated with, correlate to and/or are predictive of levels of viral RNA. In particular embodiments, the one or more parameters that are associated with, correlate to and/or are predictive of levels of viral RNA in a biological sample.

In certain embodiments, the test sample contains one or more cells. In some embodiments, the cells originate from and/or are derived from the biological sample and/or the same source as the biological sample. In particular embodiments, the test sample contains polypeptides and/or polynucleotides that are derived from cells of the biological sample or from the same source as the biological sample. In some embodiments, the test sample contains RNA. In certain embodiments, the test sample contains DNA, e.g., cDNA, that is derived from viral RNA. In some embodiments, the test sample contains protein.

In certain embodiments, the test sample contains one or more gene expression products, e.g., a polypeptide and/or polynucleotide that reflects, correlates to, and/or is associated with the presence and/or activity of a gene, e.g., a target viral RNA gene. In certain embodiments, the test sample contains one or more polypeptides that reflect, correlate to, and/or are associated with the presence and/or activity of a gene, e.g., a target viral RNA gene. In some embodiments, the polypeptides are or include modified polypeptides, e.g., a dimethylated, trimethylated, acetylated, phosphorylated, ubiquinated, palmitoylated, glycosylated, lipidated, sulfonated, and/or nitrosylatated polypeptides, that reflect, correlate to, and/or are associated with the presence and/or activity of a gene, e.g., a target viral RNA gene. In particular embodiments, the test sample contains one or more polynucleotides that reflect, correlate to, and/or is associated with the presence and/or activity of a gene, e.g., a target viral RNA gene. In some embodiments, the one or more polynucleotides are or include RNAs that encode viral genes, e.g., target viral genes. In certain embodiments, the one or more polynucleotides are or include DNAs, e.g., cDNAs, that are derived from RNAs that encode viral genes, e.g., target viral genes.

In certain embodiments, the test sample contains a parameter that is taken, derived, and/or originates from a cell. In particular embodiments, the cell is contained in the test sample. In particular embodiments, the test sample contains a cell that is taken from, originates from, and/or is derived from a biological sample and/or the same source as the biological sample. In certain embodiments, the cell is from a biological sample. In particular embodiments, the cell is from the same source as the biological sample. In some embodiments, the test sample contains RNA from a cell. In certain embodiments, the test sample contains DNA, e.g., cDNA, that is derived from RNA from a cell, e.g., a cell from a biological sample or the same source as the biological sample.

In some embodiments, the cell, e.g., a cell from a biological sample and/or from the same source as the biological sample, is one that has been generated in connection with processing and preparing engineered cells, such as for use in adoptive cell therapy and/or those formulated for such use, e.g., in a pharmaceutical composition comprising a pharmaceutically acceptable recipient and/or cryopreservative. In some embodiments, a cell, e.g., a cell from a biological sample and/or from the same source as the biological sample, assessed by the methods, which may in some aspects be a control cell, is from a viral packaging cell line (VPC), a master cell bank (MCB), or a working cell bank (WCB). In some embodiments, viral vector is produced using a VPC designed to synthesize retroviral proteins required for producing functional retroviral vector particles. In some embodiments, VPCs do not include the vector genome. In some embodiments, an MCB comprises cells, such as VPCs, established for or certified for use as a packaging cell line. Such cells are generally capable of producing high-titer or high-quality viral vector particles. In some embodiments, the WCB is used to manufacture lots or batches of viral vector particles. In some embodiments, manufacturing a viral vector lot comprises expanding seed vials from a working cell bank, a master cell bank, or a cell line in culture media under appropriate conditions. In some embodiments, the batches of supernatant that contain the vector particles are harvested over several days, as determined based on preliminary experiments that demonstrate the period of greatest vector yield. In some cases, supernatant containing viral vector may be subjected to limited purification steps to remove cell debris. In some embodiments, the bulk harvest supernatant is tested for replication competent virus as part of lot release testing.

In some embodiments, the cell, e.g., a cell from a biological sample and/or from the same source as the biological sample, is a packaging cell or host cell used to transiently produce viral vector particles. In some embodiments, viral vector particles may be produced by transient production methods that require cotransfection of plasmids that encode the vector genome and packaging constructs into a host cell. In some embodiments, transient production can be advantageous when producing lentiviral vectors since VPCs for lentiviral vectors are not widely available in part due to the potentially cytotoxic effects of certain packaging components (such as HIV gag and VSV-G). In some embodiments, transient production methods can be used to produce gammaretroviral vectors. In some embodiments, transient production bypasses the need for VPC. Cells used for transient viral vector particle production are typically expanded and characterized in a manner similar to those tests used for a master cell bank and a working cell bank of a VPC to ensure the cells produce high-titer, high quality viral vector particles.

In some embodiments, the resultant vector preparations have high levels of contaminating plasmid DNAs used during the transfection. Therefore, in some embodiments, viral vector particles produced transiently may undergo additional steps to remove the plasmid DNAs, such as DNase digestion followed by subsequent purification steps.

In some embodiments, the resultant vector preparations have detectable levels of contaminating nucleic acids, including contaminating plasmid DNAs used during the transfection and RNAs produced during viral production, including contaminating RNAs from VPCs or cells used for transient viral vector particle production. Therefore, in some embodiments, target genes selected for use in the described methods of detecting RCR are able to discriminate between background amounts, levels, or concentrations of contaminating nucleic acids and amounts, levels, or concentrations of viral RNA that indicate the presence, absence, amount, concentration, or risk of RCR in a sample.

In some embodiments, cells, e.g., cells of the test sample, of the biological sample, and/or of the same source as the biological sample, assessed by the methods and/or compositions provided have been transduced to contain a heterologous nucleic acid and/or nucleic acid encoding a heterologous protein or other nucleic acid or polypeptide product, e.g., a human or human-derived recombinant protein. In some embodiments the heterologous nucleic acid encodes a binding molecule, such as a recombinant receptor, such as a chimeric antigen receptor (CAR) or transgenic T cell receptor (TCR). In some embodiments, the cell is comprised by populations of such cells, compositions containing such cells and/or enriched for such cells, such as in which cells expressing the binding molecule make up at least 15%, 20%, 25%, 30%, 35%, 40%, 50%, 60%, 70%, 80%, 90%, 91%, 92%, 93%, 94%, 95%, 96%, 97%, 98%, 99%, or more percent of the total cells in the composition or cells of a certain type such as T cells or CD8+ or CD4+ cells. In some embodiments, the cells are primary T cells. Among the compositions are pharmaceutical compositions and formulations for administration, such as for adoptive cell therapy.

In some embodiments, the test sample comprises RNA from genetically engineered cells expressing the heterologous nucleic acid and/or nucleic acid encoding a heterologous protein or other nucleic acid or polypeptide product, e.g., a human or human-derived recombinant protein. The cells generally are eukaryotic cells, such as mammalian cells, and typically are human cells. In some embodiments, the cells, e.g., the cells of the test sample and/or of the biological sample, are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some embodiments, the cells are primary cells, such as those isolated directly from a subject and/or isolated from a subject and frozen.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells, e.g., cells from the test sample, biological sample and/or from the same source as the biological sample, include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the presence or absence of replication competent virus can be assessed at any point in the preparation, production, or manufacture of transduced or engineered cells, including cells that are or will be or have been transduced for use in adoptive cell therapy, and post-therapy monitoring of the subject. Exemplary steps for processing cells include steps involved in the isolation, separation, selection, cultivation (e.g., stimulation of the cells, for example, to induce their proliferation and/or activation), transducing, washing, suspension, dilution, concentration, and/or formulation of the cells, including those known and/or described herein. In particular embodiments, the processing steps include transduction of the cells with viral vector particles, where at least a part of the incubation with the viral vector particles is performed in a closed system or chamber to initiate transduction. The methods may further and/or alternatively include other processing steps, such as steps for the isolation, separation, selection, cultivation (e.g., stimulation of the cells, for example, to induce their proliferation and/or activation), washing, suspension, dilution, concentration, and/or formulation of the cells. In some embodiments, the test sample is obtained from cells that have been subjected to transduction and then cultured, for example at 37° C., for greater than or greater than about 1 day, 2 days or 3 days, such as generally greater than 4 days, 5 days, 6 days, 7 days, 8 days, 9 days, 10 days, 11 days, 12 days, 13 days, 14 days or more.

In some embodiments, the test sample and/or the biological sample comprises RNA from a cell at any stage of a genetic engineering manufacturing process. In some embodiments, the test sample contains DNA derived from RNA from a cell at any stage of a genetic engineering manufacturing process. For example, the test sample may comprise RNA from cells that have been transduced with a viral vector particle encoding a recombinant and/or heterologous molecule. In some embodiments, the test sample may comprise DNA derived from RNA from cells that have been transduced with a viral vector particle encoding a recombinant and/or heterologous molecule. In some embodiments, the test sample is obtained from a sample, e.g., a biological sample, containing cells, e.g. autologous or allogeneic cells, engineered by transduction with a heterologous nucleic acid encoding an antigen receptor (e.g CAR) and cultured or expanded, such as for use in connection with adoptive cell therapy. In some cases, the test sample contains RNA, or DNA derived from the RNA, from such transduced cells that have been cryopreserved, which, some aspects, is referred to as a cryopreserved drug product (CDP). In some cases, the test sample contains RNA or DNA derived from the RNA, from such transduced cells that have been formulated for administration to a subject, which, some aspects, is referred to as a formulated drug product (FDP). In some embodiments, the test sample is obtained from a subject after such subject has received a therapy comprising cells that have been transduced, such as with a viral vector particle encoding a recombinant and/or heterologous molecule, e.g. a CAR. In some embodiments, as a control, the provided methods can be performed on a patient-matched control sample that has not been subjected to transduction and/or genetic engineering, which can be a sample containing the selected or enriched cells to be used for transduction. In some embodiments, such a patient-matched control sample can be a cryopreserved sample, which, in some cases, is referred to as a cryopreserved material (CMAT). In some embodiments, test sample RNA is isolated from cells. In some cases, RNA is isolated from about $1\times10^4$, $1\times10^5$, $1\times10^6$, $1\times10^7$, or more cells. In some embodiments, RNA is isolated from $1\times10^6$ cells. In some cases, RNA is isolated from all or substantially all of the cells comprised by a sample or selected portion thereof.

In some embodiments, cells are incubated with a cell stimulating agent or agents that is/are a cell-binding agent, such as an antigen-binding reagent, such as antibody, that is able to induce intracellular signaling and/or cell proliferation. In some embodiments, cells are incubated with, including mixed with, anti-CD3/anti-CD28 beads.

b. Control Samples

In some aspects, the provided method is additionally performed on one or more control samples. In some embodiments, a plasmid standard control is used as a control for the PCR amplification portion of the assay. In some aspects, the plasmid standard control contains a control gene, such as a housekeeping gene. In some embodiments, the control gene is b-actin.

In some embodiments, the plasmid standard control comprises a nucleic acid encoding a control gene or portion thereof and the target gene or portion thereof. An exemplary plasmid standard control is or includes pActin-MMLV gag (SEQ ID NO: 30) or pActin-GaLV (SEQ ID NO: 34). In some embodiments, a plasmid encoding both the target gene and the control gene enables the transcription of similar levels of RNA encoding the target gene and the control gene. In some embodiments, the sequence encoding the control gene is operably linked to the sequence encoding the target gene such that the two sequences are co-transcribed. In some embodiments, the two sequences are co-transcribed as a single nucleic acid. In some embodiments, the two sequences are co-transcribed as separate nucleic acids at similar rates and/or with similar amounts of RNA transcripts produced. In some embodiments, transcription of the control gene and target gene is controlled by the same promoter. In some embodiments, transcription of the control gene and target gene are controlled by different promoters. In some cases, a plasmid standard control dilution series of $10^6$ to $10^1$ copies per reaction, e.g., well, is used.

In some embodiments, a no template control (NTC) is used in the assay. In some aspects, the no template control contains water and PCR reagents only. In some cases, the no template control provides information about the contamination state of the PCR reagents.

In some embodiments, a no reverse transcriptase (−RT) control is used. In some aspects, the −RT control contains the test sample or control sample, but no reverence transcriptase. As a result, the RT-PCR does not produce an amplicon. Thus, in some cases, the −RT sample is used to evaluate the purity of the RNA template and/or to detect contaminating DNA.

In some aspects, a negative control is used that does not contain copies of the target gene. In some embodiments, RNA from a cell line that does not express the target gene is used as the negative control. In some instances, the negative control may be used at a similar concentration as compared with the test sample.

In some embodiments, an in-process control containing RNA from patient-matched material that has not been transduced with the viral vector particle encoding a recombinant and/or heterologous molecule is used as a control for contamination during the RNA isolation procedure.

In some embodiments, a positive control containing the target gene RNA, e.g., first or second viral gene, is assessed. In some aspects, the positive control is established for the assay based on the limit of detection of target gene RNA levels of the assay. In some instances, for the positive control, RNA from a cell line that does express the target gene is used at a quantity at or just above the limit of detection of the assay. In some aspects, the positive control is established for the assay based on a known level or maximum acceptable level of target gene RNA. In some instances, for the positive control, RNA from a cell line that does express the target gene is used at a quantity at the known or maximum acceptable level of target gene RNA. In some embodiments, the RNA level of this positive control sample is used as the reference value for comparison with the test samples as described below. In some aspects, a no-RT control is used to confirm or assess RNA purity.

2. Primers and Probes

In some embodiments, the target gene, e.g., first viral gene and/or second viral gene, is assessed in the test sample and/or control sample using one or more oligonucleotide primers. In some instances, the one or more oligonucleotide primers are specific for a sequence of the target gene. In some instances, the one or more oligonucleotide primers are specific for a sequence of the control gene. In some aspects, the one or more oligonucleotide primers comprise a forward primer and a reverse primer. Thus, in some cases, the one or more oligonucleotide primers comprise a pair of primers. In some cases, the pair of primers contains a forward and reverse primer, each specific for a sequence of the target gene or control gene. In some aspects, the forward and reverse primers are specific for different sequences of the same target gene or control gene.

In some embodiments, the provided primers and probes are useful for detecting a target viral gene and/or viral polynucleotide sequence associated with replication competent retrovirus, such as a replication competent gammaretrovirus (RCR) or a replication competent lentivirus (RCL), in a sample, e.g., a test sample or biological sample. In particular embodiments, the provided proves and primers are useful for detecting target viral gene and/or viral polynucleotide sequence associated with a replication competent retrovirus that originates from and/or was generated from, the viral vector used to transduce cells of the biological sample. In certain embodiments, the provided primers and probes are useful for detecting target viral genes and/or viral polynucleotide sequences that are required for replication competency in the viral vector that was used to transduce the cells in the sample.

In some embodiments, the oligonucleotide primers are specific for a target gene in its DNA form. In some aspects, the oligonucleotide primers are specific for a target gene its RNA form.

In some aspects, the one or more oligonucleotide primers specific for the target gene, e.g., first or second viral gene, are specific for, e.g., bind to, a sequence of a viral env, gag, pol, or rev gene. In some embodiments the one or more oligonucleotide primers specific for the target gene, e.g., first or second viral gene, are specific for, e.g., bind to, a sequence of a viral vpr, vif, vpu, vpx, nef, and/or Tat gene.

In some instances, the one or more oligonucleotide primers are specific for a portion of a gene from a virus including, but not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). In some embodiments, the oligonucleotide primers may be specific for genes from other viruses, such as Vesicular stomatitis virus (VSV), hepatitis viruses, or influenza.

In some instances, the one or more oligonucleotide primers are specific for a portion of a GaLV env, VSVG env, or MMLV gag sequence. In some cases, the one or more oligonucleotide primers are specific for a portion of a sequence set forth in SEQ ID NO: 25, 26, or 27, or a sequence having at least or about 85, 90, 91, 92, 93, 94, 95, 96, 97, 98, or 99% identity with such a sequence or portion of such a sequence. In some cases, the one or more oligonucleotide primers comprise one or more sequences set forth in SEQ ID NOs: 4-5, 16-17, 19-20, or 22-23.

In some cases, the one or more oligonucleotide primers specific for a sequence of the target gene are specific for a portion of a GaLV env gene sequence, such as a portion of the sequence set forth in SEQ ID NO: 25, or a sequence having at least or about 85, 90, 91, 92, 93, 94, 95, 96, 97, 98, or 99% identity with such a sequence. In some such aspects, the one or more oligonucleotide primers comprise the sequence set forth in SEQ ID NO: 4 or 5. In some cases, the forward primer comprises the sequence set forth in SEQ ID NO: 4, or a sequence having at least or about 85, 90, 91, 92, 93, 94, 95, 96, 97, 98, or 99% identity with such a sequence. In some aspects, the reverse primer comprises the sequence set forth in SEQ ID NO: 5, or a sequence having at least or about 85, 90, 91, 92, 93, 94, 95, 96, 97, 98, or 99% identity with such a sequence. Thus, in some aspects, the forward primer contains the sequence set forth in SEQ ID NO: 4 and the reverse primer contains the sequence set forth in SEQ ID NO: 5.

In some cases, the one or more oligonucleotide primers are specific for a portion of a VSVG env gene sequence, such as a portion of the sequence set forth in SEQ ID NO: 26, or a sequence having at least or about 85, 90, 91, 92, 93, 94, 95, 96, 97, 98, or 99% identity with such a sequence.

In some cases, the one or more oligonucleotide primers are specific for a portion of a MMLV gag gene sequence, such as a portion of the sequence set forth in SEQ ID NO: 27, or a sequence having at least or about 85, 90, 91, 92, 93, 94, 95, 96, 97, 98, or 99% identity with such a sequence. In some such aspects, the one or more oligonucleotide primers comprise a sequence set forth in SEQ ID NO: 16-17, 19-20, or 22-23. In some cases, the forward primer comprises the sequence set forth in SEQ ID NO: 16, 19, or 22, or a sequence having at least or about 85, 90, 91, 92, 93, 94, 95, 96, 97, 98, or 99% identity with such a sequence. In some aspects, the reverse primer comprises the sequence set forth in SEQ ID NO: 17, 20, or 23, or a sequence having at least at or about 85, 90, 91, 92, 93, 94, 95, 96, 97, 98, or 99% identity with such a sequence. In some embodiments, the forward primer contains the sequence set forth in SEQ ID NO: 16 and the reverse primer contains the sequence set forth in SEQ ID NO: 17. In some embodiments, the forward primer contains the sequence set forth in SEQ ID NO: 19 and the reverse primer contains the sequence set forth in SEQ ID NO: 20. In some embodiments, the forward primer contains the sequence set forth in SEQ ID NO: 22 and the reverse primer contains the sequence set forth in SEQ ID NO: 23.

In some cases, the one or more oligonucleotide primers are specific for a portion of a rev gene sequence, such as a portion of the sequence set forth in SEQ ID NO: 33, or a sequence having at least or about 85, 90, 91, 92, 93, 94, 95, 96, 97, 98, or 99% identity with such a sequence. In some such aspects, the one or more oligonucleotide primers comprise a sequence set forth in SEQ ID NO: 38-39. In some cases, the forward primer comprises the sequence set forth in SEQ ID NO: 38, or a sequence having at least or about 85, 90, 91, 92, 93, 94, 95, 96, 97, 98, or 99% identity with such a sequence. In some aspects, the reverse primer comprises the sequence set forth in SEQ ID NO: 39, or a sequence having at least at or about 85, 90, 91, 92, 93, 94, 95, 96, 97, 98, or 99% identity with such a sequence. In some embodiments, the forward primer contains the sequence set forth in SEQ ID NO: 38 and the reverse primer contains the sequence set forth in SEQ ID NO: 39. In some aspects, the one or more oligonucleotide primers specific for the control gene, e.g., actin, bind to a portion of the control gene sequence. In some cases, where the control gene is actin, the oligonucleotide primers specific to a sequence of the control gene are specific for, e.g., bind to, a portion of an actin sequence. In some embodiments, the one or more oligonucleotide primers specific for a portion of the control gene sequence are specific for a portion of the sequence set forth in SEQ ID NO: 28. In some cases, the one or more oligonucleotide primers specific for actin comprise one or more sequences set forth in SEQ ID NOs: 1-2, 8, 10-11, or 13-14.

In some cases, the one or more oligonucleotide primers are specific for a portion of an actin gene sequence, such as a portion of a sequence set forth in SEQ ID NO: 28, or a sequence having at least at or about 85, 90, 91, 92, 93, 94, 95, 96, 97, 98, or 99% identity with such a sequence. In some such aspects, the one or more oligonucleotide primers comprise a sequence set forth in SEQ ID NO: 1-2, 7-8, 10-11, or 13-14. In some cases, the forward primer comprises the sequence set forth in SEQ ID NO: 1, 7, 10, or 13, or a sequence having at least or about 85, 90, 91, 92, 93, 94, 95, 96, 97, 98, or 99% identity with such a sequence. In some aspects, the reverse primer comprises the sequence set forth in SEQ ID NO: 2, 8, 11, or 14, or a sequence having at least or about 85, 90, 91, 92, 93, 94, 95, 96, 97, 98, or 99% identity with such a sequence. In some embodiments, the forward primer contains the sequence set forth in SEQ ID NO: 1 and the reverse primer contains the sequence set forth in SEQ ID NO: 2. In some embodiments, the forward primer contains the sequence set forth in SEQ ID NO: 1 and the reverse primer contains the sequence set forth in SEQ ID NO: 8. In some embodiments, the forward primer contains the sequence set forth in SEQ ID NO: 10 and the reverse primer contains the sequence set forth in SEQ ID NO: 11. In some embodiments, the forward primer contains the sequence set forth in SEQ ID NO: 13 and the reverse primer contains the sequence set forth in SEQ ID NO: 14.

In some embodiments, the target gene, e.g., first viral gene and/or second viral gene, and/or control gene is assessed using an oligonucleotide primer and fluorescent dye. Exemplary double strand nucleic acid specific dyes include, but are not limited to, SYBR™ Green I, SYBR™ Gold, ethidium bromide, propidium bromide, Pico Green, Hoechst 33258, YO-PRO-I and YO-YO-I, Boxto, EVAGREEN®, LC GREEN®, LC GREEN PLUS®, and SYTO® 9. In some instances, the fluorescent dye is SYBR™ Green. In some embodiments, the oligonucleotide primer is specific for a portion of the target gene sequence. In some embodiments, the oligonucleotide primer is specific for a portion of the control gene sequence. In some embodiments, the oligonucleotide primer is specific for a sequence of the same target gene or control gene as one or more of the other oligonucleotide primers. Thus, in some cases, a oligonucleotide primer specific for a sequence of a target gene or control gene is used with a forward primer and a reverse primer, e.g., primer pair, specific for the same target gene or control gene, respectively.

In some embodiments, the target gene, e.g., first viral gene and/or second viral gene, and/or control gene is assessed using a hydrolysis probe. In some instances, the hydrolysis probe is specific for a portion of the target gene sequence. In some instances, the hydrolysis probe is specific for a portion of the control gene sequence. In some aspects, the hydrolysis probe is specific for a sequence of the same target gene or control gene as one or more of the oligonucleotide primers. Thus, in some cases, a hydrolysis probe specific for a sequence of a target gene or control gene is used with a forward primer and a reverse primer, e.g., primer pair, specific for the same target gene or control gene, respectively.

In some embodiments, the hydrolysis probe comprises a fluorescent moiety or label. In some embodiments, the fluorescent moiety or label is a fluorescent resonance energy transfer (FRET) moiety or label (see, for example, U.S. Pat. Nos. 4,996,143, 5,565,322, 5,849,489, and 6,162,603). In some embodiments, when a donor fluorescent moiety and a corresponding acceptor fluorescent moiety are positioned within a certain distance of each other, energy transfer takes place between the two fluorescent moieties that can be visualized or otherwise detected and/or quantitated. The donor generally transfers the energy to the acceptor when the donor is excited by light radiation with a suitable wavelength. The acceptor generally re-emits the transferred energy in the form of light radiation with a different wavelength. In some embodiments or systems, non-fluorescent energy can be transferred between donor and acceptor moieties, by way of biomolecules that include substantially non-fluorescent donor moieties (see, for example, U.S. Pat. No. 7,741,467).

In some embodiments, an oligonucleotide probe can contain a donor fluorescent moiety and a corresponding quencher, which may or not be fluorescent. In some embodiments, the quencher dissipates the transferred energy in a form other than light. In some embodiments, when the oligonucleotide probe is intact, energy transfer occurs between the two fluorescent moieties such that fluorescent emission from the donor fluorescent moiety is quenched. In some embodiments, during an extension step of a polymerase chain reaction, an oligonucleotide probe bound to an amplification product is cleaved by the 5' to 3' nuclease activity of, e.g., a Taq polymerase such that the fluorescent emission of the donor fluorescent moiety is no longer quenched. Exemplary oligonucleotide probes for this purpose are described in, e.g., U.S. Pat. Nos. 5,210,015; 5,994,056; and 6,171,785. Commonly used donor-acceptor pairs include the FAM-TAMRA pair. Commonly used quenchers are DABCYL and TAMRA™. Commonly used dark quenchers include BlackHole Quenchers™ (BHQ), (Biosearch Technologies, Inc., Novato, Calif.), Iowa Black™, (Integrated DNA Tech., Inc., Coralville, Iowa), and BlackBerry™ Quencher 650 (BBQ-650), (Berry & Assoc., Dexter, Mich.).

In some embodiments, the hydrolysis probe specific for the target gene, e.g., first or second viral gene, is specific for, e.g., binds to, a sequence of a viral env, gag, pol, or rev gene. In some embodiments the hydrolysis probe specific for the target gene, e.g., first or second viral gene, is specific for, e.g., binds to, a sequence of a viral vpr, vif, vpu, vpx, nef, and/or Tat gene.

In some embodiments, the hydrolysis probe is specific for a portion of a sequence of a retrovirus, such as Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). In some embodiments, the hydrolysis probe is specific for a portion of a sequence of Vesicular stomatitis virus (VSV), hepatitis virus, or influenza.

In some instances, the hydrolysis probe is specific for a sequence of GaLV env, VSVG env, or MMLV gag. In some cases, the hydrolysis probe contains the sequence set forth in SEQ ID NOs: 6, 18, 21, or 24.

In some cases, the hydrolysis probe is specific for a sequence of a GaLV env gene, such as portion of the sequence set forth in SEQ ID NO: 25, or a sequence having at least at or about 85, 90, 91, 92, 93, 94, 95, 96, 97, 98, or 99% identity with such a sequence. In some such aspects, the hydrolysis probe contains the sequence set forth in SEQ ID NO: 6.

In some cases, the hydrolysis probe is specific for a sequence or portion of a sequence of a VSVG gene, such as a portion of the sequence set forth in SEQ ID NO: 26, or a sequence having at least at or about 85, 90, 91, 92, 93, 94, 95, 96, 97, 98, or 99% identity with such a sequence. In some such aspects, the hydrolysis probe contains a sequence set forth in SEQ ID NO: 40.

In some cases, the hydrolysis probe is specific for a portion of a sequence of an MMLV gag gene, such as a portion of the sequence set forth in SEQ ID NO: 27, or a sequence having at least at or about 85, 90, 91, 92, 93, 94, 95, 96, 97, 98, or 99% identity with such a sequence. In some such aspects, the hydrolysis probe contains a sequence set forth in SEQ ID NO: 18, 21, or 24.

In some cases, the hydrolysis probe is specific for a portion of a sequence of a rev gene, such as a portion of the sequence set forth in SEQ ID NO: 33, or a sequence having at least at or about 85, 90, 91, 92, 93, 94, 95, 96, 97, 98, or 99% identity with such a sequence. In some such aspects, the hydrolysis probe contains a sequence set forth in SEQ ID NO: 37.

In some embodiments, the hydrolysis probe is specific for a portion of a sequence of the control gene, e.g., actin, such as a portion of the sequence set forth in SEQ ID NO: 28, or a sequence having at least at or about 85, 90, 91, 92, 93, 94, 95, 96, 97, 98, or 99% identity with such a sequence. Thus, in some aspects, the hydrolysis probe specific for a sequence of the control gene is specific for, e.g., binds, the actin sequence. In some cases, the hydrolysis probe contains the sequence set forth in SEQ ID NOs: 3, 9, 12, or 15.

3. Reference Level or Value

In some embodiments, replication competent retrovirus may be determined to be present if the amount, level, or concentration of the one or more parameters is higher or lower than the reference value, which can be measured directly or indirectly, e.g. from a positive control sample containing the target gene. In some embodiments, the replication competent retrovirus may be determined to be present if amount, level, or concentration of one or more parameters that positively correlates to the amount, level, or concentration of one or more target genes is higher than the reference value. In particular embodiments, the replication competent retrovirus may be determined to be present if amount, level, or concentration of one or more parameters that negatively correlates to the amount, level, or concentration of one or more target genes is lower than the reference value. In some embodiments, the parameter and/or the reference level or value are and/or indicate a level or amount of a target gene. In some embodiments, the parameter and/or the reference level or value are and/or indicate a level or amount of a target gene that is a viral RNA gene.

Replication competent retrovirus may be determined to be present if RNA levels of the one or more target genes is higher than a reference value, which can be measured directly or indirectly, e.g. from a positive control sample containing the target gene, and/or containing a parameter that indicates an amount or level of the target gene.

In some cases, the replication competent virus result for the test sample is reported as "replication competent virus RNA detected." In some instances, the replication competent virus result for the test sample is reported as "replication competent virus RNA not detected." In some aspects, the replication competent virus result for the test sample is based on a comparison of the RNA levels of the target gene with a reference value.

In some embodiments, the reference value or level is an RNA level or surrogate readout of an RNA level (e.g. CT value), or is derived based on an RNA level or surrogate readout of an RNA level (e.g. CT value), that indicates a threshold for the presence of the target RNA in a sample indicative of the presence or risk of presence of RCR in a sample. In some embodiments, the reference value can be predetermined based on prior testing under similar assay conditions for detection of the target RNA in a sample, such as by using a model replication competent virus or positive RNA control for the target gene. In some embodiments, the reference value can be based on a positive control run in the same assay.

In some embodiments, the reference value is established by the positive control sample containing a parameter that is associated with and/or indicates the target gene at a known level and/or contains the parameter that is at about or just above the limit of detection of the parameter by the assay. In some embodiments, the reference value is established by calibrating the assay using a known concentration of the positive control such that the assay is sensitive enough to detect the parameter from or resulting from one or more replication competent virus-containing cell or particle in a certain volume of a sample, e.g., a biological sample, or a certain volume or amount of cells or total. In some embodiments, the reference value is calibrated to detect a parameter from one replication competent virus particle in a certain volume of test sample or a certain volume or amount of cells with a confidence interval. In some embodiments, the confidence interval is 50%, 75%, 80%, 90%, and is typically at or about or at least at or about 95%, 96%, 97% 98%, or 99%; in some aspects, it is at least 97%.

In some embodiments, the reference value is established by the positive control sample containing the target gene at a known level and/or at about or just above the limit of detection of the target gene by the assay. In some embodiments, the reference value is established by calibrating the assay using a known concentration of the positive control such that the assay is sensitive enough to detect RNA from one or more replication competent virus-containing cell or particle in a certain volume of test sample or a certain volume or amount of cells or total. In some embodiments, the reference value is calibrated to detect RNA from one replication competent virus particle in a certain volume of test sample or a certain volume or amount of cells with a confidence interval. In some embodiments, the confidence interval is 50%, 75%, 80%, 90%, and is typically at or about or at least at or about 95%, 96%, 97% 98%, or 99%; in some aspects, it is at least 97%.

In some embodiments, the reference value is calculated based on a known quantity of viral gene RNA, such as is present in a positive control and/or reference control sample. In some embodiments, a reference control sample comprises a known quantity of RNA and/or of target RNA, and/or can be used to determine the limit of detection of the assay and/or set a reference value for the assay. In some embodiments, the positive control or reference control sample comprises RNA from a sample comprising replication competent virus, such as a control virus, such as a wild type virus. In some embodiments, the control virus comprises or encodes the same sequence or reverse complement of the sequence of the target gene RNA. In some embodiments, the control virus is a wild-type virus, such as a wild-type GaLV, MMLV, or any of the viruses described herein.

In some embodiments, the reference value of RNA is determined based on the Ct value in a positive control. Thus, in some embodiments, the Ct value of the target gene in the test sample can be compared to the Ct value of the target gene in the positive control. In some embodiments, the Ct value of a sample identified as comprising or deemed to contain or possibly contain replication competent virus is lower than a reference and/or threshold Ct value. In some embodiments, the Ct value of a sample identified as not comprising or deemed not to comprise replication competent virus is higher than a reference and/or threshold Ct value.

In some embodiments, the reference value is based on a positive control containing an amount of the RNA, or a surrogate readout thereof, such as a CT value corresponding to such an amount, of the RNA, such as the target RNA e.g. the RNA of a particular viral gene, such as GaLV env, that is at or about, is above, or is just above, the limit of detection of the assay. In some embodiments, the amount of RNA is or is at or about or is just above (or alternatively is up to or up to about) or at or about 0.1, 0.2, 0.3, 0.5, 0.75, or 1.0 pg of target RNA or a readout corresponding thereto, such as a CT value corresponding thereto and in some aspects is, 2, 3, 4, 5, 7.5, 10, 15, 20, 25, 30, 35, 40, 45, 50, 75, 100, 125, 150, 175, 200, 250, 300, 400, 500, 750, or 1000 pg of target gene RNA. In some embodiments, the reference value is at or approximately or just above 0.75 pg of target gene RNA or is a CT value corresponding to such an amount. In alternative embodiments, the reference level is an amount of RNA in a given number of RCR+ cell in the test sample, per a given number of cells in the test sample, such as 1, 2, 3, 4, 5, 6, 7, 8, 9, 10, 11, 12, 13, 14, or 15 or 20, in some aspects 10 or fewer, RCR+ cells per million or per 10 million or per 100 million cells in the sample, or a CT value corresponding thereto, such as corresponding to a control with such concentration or number or relative number of RCR+ cells.

Thus, in some embodiments, replication competent virus can be detected if the amount of target gene RNA is determined to be greater than the reference value.

In some embodiments, the reference value is a delta CT (ΔCT) value. In some embodiments, the reference value is a ΔCT for a control sample, such a positive control or a negative control. In some embodiments, the ΔCT value is a CT value of a target gene normalized to a control gene within a given sample. In some embodiments, ΔCT=CT (target viral RNA)−CT (control gene) within a given sample. In some embodiments, the ΔCT value of the sample is compared to a reference value that is ΔCT value of the control sample. In some embodiments, the ΔCT value of the sample is compared to a reference value that is ΔCT value of the control sample. In some embodiments, the ΔCT value of the sample is compared to a reference value that is known or experimentally determined to be the ΔCT value at or approximately at or just above a threshold level or a minimum detectable level or readout corresponding thereto; the reference value is a ΔCT value of the parameter detected in, and/or a value of a parameter indicative of an amount of RNA in, a positive control sample; and/or the level of the parameter indicates the presence or the absence of the viral RNA in the biological sample; and/or the viral RNA includes a nucleic acid encoding a first viral gene; and/or the heterologous nucleic acid encodes a heterologous gene product In some embodiments, the ΔΔCT=ΔCT(sample)−ΔCT (control sample). In some embodiments, a sample that is deemed by the assay to have a ΔCT(sample) value that indicates the sample has the same or more target viral RNA than the corresponding ΔCT (control sample) is deemed positive. In some embodiments, a sample is deemed positive if the ΔΔCT indicates there is the same or more target viral RNA in the sample than in the control sample. In some embodiments, two or more of a plurality of viral RNAs are tested using the described methods.

In some embodiments, if the Ct value in a well (or average of replicates), e.g., for a given target, in the assay containing the test sample were to be observed to be greater than the Ct value of the positive control sample, then the target gene RNA in the test sample would be deemed to be or indicated to be lower than the reference value and the sample comprising the transduced cells is identified as "replication competent virus RNA not detected." In some embodiments, a transduced cells that are identified as "replication competent virus RNA not detected" are released, such as for further processing and/or use in therapy.

In some aspects, if the Ct value in a well (or average of replicates) of the assay containing the test sample were to be observed as less than the Ct value of the positive control sample, then the viral RNA of such a test sample would be deemed to be higher than the reference value and/or such a test sample would identified as "replication competent virus RNA detected.".

In some embodiments, the Ct value in a well (or average of replicates) of the assay containing the test sample cannot be calculated. This can occur in some embodiments when the amount of target or control amplification detected in the well does not reach the threshold level within a prescribed number of cycles. In some embodiments, such a result indicates there is no RNA from a replication competent virus present in the test sample, and/or that the amount of RNA from a replication competent virus in the test sample is undetectable using the assay. In some embodiments, such a test sample is identified as 'replication competent virus RNA not detected.' In some embodiments, transduced cells confirmed not to contain replication competent virus RNA by the provided methods are released, such as for further processing and/or use in therapy.

In some embodiments, where two or more target genes are assessed, either in a multiplex reaction or in separate reactions, RNA from a replication competent virus is detected to be present when the RNA of one of the target genes is higher than its reference value. In some aspects, where two or more target genes are assessed, either in a multiplex reaction or in separate reactions, RNA from a replication competent virus is detected to be present only when the RNA of at least two and as many as all of the two or more target genes is greater than each of the respective reference values. For examples, in some cases, two target genes, e.g., first and second viral genes, are assessed and RNA from a replication competent virus is detected to be present if the RNA of the first and second viral gene is greater than the reference value of the first and second viral gene, respectively. In some such aspects, RNA from a replication competent virus is not detected as present when the RNA of only one of the first or second viral gene is higher than the first or second reference value, respectively. In other embodiments, where two or more target genes are assessed, RNA from a replication competent virus would be deemed or detected to be present even if the RNA of only one (or less than all) target gene is greater than its corresponding reference value.

In some embodiments, when RNA from a replication competent virus is not detected in the test sample, it is deemed that replication competent virus particles were or are not present in the cells or sample from which the RNA has been isolated.

4. Assay Parameters

In some embodiments, the assay is polymerase chain reaction (PCR), including reverse transcriptase (rt) PCR, droplet digital PCR, real-time and quantitative PCR methods, a Northern blot assay; a Southern blot assay; an array based assay, including blotted arrays, microarrays, or in situ-synthesized arrays; or sequencing-based assay. In some embodiments, the assay is a next generation sequencing (NGS) assay, e.g., RNA-seq. In some embodiments, the assay is or includes immunocytochemisty or immunohistochemisty, ELISA, western blotting, peptide sequencing, mass spectrometry (such as MS/MS) optionally with HPLC.

In particular embodiments, the assay is an RT-PCR and/or real time PCR assay. In some embodiments, the RT-PCR is performed on a sample, e.g., a test sample, that is or contains RNA, e.g, viral RNA, or DNA, e.g., cDNA derived from viral RNA.

In particular embodiments, the RNA is obtained from a sample. Suitable techniques and methods for obtaining and purifying RNA from a sample are known. For example, reagents and kits for isolating RNA from a sample are commercially available, and include, but are not limited to RNeasy and RNeasy plus kits (Qiagen).

In some embodiments, cDNA is obtained or derived from RNA. The synthesis of DNA from an RNA template, via reverse transcription, produces complementary DNA (cDNA). Reverse transcriptases (RTs) use an RNA template and a short primer complementary to the 3' end of the RNA to direct the synthesis of the first strand cDNA, which can be used directly as a template for the Polymerase Chain Reaction (PCR). This combination of reverse transcription and PCR (RT-PCR) allows the detection of low abundance RNAs in a sample, and production of the corresponding cDNA, thereby facilitating the cloning of low copy genes. In some embodiments, suitable techniques and methods for generating cDNA from RNA, such as by reverse transcription, are known.

In some aspects, reverse transcription is carried out by reverse transcriptase (RT) reaction, to generate cDNA, which in some aspects is then used as a template for PCR amplification, such as using primers designed to amplify at least a portion of one or more target or control RNAs or cDNAs derived therefrom. In some aspects, a one-step quantitative RT-PCR is carried out. In some aspects, the RT-PCR is carried out using a one-step approach with a reaction mixture including reverse transcriptase (RT), and a polymerase, such as TAQ polymerase, and optionally an RNAse inhibitor. In some aspects, the mixture is RNA UltraSense™ One-Step Quantitative RT-PCR System, including the RNA UltraSense™ Enzyme Mix (including SuperScript® III RT, Platinum® Taq DNA Polymerase, and RNaseOUT™ Ribonuclease Inhibitor) (ThermoFisher Scientific).

In some embodiments, the RT-PCR is performed with one or more steps. In some embodiments, the RT-PCR includes an initial denaturation, amplification cycles, and/or a final extension step. In certain embodiments, the RT-PCR is performed to measure, detect, assess, and/or quantify target and control genes. In certain embodiments, detection of the target and control genes are performed with any suitable reagents, including but not limited to reagents from commercially availiable kits, such as but not limited to RNA UltraSense One-Step Quantitative RT-PCR Enzyme Mix and RNA UltraSense One-Step Quantitative RT-PCR 5× Reaction Mix (ThermoFisher Scientific).

In some embodiments, the RT-PCR is performed with an initial hold stage or hold step. In some embodiments, the hold step is performed for or for about 2 minutes, 3 minutes, 4 minutes, 5 minutes, 6 minutes, 7 minutes, 8 minutes, 9 minutes, 10 minutes, 12 minutes, 15 minutes, 20 minutes or greater than 10 minutes; or between about 10 minutes and 20 minutes, inclusive. In particular embodiments, the initial hold step is performed at or at about 40° C., 45° C., 46° C., 47° C., 48° C., 49° C., 50° C., 51° C., 52° C., 53° C., 54° C., or 55° C., or between 40° C. and 60° C.; 35° C. and 45° C., or 45° C. and 60° C., inclusive. In certain embodiments, the RT-PCR is performed with an initial hold step or stage at a temperature of 50° C. for 15 minutes.

In some embodiments, the RT-PCR is performed with an initial denaturation step. In some embodiments, the initial denaturation step is performed for or for about 15 seconds, 30 seconds, 45 seconds, 60 seconds, 75 seconds, 90 seconds, 105 seconds, 120 seconds, 2 minutes, 3 minutes, 4 minutes, 5 minutes, 6 minutes, 7 minutes, 8 minutes, 9 minutes, 10 minutes, or greater than 10 minutes. In particular embodiments, the initial denaturation step is performed at or at about 85° C., 86° C., 87° C., 88° C., 89° C., 90° C., 91° C., 92° C., 93° C., 94° C., 95° C., 96° C., 97° C., 98° C., 99° C., or between 85° C. and 95° C.; 90° C. and 96° C., or 94° C. and 99° C. In some embodiments, the RT-PCR is performed with an initial denaturation step at a temperature of 95° C. for 2 minutes.

In some embodiments, the RT-PCR assay includes two or more amplification cycles. In some embodiments, the RT-PCR assay includes 2, 5, 10, 15, 20, 25, 26, 27, 28, 29, 30, 31, 32, 33, 34, 35, 36, 37, 38, 39, 40, 41, 42, 43, 44, 45, or more than 45 cycles. In some embodiments, the RT-PCR assay includes between 35 and 40 amplification cycles, inclusive. In certain embodiments, the RT-PCR assay includes 40 cycles.

In some embodiments, the amplification cycle is a two-step amplification cycle. In some embodiments, the two step amplification cycle includes a first step and a second step. In some embodiments, the first step is performed at or at about 85° C., 86° C., 87° C., 88° C., 89° C., 90° C., 91° C., 92° C., 93° C., 94° C., 95° C., 96° C., 97° C., 98° C., 99° C., or between 85° C. and 95° C.; 90° C. and 96° C., or 94° C. and 99° C., inclusive. In some embodiments, the first step is performed for or for about 5 seconds, 10 seconds, 15 seconds, 20 seconds, 30 seconds, 45 seconds, 60 seconds, 75 seconds, 90 seconds, 105 seconds, 120 seconds, or between 5 seconds and 30 seconds, 15 seconds and 45 seconds, or 30 seconds and 120 seconds, inclusive. In some embodiments, the first step of the amplification cycle is a temperature of 95° C. for 15 seconds.

In certain embodiments, the second step of the two-step amplification cycle is performed at or at about 55° C., 56° C., 57° C., 58° C., 59° C., 60° C., 61° C., 62° C., 63° C., 64° C., or 65° C., or between 50° C. and 70° C., 55° C. and 65° C., or 57° C. and 63° C., inclusive. In some embodiments, the second step is performed for or for about 5 seconds, 10 seconds, 15 seconds, 20 seconds, 30 seconds, 45 seconds, 60 seconds, 75 seconds, 90 seconds, 105 seconds, 120 seconds, or between 5 seconds and 30 seconds, 15 seconds and 45 seconds, or 30 seconds and 120 seconds, inclusive. In some embodiments, the second step of the cycle is a temperature of 60° C. for 60 seconds.

In some embodiments, the RT-PCR reaction includes a final extension step. In some embodiments, the final extension step is performed at between 50° C. and 75° C., between 60° C. and 70° C., between 65° C. and 70° C., inclusive. In some embodiments, the final extension step is performed for or for about 60 seconds, 75 seconds, 90 seconds, 105 seconds, 120 seconds, 2 minutes, 3 minutes, 4 minutes, 5 minutes, 6 minutes, 7 minutes, 8 minutes, 9 minutes, 10 minutes, or greater than 10 minutes.

The some embodiments, the amplification cycle contains three steps. In some embodiments, the amplification cycle contains a denaturation step, a primer annealing step, and a primer extension step. In some embodiments denaturation step is between 5 seconds and 30 seconds, 15 seconds and 45 seconds, or 30 seconds and 120 seconds, inclusive. In certain embodiments, the denaturation step is at a temperature between 80° C. and 100° C. In particular embodiments, the primer annealing step is between 5 seconds and 30 seconds, 15 seconds and 45 seconds, or 30 seconds and 120 seconds, inclusive. In some embodiments, the primer annealing step is at a temperature between 40° C. and 60° C. In certain embodiments, the primer extension step is between 5 seconds and 30 seconds, 15 seconds and 45 seconds, or 30 seconds and 120 seconds, inclusive. In some embodiments, the primer extension step is at a temperature between 60° C. and 80° C.

In some embodiments, the RT-PCR assay is performed with is performed with an initial hold step or stage at a temperature of 50° C. for 15 minutes, an initial denaturation step at a temperature of 95° C. for 2 minutes, 40 two-step amplification cycles that contain a first step a temperature of 95° C. for 15 seconds and a second step at a temperature of 60° C. for 60 seconds.

In some embodiments, the methods include assessing or confirming the validity of the assay, as a whole or in a particular instance, such as the RT-PCR and/or real-time PCR assay. In some cases, the assay is considered valid or confirmed if one or more certain assay criteria and/or ranges are met. In some aspects, these are specific for a particular control or target sample and/or a particular pair of oligonucleotide primers.

For example, in some cases, it may be desired that no Ct value is observed in any well of the assay for a control, such as a no template control (NTC) sample, when the control gene, e.g., actin, primer set is used. In some embodiments, it is desirable that no Ct value is observed in any well of the assay for the no template control (NTC) sample when the target gene, e.g., first or second viral gene, primer set is used.

In some cases, it is desired that that the slope for the control gene, e.g., actin, in the plasmid standard samples is between a certain range, such as between about −3.1 and about −3.6. In some aspects, it is desired that that the efficiency for the control gene in the plasmid standard samples is between or between about 90 and 110%. In some aspects, the assay criteria include that the $R^2$ value for the control gene in the plasmid standard samples is about or greater than about 0.90, such as greater than or about 0.95, 0.98, or 0.99. In some embodiments, the assay criteria include that the $R^2$ value for the control gene in the plamid standard samples is about or is greater than about 0.98.

In some instances, it is desired that that the slope for the target gene, e.g., the first and/or second viral gene, in the plasmid standard samples is between or between about −3.1 and −3.6. In some cases, it is desired that that the efficiency for the target gene in the plasmid standard samples is between or between about 90 and 110%. In some aspects, the assay criteria include that the $R^2$ value for the target gene in the plasma standard samples is about or greater than about 0.90, such as greater than or about 0.95, 0.98, or 0.99. In some cases, the assay criteria include that the $R^2$ value for the target gene in the plasma standard samples is about or is greater than or about 0.98.

In some embodiments, it is desired that that the Ct value for the control gene, e.g., actin, primer set for the untransduced negative control sample is less than or less than about 22. In some cases, the assay criteria include that there is no Ct value in every well of the untransduced negative control using the target gene primer set. In some cases, it is desired that that the A260/280 value for the untransduced negative control sample is above or above about 2.000. In some aspects it is desired that that the A260/280 value for the untransduced negative control sample is between or between about 2.000 and 2.100.

In some embodiments, it is desired that that the Ct value for the control gene, e.g., actin, primer set is less than or less than about 15. In some aspects, the assay criteria include that the standard deviation of the Ct values for the control gene replicates in the test sample is less than or less than about 1, such as less than or less than about 0.75, 0.5, or 0.25. In some cases, it is desired that the standard deviation of the Ct values for the control gene replicates in the test sample is less than or less than about 0.5. In some cases, it is desired that that the A260/280 value for the test sample is above or above about 2.000. In some aspects, it is desired that the A260/280 value for the test sample is between or between about 2.000 and 2.100. In some embodiments, the Ct value for the control gene in the no reverse transcriptase (−RT) control sample is about or at least about 13.2 higher than the Ct value for the control gene in the test sample.

III. COMPOSITIONS, COMBINATIONS, KITS, AND ARTICLES OF MANUFACTURE

Provided in some aspects are compositions, combinations, and/or kits for detecting replication competent virus in a sample, e.g., a biological sample, comprising transduced cells. In some embodiments, the compositions, combinations, and/or kits comprise reagents for assessing a parameter, e.g., gene RNA levels in cells, such as transduced cells. In some embodiments, the reagents include reagents for RNA isolation, RT-PCR, qPCR, and/or RT-qPCR. In some aspects, the compositions, combinations, and/or kits comprise one or more oligonucleotide primers, one or more pairs of oligonucleotide primers, and/or one or more hydrolysis probes.

In some instances, the one or more oligonucleotide primers are specific for a sequence of the target gene. In some instances, the one or more oligonucleotide primers are specific for a sequence of the control gene. In some aspects, the one or more oligonucleotide primers comprise a forward primer and a reverse primer. Thus, in some cases, the one or more oligonucleotide primers comprise a pair of primers. In some cases, the pair of primers contains a forward and reverse primer, each specific for a sequence of the target gene or control gene. In some aspects, the forward and reverse primers are specific for different sequences of the same target gene or control gene.

In some embodiments, the composition, combination, and/or kit comprises one or more hydrolysis probes. In some embodiments, the hydrolysis probe comprises a fluorescent moiety or label. Exemplary fluorescent moieties and labels are discussed above.

In some instances, the hydrolysis probe is specific for a sequence of the target gene. In some instances, the hydrolysis probe is specific for a sequence of the control gene. In some aspects, the hydrolysis probe is specific for a sequence of the same target gene or control gene as one or more of the oligonucleotide primers. Thus, in some cases, a hydrolysis probe specific for a sequence of a target gene or control gene is used with a forward primer and a reverse primer, e.g., primer pair, specific for the same target gene or control gene, respectively.

In some embodiments, the provided compositions, combinations, and/or kits are useful for detecting replication competent retrovirus, such as a replication competent gammaretrovirus (RCR) or a replication competent lentivirus (RCL), in a sample, e.g., a test sample or biological sample. In particular embodiments, the provided compositions, combinations, and/or kits are useful for detecting replication competent retrovirus that originates from and/or was generated from, the viral vector used to transduce cells of the biological sample. In certain embodiments, the provided compositions, combinations, and/or kits are useful for detecting viral genes and/or viral polynucleotide sequences that are required for replication competency in the viral vector that was used to transduce the cells in the sample. In certain embodiments, the provided compositions, combinations, and/or kits include oligonucleotide primers and probes, e.g., hydrolysis probes, that are specific to the one or more target genes.

In some embodiments, the provided compositions, combinations, and/or kits are useful for detecting replication competent an (RCR) in a sample, e.g., a test sample or biological sample. In particular embodiments, the provided compositions, combinations, and/or kits are useful for detecting replication competent retrovirus that originates from and/or was generated from, the gammaretroviral vector used to transduce cells of the biological sample. In certain embodiments, the provided compositions, combinations, and/or kits are useful for detecting viral genes and/or viral polynucleotide sequences that are required for replication competency in the gammaretroviral vector that was used to transduce the cells in the sample. In some aspects, the one or more oligonucleotide primers specific for the target gene, e.g., first or second viral gene, are specific for, e.g., bind to, a sequence of a viral env, gag, pol, or rev gene. In some embodiments, the one or more oligonucleotide primers specific for the target gene, e.g., first or second viral gene, are specific for, e.g., bind to, a sequence of a gammaretroviral env, gag, pol, or rev gene and/or are specific for an env, gag, pol, or rev gene that is used to generate the gammaretroviral vector, e.g, a replication deficient gammaretroviral vector used for gene delivery. In some instances, the one or more oligonucleotide primers are specific for a sequence of GaLV env, VSVG, or MMLV gag. In some cases, the one or more oligonucleotide primers are specific for a sequence or portion of a sequence set forth in SEQ ID NO: 25, 26, or 27, or a sequence having at least or about 85, 90, 91, 92, 93, 94, 95, 96, 97, 98, or 99% identity with such a sequence or portion of such a sequence. In some cases, the one or more oligonucleotide primers comprise one or more sequences set forth in SEQ ID NOs: 4-5, 16-17, 19-20, or 22-23.

In some embodiments, the hydrolysis probe specific for the target gene, e.g., first or second viral gene, is specific for, e.g., binds to, a sequence of a viral env, gag, pol, or rev gene. In some instances, the hydrolysis probe is specific for a sequence of GaLV env, VSVG env, or MMLV gag. In some cases, the hydrolysis probe contains the sequence set forth in SEQ ID NOs: 6, 18, 21, or 24.

In some cases, the one or more oligonucleotide primers specific for a sequence of the target gene are specific for a sequence of a GaLV env gene, such as a portion of the sequence set forth in SEQ ID NO: 25, or a sequence having at least or about 85, 90, 91, 92, 93, 94, 95, 96, 97, 98, or 99% identity with such a sequence. In some such aspects, the one or more oligonucleotide primers comprise the sequence set forth in SEQ ID NO: 4 or 5. In some cases, the forward primer comprises the sequence set forth in SEQ ID NO: 4, or a sequence having at least or about 85, 90, 91, 92, 93, 94, 95, 96, 97, 98, or 99% identity with such a sequence. In some aspects, the reverse primer comprises the sequence set forth in SEQ ID NO: 5, or a sequence having at least or about 85, 90, 91, 92, 93, 94, 95, 96, 97, 98, or 99% identity with such a sequence. Thus, in some aspects, the forward primer contains the sequence set forth in SEQ ID NO: 4 and the reverse primer contains the sequence set forth in SEQ ID NO: 5.

In some cases, the one or more oligonucleotide primers are specific for a sequence of a MMLV gag gene, such as a portion of the sequence set forth in SEQ ID NO: 27, or a sequence having at least or about 85, 90, 91, 92, 93, 94, 95, 96, 97, 98, or 99% identity with such a sequence. In some such aspects, the one or more oligonucleotide primers comprise a sequence set forth in SEQ ID NO: 16-17, 19-20, or 22-23. In some cases, the forward primer comprises the sequence set forth in SEQ ID NO: 16, 19, or 22, or a sequence having at least or about 85, 90, 91, 92, 93, 94, 95, 96, 97, 98, or 99% identity with such a sequence. In some aspects, the reverse primer comprises the sequence set forth in SEQ ID NO: 17, 20, or 23, or a sequence having at least at or about 85, 90, 91, 92, 93, 94, 95, 96, 97, 98, or 99% identity with such a sequence. In some embodiments, the forward primer contains the sequence set forth in SEQ ID NO: 16 and the reverse primer contains the sequence set forth in SEQ ID NO: 17. In some embodiments, the forward primer contains the sequence set forth in SEQ ID NO: 19 and the reverse primer contains the sequence set forth in SEQ ID NO: 20. In some embodiments, the forward primer contains the sequence set forth in SEQ ID NO: 22 and the reverse primer contains the sequence set forth in SEQ ID NO: 23.

In some cases, the hydrolysis probe is specific for a sequence or portion of a sequence of an MMLV gag gene, such as a portion of the sequence set forth in SEQ ID NO: 27, or a sequence having at least at or about 85, 90, 91, 92, 93, 94, 95, 96, 97, 98, or 99% identity with such a portion of a sequence. In some such aspects, the hydrolysis probe contains a sequence set forth in SEQ ID NO: 18, 21, or 24.

In some embodiments, the provided compositions, combinations, and/or kits are useful for detecting RCL in a sample, e.g., a test sample or biological sample. In particular embodiments, the provided compositions, combinations, and/or kits are useful for detecting replication competent retrovirus that originates from and/or was generated from, the gammaretroviral vector used to transduce cells of the biological sample. In certain embodiments, the provided compositions, combinations, and/or kits are useful for detecting viral genes and/or viral polynucleotide sequences that are required for replication competency in the gammaretroviral vector that was used to transduce the cells in the sample. In some aspects, the one or more oligonucleotide primers specific for the target gene, e.g., first or second viral gene, are specific for, e.g., bind to, a sequence of a viral env, gag, pol, or rev gene. In some embodiments, the one or more oligonucleotide primers specific for the target gene, e.g., first or second viral gene, are specific for, e.g., bind to, a sequence of a gammaretroviral env, gag, pol, or rev gene and/or are specific for an env, gag, pol, or rev gene that is used to generate the gammaretroviral vector, e.g, a replication deficient gammaretroviral vector used for gene delivery.

In some cases, the one or more oligonucleotide primers are specific for a sequence of a VSV-G env gene, such as a portion of the sequence set forth in SEQ ID NO: 26, or a sequence having at least or about 85, 90, 91, 92, 93, 94, 95, 96, 97, 98, or 99% identity with such a sequence.

In some cases, the hydrolysis probe is specific for a sequence or portion of a sequence of a VSVG env gene, such as a portion of the sequence set forth in SEQ ID NO: 26, or a sequence having at least at or about 85, 90, 91, 92, 93, 94, 95, 96, 97, 98, or 99% identity with such a portion of a sequence.

In some cases, the one or more oligonucleotide primers are specific for a portion of a rev gene sequence, such as a portion of the sequence set forth in SEQ ID NO: 33, or a sequence having at least or about 85, 90, 91, 92, 93, 94, 95, 96, 97, 98, or 99% identity with such a sequence. In some such aspects, the one or more oligonucleotide primers comprise a sequence set forth in SEQ ID NO: 38-39. In some cases, the forward primer comprises the sequence set forth in SEQ ID NO: 38, or a sequence having at least or about 85, 90, 91, 92, 93, 94, 95, 96, 97, 98, or 99% identity with such a sequence. In some aspects, the reverse primer comprises the sequence set forth in SEQ ID NO: 39, or a sequence having at least at or about 85, 90, 91, 92, 93, 94, 95, 96, 97, 98, or 99% identity with such a sequence. In some embodiments, the forward primer contains the sequence set forth in SEQ ID NO: 38 and the reverse primer contains the sequence set forth in SEQ ID NO: 39.

In some cases, the hydrolysis probe is specific for a portion of a sequence of a rev gene, such as a portion of the sequence set forth in SEQ ID NO: 33, or a sequence having at least at or about 85, 90, 91, 92, 93, 94, 95, 96, 97, 98, or 99% identity with such a sequence. In some such aspects, the hydrolysis probe contains a sequence set forth in SEQ ID NO: 37.

In some aspects, the one or more oligonucleotide primers specific for the control gene, e.g., actin, bind to a sequence of the control gene. In some cases, where the control gene is actin, the oligonucleotide primers specific to a sequence of the control gene are specific for, e.g., bind to, a sequence of actin. In some embodiments, the one or more oligonucleotide primers specific for a sequence of the control gene are specific for a portion of the sequence set forth in SEQ ID NO: 28. In some cases, the one or more oligonucleotide primers specific for actin comprise one or more sequences set forth in SEQ ID NOs: 1-2, 8, 10-11, or 13-14.

In some cases, the one or more oligonucleotide primers are specific for a sequence of an actin gene, such as a portion of a sequence set forth in SEQ ID NO: 28, or a sequence having at least at or about 85, 90, 91, 92, 93, 94, 95, 96, 97, 98, or 99% identity with such a portion of a sequence. In some such aspects, the one or more oligonucleotide primers comprise a sequence set forth in SEQ ID NO: 1-2, 8, 10-11, or 13-14. In some cases, the forward primer comprises the sequence set forth in SEQ ID NO: 1, 10, or 13, or a sequence having at least or about 85, 90, 91, 92, 93, 94, 95, 96, 97, 98, or 99% identity with such a sequence. In some aspects, the reverse primer comprises the sequence set forth in SEQ ID NO: 2, 8, 11, or 14, or a sequence having at least or about 85, 90, 91, 92, 93, 94, 95, 96, 97, 98, or 99% identity with such a sequence. In some embodiments, the forward primer contains the sequence set forth in SEQ ID NO: 1 and the reverse primer contains the sequence set forth in SEQ ID NO: 2. In some embodiments, the forward primer contains the sequence set forth in SEQ ID NO: 1 and the reverse primer contains the sequence set forth in SEQ ID NO: 8. In some embodiments, the forward primer contains the sequence set forth in SEQ ID NO: 10 and the reverse primer contains the sequence set forth in SEQ ID NO: 11. In some embodiments, the forward primer contains the sequence set forth in SEQ ID NO: 13 and the reverse primer contains the sequence set forth in SEQ ID NO: 14.

In some embodiments, the hydrolysis probe is specific for a sequence or portion of a sequence of the control gene, e.g., actin, such as a portion of the sequence set forth in SEQ ID NO: 27, or a sequence having at least at or about 85, 90, 91, 92, 93, 94, 95, 96, 97, 98, or 99% identity with such a portion of a sequence. Thus, in some aspects, the hydrolysis probe specific for a sequence of the control gene is specific for, e.g., binds, actin. In some cases, the hydrolysis probe contains the sequence set forth in SEQ ID NOs: 3, 9, 12, or 15.

In particular embodiments, a kit provided herein is useful for the detection of a RCR in a sample. In particular embodiments, the kit includes oligonucleotide primers and probes that specific to target genes that are gammaretroviral genes and/or are genes that were used to generate a gammaretroviral vector, such as a replication deficient gammaretroviral vector used for gene delivery. In particular embodiments the kit includes oligonucleotide primers and probes that are specific to a control gene. In some embodiments, the control gene is actin. In particular embodiments, target gene is GaLV env. In certain embodiments target gene is MMLV gag. In some embodiments, the target genes are GaLV env and MMLV gag.

In certain embodiments, a kit provided herein is useful for the detection of a RCL in a sample. In particular embodiments, the kit includes oligonucleotide primers and probes that specific to target genes that are lentiviral genes and/or are genes that were used to generate a lentiviral vector, such as a replication deficient lentiviral vector used for gene delivery. In particular embodiments the kit includes oligonucleotide primers and probes that are specific to a control gene. In some embodiments, the control gene is actin. In particular embodiments, the target gene is rev, e.g., HIV rev. In certain embodiments target gene is VSV-G. In some embodiments, the target genes are rev and VSV-G.

IV. VIRAL VECTOR PARTICLES AND ENCODED RECOMBINANT AND/OR HETEROLOGOUS MOLECULES

In some aspects, the provided methods involve detecting a parameter that is associated with and/or correlated to RNA from replication competent retrovirus. In some embodiments, the parameter is measured in a test sample containing RNA or cDNA from a cell transduced with a viral vector particle encoding a recombinant and/or heterologous molecule. Thus, in some cases, the viral vector particle has been used or can be used to transduce the cells that are subsequently assessed by the provided methods.

In some embodiments, the viral vector particle, such as the lentiviral or gammaretroviral vector particle, contains a nucleic acid encoding a recombinant and/or heterologous molecule (e.g., gene product), e.g., recombinant or heterologous protein, such as a recombinant and/or heterologous receptor, such as chimeric antigen receptor (CAR) or other antigen receptor, in a genome of the viral vector. Such recombinant and/or heterologous molecules may include soluble proteins, e.g., secreted proteins, and/or cell surface proteins. In some embodiments, the molecule is or includes a recombinant receptor. Such recombinant receptors may include antigen receptors, such as functional non-TCR antigen receptors, including chimeric antigen receptors (CARs), and other antigen-binding receptors such as transgenic T cell receptors (TCRs). The receptors may also include other receptors, such as other chimeric receptors, such as receptors that bind to particular ligands and having transmembrane and/or intracellular signaling domains similar to those present in a CAR.

In some embodiments, the genome of the viral vector particle may include sequences in addition to the nucleic acid encoding the recombinant and/or heterologous molecule. Such sequences may include sequences that allow the genome to be packaged into the virus particle and/or sequences that promote expression of a nucleic acid encoding a recombinant and/or heterologous molecule, e.g., recombinant receptor, such as a CAR.

In some embodiments, the nucleic acid encodes a recombinant receptor and/or chimeric receptor, such as a heterologous receptor protein. The recombinant receptor, such as heterologous receptor, may include antigen receptors, such as functional non-TCR antigen receptors, including chimeric antigen receptors (CARs), and other antigen-binding receptors such as transgenic T cell receptors (TCRs). The receptors may also include other receptors, such as other chimeric receptors, such as receptors that bind to particular ligands and having transmembrane and/or intracellular signaling domains similar to those present in a CAR.

In some embodiments, the recombinant and/or heterologous molecule, e.g., gene product, is a soluble molecule, such as an immunomodulatory and/or immunostimulatory molecule, such as a cytokine, e.g., IL-2, IL-12, IL-6, 41BBL, CD40L, and/or soluble ligand or receptor such as a soluble ligand for an immune cell costimulatory molecule, e.g., CD40L, 41BBL, or a soluble antigen-binding molecule such as an scFv. Also among the molecules are expression or transduction markers and any other molecule(s) known for use in expression vectors and/or cassettes.

In some embodiments, the recombinant antigen receptor, e.g., CAR, specifically binds to one or more ligands on a cell or disease, such as a cancer, infectious disease, inflammatory or autoimmune disease, or other disease or condition, including those described herein. Exemplary antigens include $\alpha v\beta 6$ integrin (avb6 integrin), B cell maturation antigen (BCMA), B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRHS), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-AD, Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the antigen is a pathogen-specific antigen. In some embodiments, the antigen is a viral antigen (such as a viral antigen from HIV, HCV, HBV, etc.), bacterial antigens, and/or parasitic antigens.

Antigen receptors, including CARs and recombinant TCRs, and production and introduction thereof, in some embodiments include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75.

In some embodiments, the recombinant or heterologous molecule(s) encoded by the nucleic acid within the viral vector particle is or includes a nucleic acid molecule, such as an RNA, DNA, or artificial nucleic acid sequence, such as one designed for interference with expression or activity of a target mRNA, such as an short-interfering RNA (siRNA), short hairpin RNA (shRNA), or micro-RNA (miRNA). Such molecules may include those designed to interfere with expression or activity of molecules associated with, promoting, or inhibiting the activity of immune cells, such as immunomodulators, immunoinhibitory molecules, and immune checkpoint molecules. In some embodiments, a nucleotide siRNA or miRNA sequence (e.g. 21-25 nucleotides in length) can, for example, be produced from an expression vector by transcription of a short-hairpin RNA (shRNA) sequence, a longer (e.g. 60-80 nucleotide) precursor sequence, which is subsequently processed by the cellular RNAi machinery to produce either a siRNA or miRNA sequence. Alternatively, a nucleotide siRNA or miRNA sequence (e.g. 21-25 nucleotides in length) can, for example, be synthesized chemically. Chemical synthesis of siRNA or miRNA sequences is commercially available from such corporations as Dharmacon, Inc. (Lafayette, Colo.), Qiagen (Valencia, Calif.), and Ambion (Austin, Tex.). The RNA can be 10 to 30 nucleotides long, such as 19-25 or 21-25 nucleotides in length. For example, an siRNA sequence typically binds a unique sequence within a target mRNA with exact complementarity and results in the degradation of the target mRNA molecule. A siRNA sequence can bind anywhere within the mRNA molecule; sequences targeted by the siRNA include genes expressing a polypeptide of interest, or an upstream or downstream modulator of such a gene, e.g. an upstream or downstream modulator of a gene, such as a transcription factor that binds a gene promoter, a kinase or phosphatase that interacts with a polypeptide of interest, and polypeptides involved in regulatory pathways capable of influencing the polypeptide of interest. A miRNA sequence typically binds a unique sequence within a target mRNA with exact or less than exact complementarity and results in the translational repression of the target mRNA molecule. A miRNA sequence can bind anywhere within mRNA sequence, but generally binds within the 3' untranslated region of the mRNA molecule.

A. Chimeric Antigen Receptors

In some embodiments, the recombinant and/or heterologous molecule is or includes a chimeric antigen receptor (CAR). The CAR is generally a genetically engineered receptor with an extracellular ligand binding domain linked to one or more intracellular signaling components. Such molecules typically mimic or approximate a signal through a natural antigen receptor and/or signal through such a receptor in combination with a costimulatory receptor.

In some embodiments, CARs are constructed with specificity for a particular marker, such as a marker expressed in a particular cell type to be targeted by adoptive therapy, e.g., a cancer marker and/or any of the antigens described. Thus, the CAR typically includes one or more antigen-binding fragment, domain, or portion of an antibody, or one or more antibody variable domains, and/or antibody molecules. In some embodiments, the CAR includes an antigen-binding portion or portions of an antibody molecule, such as a variable heavy chain (VH) or antigen-binding portion thereof, or a single-chain antibody fragment (scFv) derived from the variable heavy (VH) and variable light (VL) chains of a monoclonal antibody (mAb).

In some embodiments, the extracellular portion of the CAR, such as an antibody portion thereof, further includes a spacer, such as a spacer region between the antigen-recognition component, e.g. scFv, and a transmembrane domain. The spacer may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer* Res., 19:3153 or international patent application publication number WO2014031687.

The extracellular ligand binding domain, such as antigen recognition domain, generally is linked to one or more intracellular signaling components, such as signaling components that mimic activation through an antigen receptor complex, such as a TCR complex, in the case of a CAR, and/or signal via another cell surface receptor. In some embodiments, a transmembrane domain links the extracellular ligand binding and intracellular signaling domains. In some embodiments, the CAR includes a transmembrane domain fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The antigen-specific binding or recognition component is generally linked to one or more transmembrane and intracellular signaling domains. In some embodiments, the CAR includes a transmembrane domain fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD154. The transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor y, CD8, CD4, CD25, or CD16. For example, in some aspects, the CAR or other chimeric receptor includes a chimeric molecule between CD3-zeta (CD3-ζ) or Fc receptor y and CD8, CD4, CD25 or CD16.

In some embodiments, upon ligation of the CAR or other chimeric receptor, the cytoplasmic domain or intracellular signaling domain of the receptor activates at least one of the normal effector functions or responses of the cell, e.g., immune cell, e.g., T cell, engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, and costimulatory CARs, both expressed on the same cell (see WO2014/055668). In some aspects, the CAR is the stimulatory or activating CAR; in other aspects, it is the costimulatory CAR. In some embodiments, the cells further include inhibitory CARs (iCARs, see Fedorov et al., *Sci. Transl. Medicine,* 5(215) (December, 2013), such as a CAR recognizing a different antigen, whereby an activating signal delivered through a CAR recognizing a first antigen is diminished or inhibited by binding of the inhibitory CAR to its ligand, e.g., to reduce off-target effects.

In certain embodiments, the intracellular signaling domain comprises a CD28 transmembrane and signaling domain linked to a CD3 intracellular domain. In some embodiments, the intracellular signaling domain comprises a chimeric CD28 and CD137 co-stimulatory domains, linked to a CD3 intracellular domain.

In some embodiments, a CAR can also include a transduction marker (e.g., tEGFR). In some embodiments, the intracellular signaling domain of the $CD8^+$ cytotoxic T cells is the same as the intracellular signaling domain of the $CD4^+$ helper T cells. In some embodiments, the intracellular signaling domain of the $CD8^+$ cytotoxic T cells is different than the intracellular signaling domain of the $CD4^+$ helper T cells.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the recombinant and/or heterologous molecule encoded by nucleic acid(s) within the viral vector particle further include one or more marker, e.g., for purposes of confirming transduction or engineering of the cell to express the receptor and/or selection and/or targeting of cells expressing molecule(s) encoded by the nucleic acid. In some aspects, such a marker may be encoded by a different nucleic acid or polynucleotide, which also may be introduced during the genetic engineering process, typically via the same method, e.g., transduction by the same vector or type of vector.

In some aspects, the marker, e.g., transduction marker, is a protein and/or is a cell surface molecule. Exemplary markers are truncated variants of a naturally-occurring, e.g., endogenous markers, such as naturally-occurring cell surface molecules. In some aspects, the variants have reduced immunogenicity, reduced trafficking function, and/or reduced signaling function compared to the natural or endogenous cell surface molecule. In some embodiments, the marker is a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO2014031687. In some embodiments, the marker is a molecule, e.g., cell surface protein, not naturally found on T cells or not naturally found on the surface of T cells, or a portion thereof.

In some embodiments, the marker is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular ligand-binding portion, such as an antigen-binding portion, such as an antibody or fragment thereof and in intracellular domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

In some embodiments, the transmembrane domain of the receptor, e.g., CAR, is a transmembrane domain of human CD28 or variant thereof, e.g., a 27-amino acid transmembrane domain of a human CD28 (Accession No.: P10747.1). In some embodiments, the intracellular domain comprises an intracellular costimulatory signaling domain of human CD28 or functional variant thereof, such as a 41 amino acid domain thereof and/or such a domain with an LL to GG substitution at positions 186-187 of a native CD28 protein. In some embodiments, the intracellular domain comprises an intracellular costimulatory signaling domain of 41BB or functional variant thereof, such as a 42-amino acid cytoplasmic domain of a human 4-1BB (Accession No. Q07011.1). In some embodiments, the intracellular signaling domain comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190. In some aspects, the spacer contains only a hinge region of an IgG, such as only a hinge of IgG4 or IgG1. In other embodiments, the spacer is an Ig hinge, e.g., and IgG4 hinge, linked to a CH2 and/or CH3 domains. In some embodiments, the spacer is an Ig hinge, e.g., an IgG4 hinge, linked to CH2 and CH3 domains. In some embodiments, the spacer is an Ig hinge, e.g., an IgG4 hinge, linked to a CH3 domain only. In some embodiments, the spacer is or comprises a glycine-serine rich sequence or other flexible linker such as known flexible linkers.

For example, in some embodiments, the CAR includes: an extracellular ligand-binding portion, such as an antigen-binding portion, such as an antibody or fragment thereof, including sdAbs and scFvs, that specifically binds an antigen, e.g., an antigen described herein; a spacer such as any of the Ig-hinge containing spacers; a transmembrane domain that is a portion of CD28 or a variant thereof an intracellular signaling domain containing a signaling portion of CD28 or functional variant thereof; and a signaling portion of CD3 zeta signaling domain or functional variant thereof. In some embodiments, the CAR includes: an extracellular ligand-binding portion, such as an antigen-binding portion, such as an antibody or fragment thereof, including sdAbs and scFvs, that specifically binds an antigen, e.g. an antigen described herein; a spacer such as any of the Ig-hinge containing spacers; a transmembrane domain that is a portion of CD28 or a variant thereof, an intracellular signaling domain containing a signaling portion of 4-1BB or functional variant thereof; and a signaling portion of CD3 zeta signaling domain or functional variant thereof. In some embodiments, such CAR constructs further includes a T2A ribosomal skip element and/or a tEGFR sequence, e.g., downstream of the CAR.

B. T Cell Receptors (TCRs)

In some embodiments, the recombinant and/or heterologous molecule encoded by the viral vector particle is or includes a recombinant T cell receptor (TCR). In some embodiments, the recombinant TCR is specific for an antigen, generally an antigen present on a target cell, such as a tumor-specific antigen, an antigen expressed on a particular cell type associated with an autoimmune or inflammatory disease, or an antigen derived from a viral pathogen or a bacterial pathogen.

In some embodiments, the TCR is one that has been cloned from naturally occurring T cells. In some embodiments, a high-affinity T cell clone for a target antigen (e.g., a cancer antigen) is identified and isolated from a patient. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15:169-180 and Cohen et al. (2005) *J Immunol.* 175:5799-5808. In some embodiments, phage display is used to isolate TCRs against a target antigen (see, e.g., Varela-Rohena et al. (2008) *Nat Med.* 14:1390-1395 and Li (2005) *Nat Biotechnol.* 23:349-354.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, the nucleic acid encoding a TCR further includes a marker to confirm transduction or engineering of the cell to express the receptor.

C. Viral Vector Particles

In some embodiments, the cells being tested for replication competent virus were transduced with viral vector particle includes a nucleic acid encoding the recombinant and/or heterologous molecule, e.g., gene product. In some embodiments, the nucleic acid, i.e., polynucleotide, is contained within an expression cassette. The nucleic acid or expression cassette can be contained in an expression vector, such as a viral vector, for expression of the recombinant and/or heterologous molecule encoded by the nucleic acid in the viral vector particle.

1. Expression Cassette

In some embodiments, the expression cassette can contain the nucleic acid encoding the heterologous and/or recombinant molecule under the control of a promoter. The expression cassette also can contain one or more other regulatory elements. In some cases, the nucleic acid may be operably linked to other nucleic acid sequences, including but not limited to, promoters, enhancers, other post-transcriptional regulatory elements, polyadenylation signals, restriction enzyme sites, multiple cloning sites or coding segments.

a. Promoters

In some embodiments, the expression cassette includes a promoter operably linked to the nucleic acid molecule encoding the recombinant or heterologous protein. The promoter can comprise any promoter desired by the user as appropriate for the expression context. In some embodiments, a promoter can comprise a promoter of eukaryotic or prokaryotic origin that can provide high levels of constitutive expression across a variety of cell types and will be sufficient to direct the transcription of nucleic acid encoding the recombinant or heterologous protein in a cell. In some embodiments, the nucleic acid encoding the recombinant or heterologous protein is a distally located sequence, which is a sequence operably linked to the 5' end of the promoter sequence. The promoter region can also include control elements for the enhancement or repression of transcription and can be modified as desired by the user and depending on the context.

In some embodiments, a promoter comprises a sequence that functions to position the start site for RNA synthesis. In some embodiments, the promoter comprises the TATA box. In some embodiments, the promoter lacks a TATA box, such as, for example, the promoter for the mammalian terminal deoxynucleotidyl transferase gene and the promoter for the SV40 late genes. In such an embodiment, the promoter can contain a discrete element overlying the start site itself helps to fix the place of initiation. Additional promoter elements regulate the frequency of transcriptional initiation. In some embodiments, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

In some embodiments, the spacing between promoter elements is flexible, so that promoter function is preserved when elements are inverted or moved relative to one another. In some embodiments in which the promoter is the tk promoter, the spacing between promoter elements can be increased to 50 bp apart before activity begins to decline. Depending on the promoter, individual elements can function either cooperatively or independently to activate transcription. In some embodiments, a promoter may be used in conjunction with an "enhancer," which refers to a cis-acting regulatory sequence involved in the transcriptional activation of a nucleic acid sequence.

In some embodiments a promoter may be one that is naturally associated with a nucleic acid sequence, as may be obtained by isolating the 5' non-coding sequences located upstream of the coding segment and/or exon. Such a promoter can be referred to as "endogenous." In some embodiments an enhancer may be one naturally associated with a nucleic acid sequence, located either downstream or upstream of that sequence.

Alternatively, in some embodiments the coding nucleic acid segment may be positioned under the control of a recombinant and/or heterologous promoter and/or enhancer, which is not normally associated with the coding nucleic acid sequence in the natural setting. Such promoters or enhancers may include promoters or enhancers which in nature are operably linked to other genes within the species from which the nucleic acid is derived, and promoters or enhancers isolated from other species, such as from other prokaryotic or eukaryotic cells, and promoters or enhancers that are not "naturally occurring," i.e., that contain different elements of different transcriptional regulatory regions, and/or mutations that alter expression compared with those found in any promoter or enhancer in nature. For example, exemplary promoters used in recombinant DNA construction include, but are not limited to, the β-lactamase (penicillinase), lactose, tryptophan (trp), RNA polymerase (pol) III promoters including, the human and murine U6 pol III promoters as well as the human and murine H1 RNA pol III promoters; RNA polymerase (pol) II promoters; cytomegalovirus immediate early promoter (pCMV), elongation factor-1 alpha (EF-1 alpha), and the Rous Sarcoma virus long terminal repeat promoter (pRSV) promoter systems. In addition to producing nucleic acid sequences of promoters and enhancers synthetically, sequences may be produced using recombinant cloning and/or nucleic acid amplification technology, including PCR™, in connection with the compositions and methods disclosed herein (see U.S. Pat. Nos. 4,683,202 and 5,928,906, each incorporated herein by reference). Furthermore, in some embodiments the control sequences that direct transcription and/or expression of sequences within non-nuclear organelles such as mitochondria, chloroplasts, and the like, can be employed as well. Control sequences comprising promoters, enhancers and other locus or transcription controlling/modulating elements are also referred to as "transcriptional cassettes".

In some embodiments, the promoter and/or enhancer is operably linked to effectively direct the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous for gene therapy or for applications such as the large-scale production of recombinant proteins and/or peptides. The promoter may be heterologous or endogenous.

In some embodiments, a T3, T7 or SP6 cytoplasmic expression system can be employed. Eukaryotic cells can support cytoplasmic transcription from certain bacterial promoters if the appropriate bacterial polymerase is provided, either as part of the delivery complex or as an additional genetic expression construct.

In some embodiments, an inducible promoter can be used. As used herein, an "inducible promoter" refers to a transcriptional control element that can be regulated in response to specific signals. An inducible promoter is transcriptionally active when bound to a transcriptional activator, which in turn is activated under a specific set of conditions, for example, in the presence of a particular combination of chemical signals that affect binding of the transcriptional activator to the inducible promoter and/or affect function of the transcriptional activator itself. Thus, an inducible promoter is a promoter that, either in the absence of an inducer, does not direct expression, or directs low levels of expression, of a nucleic acid sequence to which the inducible promoter is operably linked; or exhibits a low level of expression in the presence of a regulating factor that, when removed, allows high-level expression from the promoter, for example, the tet system. In the presence of an inducer, an inducible promoter directs transcription at an increased level.

In some embodiments, the tetracycline-(tet)-regulatable system, which is based on the inhibitory action of the tet repression (tetr) of *Escherichia coli* on the tet operator sequence (TECO), can be modified for use in mammalian systems and used as a regulatable element for expression cassettes. These systems are well known to those of ordinary skill in the art. (See, Goshen and Badgered, Proc. Natl. Acad. Sci. USA 89: 5547-51 (1992), Shockett et al., Proc. Natl. Acad. Sci. USA 92:6522-26 (1996), Lindemann et al., Mol. Med. 3:466-76 (1997)).

b. Other Regulatory Elements

In some embodiments, the expression cassette can additionally include an enhancer that is operably linked to the nucleic acid encoding the recombinant protein or heterologous gene product.

In some embodiments, internal ribosome binding sites (IRES) elements are operably linked to expression cassettes to create multigene, or polycistronic, messages. IRES elements are able to bypass the ribosome scanning model of 5'-methylated cap-dependent translation and begin translation at internal sites (see Pelletier and Sonenberg, (1988) *Nature*. 334:320-325). Non-limiting examples of IRES elements include, but are not limited to, IRES elements of the picornavirus family (polio and encephalomyocarditis) (see Pelletier and Sonenberg, (1988) Nature. 334:320-325) or an IRES from a mammalian message (see Macejak and Sarnow, (1991) Nature, 353:90-94). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In some embodiments involving eukaryotic gene expression, the expression cassette may be operably linked to a polyadenylation signal to effect proper polyadenylation of the transcript. Any such sequence may be employed. Some examples include the SV40 polyadenylation signal or the bovine growth hormone polyadenylation signal, convenient and known to function well in various target cells. Polyadenylation may increase the stability of the transcript or may facilitate cytoplasmic transport.

In some embodiments, the expression cassette or vector contains one or more origins of replication sites (often termed "ori") in order to propagate in a host cell. An origin of replication is a specific nucleic acid sequence at which replication is initiated. Alternatively an autonomously replicating sequence (ARS) can be employed if the host cell is yeast.

In some embodiments, the nucleic acid sequence contained in the viral vector genome encoding an recombinant receptor, such as an antigen receptor, for example a CAR, is operably linked in a functional relationship with other genetic elements, for example transcription regulatory sequences including promoters or enhancers, to regulate expression of the sequence of interest in a particular manner. In certain instances, such transcriptional regulatory sequences are those that are temporally and/or spatially regulated with respect to activity. Expression control elements that can be used for regulating the expression of the components are known and include, but are not limited to, inducible promoters, constitutive promoters, secretion signals, enhancers and other regulatory elements.

In some embodiments, the nucleic acid sequence encoding a recombinant receptor, such as an antigen receptor, for example a CAR, is operably linked with internal promoter/enhancer regulatory sequences. The promoters employed may be constitutive, tissue-specific, inducible, and/or useful under the appropriate conditions to direct high level expression of the introduced DNA segment. The promoter may be heterologous or endogenous. In some embodiments, a promoter and/or enhancer is produced synthetically. In some embodiments, a promoter and/or enhancer is produced using recombinant cloning and/or nucleic acid amplification technology.

In some embodiments a promoter and/or enhancer may be one that is naturally associated with a nucleic acid sequence, as may be obtained by isolating the 5' non-coding sequences located upstream of the coding segment and/or exon. Alternatively, in some embodiments the coding nucleic acid segment may be positioned under the control of a recombinant and/or heterologous promoter and/or enhancer, which is not normally associated with the coding nucleic acid sequence in the natural setting. For example, exemplary promoters used in recombinant DNA construction include, but are not limited to, the β-lactamase (penicillinase), lactose, tryptophan (trp), RNA polymerase (pol) III promoters including, the human and murine U6 pol III promoters as well as the human and murine H1 RNA pol III promoters; RNA polymerase (pol) II promoters; cytomegalovirus immediate early promoter (pCMV), elongation factor-1 alpha (EF-1 alpha), and the Rous Sarcoma virus long terminal repeat promoter (pRSV) promoter systems. In some embodiments, the promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system.

In some embodiments, the promoter may be constitutively active. Non-limiting examples of constitutive promoters that may be used include the promoter for ubiquitin (U.S. Pat. No. 5,510,474; WO 98/32869), CMV (Thomsen et al., *PNAS* 81:659, 1984; U.S. Pat. No. 5,168,062), beta-actin (Gunning et al. 1989 *Proc. Natl. Acad. Sci. USA* 84:4831-4835) and pgk (see, for example, Adra et al. 1987 Gene 60:65-74; Singer-Sam et al. 1984 Gene 32:409-417; and Dobson et al. 1982 *Nucleic Acids Res.* 10:2635-2637).

In some embodiments, the promoter may be a tissue specific promoter and/or a target cell-specific promoter. In some embodiments, the promoters may be selected to allow for inducible expression of the sequence of interest. A number of systems for inducible expression are known, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. In some embodiments, the tetracycline-(tet)-regulatable system, which is based on the inhibitory action of the tet repression (tetr) of *Escherichia coli* on the tet operator sequence (TECO), can be modified for use in mammalian systems and used as a regulatable element for expression cassettes. These systems are well known. (See, Goshen and Badgered, Proc. Natl. Acad. Sci. USA 89: 5547-51 (1992), Shockett et al., Proc. Natl. Acad. Sci. USA 92:6522-26 (1996), Lindemann et al., Mol. Med. 3:466-76 (1997)).

A combination of promoters may also be used to obtain the desired expression of the gene of interest. The artisan of ordinary skill will be able to select a promoter based on the desired expression pattern of the gene in the organism or the target cell of interest.

In some embodiments, an enhancer may also be present in the viral construct to increase expression of the gene of interest. Enhancers are typically cis-acting nucleic acid elements, usually about 10 to 300 by in length, that act on a promoter to increase its transcription. Many enhancers in viral genomes, such as HIV or CMV are known. For example, the CMV enhancer (Boshart et al. Cell, 41:521, 1985) can be used. Other examples include, for example, the SV40 enhancer on the late side of the replication origin (bp 100-270), the cytomegalovirus early promoter enhancer, the polyoma enhancer on the late side of the replication origin, and adenovirus enhancers. In some cases, an enhancer is from a mammalian gene, such as an enhancer from a globin, elastase, albumin, alpha-fetoprotein or insulin). An enhancer can be used in combination with a heterologous promoter. The enhancer may be spliced into the vector at a position 5' or 3' to the polynucleotide sequence encoding the gene of interest, but is generally located at a site 5' from the promoter. One of ordinary skill in the art will be able to select the appropriate enhancer based on the desired expression pattern.

The viral vector genome may also contain additional genetic elements. The types of elements that can be included in the constructs are not limited in any way and can be chosen by one with skill in the art. For example, a signal that facilitates nuclear entry of the viral genome in the target cell may be included.

In some instances, more than one open reading frame encoding separate heterologous proteins can be included.

For example, in some embodiments, if a reporter and/or detectable and/or selectable gene is included in the expression construct, an internal ribosomal entry site (IRES) sequence can be included. Typically, the additional genetic elements are operably linked with and controlled by an independent promoter/enhancer. The additional genetic element can be a reporter gene, a selectable marker or other desired gene.

In some embodiments, other various regulatory elements can include a transcription initiation region and/or a termination region. Expression vectors may also contain sequences for the termination of transcription and for stabilizing the mRNA. Such sequences are known and are often found naturally in the 5' and, occasionally 3', untranslated regions of eukaryotic or viral DNAs or cDNAs. Examples of transcription termination region include, but are not limited to, polyadenylation signal sequences. Examples of polyadenylation signal sequences include, but are not limited to, Bovine growth hormone (BGH) poly(A), SV40 late poly(A), rabbit beta-globin (RBG) poly(A), thymidine kinase (TK) poly(A) sequences, and any variants thereof 2. Viral Vectors In some embodiments, the viral vector particles used to transduce the cells to be tested contain a genome derived from a retroviral genome based vector, such as derived from a gammaretroviral or lentiviral genome based vector. Any of a large number of such suitable vector genomes are known ((see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557; Pfeifer and Verma (2001) Annu. Rev. Genomics Hum. Genet., 2:177-211). In some aspects of the provided viral vectors, the heterologous nucleic acid encoding a recombinant receptor, such as an antigen receptor, such as a CAR, is contained and/or located between the 5' LTR and 3' LTR sequences of the vector genome. In some embodiments, the vector genome is referred to as the transfer vector and/or transfer plasmid.

Exemplary viral vectors include retroviral vectors, such as lentiviral or gammaretroviral vectors, vectors derived from simian virus 40 (SV40), adenoviruses, and adeno-associated virus (AAV). In some embodiments, recombinant nucleic acids are transferred into cells using retroviral vectors, such as lentiviral vectors or gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557. Retroviruses are useful as delivery vectors because of their ability to integrate their genes into the host genome, transferring a large amount of foreign genetic material, infecting a broad spectrum of species and cell types and of being packaged in special cell lines (Miller, 1992).

In some embodiments, genetic transfer is accomplished via gammaretroviral vectors. Thus, in some cases, the viral vector genome is a gammaretrovirus genome, such as a murine leukemia virus (MLV), Gibbon ape leukemia virus (GALV), Endogenous Xenotropic murine leukemia virus-related virus (XMRV), or feline leukemia virus (FLV) genome.

In some embodiments, genetic transfer is accomplished via lentiviral vectors. In some aspects, lentiviruses may be used for transducing certain non-dividing cells.

Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu, vpx, and nef are deleted, which in some embodiments may render a vector safer, more accepted as safe or more desirable for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In some embodiments, the viral vectors include, but are not limited to, one derived from an HIV-1, SIVmnd1, SIVlst, SIVsun, SIVolc or SIVwrc lentivirus.

In some embodiments, two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components. In some embodiments, the packaging plasmid can contain all HIV-1 proteins other than envelope proteins (Naldini et al., 1998). In some embodiments, viral vectors can lack additional viral genes, such as those that are associated with virulence, e.g. vpr, vif, vpu, vpx, and nef, and/or Tat, a primary transactivator of HIV. In some embodiments, packaging systems for lentiviral vectors, such as HIV-based lentiviral vectors, include separate packaging plasmids that together comprise only three genes of the parental virus: gag, pol and rev, which reduces or eliminates the possibility of reconstitution of a wild-type virus through recombination.

In some aspects of the provided methods, the heterologous nucleic acid encoding a recombinant protein, such as provided as part of an expression cassette containing the transgene under the control of a promoter, is contained and/or located between the 5' LTR and 3' LTR sequences of the vector genome, including wildtype LTRs or portions or chimeric portions thereof. In some embodiments, the viral vector genome can contain sequences of the 5' and 3' LTRs of a retrovirus. In some aspects, the viral genome construct may contain sequences from the 5' and 3' LTRs of a retrovirus, and in particular can contain the R and U5 sequences from the 5' LTR of a retrovirus and an inactivated or self-inactivating 3' LTR from a retrovirus. The LTR sequences can be LTR sequences from any retrovirus from any species. For example, they may be LTR sequences from HIV, SIV, FIV or BIV.

The vector genome can contain an inactivated or self-inactivating 3' LTR (Zufferey et al. *J Virol* 72: 9873, 1998; Miyoshi et al., *J Virol* 72:8150, 1998). For example, deletion in the U3 region of the 3' LTR of the nucleic acid used to produce the viral vector RNA can be used to generate self-inactivating (SIN) vectors. This deletion can then be transferred to the 5' LTR of the proviral DNA during reverse transcription. A self-inactivating vector generally has a deletion of the enhancer and promoter sequences from the 3' long terminal repeat (LTR), which is copied over into the 5' LTR during vector integration. In some embodiments enough sequence can be eliminated, including the removal of a TATA box, to abolish the transcriptional activity of the LTR. This can prevent production of full-length vector RNA in transduced cells. In some aspects, the U3 element of the 3' LTR contains a deletion of its enhancer sequence, the TATA box, Sp1 and NF-kappa B sites. As a result of the self-inactivating 3' LTR, the provirus that is generated following entry and reverse transcription contains an inactivated 5' LTR. This can improve safety by reducing the risk of mobilization of the vector genome and the influence of the LTR on nearby cellular promoters. The self-inactivating 3' LTR can be constructed by any method known in the art. In some embodiments, this does not affect vector titers or the in vitro or in vivo properties of the viral vector particle.

Optionally, the U3 sequence from the lentiviral 5' LTR can be replaced with a promoter sequence in the viral construct, such as a heterologous promoter sequence. This can increase the titer of virus recovered from the packaging cell line. An enhancer sequence can also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062).

In some embodiments, the viral vector genome may also contain additional genetic elements. The types of elements that can be included in the constructs are not limited in any way and can be chosen by one with skill in the art. In some embodiments, the vector genome contains sequences derived from a viral genome (e.g. retroviral genome) that are non-coding regions of the genome that facilitate or provide recognition signals for DNA or RNA synthesis and processing. In some embodiments, such sequences can include cis-acting sequences that can be involved in packaging or encapsidation, reverse transcription and transcription and/or gene transfer or integration. In some embodiments, cis-activating sequences provided as part of the viral vector are derived from the same lentivirus or retrovirus-like organism.

In some embodiments, the retroviral vector genome can contain elements selected among a splice donor site (SD), a splice acceptor site (SA) and/or a Rev-responsive element (RRE). In some embodiments, RRE is provided to allow export of viral messenger RNA from the nucleus to the cytosol after binding of the Rev protein provided as part of a helper plasmid during viral packaging. In some embodiments, the vector genome can contain the psi (ψ) packaging signal, which, in some cases, can be derived from the N-terminal fragment of the gag ORF. In some embodiments, the psi packaging signal sequence can be modified by frameshift mutation(s) in order to prevent any interference of a possible transcription/translation of gag peptide, with that of the transgene.

In certain embodiments, the viral vector genome, such as gammaretroviral or lentiviral vector genome, or other viral genome, is engineered to be integration defective. A variety of approaches can be pursued to produce a non-integrating vector genome. In some embodiments, a mutation(s) can be engineered into the integrase enzyme component of the pol gene, such that it encodes a protein with an inactive integrase. In some embodiments, the vector genome itself can be modified to prevent integration by, for example, mutating or deleting one or both attachment sites, or making the 3' LTR-proximal polypurine tract (PPT) non-functional through deletion or modification. In some embodiments, non-genetic approaches are available; these include pharmacological agents that inhibit one or more functions of integrase. The approaches are not necessarily mutually exclusive; that is, more than one of them can be used at a time. For example, both the integrase and attachment sites can be non-functional, or the integrase and PPT site can be non-functional, or the attachment sites and PPT site can be non-functional, or all of them can be non-functional. Such methods and viral vector genomes are known and available (see Philpott and Thrasher, *Human Gene Therapy* 18:483, 2007; Engelman et al. J Virol 69:2729, 1995; Brown et al *J Virol* 73:9011 (1999); WO 2009/076524; McWilliams et al., *J Virol* 77:11150, 2003; Powell and Levin *J Virol* 70:5288, 1996).

In some embodiments, the vector also can contain sequences for propagation in a host cell, such as a prokaryotic host cell. In some embodiments, the nucleic acid of the viral vector contains one or more origins of replication for propagation in a prokaryotic cell, such as a bacterial cell. In some embodiments, vectors that include a prokaryotic origin of replication also may contain a gene whose expression confers a detectable or selectable marker such as drug resistance.

3. Preparation of Viral Vector Particles

In some embodiments of the provided methods, a nucleic acid encoding the recombinant and/or heterologous molecule is inserted into the viral genome in the place of certain viral sequences to produce a virus that is replication defective. In order to produce virions, a packaging cell line containing the gag, pol, and env genes but without the LTR and packaging components may be constructed. When a recombinant plasmid together with the retroviral LTR and packaging sequences is introduced into a special cell line (e.g., by calcium phosphate precipitation for example), the packaging sequence may permit the RNA transcript of the recombinant plasmid to be packaged into viral particles, which then may be secreted into the culture media. The media containing the recombinant retroviruses in some embodiments is then collected, optionally concentrated, and used for gene transfer.

The viral vector genome is typically constructed in a plasmid form that can be transfected into a packaging or producer cell line. Any of a variety of known methods can be used to produce viral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all viral proteins other than envelope proteins (Naldini et al., 1998). In other embodiments, viral vectors can lack additional viral genes, such as those that are associated with virulence, e.g. vpr, vif, vpu, vpx, and nef, and/or Tat, a primary transactivator of HIV.

In some embodiments, lentiviral vectors, such as HIV-based lentiviral vectors, comprise only three genes of the parental virus: gag, pol and rev, which reduces or eliminates the possibility of reconstitution of a wild-type virus through recombination.

As described above, in some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. The packaging cell line can express or be made to express essential retroviral genes to allow the generation of viral vector particles. These genes can be expressed by several plasmids. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; one or more helper plasmids encoding the virus enzymatic and/or structural components, such as Gag, pol and/or rev. In some embodiments, multiple vectors are utilized to separate the various genetic components that generate the viral vector particles. In some such embodiments, providing separate vectors to the packaging cell reduces the chance of recombination events that might otherwise generate replication competent viruses. In some embodiments, a single plasmid vector having all of the viral components can be used.

In some embodiments, a packaging cell line can be transfected with a lentiviral expression plasmid containing a cis-acting psi (Y) packaging sequence and the transgene gene inserted between the lentiviral LTRs to allow target cell integration; a packaging plasmid or plasmids encoding the pol, gag, rev and/or tat viral genes and, in some cases, containing the rev-response element (RRE) and a pseudotyping plasmid, such as a plasmid encoding an envelope protein, such as the G protein of the Vesicular Stomatitis Virus (VSV-G) envelope gene.

In some embodiments, a packaging cell line is transfected with a plasmid containing the viral vector genome, including the LTRs, the cis-acting packaging sequence and the sequence of interest, i.e. a nucleic acid encoding a recombinant protein, (e.g. an antigen receptor, such as a CAR) along with several helper plasmids encoding the virus enzymatic and/or structural components, such as Env, Gag, pol and/or rev. In some embodiments, a GagPol packaging plasmid containing the gag and pol genes encoding for structural and enzymatic components and a Rev plasmid containing the rev gene encoding for Rev regulatory protein are separately introduced into a packaging cell line. In some embodiments, a single plasmid vector having all of the retroviral components can be used. In some embodiments, an envelope plasmid encoding an env gene also can be introduced, which, in some cases, can result in viral particles pseudotyped with alternative Env proteins. In some embodiments, the viral vector particle, such as gammaretroviral or lentiviral vector particle, is pseudotyped to increase the transduction efficiency of host cells. For example, a viral vector particle can be pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

The env gene can be derived from any appropriate virus, such as a retrovirus. In some embodiments, the env is an amphotropic envelope protein which allows transduction of cells of human and other species. Some embodiments use retroviral-derived env genes, including, but not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). In some embodiments, other env genes such as Vesicular stomatitis virus (VSV) protein G (VSVG), that of hepatitis viruses, and of influenza also can be used.

In some embodiments, the packaging plasmid providing the viral env nucleic acid sequence is associated or operably linked with regulatory sequences, e.g., a promoter or enhancer. The regulatory sequence in some embodiments can be any eukaryotic promoter or enhancer, including for example, EF1$\alpha$, PGK, the Moloney murine leukemia virus promoter-enhancer element, the human cytomegalovirus enhancer, the vaccinia P7.5 promoter or the like. In some cases, such as the Moloney murine leukemia virus promoter-enhancer element, the promoter-enhancer elements are located within or adjacent to the LTR sequences. In some embodiments, the regulatory sequence is one which is not endogenous to the lentivirus from which the vector is being constructed. Thus, if the vector is being made from SIV, the SIV regulatory sequence found in the SIV LTR may be replaced by a regulatory element which does not originate from SIV.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing retroviral proteins and producing functional viral vector particles. In some aspects, suitable packaging cell lines include 293 (ATCC CCL X), 293T, HeLA (ATCC CCL 2), D17 (ATCC CCL 183), MDCK (ATCC CCL 34), BHK (ATCC CCL-10) and Cf2Th (ATCC CRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a recombinant and/or heterologous molecule, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection. When a recombinant plasmid and the viral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art. Thus, the packaging plasmids in some embodiments are introduced into human cell lines by these methods, generally together with a dominant selectable marker, such as neomycin, DHFR, Glutamine synthetase or ADA, followed by selection in the presence of the appropriate drug and isolation of clones. The selectable marker gene can be linked physically to the packaging genes in the construct.

In some embodiments, viral vector particles can be produced by stable cell lines wherein the packaging functions are configured to be expressed. Suitable packaging cells are known including, for example, U.S. Pat. No. 5,686,279; and Ory et al., *Proc. Natl. Acad. Sci*. (1996) 93:11400-11406. In some instances, the packaging cells with a viral vector incorporated in them form producer cells. Producer cells are thus typically cells or cell-lines that can produce or release viral vector particles carrying the gene of interest. In some embodiments, these cells can further be anchorage dependent, which means that these cells will grow, survive, or maintain function optimally when attached to a surface such as glass or plastic. In some embodiments, the producer cells may be neoplastically transformed cells. In some embodiments, host cells for transfection with the lentiviral vector and packaging plasmids include, for example, mammalian primary cells; established mammalian cell lines, such as COS, CHO, HeLa, NIH3T3, 293T and PC12 cells; amphibian cells, such as *Xenopus* embryos and oocytes; other vertebrate cells; insect cells (for example, *Drosophila*), yeast cells (for example, *S. cerevisiae, S. pombe*, or *Pichia pastoris*) and prokaryotic cells (for example, *E. coli*).

In some embodiments, viral vector particles can be produced in a packaging cell line, such as an exemplary HEK 293T cell line, by introduction of plasmids to allow generation of viral vector particles. In some embodiments, a packaging cell is transfected and/or contains a polynucleotide encoding gag and pol, and a polynucleotide encoding a recombinant and/or heterologous molecule, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g. HEK 293T cells, the cell supernatant contains recombinant viral vector particles, which can be recovered and titered. Recovered and/or produced viral vector particles can be used to transduce target cells, such as immune cells, for example T cells, as described. In some aspects, once in the target cells, the viral RNA is reverse-transcribed, imported into the nucleus and stably integrated into the host genome. In some aspects, one or two days after the integration of the viral RNA, the expression of the recombinant and/or heterologous molecule can be detected.

In some embodiments, the isolated viral vector particles can be assessed for replication competent virus by any of the methods described herein.

4. Transduction of Cells

In some embodiments, the test sample comprises cells and/or RNA of or from such cells, e.g., immune cells, such as T cells, that are or have been transduced by incubating and/or contacting a population of cells containing such cells with a viral vector particle, such as lentiviral or gammaretroviral vector particle, that contains: a nucleic acid encoding a recombinant and/or heterologous molecule, such as a CAR or other antigen receptor in a genome of the viral vector. The viral vector particle, such as lentiviral or gammaretroviral vector particle, can be any as described. In some such embodiments, the resulting transduced cells, such as transduced T cells, express the recombinant and/or heterologous molecule, such as a CAR, and can be used in adoptive immunotherapy methods. The presence or absence of replication competent virus in some embodiments can be assessed at any point in the processing of cells, including cells that are or will be transduced, including cells for use in adoptive cell therapy. Steps for processing cells, including steps involved in the isolation, separation, selection, cultivation (e.g., stimulation of the cells, for example, to induce their proliferation and/or activation), transducing, washing, suspension, dilution, concentration, and/or formulation of the cells, are described in detail below.

In some embodiments, the processing steps can be carried out in an order in which: cells, e.g. primary cells, are first isolated, such as selected or separated, from a biological sample; resulting isolated or selected cells are stimulated in the presence of a stimulation reagent; stimulated cells are incubated with viral vector particles for transduction; and transduced cells are formulated in a composition. In some embodiments, the stimulation is additionally or alternatively performed during at least a part of the incubation with the viral vector particles. In some cases, stimulation is additionally or alternatively carried out after incubation of cells with the viral vector particles. In some cases, the methods do not include a step of stimulating the cells. In some embodiments, the method can include one or more processing steps from among washing, suspending, diluting and/or concentrating cells, which can occur prior to, during or simultaneous with or subsequent to one or more of the isolation, such as separation or selection, stimulation, transduction, cultivation, culture or expansion, cryopreservation and/or formulation steps. The provided methods can be used to determine the presence or absence of, or risk of, a replication competent virus in a sample collected at any of the above steps in accord with the provided methods.

a. Closed Systems

All or a portion of each of the processing steps may be performed in a closed system. In aspects of the methods, the processes need not be performed in the same closed system, but can be performed under a different closed system.

In some embodiments, the methods of transducing a cell include one or more of (a) washing a biological sample containing cells (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product) in a cavity of a chamber, (b) isolating, e.g. selecting, from the sample a desired subset or population of cells (e.g., CD4+ or CD8+ T cells) in a cavity of a chamber, for example, by incubation of cells with a selection or immunoaffinity reagent for immunoaffinity-based separation; c) incubating the isolated, such as selected cells, with viral vector particles, such as in accord with methods described above and d) formulating the transduced cells, such as in a pharmaceutically acceptable buffer, cryopreservative or other suitable medium. In some embodiments, the methods of transducing a cell can further include (e) stimulating cells in a cavity of a chamber by exposing cells to stimulating conditions, thereby inducing cells to proliferate. In some embodiments, the step of stimulating the cells is performed prior to, during and/or subsequent to the incubation of cells with viral vector particles. In some embodiments, one or more further step of washing or suspending step, such as for dilution, concentration and/or buffer exchange of cells, can also be carried out prior to or subsequent to any of the above steps.

Thus, in some embodiments, the methods of transducing a cell include performing one, more, or all steps in the preparation of cells for clinical use, e.g., in adoptive cell therapy, without exposing the cells to non-sterile conditions and without the need to use a sterile room or cabinet. In some embodiments of such a process, the cells are isolated, separated or selected, stimulated, transduced, washed, and formulated, all within a closed system. In some embodiments, the methods of transducing a cell are carried out in an automated fashion. In some embodiments, one or more of the steps is carried out apart from the closed system.

b. Samples and Cell Preparations

In aspects of the provided methods, the population of cells includes primary cells, such as a population of primary cells containing T cells, that are obtained from a subject. In some embodiments, the subject is a mammalian subject, such as a primate, such as a human.

In some embodiments, prior to incubating and/or contacting a viral vector with a population of cells, the population of cells is isolated or obtained from a subject. Such cells in some embodiments are derived from samples, e.g., biological samples, such as those obtained from a subject destined to receive the adoptive therapy or from another subject.

In some embodiments, the processing steps include isolation of cells or compositions thereof from biological samples, such as those obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

The samples generally include T cells. In some examples, the samples or T cell populations include a population of unfractionated T cells, unfractionated $CD4^+$ cells and/or unfractionated $CD8^+$ T cells, and/or one or more sub-type thereof, such as those defined by function, lack of an activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation or lack of differentiation. Such subtypes can be selected by positive or negative selection methods.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the provided methods include processing, in whole or in part, one or more of the samples in a closed system. In some embodiments, the processing step can involve washing of the sample, e.g., blood cell-containing sample, from the subject, e.g., to remove the plasma fraction and/or replacing the cells in an appropriate buffer or media for subsequent processing steps and/or performing a density-based cell separation methods, such as in the preparation of white blood cells from peripheral blood by lysing the red blood cells and centrifugation through a Percoll or Ficoll gradient.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

c. Affinity-Based Selection

The processing steps may include isolation of cells from mixed populations and/or compositions, such as using one of various selection steps including density-based or other physical property-based separation methods and affinity-based selection. In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to a subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same patient, before or after cryopreservation, and/or before or after testing for replication competent virus.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, T cells are separated from a PBMC sample or other sample by negative selection of markers expressed on non-T cells, such as B cells, monocytes, or other white blood cells. In some embodiments, T cells can be enriched from a population of cells by negative selection methods to select non-T cells from the population based on surface expression of one or more of markers CD11b, CD14, CD15, CD16, CD19, CD20, CD34, CD36, CD56, CD123 and CD235a. In some embodiments, pan T cell selection is performed, such as by using a commercially available Pan T cell isolation kit against a cocktail of markers (e.g. Miltenyi No. 130-096-535). Such a selection strategy provides for a population of T cells that have been untouched by an antibody or other reagent used in the selection process.

In some aspects, a $CD4^+$ and/or $CD8^+$ selection step is used to separate $CD4^+$ helper and $CD8^+$ cytotoxic T cells. In some embodiments, a $CD4^+$ selection step is performed. In some embodiments, a $CD8^+$ selection step is performed.

In some embodiments, such $CD4^+$ and $CD8^+$ populations can be further sorted into sub-populations by positive or negative selection for markers expressed or expressed to a relatively higher degree on one or more naive, memory, and/or effector T cell subpopulations. For example, in some aspects, specific subpopulations of T cells, such as cells positive or negative for one or more surface markers, e.g., CD28, CD62L, CCR7, CD27, CD127, CD4, CD8, CD45RA, and/or CD45RO, are isolated by positive or negative selection techniques. For example, one or more of naïve (e.g. one or more markers $CD45RO^-$, $CD44^{low}$, $CD62L^{high}$), memory (e.g. one or more markers $CD45RO^+$, $CCR7^+$, $CD27^+$, $CD28^+$, and/or $CD62L^+$) and/or effector (e.g. one or more markers $CD45RO^+$, $CD62L^-$, $CCR7^-$) T cell populations can be selected.

In some embodiments, the methods do not comprise selection and/or enrichment for effector T cells. In some embodiments, the methods comprise removing or depleting effector T cells from the cell population.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$. In some embodiments, the methods do not comprise selection and/or enrichment for effector $CD4^+$ T cells. In some embodiments, the methods comprise removing or depleting effector $CD4^+$ T cells from the cell population.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the selection is carried out by affinity-based selection by incubating the sample or cells with a magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference, in their entirety. Colloidal sized particles, such as those described in Owen U.S. Pat. No. 4,795,698, and Liberti et al., U.S. Pat. No. 5,200,084 are other examples, which are also incorporated by reference in their entirety.

The incubation step is generally carried out under conditions whereby the antibodies, other binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US Publication Number 20110003380 A1.

In some embodiments, the system or apparatus carries out one or more, e.g., all, of the preparation, selection, cultivation, engineering, and/or formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the compositions for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al (2012) J Immunother. 35(9): 651-660, Terakura et al. (2012) Blood. 1:72-82, and Wang et al. (2012) J Immunother. 35(9):689-701.

In some embodiments, the separation or selection is carried out via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale FACS and/or microelectromechanical systems (MEMS) chips, e.g., in combination with a flow-cytometric detection system. Such methods allow for positive and negative selection based on multiple markers simultaneously.

d. Freezing and Cyropreservation

In some embodiments, the provided methods include steps for freezing, e.g., cryopreserving, the cells, either before or after preparation, cultivation, and/or engineering. In some embodiments, cells are frozen while a sample of such cells are tested for replication competent virus. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank. In some embodiments, the cells are frozen, e.g., cryopreserved, either before, during, or after said methods of assessing the cells for replication competent virus. In some embodiments, the cells are frozen, e.g., cryopreserved, either before, during, or after said methods for processing.

e. Incubation of Viral Vector Particles with Cells

In some aspects, the cells, e.g., population of cells, such as a population of cells obtained and/or isolated as described, can be or have been incubated and/or contacted with a viral vector particle under conditions that permit gene transfer. In any of such some embodiments, the viral vector particle is incubated and/or contacted with the population of cells under conditions, e.g. viral input, that allow for transfer of the viral particle into the cell and/or expression of the nucleic acid encoding the recombinant and/or heterologous molecule, e.g., recombinant receptor, such as a CAR, in the cell.

Methods of viral transduction, such as gammaretroviral or lentiviral transduction, are known. Exemplary methods are described in, e.g., Wang et al. (2012) *J. Immunother.* 35(9): 689-701; Cooper et al. (2003) *Blood.* 101:1637-1644; Verhoeyen et al. (2009) *Methods Mol Biol.* 506: 97-114; and Cavalieri et al. (2003) Blood. 102(2): 497-505.

In some embodiments, the population of cells can be a population of cells that has previously been subject to cryopreservation.

The composition that contains the viral vector particles and cells during the transduction step) may further include one or more additional agents, such as those to promote transduction efficiency, such as polycations including protamine (e.g. protamine sulfate), hexadimethrine bromide (POLYBRENE®, Abbott Laboratories Corp), and CH-296 (RETRONECTIN®, Clontech). In some embodiments, the polycation can be present in the input composition at a final concentration of 1 μg/mL to 100 μg/mL, such as 5 μg/mL to 50 μg/mL. The composition may also include media, including cell culture medium including medium designed for culture of the cell type to be processed, such as hematopoietic stem cell medium, e.g., serum free medium.

In some embodiments, transduction can be achieved at a multiplicity of infection (MOI) of less than 100, such as generally less than 60, 50, 40, 30, 20, 10, 5 or less.

In some embodiments, the cells can be or have been transduced and/or genetically engineered with a nucleic acid encoding a recombinant receptor, such as a chimeric receptor, such as an antigen receptor, for example a CAR or transgenic TCR. In some aspects, at least 7.5%, 10%, 15%, 20%, 25%, 30%, 35%, 40%, 50% or more T cells are transduced with the nucleic acid.

f. Cultivation and Stimulation

In some embodiments, the cells are stimulated and/or proliferated and/or expanded in connection with or subsequent to genetic engineering. In some embodiments, the processing steps include incubations of cells, such as selected cells and/or transduced cells, in which the incubation steps can include culture, cultivation, stimulation, activation, and/or propagation of cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

In some embodiments, isolated cells, such as selected cell populations, are stimulated or activated. In some embodiments, the processing steps include incubation of a composition containing the cells under stimulating conditions. The incubation may be prior to or in connection with genetic engineering, such as genetic engineering resulting from embodiments of the transduction method described above. In some embodiments, the stimulation results in activation and/or proliferation of the cells, for example, prior to transduction.

In some embodiments, the proliferation and/or expansion is performed subsequent to transduction to culture the transduced cells to numbers sufficient for clinical applications. In some embodiments, transduced cells are incubated or cultured under conditions to induce expansion for at least or about at least 1 days, 2 days, 3 days, 4 days, 5 days, 6 days, 7 days, 8 days, 9 days, 10 days, 11 days, 12 days, 13 days, 14 days or more. In some cases, cells are expanded by culturing for 7-10 days. In some embodiments, incubation or culturing of cells is carried out at or about 37° C.±2° C. in the presence of one or more stimulating agents.

In some embodiments, the conditions for stimulation and/or activation can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some embodiments, the T cells are expanded by adding to the composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions generally include a temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some embodiments, at least a portion of the incubation with one or more stimulating conditions or stimulatory agents, such as any described above, is performed in a closed system.

In some embodiments, the total duration of the incubation with the stimulating agent is from or from about 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some cases, the total duration of the incubation is from or from about 5 minutes to 6 hours, such as 30 minutes to 3 hours, for example, at least or about at least 30 minutes, 60 minutes, 120 minutes or 180 minutes.

In some embodiments, the population of cells transduced with a viral vector particle is subjected to one or more steps and/or selections to enrich for genetically engineered cells. For example, in some aspects, a transduction marker within the viral vector can be used to confirm transduction or engineering of the cell to express the receptor and/or selection of the engineered cells expressing the receptor. In some aspects, such a marker may be encoded by a different nucleic acid or polynucleotide, which also may be introduced during the genetic engineering process, typically via the same method, e.g., transduction by the same vector or type of vector.

5. Formulation

In some embodiments, the process steps may include formulation of cells, such as formulation of genetically engineered cells resulting from the provided transduction processing steps and/or one or more other processing steps as described. In some embodiments, the cells are formulated as a formulated drug product (FDP). In some embodiments, the provided methods associated with formulation of cells include processing transduced cells, such as cells transduced and/or expanded using the processing steps described above, in a closed system.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the transduced and/or expanded cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the disease or condition, such as a therapeutically effective or prophylactically effective amount.

In some embodiments, the formulation buffer contains a cryopreservative. In some embodiments, the cell are formulated with a cyropreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the transduced and/or expanded cells to replace the cells in a cryopreservative solution.

In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired.

In some embodiments, the processing includes adding a volume of a formulation buffer to transduced and/or expanded cells. In some embodiments, the volume of formulation buffer is from or from about 10 mL to 1000 mL, such as at least or about at least or about or 50 mL, 100 mL, 200 mL, 300 mL, 400 mL, 500 mL, 600 mL, 700 mL, 800 mL, 900 mL or 1000 mL.

In some embodiments, the closed system, such as associated with a cell processing system, can express the process cells into a desired number or plurality of output containers, e.g., bags. In some aspects, cells can be expressed to the one or more of the plurality of output bags in an amount for dosage administration, such as for a single unit dosage administration or multiple dosage administration. For example, in some embodiments, the output bags may each contain the number of cells for administration in a given dose or fraction thereof. Thus, each bag, in some aspects, may contain a single unit dose for administration or may contain a fraction of a desired dose such that more than one of the plurality of output bags, such as two of the output bags, or 3 of the output bags, together constitute a dose for administration.

Thus, the containers, e.g., bags, generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, each of the containers, e.g., bags, individually comprises a unit dose of the cells. Thus in some embodiments, each of the containers comprises the same or approximately or substantially the same number of cells. In some embodiments, the unit dose includes less than about $1\times10^8$, less than about $5\times10^7$, less than about $1\times10^6$ or less than about $5\times10^5$ of cells, per kg of the subject to be treated and/or from which the cells have been derived. In some embodiments, each unit dose contains at least or about at least $1\times10^6$, $2\times10^6$, $5\times10^6$, $1\times10^7$, $5\times10^7$, or $1\times10^8$ engineered cells, total cells, T cells, or PBMCs. In some embodiments, the volume of the formulated cell composition in each bag is 10 mL to 100 mL, such as at least or about at least 20 mL, 30 mL, 40 mL, 50 mL, 60 mL, 70 mL, 80 mL, 90 mL or 100 mL.

In some embodiments, one or more of the plurality of output bags can be used for testing, such as for detecting replication competent vectors or assessing transduction efficiency. Replication competent vectors can be detected using any of the methods described herein. The transduction efficiency in some aspects may be assessed by measuring the level of expression of a recombinant protein, such as a heterologous protein, encoded by a nucleic acid contained in the genome of the viral vector particle following transduction using embodiments of the provided methods. Thus, in some embodiments, the expression level of recombinant molecules may be assessed by any of a number of well-known methods such as detection by affinity-based methods, e.g., immunoaffinity-based methods, e.g., in the context of cell surface proteins, such as by flow cytometry. In some aspects, the cells contained in one or more of the plurality of containers, e.g., bags, is tested for the expression level of recombinant molecules by detection of a transduction marker and/or reporter construct. In other embodiments, expression is assessed using a nucleic acid encoding a truncated surface protein included within the vector as a marker.

V. DEFINITIONS

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

VI. EXEMPLARY EMBODIMENTS

Among the embodiments herein are:

1. A method including:

a) determining a level of a parameter in a test sample, wherein the parameter or level indicates or correlates (optionally positively or inversely) with a presence, absence, or amount or concentration of a viral RNA in a biological sample, the biological sample including at least one cell that contains a heterologous nucleic acid and/or a nucleic acid encoding a heterologous protein, wherein:

the presence, absence or amount or concentration of the viral RNA in the biological sample indicates a presence or absence of, or risk of, a replication competent virus in the biological sample, or a sample from which the biological sample is derived; and/or the viral RNA is required for, or encodes a gene product or specifically identifiable portion thereof that is required for, replication competency of a replication competent virus.

2. The method of embodiment 1, further including determining the presence, absence, concentration, or amount of the viral RNA in the biological sample or risk thereof, based on said level so-determined.

3. The method of embodiment 1 or embodiment 2, further including the steps of:

b) comparing the level of the parameter, determined in (a), to a first reference value for the parameter.

4. The method of embodiment 3, wherein the comparison indicates the presence, absence, concentration or amount of the viral RNA in the biological sample or sample derived therefrom, or risk of any of the foregoing.

5. The method of any of embodiments 1-4, further including:

determining the presence, absence, or amount or concentration of the viral RNA, or risk of any of the foregoing, in the biological sample or portion thereof; and/or determining whether replication competent virus is (or is potentially or is likely to be) present or at risk for being present in the biological sample, or a portion thereof.

6. The method of any of embodiments 1-5, wherein:

the biological sample is deemed to have, to potentially have, or to be at risk for, presence of the replication competent virus, and/or to have the presence or at least a threshold amount of the viral RNA, if, and optionally only if, the level of the parameter determined in (a) is at or is above the first reference value, optionally wherein the level of the parameter positively correlates with the amount of the RNA in the biological sample; and/or the biological sample is deemed to have, or to be at risk for, the presence of the replication competent virus, and/or to have the presence or at least a threshold amount of the viral RNA, if, and optionally only if, the level of the parameter determined in (a) is at or below the first reference value, optionally wherein the level of the parameter inversely correlates with the amount of viral RNA in the biological sample; the biological sample, and/or one or more of the at least one cell, is deemed RCR negative, or is deemed to not have, to not be at risk for, or to not potentially contain the presence of replication competent virus, if, and optionally only if, the level of the parameter determined in (a) is below the first reference value, optionally wherein the level of the parameter positively correlates with the amount of the RNA in the biological sample; and/or the biological sample and/or one or more of the at least one cell is deemed not to have or not to be at risk for the presence of the replication competent virus, and/or not to have the presence or at least a threshold amount of the viral RNA, if, and optionally only if, the level of the parameter determined in (a) is above the first reference value, optionally wherein the level of the parameter inversely correlates with the amount of viral RNA in the biological sample.

7. The method of embodiment 4, wherein:

the biological sample is so-deemed negative, not to have, or not to be at risk, even if another replication competent-required viral RNA is determined to be present in the biological sample;

the biological sample is so-deemed negative, not to have, or not to be at risk, even if a level, at or above a second reference value, of a second parameter that is positively correlated with an amount of another replication competent-required viral RNA in the biological sample, is or has been detected in the test sample or a second test sample derived from or containing nucleic acid from the biological sample; and/or the biological sample is so-deemed negative, not to have, or not to be at risk, even if a level, at or below a second reference value, of a second parameter negatively correlated with an amount of another replication competent-required viral RNA, is or has been detected in the test sample or another test sample derived from or containing nucleic acid from the biological sample.

8. The method of any of embodiments 1-7, wherein:

the biological sample is deemed to have, to potentially have, or to be at risk for the presence of the replication competent virus, if (and optionally only if) the presence of the viral RNA in the biological sample is determined, and/or if (and optionally only if) an amount, which optionally is at or above a threshold amount, of the viral RNA is determined to be in the biological sample;

the biological sample is deemed to potentially have or to be at risk for the presence of the replication competent virus if (and optionally only if) the presence of the viral RNA in the biological sample is determined, and/or if (and optionally only if) an amount, which optionally is at or above a threshold amount, of the viral RNA is determined to be in the biological sample, but is not deemed to contain the presence of the replication competent virus without further indication of risk and/or without assessing another parameter indicative of another viral RNA; and/or the biological sample is deemed not to have, not to potentially have, and/or not to be at risk for the presence of the replication competent virus, if the absence of the viral RNA in the biological sample is determined, and/or if an amount (or no more than the amount), which amount optionally is at or below a threshold amount, of the viral RNA is determined to be in the biological sample, optionally even if the presence of another RNA required for replication competency of the virus is determined to be present in the biological sample; and/or the biological sample is deemed replication competent virus negative if the parameter and/or the viral RNA is undetectable or is not detected in the test sample and/or is not determined to be present in the biological sample.

9. The method of any of embodiments 1-8, wherein the first reference value is a value at or approximately at or just above a threshold level or a minimum detectable level or readout corresponding thereto;

the first reference value is a value of the parameter detected in, and/or a value of a parameter indicative of an amount of RNA in, a positive control sample; and/or the level of the parameter indicates the presence or the absence of the viral RNA in the biological sample; and/or the viral RNA includes a nucleic acid encoding a first viral gene; and/or the heterologous nucleic acid encodes a heterologous gene product.

10. The method of any of embodiments 1-9, wherein the parameter assessed in the test sample is or includes an amount or relative amount of the viral RNA, or a product expressed therefrom or from a viral gene corresponding to the RNA, which optionally is a relative copy number, or a relative weight, or is or includes a concentration, or relative concentration, of the viral RNA, or of a product expressed therefrom or from a viral gene corresponding to the RNA.

11. The method of embodiment 10, wherein the amount is an absolute or relative amount.

12. The method of any of embodiments 1-11, wherein the parameter and/or level is or includes a surrogate or relative value, which optionally is a cycle threshold (Ct) value.

13. The method of embodiment 12, wherein the viral RNA or the expression thereof is determined to be present or at risk of being present in the biological sample or in the test sample, if the CT value for the test sample is below a first reference value, which is a reference Ct score.

14. The method of any of embodiments 1-13, wherein the test sample is or is derived from the biological sample or a portion thereof.

15. A method including:

a) determining or assessing a first level of a first parameter in a test sample, wherein said first level or first parameter correlates (optionally positively or inversely) with a presence, absence, amount or concentration, in a biological sample, of a first viral RNA and/or a first nucleic acid encoding a first viral gene that encodes the first viral RNA;

b) determining or assessing a second level of a second parameter in a test sample, which optionally is the same or a different test sample, wherein said second level or second parameter correlates (optionally positively or inversely) with a presence, absence, amount or concentration, in the biological sample, of a second viral RNA distinct from the first viral RNA and/or a second nucleic acid encoding a second and distinct viral gene encoding said second viral RNA;

wherein at least one cell that contains a heterologous nucleic acid, a heterologous gene product, and/or a nucleic acid encoding a heterologous protein and/or has been transduced with a viral vector;

wherein:

the presence, absence or amount or concentration of the first viral RNA or gene or the second viral RNA or gene, and/or the presence, absence, or amount or concentration of both the first and the second viral RNA or gene, in the biological sample indicates a presence or absence of, or risk of, a replication competent virus in the biological sample, or a sample from which the biological sample is derived; and/or the first viral RNA, the second viral RNA, and/or both the first and the second viral RNA, is required for, or encodes a gene product or specifically identifiable portion thereof that is required for, replication competency of a replication competent virus.

16. The method of embodiment 15 or 20, further including determining the presence, absence, concentration, or amount of the first and/or the second viral RNA or gene product in the biological sample, or risk thereof, based on said level(s) so-determined.

17. The method of embodiment 16, further including:

c) comparing the level of the first and/or the second parameter determined in (a) and/or (b) to a first and/or a second reference value, wherein the comparison optionally indicates the presence, absence, concentration or amount of the viral RNA in the biological sample or sample derived therefrom, or risk of any of the foregoing.

18. The method of any of embodiments 15-17 and 20, further including:

c) determining the presence, absence, or amount or concentration of the first viral RNA or expression, or risk of any of the foregoing, in the biological sample or portion thereof, and/or determining the presence, absence, or amount or concentration of the second viral RNA or expression, or risk of any of the foregoing, in the biological sample or portion thereof; and/or d) determining whether a replication competent virus is (or is potentially or is likely to be) present or at risk for being present in the biological sample or a portion thereof, optionally based on the determination in c).

19. The method of any of embodiments 1-19, wherein the viral RNA is from and/or the first viral RNA is from and/or the first viral gene is env, gag, pol, or rev; and/or the viral RNA is from and/or the second viral RNA is from, and/or the second viral gene is, env, gag, pol, or rev.

20. A method including:

a) assessing a level of a first parameter in a test sample, which is indicative of or correlates (optionally positively or inversely) with of an amount or presence or absence of a first viral RNA in a biological sample, wherein the first viral RNA is from a first viral gene that is an env gene, and assessing a level of a second parameter in a test sample, which optionally is the same or a different test sample, wherein the second viral parameter is indicative of or correlates (optionally positively or inversely) with a presence, absence or amount of a second viral RNA in the biological sample, wherein the second viral RNA is from a gene selected from a gag, pol, and rev gene, wherein the biological sample includes a cell transduced with a viral vector particle, optionally including a heterologous gene product and/or includes a cell with a heterologous gene product;

wherein at least one cell that contains a heterologous nucleic acid, a heterologous gene product, and/or a nucleic acid encoding a heterologous protein and/or has been transduced with a viral vector;

wherein:

the presence, absence or amount or concentration of the first viral RNA or gene or the second viral RNA or gene, and/or the presence, absence, or amount or concentration of both the first and the second viral RNA or gene, in the biological sample indicates a presence or absence of, or risk of, a replication competent virus in the biological sample, or a sample from which the biological sample is derived; and/or the first viral RNA, the second viral RNA, and/or both the first and the second viral RNA, is required for, or encodes a gene product or specifically identifiable portion thereof that is required for, replication competency of a replication competent virus.

21. The method of any of embodiments 1-20, wherein parameter is a presence or absence of viral RNA.

22. The method of any of embodiments 1-21, wherein the reference value, the first reference value and/or the second reference value is or corresponds to a threshold level or a minimum detectable level.

23. The method of any of embodiments 1-22, wherein the reference value, the first reference value and/or the second reference value is a value corresponding to or for the parameter in a positive control test sample, which optionally contains a known amount or concentration of the viral RNA, the second viral RNA and/or the first viral RNA.

24. The method of any of embodiments 15-23, wherein:

the biological sample is deemed to contain or to be at risk for containing or to potentially contain a replication competent virus if the method determines the presence or an amount above a threshold amount of the first and the second viral RNA in the biological sample, and optionally not if the method determines the presence or an amount above a threshold amount for one but not both the first and second RNAs; and/or the biological sample is deemed negative for or not to contain or to not be at risk for containing or not potentially containing a replication competent virus, if the method determines the absence of, the absence of a detectable amount of, or an amount below a threshold amount of, the first viral RNA, or the second viral RNA, and/or both the first and the second viral RNA, in the biological sample.

25. The method of any of embodiments 15-24, wherein the biological sample is deemed replication competent virus negative if the level of viral RNA encoding the first and second viral genes is undetectable in the test sample and/or is not determined to be present or present above a threshold level in the biological sample.

26. The method of any of embodiments 1-25, further including a step of isolating RNA from the biological sample or a portion therefrom or a sample or portion thereof derived from the biological sample, prior to step a), wherein the RNA contains RNA from one or more of the at least one cell.

27. The method of any of embodiments 1-26, wherein the replication competent virus is or includes a retrovirus, and/or wherein the viral RNA or the first and/or the second viral RNA is expressed by a retrovirus.

28. The method of embodiment 27, wherein the retrovirus is a gammaretrovirus.

29. The method of any embodiment 28, wherein the retrovirus is a lentivirus.

30. The method of any of embodiments 1-29, wherein the biological sample is from a human or mammal and/or the one or more cell is a primary cell, which is optionally a human or mammalian cell.

31. The method of any of embodiments 1-30, wherein the one or more cell and/or biological sample is from a master cell bank (MCB), a working cell bank (WCB), or a cell line, or a sample thereof.

32. The method of any of embodiments 1-24, wherein the at least one cell or biological sample is or is from a cryopreserved material (CMAT), a cryopreserved drug product (CDP), or a formulated drug product (FDP) for autologous cell therapy, or a sample thereof.

33. The method of any of embodiments 1-32, wherein the heterologous nucleic acid or heterologous gene product is or encodes a recombinant receptor, a chimeric receptor, optionally a chimeric antigen receptor, or a transgenic T cell receptor.

34. The method of any of embodiments 1-33, wherein the determining or assessing is carried out using one or more oligonucleotide primers specific for a sequence of the viral RNA, the first viral RNA and/or the second viral RNA.

35. The method of any of embodiments 15-34, where the level of viral RNA encoding the second viral gene is assessed using one or more oligonucleotide primers specific for a sequence of the second viral gene.

36. The method of any of embodiments 1-35, wherein the level of viral RNA is assessed by real-time polymerase chain reaction (PCR).

37. The method of any of embodiments 1-36, wherein the determining or assessing includes carrying out reverse transcriptase quantitative PCR (RT-qPCR).

38. The method of any of embodiments 1-37, wherein the viral RNA and/or the first and/or second viral RNA and/or viral RNA and/or gene is from a retrovirus.

39. The method of any of embodiments 1-38, wherein the viral RNA, the first viral RNA and/or second viral RNA (or gene encoding any of the foregoing) is or is encoded by a gene involved in virion replication and/or packaging.

40. The method of any of embodiments 1-39, wherein the viral RNA and/or the first viral RNA and/or the second viral RNA (or gene encoding one or more of the foregoing) is not a gene encoded by a transfer vector that has been used to transduce the transduced cell.

41. The method of any of embodiments 1-40, wherein viral RNA, the first viral RNA and/or the second viral RNA encodes a viral surface protein, an envelope protein, a group-specific antigen, a virally-derived polymerase, a virally-derived reverse transcriptase, a virally-derived regulatory element, a transactivator of transcription, or a response element.

42. The method of any of embodiments 1-41, wherein the gag gene is selected from the group consisting of murine leukemia virus (MMLV) gag and Human Immunodeficiency Virus (HIV) gag.

43. The method of any of embodiments 1-42, wherein the env gene is selected from GaLV env and VSVG env.

44. The method of any of embodiments 34-43, wherein the one or more oligonucleotide primers specific for a sequence of the first viral gene include one or more sequences set forth in SEQ ID NOs: 4-5.

45. The method of any of embodiments 34-44, wherein the one or more oligonucleotide primers specific for a sequence of the first viral gene include one or more sequences set forth in SEQ ID NOs: 16-24.

46. The method of any of embodiments 34-45, wherein the one or more oligonucleotide primers specific for a sequence of the second viral gene include one or more sequences set forth in SEQ ID NOs: 4-5.

47. The method of any of embodiments 34-45, wherein the one or more oligonucleotide primers specific for a sequence of the second viral gene include one or more sequences set forth in SEQ ID NOs: 16-24.

48. The method of any of embodiments 1-47, wherein the assessing or determining includes use of a hydrolysis probe specific for a sequence of the viral RNA, the viral gene, the first viral RNA or the first viral gene, or the second viral RNA or second viral gene.

49. The method of embodiment 48, wherein the hydrolysis probe specific for a sequence of the first viral gene includes a sequence set forth in SEQ ID NO: 6.

50. The method of embodiment 49, wherein the hydrolysis probe specific for a sequence of the first viral gene includes a sequence set forth in SEQ ID NO: 18, 21, or 24.

51. The method of any of embodiments 1-50, wherein the assessing, determining or detecting includes using a hydrolysis probe specific for a sequence of one or more of the viral RNA, second viral RNA, first viral RNA, and/or second viral gene.

52. The method of embodiment 51, wherein the hydrolysis probe comprises a sequence set forth in SEQ ID NO: 6.

53. The method of embodiment 51, wherein the hydrolysis probe specific for a sequence of the first viral gene comprises a sequence set forth in SEQ ID NO: 18, 21, or 24.

54. The method of any of embodiments 1-53, further comprising assessing in the test sample a level of, or a level of a parameter indicative of or correlative with, an RNA encoding a control gene in the test or biological sample, optionally wherein the control gene is or comprises β-actin and/or optionally wherein the level of the parameter or control gene is assessed using one or more oligonucleotide primers specific to a sequence of the control gene, which individually optionally comprise one or more sequences set forth in SEQ ID NO: 1 or 2 or one of 8-15, optionally wherein the level is assessed using a hydrolysis probe specific for a sequence of the control gene, which optionally comprises a sequence set forth in SEQ ID NO: 3, 9, 12, or 15.

55. The method of any of embodiments 1-54, wherein the assessment or determining comprises carrying out a multiplex reaction, wherein optionally the level, the first level, and/or the second level; and optionally the level or parameter indicative or correlative with the control gene, is assessed in the multiplex reaction.

56. The method of any of embodiments 1-55, wherein the parameter, the first parameter, and/or the second parameter, individually, is or comprises an amount or relative amount of the viral RNA (or first or second viral RNA), or a product expressed therefrom or from a viral gene corresponding to the RNA, which optionally is a relative copy number, or a relative weight, or is or comprises a concentration, or relative concentration, of the viral RNA (or first or second viral RNA) or of a product expressed therefrom or from a viral gene corresponding to the RNA (or first or viral RNA).

57. The method of embodiment 56, wherein the amount is an absolute or relative amount.

58. The method of any of embodiments 1-57, wherein the parameter and/or level is or comprises a cycle threshold (Ct) value.

59. The method of embodiment 58, wherein the viral RNA or the expression thereof is determined to be present or at risk of being present in the biological sample or in the test sample, if the CT value for the test sample is below a first reference value, which is a reference Ct score.

60. The method of any of embodiments 1-59, wherein the biological sample and/or the one or more cells is or are from a subject.

61. The method of any of embodiments 1-60, wherein said at least one cell comprises a plurality of cells, and wherein:

said plurality of cells and/or said biological sample comprises suspension cells;

said plurality of cells and/or said biological sample comprises white blood cells; and/or said plurality of cells and/or said biological sample comprises T cells or NK cells.

62. The method of any of embodiments 15-61, wherein one or both of the first test sample and the second test sample, individually is derived from or contains RNA derived from the biological sample or a portion thereof.

63. The method of any of embodiments 15-61, wherein the test sample assessed for the first viral RNA and the test sample assessed for the second RNA are the same or are portions of the same sample or composition.

64. The method of embodiment 61, wherein said plurality of cells comprises unfractionated T cells, isolated CD8+ T cells, or isolated CD4+ T cells.

65. The method of any of embodiments 1-64, wherein said at least one cell is a human cell.

66. The method of any of embodiments 29-65, wherein acceptance criteria are set to assess validity of the real-time PCR.

67. The method of embodiment 66, wherein the acceptance criteria comprise a percent efficiency of between or between about 90% and 110%.

68. The method of any of embodiments 66-67, wherein the acceptance criteria comprise an $R^2$ value of about or greater than at or about 0.95, 0.96, 0.97, 0.99 or 0.99.

69. The method of any of embodiments 1-68, further comprising assessing the purity, integrity, and/or concentration of the RNA.

70. A primer comprising an oligonucleotide comprising a sequence set forth in any of SEQ ID NOs: 1-24 or 35-41.

71. The primer of embodiment 70, further comprising a fluorescent moiety or label.

72. A kit comprising one or more primers according to embodiment 70 and/or embodiment 71.

73. The kit of embodiment 71, further comprising one or more of nuclease-free water, a reverse transcriptase, a polymerase, deoxynucleotide triphosphates, a buffer, and a DNase.

74. The method of any of embodiments 1-73, wherein the test sample is or is a portion of the biological sample.

75. The method of any of embodiments 1-69 and 74, wherein the method is capable of detecting the viral RNA or the first and/or the second viral RNA in a test sample in which at least 5 or at least 10 or at least 20 or at least 50 or at least 100 cells in the sample, or per 10 million cells in the test sample or biological sample; and/or wherein the method is capable of detecting an amount of target RNA that is no more than at or about 1.5 pg, 1 pg, or 0.75 pg or less of the viral target, in the test sample and/or the biological sample.

76. The method of any of embodiments 1-69, 74 and 75, wherein the one or more cell and/or biological sample is collected from a process in which transduced cells have been cultured under conditions to expand the cells, optionally at or about 37° C. and/or in the presence of one or more stimulating agents.

77. The method of embodiment 76, wherein the transduced cells have been cultured for at least 1 day, 2 days, 3 days, 4 days, 5 days, 6 days, 7 days, 8 days, 9 days, 10 days, 11 days, 12 days, 13 days or 14 days; or from or from about 2 to 14 days, 2 to 10 days, 4 to 14 days, 4 to 10 days or 7 to 10 days.

78. A method comprising:

a) assessing a level of viral RNA in a test sample, wherein the test sample comprises RNA from a sample comprising at least one cell comprising a heterologous nucleic acid; and wherein the level of viral RNA indicates the presence, absence, or amount of a replication competent virus in the test sample.

79. The method of embodiment 78, further comprising the steps of:

b) comparing the level of viral RNA in the test sample to a first reference value; and c) determining whether replication competent virus is present in the test sample, wherein the sample is deemed replication competent virus positive if the amount of the viral RNA is above the first reference value.

80. The method of embodiment 79, wherein the test sample cell is deemed RCR negative if the level of the viral RNA is below the first reference value.

81. The method of any of embodiments 78-80, wherein the test sample is deemed replication competent virus negative if the level of the viral RNA is undetectable.

82. The method of any of embodiments 78-81, wherein the first reference value is a threshold level or a minimum detectable level.

83. The method of any of embodiments 78-82 wherein the first reference value is a positive control.

84. The method of any of embodiments 78-83, wherein the level of viral RNA is a presence or absence of viral RNA.

85. The method of any of embodiments 78-84, wherein the viral RNA comprises a nucleic acid encoding a first viral gene.

86. The method of any of embodiments 78-85, wherein the heterologous nucleic acid encodes a heterologous gene product.

87. A method comprising:

a) assessing a level of viral RNA encoding a first viral gene and a level of a viral RNA encoding a second viral gene in a test sample, wherein the test sample comprises RNA from a sample comprising at least one cell transduced with a viral vector particle comprising a heterologous gene product, and wherein the first and second viral genes are not the same;

b) comparing the level of the first and second viral genes in the test sample to a first and second reference value, respectively; and c) determining whether a replication competent virus is present in the test sample, wherein the test sample cell is deemed replication competent virus positive if the levels of the first and/or second viral genes are above the first and/or second reference values, respectively.

88. The method of any of embodiments 85-87, wherein the first viral gene is env, gag, pol, or rev.

89. The method of embodiment 86 or embodiment 88, wherein the second viral gene is env, gag, pol, or rev.

90. A method comprising:

a) assessing a level of viral RNA encoding a first viral gene, wherein the first viral gene is an env gene, and assessing a level of viral RNA encoding a second viral gene, wherein the second viral gene is selected from a gag, pol, or rev gene in a test sample, wherein the test sample comprises RNA from sample comprising a cell transduced with a viral vector particle comprising a heterologous gene product;

b) comparing the level of viral RNA encoding the first and second viral genes in the test sample to a first and second reference value, respectively; and c) determining whether a replication competent virus is present in the test sample, wherein the replication competent virus is present if the levels of viral RNA of the first and/or second viral genes is above the first and second reference value, respectively.

91 The method of any of embodiments 78-90, wherein assessing the level of viral RNA or expression of the viral gene comprises calculating a cycle threshold (Ct) value.

92. The method of claim 91, wherein the level of the viral RNA or the expression of the viral gene is below the first reference value if the Ct score is above a maximum Ct value.

VII. EXAMPLES

The following examples are included for illustrative purposes only and are not intended to limit the scope of the invention.

Example 1: Exemplary Assay Assessing Levels of Parameters Indicative of Viral RNA Targets, Such as GaLV Env and/or MMLV Gag This Example describes an exemplary method for assessing a level of one or more parameters in a test sample indicative of the presence, absence, level, or other readout of viral RNAs and/or existing or potential presence or risk of replication competent retrovirus (RCR) in a biological sample. The biological sample generally includes at least one cell, such as a cell comprising a heterologous nucleic acid or nucleic acid encoding all or part of a heterologous gene product, such as a heterologous, exogenous and/or recombinant nucleic acid and/or protein. Such cells in some aspects have been subject to the introduction of nucleic acids or other biomolecules, generally that are encoded by and/or contained in a retroviral vector, retroviral vector particle, or retrovirus, such as by transduction. The test sample generally comprises RNA, or product produced therefrom, such as cDNA, the RNA having been isolated from or present in the cell(s) in the biological sample, such as the cells transduced with a viral vector particle comprising a heterologous gene product. The cell(s) in the biological sample can be mammalian cells, such as human cells.

In one aspect of the method, detection of the parameter is or includes the presence or absence of or amount or relative amount of a GaLV env RNA or nucleic acid transcribed from or encoded thereby, or a parameter that is a surrogate, e.g., that inversely or positively correlates with such RNA, either in the test or biological sample. In some aspects, the level of such parameter serves as a marker for the determination of the potential for, risk of, presence of, or absence of, RCR in the sample. In general, GaLV env gene encodes a viral envelope protein present in replication competent retroviruses and in some aspects is required or necessary, but not sufficient, for replication competent virus or replication competency thereof.

In some aspects, of the method, the level of the parameter is or includes the presence or absence of or amount of an MMLV gag RNA, or nucleic acid or other product transcribed from or encoded thereby, or a parameter that is a surrogate for such RNA or nucleic acid, e.g., that inversely or positively correlates with such RNA, either in the test or biological sample. In some aspects, the level of such parameter serves as a marker for the determination of the potential for, risk of, presence of, or absence of, RCR in the sample. In general, MMLV gag gene encodes a viral protein comprising viral matrix, capsid and nucleocapsid proteins, and in some aspects is required or necessary, but not sufficient, for replication competent virus or replication competency thereof.

In some aspects, a level, presence, amount, concentration, absence, or relative amount or concentration, of each of one or more of the viral RNA, such as the GaLV env RNA or the MMLV gag RNA, is indicated or determined by a level of a corresponding parameter in the test sample, where the parameter is inversely or positively correlates with the level, presence, amount, concentration, absence, or relative amount or concentration, of the respective RNA, e.g., in the test sample and/or in the biological sample.

Generally, transduced cells harboring RCR may transcribe various viral genes required for the production of infectious viral particles, such as those required for replication competent virus. In general, such genes (and/or a sufficient number or group of such genes) are or is not present in the heterologous or virally-derived nucleic acid(s) present in a transduced cell into which the heterologous or recombinant molecule has been inserted using a viral vector. Such genes can include env and gag genes, such as GaLV env and/or the MMLV gag.

An exemplary assay (which, as described in Example 2, 4, or 6 was performed to assess or confirm absence of RCR in particular samples, including test samples or control samples), is carried out on one or more test samples. The test samples include one or more test samples containing RNA isolated and/or derived from or more biological samples, respectively. Among the biological samples are generally those containing one or more cell, such as a human cell or mammalian cell, such as formulated for cell therapy or administration, for which it is desired to confirm the absence of replication competent virus; also among the biological samples or reference test samples can be those known to contain or not to contain certain reference amounts of viral RNA(s) and/or control nucleic acids, being assessed in the assay. Combinations of such samples may be used as biological samples or test samples in the assay, such as in spike-in samples.

In certain applications, such as that in the studies described in Examples 4 or 6, the biological sample being assessed contains cells transduced using a retroviral vector with heterologous nucleic acid encoding a chimeric antigen receptor (CAR); the samples used in the assay also generally include one or more control sample, such as control biological and/or control test samples.

One or a plurality of biological samples, such as those comprising transduced cells, are optionally thawed, and RNA extracted from the samples to generate one or a plurality of test samples. Test samples may be prepared in triplicate or duplicate or more. RNA is used as a template to generate cDNA by reverse transcription.

Control samples may be run in parallel, including negative controls and/or those containing known amounts of one or both targets/portions. In some aspects, the control RNA is or comprises at least a portion of actin and or the viral RNA comprises all or a portion of a GaLV env RNA and/or all or a portion of an MMLV gag RNA. In such aspects, primers and hydrolysis probes specific for actin and/or GaLV env (or the MMLV gag) are used in the reaction; in some cases, such as those in which dual constructs containing both target and control RNA are spiked in to control samples, primers/probes specific for both the control and target RNA are included or multiplexed in the same reaction. Exemplary actin and GaLV env primers and probes are shown in Table 1.

TABLE 1

Exemplary Actin and env Primer and Probe Sequences

| Description | Sequence | SEQ ID NO. |
|---|---|---|
| Actin forward primer | 5'-GCGAGAAGATGACCCAGATC-3' | 1 |
| Actin reverse primer | 5'-CCA GTG GTA CGG CCA GAG G-3' | 2 |

TABLE 1-continued

| Exemplary Actin and env Primer and Probe Sequences | | |
|---|---|---|
| Description | Sequence | SEQ ID NO. |
| VIC-labeled actin probe with a Minor Groove Binder/Non-fluorescent quencher (MGBNFQ) | VIC-CCA GCC ATG TAC GTT GCT ATC CAG GC-MGBNFQ | 3 |
| GaLV env forward primer | 5'-TCT GGG ATA CAA AGG CAG TCC A-3' | 4 |
| GaLV env reverse primer | 5'-GCC AAG GCA CAT ACA TCA GGT T-3' | 5 |
| FAM-labeled GaLV env probe with a Minor Groove Binder/Non-fluorescent quencher (MGBNFQ) | FAM-CCC TTG GAC TTG GTG GCC CAC ACT-MGBNFQ | 6 |

In some embodiments, e.g., where a multiplexed real-time PCR assay is used, e.g., for actin (as a control) and MMLV gag and/or RNA sequences. Sequences of exemplary actin (HuActin) and MMLV gag (gag) forward (F) and reverse (R) primers and hydrolysis probes are shown in Table 2.

TABLE 2

| Exemplary Actin and MMLV gag Primer and Probe Sequences | | |
|---|---|---|
| Description | Sequence | SEQ ID NO. |
| Actin forward primer | GCGAGAAGATGACCCAGATC | 1 |
| Actin reverse primer | CCA GTG GTA CGG CCA GAC C | 8 |
| Vic-labeled Actin hydrolysis probe | CCA GCC ATG TAC GTT GCT ATC CAG GC | 9 |
| Actin forward primer | AAGGCCAACCGCGAGAAG | 10 |
| Actin reverse primer | ACAGCCTGGATAGCAACGTACA | 11 |
| HEX-labeled Actin hydrolysis probe | TGACCCAGATCATGTTT | 12 |
| Actin forward primer | TTCTACAATGAGCTGCGTG | 13 |
| Actin reverse primer | CCTGGATAGCAACGTACATGG | 14 |
| HEX-labeled Actin hydrolysis probe | CTGAACCCCAAGGCCAACCG | 15 |
| MMLV gag forward primer | ACTCCACTACCTCGCAGGCAT | 16 |
| MMLV gag reverse primer | AGA GGA GAA CGG CCA GTA TTG | 17 |
| FAM-labeled MMLV gag hydrolysis probe | CCGCGCAGGAGGAAACGGACA | 18 |
| MMLV gag forward primer | CTCCTTCTCTAGGCGCCAAA | 19 |
| MMLV gag reverse primer | GCG GCC CCC CAC TGT | 20 |
| FAM-labeled MMLV gag hydrolysis probe | CTAAACCTCAAGTTCTTTC | 21 |
| MMLV gag forward primer | GGACAGAAACAGGATAGACAGG | 22 |
| MMLV gag reverse primer | TCGTGGTTTCTTGGGACAATC | 23 |
| FAM-labeled MMLV gag hydrolysis probe | CCAGTGCCCCTTTTCTTTGCAGT | 24 |

A control sample, such as a control test sample such as a plasmid standard control is used as a control for the PCR amplification portion of the assay. In one example, the control samples include a sample containing cells and further containing (e.g., spiked with) a known quantity or concentration (e.g., reference value) of the standard, such as a known quantity/concentration/amount of, the viral RNA or portion thereof, the control RNA or portion thereof e.g., in the form of a plasmid standard control, optionally both, on the same construct. In some examples, controls (or sample used to calibrate the assay) include a sample with a known number or relative number of target-positive cells (e.g., target+ cells per total number of cells).

In some contexts where a plasmid standard control is used, the plasmid includes the positive and negative control nucleic acids on the same construct, for improved control. In aspects of the method, the plasmid standard control includes a pActin-GaLVgag construct (SEQ ID NO: 34). In aspects of the method, the plasma standard control(s) includes a pActin-MMLVgag construct (SEQ ID NO: 30).

In one example, the known amount or concentration to be used in the assay is determined empirically, such as by carrying out studies to determine the sensitivity and/or specificity of the assay for a particular plasmid standard. In one such example, a plasmid standard control sample dilution series, including various concentrations or amounts, such as within the range of $10^6$ to $10^1$ copies per reaction is used. A plasmid standard control sample dilution series of $10^6$ to $10^1$ copies per 7 μL is used.

A no template control containing water and PCR reagents only is used to provide information about any potential contamination and/or contamination state, e.g., of one or more of the PCR reagents. A no reverse transcriptase (−RT) control is used to evaluate the purity of the RNA template and to verify or confirm the absence of, and/or to detect any potential, contaminating DNA.

RNA from a cell line that does not express the target viral gene, e.g. does not express GaLV env, is used as a negative control. The negative control is used at a similar concentration or amount, e.g., of total RNA and/or cells, as compared with the test sample.

A positive control is established for the assay based on a reference value, such as an exemplary limit of detection, which in some aspects is determined empirically, e.g., by selecting a desired confidence interval and assessing samples with a series of known quantities of GaLV env RNA.

In some embodiments, as a positive control, RNA from a cell line that does express the target viral gene, such as does not express GaLV env (e.g., 293Vec-GaLV), is used at a quantity at or around or just above an exemplary limit or level of detection of the assay. In an assay carried out in Example 2, a positive control contained 0.75 pg of GaLV RNA. The RNA level of this positive control is used as a reference value for comparison with the test samples.

Detection of actin is multiplexed with detection of the target viral gene, e.g. GaLV env, in each well of the assay. This parameter controls for RNA quality. Presence of actin in each well confirms that RNA is present and is of sufficient quality to be capable of undergoing reverse transcription and PCR amplification. Actin in some aspects is not evaluated in the positive control reactions because it may typically not be detectable.

In some exemplary methods, RNA from patient-matched material that has not been transduced with the viral vector particle comprising the heterologous gene product is used as a control for contamination during the RNA isolation procedure.

For the test samples, RNA isolated from $10\times10^6$ cells is tested with 7 μL used per well. In an exemplary method, each control and test sample is assigned to one or more wells in a 96-well format. Control and test samples are run in triplicate. The samples are mixed with the actin and GaLV env forward and reverse primers, hydrolysis probes, and components for carrying out RT-PCR provided by RNA UltraSense One-Step Quantitative RT-PCR Enzyme Mix and RNA UltraSense One-Step Quantitative RT-PCR 5× Reaction Mix (ThermoFisher Scientific).

In some aspects, the assay is carried out using a commercially available one-step quantitative RT-PCR system. The multiplexed real-time PCR assay may be run for 40 cycles. Generally, probe hydrolysis that occurs with amplicon generation released a fluorescent molecule, which is detected by the real-time PCR machine. A threshold level is set and threshold cycle (Ct) values are obtained for each well of the assay. Ct values of replicates are averaged.

The assay in some aspects is considered appropriate for a particular use and/or valid based on certain criteria. In some aspects, the template control is desired to have no or little Ct value in every well. The plasmid standard parameters in some aspects are within appropriate ranges for the method of detection used. The un-transduced negative control in some aspects should have no Ct value in every well, and an appropriate A260/280 value indicative of appropriate RNA quality. Test samples generally should likewise have an appropriate A260/280 value (e.g. between 2-2.1, inclusive), an appropriate Ct value for actin, and other control parameters as desired for a particular assay.

Hypothetical results for an assay carried out on hypothetical samples having particular conditions are listed below, to illustrate results that may be obtained if the methods were used to assess a test sample derived from a biological sample which did contain replication competent virus. In this example, the actin and GaLV env amplicons are detected by real-time PCR, and results for the test samples are reported as 'RCR-associated RNA detected' or 'RCR-associated RNA not detected' based on a comparison of a level of a parameter (e.g., a Ct value or ΔCt value or ΔΔCt value) detected or determined for such test sample(s) and a corresponding reference value, e.g., the corresponding level for such parameter (e.g., Ct value or ΔCt value or ΔΔCt value) determined for a positive control with the known quantity of the target RNA (containing for example 1.5, 1, or 0.75 or 0.5 pg of GaLV env RNA). For example, in some embodiments, if the Ct value in a well (or average of replicates) for the test sample is deemed to be greater than the Ct value determined for the positive control (containing of the known or predetermined quantity of GaLV env RNA), then the GaLV env RNA may be deemed not present in the corresponding biological sample that is the test sample or from which the test sample is derived, and generally, such test sample is identified as 'RCR-associated RNA not detected'. In some examples, whether the test sample is identified as "RCR-associated RNA detected" or "RCR-associated RNA not detected" is determined based on a comparison of delta Ct or delta delta Ct values, for example, based on the degree of difference (delta) between the Ct value or delta CT value obtained for a negative control sample (such as one known not to have been exposed to the viral particle of interest or replicating virus) and the Ct value or delta CT value obtained for a given test sample. In some aspects, a threshold level for the assay (such as the level above or below which a test sample is deemed positive or negative and/or is deemed or is not deemed RCR-associated RNA containing) is expressed as the degree of such a difference or delta for a positive control sample, such as one known to contain the viral RNA in question at or about at the limit of detection (LOD) for the assay. For example, the threshold value may be set at the difference (or delta) between the Ct value or delta CT value for such positive control sample and the Ct value or delta CT value for the negative control sample, or the threshold value may be set at some point relative to such control difference or delta, such as a multiple thereof.

In some embodiments, the difference between the Ct value for a positive control (such as one known to contain viral RNA at or about the limit of detection (LOD) and the Ct value for a negative control sample, such as sample (or sample derived from a sample) known not to have been exposed to the viral vector particle comprising the heterologous gene product or any replicating virus) is determined; in some aspects, such difference, or multiple or fold-difference thereof, is set as a threshold value. In some examples, for a given test sample and/or each test sample, the difference between the Ct value for that test sample and the Ct value for the for the negative control sample, such as the sample (or sample derived from a sample) known not to have been exposed to the viral vector particle comprising the heterologous gene product or any replicating virus) is determined, and in some aspects compared to such threshold value. In some examples, the given test sample is considered "RCR-associated RNA detected" if such difference is at or below the threshold value.

In some examples, if the Ct value in a well (or average of replicates) for the test sample is determined to be less than the Ct value determined for the positive control (containing known quantity of of GaLV env RNA), (or the difference—or delta—between the Ct value or delta Ct value for the test sample and Ct value or delta Ct value for the negative control is at or above the threshold value that is or corresponds to the difference between the Ct or delta Ct for the positive control (e.g., Ct or delta Ct for the sample with viral RNA at or about the LOD) and the Ct or delta Ct value for the negative control) then the viral RNA may be deemed to be potentially present or present in the test sample and/or the biological sample, and, in this exemplary assay, such a test sample would be identified as 'RCR-associated RNA detected', which in some aspects may indicate a risk of the presence of RCR or potential RCR.

In some such aspects, the method would further include further assays, such as carrying out or analyzing results for an assay similar but directed to a different RCR-associated RNA such as MMLV gag.

Example 2: Design of a Reverse Transcriptase-PCR (RT-PCR) Assay for Detecting the Gene Encoding Gibbon Ape Leukemia Virus (GaLV) Envelope (Env)

To carry out the assay as described in Example 1, an assay was designed to detect the gene encoding Gibbon Ape Leukemia Virus (GaLV) envelope (env). GaLV env was chosen as a target in part because its presence in a transduced human cell composition could indicate recombination events based on the transduction, rather than the presence of endogenous, viral sequences.

1. Primer/Probe Sets

A positive amplification control plasmid was generated to contain the GaLV env sequence and a fragment of a human beta actin sequence to provide templates for both primer and probe sets for use in RT-PCR. A sequence of the pActin-GaLV plasmid is set forth in SEQ ID NO:34. Four candidate primer and probe sets were designed to amplify across different regions of the GaLV env sequence and two candidate primer and probe sets were also designed around the actin fragment target. Quantitative Reverse Transcriptase-PCR (RT-PCR) was carried out in the presence of an RT and a TAQ polymerase. The amplification conditions used for the RT-PCR are set forth in Table 3.

TABLE 3

| PCR cycles | | |
|---|---|---|
| | | RT-PCR Run Program |
| Hold Stage | Step 1 | 50.0° C. for 15 minutes |
| | Step 2 | 95.0° C. for 2 minutes |
| PCR Stage | Step 1 | 95.0° C. for 15 seconds |
| | Step 2 | 60.0° C. for 1 minute |

Primer/probe sets were initially tested using a no template control (negative control) and a dilution series of the pActin-GaLV plasmid as a template. In addition, RNA isolated from a 293 Vec-GaLV viral packaging cell line (BioVec), which stably expresses the GaLV envelope and the MMLV gag/pol, was used as a positive control for the reverse transcription reaction and PCR amplification steps. As a further control, RNA from a thawed cryopreserved cell composition (cryopreserved material, CMAT), generated by a process that included immunoaffinity-based selection of CD4+ and CD8+ T cells from a leukapheresis sample of an individual subject followed by cryopreservation of isolated cells, was used. The CMAT sample, which did not undergo transduction with a viral vector and thus had not been exposed to viral stock, was used as a positive control for the actin primer/probe set but should not generate an amplification signal for the GaLV env primer/probe set.

The top two GaLV env primer probe sets were selected based on acceptance criteria for standard curve performance parameters shown in Table 4.

TABLE 4

| Acceptance Criteria | | |
|---|---|---|
| Sample | Parameter | Criteria |
| No template control | $C_T$: Actin | Not detected |
| No template control | $C_T$: GaLV env | Not detected |
| Plasmid Standard | Slope: Actin | −3.1 to −3.6 |
| Plasmid Standard | Efficiency: Actin | 90-110% |
| Plasmid Standard | $R^2$: Actin | ≥0.98 |
| Plasmid Standard | Slope: GaLV env | −3.1 to −3.6 |
| Plasmid Standard | Efficiency: GaLV env | 90-110% |
| Plasmid Standard | $R^2$: GaLV env | ≥0.98 |
| Positive Control | $C_T$: GaLV env | 32.9-37.0 |
| CMAT | $C_T$: Actin | ≤22 |
| CMAT | $C_T$: GaLV env | Not detected |

Primer/probe sets were then tested individually and combined to verify that multiplexing between selected GaLV env and actin primer/probe pairings did not impact amplification performance on target detection. The exemplary GaLV env and actin primer/probe pairs set forth in Table 1 was selected and used for subsequent assay development.

2. RNA Isolation and Sample Quality

Different methodologies were compared for obtaining isolation of high quality RNA template with minimal DNA contamination. RNA was isolated from CMAT samples generated as described above. RT-PCR \was carried out with (+RT) and without reverse transcriptase (−RT) (in each case in the presence of Taq polymerase) in order to distinguish between signal originating from RNA template and from contaminating DNA template.

The amplification signal for the actin template was compared among the samples. A high level of amplification at a low cycle number indicates a high concentration of template present in a sample.

As an exemplary criterion related to purity of the RNA sample, an exemplary threshold value of ≥2.0 (for the A260/A280 ratio measured on a spectrophotometer) was set; threshold values also were set based on the inclusion of the primer/probe set targeting the housekeeping gene, actin. A cycle number ($C_T$) maximum threshold value was set, related to concentration and quality of the RNA samples to be evaluated in the assay for the presence of the GaLV env target. Further, a minimum value for standard deviation for the actin $C_T$ values between replicates also was set, for example, for confirming consistency across replicates. A threshold value also was set for signal for the no reverse transcriptase control (−RT) (indicative of the presence of any DNA contamination) also was set. An exemplary threshold minimum level for the difference in the number of cycles with (+RT) and without (−RT) reverse transcriptase was set at ≥13.2. Table 5 summarizes the RNA sample threshold levels.

TABLE 5

| RNA Sample Criteria | |
|---|---|
| Parameter | Criteria |
| A260/A280 | ≥2.0 |
| $C_T$: actin primer set | ≤15 |
| Actin $C_T$ value between replicates | SD ≤ 0.5 |
| Actin $C_T$ values in the "no reverse transcriptase" control | (−RT) − (+RT) ≥ 13.2 |

A cellular control was chosen to include in each assay to ensure proper performance of the RNA isolation procedure. In some embodiments, an exemplary cellular control for inclusion across assays is an aliquot of the same cell composition stored as single use aliquots in liquid nitrogen, in which, in each assay, RNA was isolated from the same number of cells, e.g. $5\times10^6$ cells. In some aspects, a threshold value is set for such control. An exemplary criterion for the RNA control was the mean of the expected RNA concentration (e.g. as determined from a plurality of aliquots)±4 standard deviations.

3. Detection of GaLV Env RNA by RT-PCR

The GaLV env RT-PCR assay carried out on RNA isolated from the 293Vec-GaLV cell line or the pActin-GaLV plasmid positive control. RNA also was isolated from a cryopreserved cell composition (CCC) that had been transduced with a gammaretroviral vector produced using a plasmid encoding the GaLV env packaging element. Various parameters were evaluated for the assay in this study, including exemplary specificity, linearity, range matrix interference, precision and sample and plasmid control stability.

Amplicons generated from singleplex RT-PCR with GaLV or actin primers/probes on pActin-GaLV plasmid template were sequenced and were 100% identical to the predicted GaLV and actin sequences. In clones from 293Vec-GaLV cells or CMAT control approximately 11% (1/9) of sequenced amplicons contained a single base pair mismatch to the predicted GaLV or actin sequence, respectively, likely due to reverse transcriptase error.

In an RT-PCR carried out with a dilution series with pActin-GaLV plasmid standard, the assay could quantify as few as 10 copies per reaction; detection of target at or above that number of copies was observed in 100% of wells meeting this limit, with a standard deviation ≤1.5. A linear range of detection was observed at $10^1$ to $10^6$ copies/μL with detection in 100% of wells and a standard deviation of ≤0.5, except at 10 copies per reaction.

In another series of experiments, RT-PCR was performed on a dilution series of RNA isolated from 293Vec-GaLV cell line. Greater than 95% of positive samples with at least 0.5 to 0.75 pg GalV+ RNA were detected as positive in the assay. In another series of experiments, the dilution series of RNA isolated from 293Vec-GaLV cell line was spiked into RNA isolated from a CCC sample. As few as ten GALV+ cells spiked into $10\times10^6$ CCC cells (0.001%) were detectable in the assay, with detection in 100% of wells and $C_T$ value ≤$C_T$ value of the positive control.

To assess stability of the RNA in the assay, 293 Vec-GaLV cells were spiked into a CCC sample and samples were incubated at room temperature for 0, 2, 6 or 25 hours and then RNA was isolated. RNA was analyzed for RNA Integrity Number (RIN) using standard methods, and to assess A260/A280 and degradation. The time course study confirmed that the RNA remained stable at room temperature for up to 25 hours (for example, which may be desirable in certain settings for example to account for operator variability in sample handling). While still high quality RNA was observed at up to 25 hours, a decrease in RNA concentration was observed at the 25 hour time point, while the earlier time points were comparable. The RIN decreased from 10 to 9 only at the 25 hour time point. GaLV detection was determined to be stable over the time course at room temperature, while actin detection decreased over the time course at room temperature.

These results demonstrated that the GaLV RT-PCR assay was able to detect 10 spiked in GaLV positive cells in a matrix of 10 million CCC cells and was robust enough so that GaLV signal was still detectable in stressed samples left at room temperature for up to 25 hours. In these studies, acceptable levels of inter-assay and intra-assay variability was observed.

Example 3: Assessment of Viral RNA Target(s) Indicative of or Associated with or Required for Replication Competent Retrovirus in Samples with a GaLV Env and MMLV Gag Dual-Target Assay An exemplary dual-target method in some embodiments is used to evaluate the absence or presence of replication competent retrovirus (RCR) in transduced or other cells. The assay is carried out substantially as described in Example 1, where the target RNAs assessed include GaLV env RNA and MMLV gag RNA, each assessed in test samples, with the use of each of the respective viral RNA-actin plasmid standard, such that the same control RNA is used in each assay, which can provide improved control. A risk of RCR in some aspects is identified in the biological sample only if both the GaLV env and the MMLV gag RNA are determined by the method to be present or above reference amount in the sample. In some aspects, the determination that one of the RNAs is present or above reference is followed by further assays before confirming a sample as negative.

Example 4: Assessment of Viral RNA Target(s) Indicative of or Associated with or Required for Replication Competent Retrovirus in Samples with a GaLV Env Target Assay T cells transduced with retroviral vectors and processed were assessed by the method, confirming the absence of RCR-associated RNA. Samples were prepared and a RT-PCR-based RCR detection method was performed substantially as described in Example 1. Briefly, RNA was isolated from biological samples comprising transduced cells in triplicate. The resulting RNA-containing test samples were analyzed for RNA quality using A260/280 measurements, tested for contaminating DNA using a spectrophotometer as well as a "no reverse transcriptase" control PCR. All samples were determined to have functionally 99.999% pure RNA. The linearity of RNA template used in the assay was validated using positive control RNA from a −GaLV cell line (for GaLV env) and a sample of transduced cells (for actin).

Reference values of assessed parameters were determined using samples with RNA derived from transduced cells spiked with a known quantity (e.g., approximately 0.75 pg) plasmid control (pActin-GaLV; SEQ ID NO: 34) per reaction.

Non-spiked transduced cell RNA samples (three samples, in triplicate) were evaluated in parallel with the spiked samples using the GaLV/actin RT-PCR method substantially as described in Example 2. In each of the test samples containing RNA from biological samples containing the transduced cells, Ct values observed indicated the absence of the target RNA in the biological samples, and as such, none of the assessed transduced cell samples were determined to be RCR-positive. All of the samples tested positive for actin. Results for positive control cell-derived samples confirmed sensitivity and function of the assay.

Example 5: Testing During Process

In an exemplary process, testing for RCR is performed at multiple stages throughout a product manufacturing process for engineering cells by transducing with a viral vector particle encoding a heterologous gene product. In an exemplary method for engineering cells, leukapheresis is performed to harvest peripheral blood mononuclear cells (PBMC), cells are washed and T cells are further enriched by immunoaffinity-based enrichment. Optionally, the isolated cells are cryopreserved and subsequently thawed. The cells, e.g., thawed cells, are cultured in the presence of anti-CD3/-CD28 beads, followed by transduction with a GaLV-pseudotyped retroviral vector encoding a heterologous gene product, such as a chimeric antigen receptor (CAR). After transduction, cells are expanded in culture for a period of time, such as up to 10 days. Optionally, transduced cells are frozen by cryopreservation. Expanded and transduced cells, which optionally are thawed, are further formulated for administration to a subject.

The assay, such as described in the above Examples, is carried out, for example, to assess one or more the following biological samples: isolated viral vector particles, vector supernatants, a master cell bank for vector producer cells, end-of-production cells (EOPC), final vector-transduced cells (including cells during various periods of ex-vivo expansion and/or that undergo a period of ex-vivo expansion), cryopreserved material (CMAT), cryopreserved drug product (CDP), and a formulated drug product (FDP). Further, biological samples also can include samples derived from a subject after administration of a formulated drug product. The assay of any one or more of Examples 1-3 is used to detect RCR in samples comprising the transduced cells at the various stages of the product manufacturing process.

Example 6: Detection of Replication-Competent Virus in T Cells Spiked with a Model Virus The RT-PCR-based methods described in Examples 1, 2 and 4 were used to detect the presence or absence of GaLV viral RNA in a test sample obtained from T cell samples spiked with a replicating wild-type GaLV at varying numbers of infectious units and subjected to an in vitro process. CD3+ T cells were isolated by immunoaffinity-based enrichment from leukapheresis of human Peripheral Blood Mononuclear Cells (PBMC) from three different human subjects. Isolated T cells from each subject were then cryopreserved.

An initial study was carried out to assess the degree or absence of replication by different known low amounts of spiked-in replication-competent retrovirus, during an ex vivo process involving the culture and expansion of CD3+ T cells. Isolated T cells were thawed, activated with anti-CD3/anti-CD28 beads, spiked by addition of a wild-type GaLV replicating virus at 0, 10, 100, or 1000 infectious units (IU) and expanded at 37° C. for 10 days. As a positive control, samples containing permissive HEK293 cells, into which had been spiked the same IUs of the virus, were cultured in parallel.

In an initial experiment, supernatants were collected at days 4 and 10 following initiation of the culture, and assessed for viral titer using the PG4 S+L indicator cell line according to standard techniques. For the test samples, only when the highest amount (IU) of virus (1000 infectious units (IU)) was spiked into cultures, was replicating virus observed at day 10 as detected by the standard PG4 S+L indicator cell line plaque assay. In the control samples in which permissive HEK293 cells had been spiked with the same viral amounts, replicating virus was observed to be detected in supernatants for each of the spiked-in amounts, determined using the PG4 S+L indicator cell line plaque assay, further confirming the ability of the assay to detect viral replication following the addition of each amount of virus.

Similar conditions were used in a study performed to confirm the ability of the exemplary provided RT-PCR-based RCR assay to detect low levels of replicating virus in samples in an ex vivo T cell culture process. Isolated T cells were thawed and activated with anti-CD3/anti-CD28 beads and were spiked with none of or with varying amounts of the wild-type GaLV replicating virus as described above, except that during the process, cells of some samples were transduced with a heterologous gene product using a GaLV-pseudotyped viral vector particle encoding the gene product (vector). The cells were cultured at 37° C. over a period of 10 days. Supernatant from expanded cultures was collected at days 4, 7 and 10 and assessed for viral titer using the PG4 S+L indicator cell line as described above. In addition, RNA was harvested from expanded T cells on days 4, 7, and 10 and assessed for the presence of viral RNA indicative of replicating virus using an exemplary RT-PCR assay essentially as described in Example 2 for GaLV viral RNA encoding env. In the RT-PCR assay, assay results were normalized by calculating delta $C_T$ values by substracting the GaLV $C_T$ value for an individual RNA sample from the $C_T$ value of the assay RNA positive control. As a comparison, an RCR co-culture assay was carried out by harvesting T cells at days 4, 7 and 10 and co-culturing the T cells with a HEK293 permissive cell line for an amplification period, followed by detection of the presence or absence of virus in supernatant of co-cultured cells using the PG4 S+L indicator cell line.

The study demonstrated that the assay could detect low levels of replicating virus, including with the same or greater sensitivity as compared to a standard co-culture plaque assay. The results for three different runs of each condition are set forth in Table 6. The PG4S+L− harvest titer is included to highlight that the PG4 S+L− indicator line is only able to detect RCR in some unamplified samples spiked with high levels of GaLV virus (1000 IU). As shown, the presence of replicating spiked-in virus, in samples following spike-in of replication-competent GaLV virus, was detectable in samples collected at 7 and 10 days post-culture initiation, using both the exemplary provided RT-PCR assay and the co-culture method. In samples collected at day 4, evidence of such replicating virus (in samples into which replication competent GaLV had been spiked) could be detected using the RT-PCR method, even in cases in which such replication was not detected using the co-culture assay.

TABLE 6

Comparison of RCR Co-Culture Assay Results to RT-PCR Results for Corresponding Samples

| | Run 1 | | | Run 2 | | | Run 3 | | |
|---|---|---|---|---|---|---|---|---|---|
| Sample | PG4 $S^+L^-$ Titer (Harvest) | RCR Co-Cult | GaLV RT-PCR | PG4 $S^+L^-$ Titer (Harvest) | RCR Co-cult | GaLV RT-PCR | PG4 $S^+L^-$ Titer (Harvest) | RCR Co-cult | GaLV RT-PCR |
| D4 Negative | | | | 0 | 0 | − | 0 | 0 | − |
| D4 10 IU GaLV | | | | 0 | 0 | + | 0 | 0 | − |
| D4 100 IU GaLV | | | | 0 | + | + | 0 | + | + |
| D4 1000 IU GaLV | | | | 0 | + | + | 0 | + | + |
| D4 10 IU GaLV + vector | | | | 0 | 0 | + | 0 | 0 | + |
| D4 100 IU GaLV + vector | | | | 0 | + | + | 0 | + | + |
| D4 1000 IU GaLV + vector | | | | 5 | + | + | 0 | + | + |
| D7 Negative | 0 | 0 | − | | 0 | − | 0 | 0 | − |
| D7 10 IU GaLV | | | | | 0 | − | 0 | 0 | − |
| D7 100 IU GaLV | 0 | + | + | | + | + | 0 | 0 | − |
| D7 1000 IU GaLV | 0 | + | + | | + | + | 0 | + | + |
| D7 10 IU GaLV + vector | | | | | + | + | 0 | 0 | − |
| D7 100 IU GaLV + vector | 0 | + | + | | + | + | 0 | 0 | + |
| D7 1000 IU GaLV + vector | 0 | + | + | | + | + | 0 | + | + |
| D10 Negative | 0 | 0 | − | 0 | 0 | − | 0 | 0 | − |
| D10 10 IU GaLV | | | | 0 | 0 | − | 0 | 0 | − |
| D10 100 IU GaLV | 0 | + | + | 0 | + | + | 0 | 0 | − |
| D10 1000 IU GaLV | 0 | + | + | TNTC | + | + | 25 | + | + |
| D10 10 IU GaLV + vector | | | | 0 | 0 | − | 0 | 0 | − |
| D10 100 IU GaLV + vector | 0 | + | + | 0 | + | + | 0 | 0 | − |
| D10 1000 IU GaLV + vector | 4 | + | + | TNTC | + | + | 50 | + | + |

TNTC = Too Numerous To Count

As shown in Table 6, the results for the RCR co-culture assay and the RT-PCR assay were aligned, with the exception of the four runs that are shaded. The RT-PCR assay detected GaLV virus RNA in samples spiked with 10 IU of GaLV virus at day 4 in one of the runs, but not at days 7 and 10, while the RCR co-culture assay for these samples did not detect GaLV RNA at any time points. Without wishing to be bound by theory, it is possible that the positive result at day 4 reflected detection of either a low level of RCR that did not replicate or residual RNA from the viral spikes. It is also possible that the negative results at days 7 and 10 reflected a dilution of the RCR or viral RNA below the detection threshold of the RT-PCR assay that occurred during media feeds of the cell cultures.

The RT-PCR and RCR co-culture assay also produced different results for the samples spiked with 10 IU of GaLV virus that were transduced with the gene encoding viral vector (vector). The RT-PCR assay was positive at days 4 and 7 but not day 10, while the RCR co-culture assay transitions were only positive on day 7. Without wishing to be bound by theory, it is possible that these results reflected an initial presence of RCR in the samples that did not sufficiently replicate to be detectable by day 10. Furthermore, it is possible that the inconsistent results of the RCR co-culture assay at days 4 and 7 indicated that the virus was near the detection limit for the assay. These results supported finding of the sensitivity of the GaLV RT-PCR assay.

Similar results were observed in samples spiked with 100 IU of GaLV virus and transduced with the viral gene vector. Both the RT-PCR and RCR co-culture assays detected virus at day 4, but only the GaLV RT-PCR assay detected GaLV RNA at day 7. Neither assay detected GaLV RNA on Day 10. As with the samples spiked with 10 IU of GaLV virus and transduced, it is possible that the initial levels of the GaLV virus did not sufficiently replicate to avoid dilution by the cell culture expansion. The detection of GaLV RNA at day 7 supported the increased sensitivity of the RT-PCR assay.

The results demonstrated the ability of the RT-PCR method to detect the presence of replication-competent retrovirus present in a T cell sample subjected to ex vivo culture, with the same or greater sensitivity as compared to a standard co-culture assay. In contrast to the co-culture assay involving a multi-week amplification for detection of GaLV virus, the GaLV RT-PCR assay was able to achieve detection of RCR in samples directly from cell composition samples.

Example 7: Exemplary Assay Assessing Levels of Parameters Indicative of Viral RNA Targets, Such as VSV-G and/or Rev Gag Primers and labeled probes directed to a VSV-G and rev present in a VSV-G pseudotyped replication competent lentivirus (RCL), as well as to a beta-actin (ACTB) control, were designed as shown in Table 7. The probes were labeled with either FAM or HEX-dye labels and were quenched with Iowa black non-fluorescent quenchers.

TABLE 7

Exemplary VSV-G, rev, and Actin Primer and Probe Sequences

| Primer | DNA Sequence | SEQ ID NO |
|---|---|---|
| VSV-G Forward Primer | ATTGCCCGTCAAGCTCAGAT | 35 |
| VSV-G Reverse Primer | GTGACTCTTGGGCATTTTGACTT | 36 |
| VSV-G Probe | TGGCATAATGACTTAATAGGCACAGCCTTA | 37 |
| rev Forward Primer | AGCGACGAAGACCTCCTCAAG | 38 |
| rev Reverse Primer | CTCTCCACCTTCTTCTTCTATTCCTTC | 39 |
| rev Probe | CAAGTTTCTCTATCAAAGCAACCCACCTCC | 40 |
| ACTB Forward Primer | GCGAGAAGATGACCCAGATCA | 41 |
| ACTB Reverse Primer | CCAGTGGTACGGCCAGAGG | 2 |
| ACTB Probe | CCAGCCATGTACGTTGCTATCCAGGC | 7 |

RT-PCR runs performed on vector production plasmids containing pol gene, rev gene and VSV-G gene verified that the primers and probes could selectively bind and detect the target genes. RT-PCR on RNA extracted from exemplary cell lines that express target RNA also was evaluated and confirmed detection of the target genes using the above primers and probes.

The primers and probes described in Table 4 are used in an RT-PCR assay performed on a cell composition containing heterologous nucleic acid introduced by transduction with VSV-G-expressing lentivirus. The RT-PCR assay is performed to assess if one or both of VSV-G and rev encoding viral RNA are present.

RNA is extracted from cell compositions, converted into complimentary DNA (cDNA), and amplified by conventional techniques. In an exemplary method, RNA is extracted with Qiagen RNeasy-Plus Mini Kit. Multiplex RT-PCR reactions are performed with the primers and probes for VSV-G and/or rev and ACTB that are displayed in Table 4. Isolated RNA from the each sample is mixed with forward and reverse primers and hydrolysis probes for VSV-G and/or rev and ACTB displayed in Table 4, and components for carrying out RT-PCR are added. In an exemplary method, components for carrying out the RT-PCR are provided by RNA UltraSense One-Step Quantitative RT-PCR Enzyme Mix and RNA UltraSense One-Step Quantitative RT-PCR 5× Reaction Mix (ThermoFisher Scientific). In some cases, PCR reactions for VSV-G and rev are run in multiplex in the same PCR wells. Inclusion of primers for detecting ACTB is used as a control to confirm RNA is present and verify RNA quality. Various controls are used in the assay, such as a plasmid based standard curve for VSV-G and/or rev, a cell culture based RNA control for VSV-G and/or rev and ACTB, no template control, and No-Reverse Transcriptase control reactions. The results of the RT-PCR reactions indicate if detectable levels of VSV-G and/or rev are present in the cell compositions.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| # | SEQUENCE | ANNOTATION |
|---|---|---|
| 1 | GCGAGAAGATGACCCAGATC | Actin forward primer |
| 2 | CCAGTGGTACGGCCAGAGG | Actin reverse primer |
| 3 | CCAGCCATGTACGTTGCTATCCAGGC | VIC-labeled actin probe |
| 4 | TCTGGGATACAAAGGCAGTCCA | GaLV env forward primer |
| 5 | GCCAAGGCACATACATCAGGTT | GaLV env reverse primer |
| 6 | CCCTTGGACTTGGTGGCCCACACT | FAM-labeled GaLV env probe |
| 7 | CCAGCCATGTACGTTGCTATCCAGGC | beta Actin probe |
| 8 | CCA GTG GTA CGG CCA GAC C | Actin reverse primer |
| 9 | CCA GCC ATG TAC GTT GCT ATC CAG GC | Vic-labeled Actin hydrolysis probe |
| 10 | AAGGCCAACCGCGAGAAG | Actin forward primer |
| 11 | ACAGCCTGGATAGCAACGTACA | Actin reverse primer |
| 12 | TGACCCAGATCATGTTT | HEX-labeled Actin hydrolysis probe |
| 13 | TTCTACAATGAGCTGCGTG | Actin forward primer |
| 14 | CCTGGATAGCAACGTACATGG | Actin reverse primer |
| 15 | CTGAACCCCAAGGCCAACCG | HEX-labeled Actin hydrolysis probe |
| 16 | ACTCCACTACCTCGCAGGCAT | MMLV gag forward primer |
| 17 | AGA GGA GAA CGG CCA GTA TTG | MMLV gag reverse primer |
| 18 | CCGCGCAGGAGGAAACGGACA | Fam-labeled MMLV gag hydrolysis probe |

-continued

SEQUENCES

| # | SEQUENCE | ANNOTATION |
|---|---|---|
| 19 | CTCCTTCTCTAGGCGCCAAA | MMLV gag forward primer |
| 20 | GCG GCC CCC CAC TGT | MMLV gag reverse primer |
| 21 | CTAAACCTCAAGTTCTTTC | Fam-labeled MMLV gag hydrolysis probe |
| 22 | GGACAGAAACAGGATAGACAGG | MMLV gag forward primer |
| 23 | TCGTGGTTTCTTGGGACAATC | MMLV gag reverse primer |
| 24 | CCAGTGCCCCTTTTCTTTGCAGT | Fam-labeled MMLV gag hydrolysis probe |
| 25 | atggtattgctgcctgggtccatgcttctcacctcaaacctgcaccaccttcggcaccagatgagtcctgggagct<br>ggaaaagactgatcatcctcttaagctgcgtattcggcggcggcgggacgagtctgcaaaataagaacccccac<br>cagcccatgaccctcacttggcaggtactgtcccaaactggagacgttgtctgggatacaaaggcagtccagcc<br>cccttggacttggtggcccacacttaaacctgatgtatgtgccttggcggctagtcttgagtcctgggatatcccgg<br>gaaccgatgtctcgtcctctaaacgagtcagacctccggactcagactatactgccgcttataagcaaatcacctg<br>gggagccatagggtgcagctaccctcgggctaggactagaatggcaagctctaccttctacgtatgtccccggg<br>atggccggaccctacagaagctagaaggtgcggggggctagaatccctatactgtaaagaatgggattgtgag<br>accacggggaccggttattggctatctaaatcctcaaaagacctcataactgtaaaatgggaccaaaatagcgaa<br>tggactcaaaaatttcaacagtgtcaccagaccggctggtgtaaccccttaaaatagatttcacagacaaagga<br>aaattatccaaggactggataacgggaaaaacctggggattaagattctatgtgtctggacatccaggcgtacag<br>ttcaccattcgcttaaaaatcaccaacatgccagctgtggcagtaggtcctgacctcgtccttgtggaacaaggac<br>ctcctagaacgtccctcgctctcccacctcctcttcccccaagggaagcgccaccgccatctctccccgactctaa<br>ctccacagccctggcgactagtgcacaaactcccacggtgagaaaaacaattgttaccctaaacactccgcctcc<br>caccacaggcgacagactattgatcttgtgcagggggcatcctaaccttaaatgctaccaacccaggggccac<br>tgagtcttgctggctagtaggccatgggcccccttattatgaagcaatagcctcatcaggagaggtcgcctact<br>ccaccgaccttgaccggtgccgctgggggacccaaggaaagctcaccctcactgaggtctcaggacacgggtt<br>gtgcataggaaaggtgccctttacccatcagcatctctgcaatcagaccctatccatcaattcctccggagaccat<br>cagtatctgctcccctccaaccatagctggtgggcttgcagcactggcctcaccccttgcctctccacctcagttta<br>aatcagactagagatactgtatccaggtccagctgattcctcgcatctattactatcctgaagaagttagttacagg<br>cctatgacaattctcaccccaggactaaaagagaggctgtctcacttaccctagctgttttactggggttgggaatc<br>acggcgggaataggtactggacaactgccttaattaaaggacctatagacctccagcaaggcctgacaagcctc<br>cagatcgccatagatgctgacctccgggccctccaagactcagtcagcaagttagaggactcactgacttccctg<br>tccgaggtagtgctccaaaataggagaggccttgacttgctgtactaaaagaaggtggcctctgtgcggccctaa<br>aggaagagtgctgtttttacatagaccactcaggtgcagtacgggactccatgaaaaaactcaaagaaaaactgg<br>ataaaagacagttagagcgccagaaaagccaaaactggtatgaaggatggacaataactcccatggacacta<br>ccctgctatcaaccatcgctgggcccctattactcctccttctgttgctcatcctcgggccatgcatcatcaataagtt<br>agttcaattcatcaatgataggataagtgcagttaaaattctggtccttagacagaaatatcaggccctagagaacg<br>aaggtaacctttaa | GaLV env NC_001885.2 Nucleotides 5552-7609 |
| 26 | AACAGAGATCGATCTGTTTCCTTGACACTATGAAGTGCCTTTTGTAC<br>TTAGCCTTTTTATTCATTGGGGTGAATTGCAAGTTCACCATAGTTTT<br>TCCACACAACCAAAAAGGAAACTGGAAAAATGTTCCTTCTAATTAC<br>CATTATTGCCCGTCAAGCTCAGATTTAAATTGGCATAATGACTTAAT<br>AGGCACAGCCATACAAGTCAAAATGCCCAAGAGTCACAAGGCTATT<br>CAAGCAGACGGTTGGATGTGTCATGCTTCCAAATGGGTCACTACTT<br>GTGATTTCCGCTGGTATGGACCGAAGTATATAACACAGTCCATCCG<br>ATCCTTCACTCCATCTGTAGAACAATGCAAGGAAAGCATTGAACAA<br>ACGAAACAAGGAACTTGGCTGAATCCAGGCTTCCCTCCTCAAAGTT<br>GTGGATATGCAACTGTGACGGATGCCGAAGCAGTGATTGTCCAGGT<br>GACTCCTCACCATGTGCTGGTTGATGAATACACAGGAGAATGGGTT<br>GATTCACAGTTCATCAACGGAAAATGCAGCAATTACATATGCCCCA<br>CTGTCCATAACTCTACAACCTGGCATTCTGACTATAAGGTCAAAGG<br>GCTATGTGATTCTAACCTCATTTCCATGGACATCACCTTCTTCTCAG<br>AGGACGGAGAGCTATCATCCCTGGGAAAGGAGGGCACAGGGTTCA<br>GAAGTAACTACTTTGCTTATGAAACTGGAGGCAAGGCCTGCAAAAT<br>GCAATACTGCAAGCATTGGGGAGTCAGACTCCCATCAGGTGTCTGG<br>TTCGAGATGGCTGATAAGGATCTCTTTGCTGCAGCCAGATTCCCTGA<br>ATGCCCAGAAGGGTCAAGTATCTCTGCTCCATCTCAGACCTCAGTG<br>GATGTAAGTCTAATTCAGGACGTTGAGAGGATCTTGGATTATTCCCT<br>CTGCCAAGAAACCTGGAGCAAAATCAGAGCGGGTCTTCCAATCTCT<br>CCAGTGGATCTCAGCTATCTTGCTCCTAAAAACCCAGGAACCGGTC | VSVG env gi\|9627229: 3049-4713 |

-continued

SEQUENCES

| # | SEQUENCE | ANNOTATION |
|---|---|---|
| | CTGCTTTCACCATAATCAATGGTACCCTAAAATACTTTGAGACCAG<br>ATACATCAGAGTCGATATTGCTGCTCCAATCCTCTCAAGAATGGTC<br>GGAATGATCAGTGGAACTACCACAGAAAGGGAACTGTGGGATGAC<br>TGGGCACCATATGAAGACGTGGAAATTGGACCCAATGGAGTTCTGA<br>GGACCAGTTCAGGATATAAGTTTCCTTTATACATGATTGGACATGGT<br>ATGTTGGACTCCGATCTTCATCTTAGCTCAAAGGCTCAGGTGTTCGA<br>ACATCCTCACATTCAAGACGCTGCTTCGCAACTTCCTGATGATGAG<br>AGTTTATTTTTTGGTGATACTGGGCTATCCAAAAATCCAATCGAGCT<br>TGTAGAAGGTTGGTTCAGTAGTTGGAAAAGCTCTATTGCCTCTTTTT<br>TCTTTATCATAGGGTTAATCATTGGACTATTCTTGGTTCTCCGAGTT<br>GGTATCCATCTTTGCATTAAATTAAAGCACACCAAGAAAAGACAGA<br>TTTATACAGACATAGAGATGAACCGACTTGGAAAGTAACTCAAATC<br>CTGCACAACAGATTCTTCATGTTTGGACCAAATCAACTTGTGATACC<br>ATGCTCAAAGAGGCCTCAATTATATTTGAGTTTTTAATTTTTATG | |
| 27 | atgggccagactgttaccactcccttaagtttgaccttaggtcactggaaagatgtcgagcggatcgctcacaacc<br>agtcggtagatgtcaagaagagacgttgggttaccttctgctctgcagaatggccaacctttaacgtcggatggcc<br>gcgagacggcacctttaaccgagacctcatcacccaggttaagatcaaggtcttttcacctggcccgcatggaca<br>cccagaccaggtcccctacatcgtgacctgggaagccttggcttttgacccccctccctgggtcaagccctttgta<br>caccctaagcctccgcctcctcttcctccatccgccccgtctctccccctgaacctcctcgttcgaccccgcctcg<br>atcctccctttatccagccctcactccttctctaggcgccaaacctaaacctcaagttctttctgacagtgggggc<br>cgctcatcgacctacttacagaagacccccgccttatagggacccaagaccaccccttccgacagggacgg<br>aaatggtggagaagcgacccctgcgggagaggcaccggacccctccccaatggcatctcgcctacgtgggag<br>acgggagcccccctgtggccgactccactacctcgcaggcattccccctccgcgcaggaggaaacggacagct<br>tcaatactggccgttctcctcttctgacctttacaactggaaaaataataaccatctattctgaagatccaggtaaac<br>tgacagctctgatcgagtctgttctcatcacccatcagcccacctgggacgactgtcagcagctgttggggactct<br>gctgaccggagaagaaaaacaacgggtgctcttagaggctagaaaggcggtgcggggcgatgatgggcgcc<br>ccactcaactgcccaatgaagtcgatgccgcttttcccctcgagcgcccagactgggattacaccacccaggca<br>ggtaggaaccacctagtccactatcgccagttgctcctagcgggtctccaaaacgcgggcagaagccccacca<br>atttggccaaggtaaaaggaataacacaagggcccaatgagtctccctcggccttcctagagagacttaaggaa<br>gcctatcgcaggtacactccttatgaccctgaggacccagggcaagaaactaatgtgtctatgtctttcatttggca<br>gtctgccccagacattgggagaaagttagagaggttagaagatttaaaaaacaagacgcttggagatttggttag<br>agaggcagaaaagatctttaataaacgagaaaccccggaagaaagagaggaacgtatcaggagagaaacag<br>aggaaaaagaagaacgccgtaggacagaggatgagcagaaagagaaagaaagagatcgtaggagacatag<br>agagatgagcaagctattggccactgtcgttagtggacagaaacaggatagacagggaggagaacgaaggag<br>gtcccaactcgatcgcgaccagtgtgcctactgcaaagaaaaggggcactgggctaaagattgtcccaagaaa<br>ccacgaggacctcggggaccaagaccccagacctccctcctgaccctagatgactag | MMLV gag<br>NC_001501.1<br>Nucleotides<br>357_1973 |
| 28 | ACCGCCGAGACCGCGTCCGCCCCGCGAGCACAGAGCCTCGCCTTTG<br>CCGATCCGCCGCCCGTCCACACCCGCCGCCAGGTAAGCCCGGCCAG<br>CCGACCGGGGCAGGCGGCTCACGGCCCGGCCGCAGGCGGCCGCGG<br>CCCCTTCGCCCGTGCAGAGCCGCCGTCTGGGCCGCAGCGGGGGGCG<br>CATGGGGGGGGAACCGGACCGCCGTGGGGGGCGCGGGAGAAGCCC<br>CTGGGCCTCCGGAGATGGGGGACACCCCACGCCAGTTCGGAGGCGC<br>GAGGCCGCGCTCGGGAGGCGCGCTCCGGGGGTGCCGCTCTCGGGGC<br>GGGGGCAACCGGCGGGGTCTTTGTCTGAGCCGGGCTCTTGCCAATG<br>GGGATCGCAGGGTGGGCGCGGCGGAGCCCCCGCCAGGCCCGGTGG<br>GGGCTGGGGCGCCATTGCGCGTGCGCGCTGGTCCTTTGGGCGCTAA<br>CTGCGTGCGCGCTGGGAATTGGCGCTAATTGCGCGTGCGCGCTGGG<br>ACTCAAGGCGCTAACTGCGCGTGCGTTCTGGGGCCCGGGGTGCCGC<br>GGCCTGGGCTGGGGCGAAGGCGGGCTCGGCCGGAAGGGGTGGGGT<br>CGCCGCGGCTCCCGGGCGCTTGCGCGCACTTCCTGCCCGAGCCGCT<br>GGCCGCCCGAGGGTGTGGCCGCTGCGTGCGCGCGCGCCGACCCGGC<br>GCTGTTTGAACCGGGCGGAGGCGGGGCTGGCGCCCGGTTGGGAGG<br>GGGTTGGGGCCTGGCTTCCTGCCGCGCGCCGCGGGGACGCCTCCGA<br>CCAGTGTTTGCCTTTTATGGTAATAACGCGGCCGGCCCGGCTTCCTT<br>TGTCCCCAATCTGGGCGCGCGCCGGCGCCCCCTGGCGGCCTAAGGA<br>CTCGGCGCGCCGGAAGTGGCCAGGGCGGGGGCGACCTCGGCTCAC<br>AGCGCGCCCGGCTATTCTCGCAGCTCACCATGGATGATGATATCGC<br>CGCGCTCGTCGTCGACAACGGCTCCGGCATGTGCAAGGCCGGCTTC<br>GCGGGCGACGATGCCCCCCGGGCCGTCTTCCCCTCCATCGTGGGGC<br>GCCCCAGGCACCAGGTAGGGGAGCTGGCTGGGTGGGGCAGCCCCG<br>GGAGCGGGCGGGAGGCAAGGGCGCTTTCTCTGCACAGGAGCCTCCC<br>GGTTTCCGGGGTGGGGGCTGCGCCCGTGCTCAGGGCTTCTTGTCCTT<br>TCCTTCCCAGGGCGTGATGGTGGGCATGGGTCAGAAGGATTCCTAT<br>GTGGGCGACGAGGCCCAGAGCAAGAGAGGCATCCTCACCCTGAAG<br>TACCCCATCGAGCACGGCATCGTCACCAACTGGGACGACATGGAGA<br>AAATCTGGCACCACACCTTCTACAATGAGCTGCGTGTGGCTCCCGA<br>GGAGCACCCCGTGCTGCTGACCGAGGCCCCCCTGAACCCCAAGGCC<br>AACCGCGAGAAGATGACCCAGGTGAGTGGCCCGCTACCTCTTCTGG<br>TGGCCGCCTCCCTCCTTCCTGGCCTCCCGGAGCTGCGCCCTTTCTCA<br>CTGGTTCTCTCTTCTGCCGTTTTCCGTAGGACTCTCTTCTCTGACCTG<br>AGTCTCCTTTGGAACTCTGCAGGTTCTATTTGCTTTTTCCCAGATGA<br>GCTCTTTTTCTGGTGTTTGTCTCTCTGACTAGGTGTCTAAGACAGTG<br>TTGTGGGTGTAGGTACTAACACTGGCTCGTGTGACAAGGCCATGAG | Human beta<br>actin |

-continued

SEQUENCES

| # | SEQUENCE | ANNOTATION |
|---|---|---|
| | GCTGGTGTAAAGCGGCCTTGGAGTGTGTATTAAGTAGGTGCACAGT<br>AGGTCTGAACAGACTCCCCATCCCAAGACCCCAGCACACTTAGCCG<br>TGTTCTTTGCACTTTCTGCATGTCCCCCGTCTGGCCTGGCTGTCCCCA<br>GTGGCTTCCCCAGTGTGACATGGTGTATCTCTGCCTTACAGATCATG<br>TTTGAGACCTTCAACACCCCAGCCATGTACGTTGCTATCCAGGCTGT<br>GCTATCCCTGTACGCCTCTGGCCGTACCACTGGCATCGTGATGGACT<br>CCGGTGACGGGGTCACCCACACTGTGCCCATCTACGAGGGGTATGC<br>CCTCCCCCATGCCATCCTGCGTCTGGACCTGGCTGGCCGGGACCTG<br>ACTGACTACCTCATGAAGATCCTCACCGAGCGCGGCTACAGCTTCA<br>CCACCACGGCCGAGCGGGAAATCGTGCGTGACATTAAGGAGAAGC<br>TGTGCTACGTCGCCCTGGACTTCGAGCAAGAGATGGCCACGGCTGC<br>TTCCAGCTCCTCCCTGGAGAAGAGCTACGAGCTGCCTGACGGCCAG<br>GTCATCACCATTGGCAATGAGCGGTTCCGCTGCCCTGAGGCACTCTT<br>CCAGCCTTCCTTCCTGGGTGAGTGGAGACTGTCTCCCGGCTCTGCCT<br>GACATGAGGGTTACCCCTCGGGGCTGTGCTGTGGAAGCTAAGTCCT<br>GCCCTCATTTCCCTCTCAGGCATGGAGTCCTGTGGCATCCACGAAAC<br>TACCTTCAACTCCATCATGAAGTGTGACGTGGACATCCGCAAAGAC<br>CTGTACGCCAACACAGTGCTGTCTGGCGGCACCACCATGTACCCTG<br>GCATTGCCGACAGGATGCAGAAGGAGATCACTGCCCTGGCACCCAG<br>CACAATGAAGATCAAGGTGGGTGTCTTTCCTGCCTGAGCTGACCTG<br>GGCAGGTCGGCTGTGGGGTCCTGTGGTGTGTGGGGAGCTGTCACAT<br>CCAGGGTCCTCACTGCCTGTCCCCTTCCCTCCTCAGATCATTGCTCC<br>TCCTGAGCGCAAGTACTCCGTGTGGATCGGCGGCTCCATCCTGGCC<br>TCGCTGTCCACCTTCCAGCAGATGTGGATCAGCAAGCAGGAGTATG<br>ACGAGTCCGGCCCCTCCATCGTCCACCGCAAATGCTTCTAGGCGGA<br>CTATGACTTAGTTGCGTTACACCCTTTCTTGACAAAACCTAACTTGC<br>GCAGAAAACAAGATGAGATTGGCATGGCTTTATTTGTTTTTTTTGTT<br>TTGTTTTGGTTTTTTTTTTTTTTTTGGCTTGACTCAGGATTTAAAAAC<br>TGGAACGGTGAAGGTGACAGCAGTCGGTTGGAGCGAGCATCCCCC<br>AAAGTTCACAATGTGGCCGAGGACTTTGATTGCACATTGTTGTTTTT<br>TTAATAGTCATTCCAAATATGAGATGCGTTGTTACAGGAAGTCCCTT<br>GCCATCCTAAAAGCCACCCCACTTCTCTCTAAGGAGAATGGCCCAG<br>TCCTCTCCCAAGTCCACACAGGGGAGGTGATAGCATTGCTTTCGTGT<br>AAATTATGTAATGCAAAATTTTTTTAATCTTCGCCTTAATACTTTTTT<br>ATTTTGTTTTATTTTGAATGATGAGCCTTCGTGCCCCCCCTTCCCCCT<br>TTTTTGTCCCCCAACTTGAGATGTATGAAGGCTTTTGGTCTCCCTGG<br>GAGTGGGTGGAGGCAGCCAGGGCTTACCTGTACACTGACTTGAGAC<br>CAGTTGAATAAAAGTGCACACCTTAAAAATGA | |
| 29 | ctagggaggtcagggtcaggagcccccccctgaacccaggataaccctcaaagtcgggggcaacccgtca<br>ccttcctggtagatactggggcccaacactccgtgctgacccaaaatcctggaccccctaagtgataagtctgcct<br>gggtccaaggggctactggaggaaagcggtatcgctggaccacggatcgcaaagtacatctagctaccggtaa<br>ggtcacccactctttcctccatgtaccagactgtccctatcctctgttaggaagagatttgctgactaaactaaaagc<br>ccaaatccactagagggatcaggagctcaggttatgggaccaatggggcagcccctgcaagtgttgaccctaa<br>atatagaagatgagcatcggctacatgagacctcaaaagagccagatgtactctagggtccacatggctgtctga<br>ttacctcaggcctgggcggaaaccgggggcatgggactggcagttcgccaagctcctctgatcatacctctgaa<br>agcaacctctaccccgtgtccataaaacaataccccatgtcacaagaagccagactggggatcaagccccac<br>atacagagactgttggaccagggaatactggtaccctgccagtcccctggaacacgcccctgctacccgttaa<br>gaaaccagggactaatgattataggcctgtccaggatctgagagaagtcaacaagcgggtggaagacatccac<br>cccaccgtgcccaacccttacaacctcttgagcgggctcccaccgtcccaccagtggtacactgtgcttgatttaa<br>aggatgcctttttctgcctgagactccaccccaccagtcagcctctcttcgcctagagtggagagatccagagat<br>gggaatctcaggacaattgacctggaccagactcccacagggtacaaaaacagtcccaccctgtagatgaggc<br>actgcacagagacctagcagacttccggatccagcacccagacttgatcctgctacagtacgtggatgacttact<br>gctggccgccacttctgagctagactgccaacaaggtactcgggccctgttacaaaccctagggaacctcgggt<br>atcgggcctcggccaagaaagcccaaatttgccagaaacaggtcaagtatctggggtatcttctaaaagagggt<br>cagagatggctgactgaggccagaaaagagactgtgatggggcagcctactccgaagacccctcgacaacta<br>agggagttcctagggacggcaggcttctgtcgcctctggatccctgggtttgcagaaatggcagccccttgtac<br>cctctcaccaaaacggggactctgtttaattggggcccagaccaacaaaaggcctatcaagaaatcaagcaagc<br>tcttctaactgccccagccctggggttgccagatttgactaagccctttgaactctttgtcgacgagaagcagggct<br>acgccaaaggtgtcctaacgcaaaaactgggaccttggcgtcggccggtggcctacctgtccaaaaagctaga<br>cccagtagcagctgggtggccccttgcctacggatggtagcagccattgccgtactgacaaaggatgcaggc<br>aagctaaccatgggacagccactagtcattctggccccccatgcagtagaggcactagtcaaacaaccccccg<br>accgctggctttccaacgcccggatgactcactatcaggccttgcttttggacacggaccgggtccagttcggac<br>cggtggtagccctgaacccggctacgctgctcccactgcctgaggaagggctgcaacacaactgccttgatatc<br>ctggccgaagcccacggaacccgacccgacctaacggaccagccgctcccagacgccgaccacacctggta<br>cacggatggaagcagtctcttacaagagggacagcgtaaggcgggagctgcggtgaccaccgagaccgagg<br>taatctgggctaaagccctgccagccgggacatccgctcagcgggctgaactgatagcactcacccaggccct<br>aaagatggcagaaggtaagaagctaaatgtttatactgatagccgttatgcttttgctactgcccatatccatggag<br>aaatatacagaaggcgtgggttgctcacatcagaaggcaaagagatcaaaaataaagacgagatcttggcccta<br>ctaaaagccctctttctgcccaaaagacttagcataatccattgtccaggacatcaaaagggacacagcgccgag<br>gctagaggcaaccggatggctgaccaagcggcccgaaaggcagccatcacagagactccagacacctctac<br>cctcctcatagaaaattcatcaccctacacctcagaacattttcattacacagtgactgatataaaggacctaacca<br>agttgggggccatttatgataaaacaaagaagtattgggtctaccaaggaaaacctgtgatgcctgaccagtttac<br>ttttgaattattagactttcttcatcagctgactcacctcagcttctcaaaaatgaaggctctcctagagagaagccac<br>agtccctactacatgctgaaccgggatcgaacactcaaaaatatcactgagacctgcaaagcttgtgcacaagtc | MLV pol<br>NC_001501.1<br>Nucleotides<br>1970-5573 |

-continued

SEQUENCES

| # | SEQUENCE | ANNOTATION |
|---|---|---|
| | aacgccagcaagtctgccgttaaacagggaactagggtccgcgggcatcggcccggcactcattgggagatc<br>gatttcaccgagataaagcccggattgtatggctataaatatcttctagtttttatagatacctttttctggctggatagaa<br>agccttcccaaccaagaaagaaaccgccaaggtcgtaaccaagaagctactagaggagatcttccccaggttc<br>ggcatgcctcaggtattgggaactgacaatgggcctgccttcgtctccaaggtgagtcagacagtggccgatctg<br>ttggggattgattggaaattacattgtgcatacagaccccaaagctcaggccaggtagaaagaatgaatagaacc<br>atcaaggagactttaactaaattaacgcttgcaactggctctagagactgggtgctcctactccccttagccctgta<br>ccgagcccgcaacacgccgggccccccatggcctcaccccatatgagatcttatatggggcacccccgcccctt<br>gtaaacttccctgaccctgacatgacaagagttactaacagcccctctctccaagctcacttacaggctctctactt<br>agtccagcacgaagtctggagacctctggcggcagcctaccaagaacaactggaccgaccggtggtacctca<br>cccttaccgagtcggcgacacagtgtgggtccgccgacaccagactaagaacctagaacctcgctggaaagg<br>accttacacagtcctgctgaccacccccaccgccctcaaagtagacggcatcgcagcttggatacacgccgccc<br>acgtgaaggctgccgaccccgggggtggaccatcctctagactgacatggcgcgttcaacgctctcaaaaccc<br>cttaaaaataaggttaacccgcgaggcccccctaa | |
| 30 | tcgacatgggccagactgttaccactcccttaagtttgaccttaggtcactggaaagatgtcgagcggatcgctca<br>caaccagtcggtagatgtcaagaagagacgagggttaccttctgctctgcagaatggccaacctttaacgtcgg<br>atggccgcgagacggcacctttaaccgagacctcatcacccaggttaagatcaaggtcttttcacctggcccgca<br>tggacacccagaccaggtcccctacatcgtgacctgggaagccttggcttttgacccccctccctgggtcaagcc<br>ctttgtacaccctaagcctccgcctcctcttcctccatccgccccgtctctccccccttgaacctcctcgttcgacccc<br>gcctcgatcctccctttatccagccctcactccttctctaggcgccaaacctaaacctcaagttctttctgacagtgg<br>ggggccgctcatcgacctacttacagaagaccccccgccttatagggacccaagaccaccccccttccgacagg<br>gacggaaatggtggagaagcgacccctgcgggagaggcaccggacccctccccaatggcatctcgcctacgt<br>gggagacgggagcccccctgtggccgactccactacctcgcaggcattccccctccgcgcaggaggaaacgg<br>acagcttcaatactggccgttctcctcttctgacctttacaactggaaaaataataacccttctttttctgaagatccag<br>gtaaactgacagctctgatcgagtctgttctcatcacccatcagcccacctgggacgactgtcagcagctgttggg<br>gactctgctgaccggagaagaaaaacaacgggtgctcttagaggctagaaaggcggtgcggggcgatgatgg<br>gcgccccactcaactgcccaatgaagtcgatgccgcttttcccctcgagcgcccagactgggattacaccaccc<br>aggcaggtaggaaccacctagtccactatcgccagttgctcctagcgggtctccaaaacgcgggcagaagccc<br>caccaatttggccaaggtaaaaggaataacacaagggcccaatgagtctccctcggccttcctagagagactta<br>aggaagcctatcgcaggtacactccttatgaccctgaggacccagggcaagaaactaatgtgtctatgtctttcatt<br>tggcagtctgccccagacattgggagaaagttagagaggttagaagatttaaaaaacaagacgcttggagatttg<br>gttagagaggcagaaaagatctttaataaacgagaaaccccggaagaaagagaggaacgtatcaggagagaa<br>acagaggaaaaagaagaacgccgtaggacagaggatgagcagaaagagaaagaaagagatcgtaggagac<br>atagagagatgagcaagctattggccactgtcgttagtggacagaaacaggatagacagggaggagaacgaa<br>ggaggtcccaactcgatcgcgaccagtgtgcctactgcaaagaaaaggggcactgggctaaagattgtcccaa<br>gaaaccacgaggacctcggggaccaagaccccagacctccctcctgaccctagatgactagaagcttatcagtt<br>ctggaccagcgagctgtgctgcgactcgtggcgtaatcatggtcatagctgtttcctgtgtgaaattgttatccgct<br>cacaattccacacaacatacgagccggaagcataaagtgtaaagcctggggtgcctaatgagtgagctaactca<br>cattaattgcgttgcgctcactgcccgctttccagtcgggaaacctgtcgtgccagctgcattaatgaatcggcca<br>acgcgcggggagaggcggtagcgtattgggcgctcttccgcttcctcgctcactgactcgctgcgctcggtcgt<br>tcggctgcggcgagcggtatcagctcactcaaaggcggtaatacggttatccacagaatcaggggataacgca<br>ggaaagaacatgtgagcaaaaggccagcaaaaggccaggaaccgtaaaaaggccgcgttgctggcgtttttcc<br>ataggctccgcccccctgacgagcatcacaaaaatcgacgctcaagtcagaggtggcgaaacccgacaggac<br>tataaagataccaggcgtttccccctggaagctccctcgtgcgctctcctgttccgaccctgtcgcttaccggatac<br>ctgtccgcctactcccttcgggaagcgtggcgctactcatagctcacgctgtaggtatctcagttcggtgtaggtc<br>gttcgctccaagctgggctgtgtgcacgaaccccccgttcagcccgaccgctgcgccttatccggtaactatcgt<br>cttgagtccaacccggtaagacacgacttatcgccactggcagcagccactggtaacaggattagcagagcga<br>ggtatgtaggcggtgctacagagttcttgaagtggtggcctaactacggctacactagaagaacagtatttggtat<br>ctgcgctctgctgaagccagttaccttcggaaaaagagttggtagctcttgatccggcaaacaaaccaccgctgg<br>tagcggtggtttttttgtttgcaagcagcagattacgcgcagaaaaaaaggatctcaagaagatcctttgatcttttct<br>acggggtctgacgctcagtggaacgaaaactcacgttaagggattttggtcatgagattatcaaaaaggatcttca<br>cctagatccttttaaattaaaaatgaagttttaaatcaatctaaagtatatatgagtaaacttggtctgacagttaccaa<br>tgcttaatcagtgaggcacctatctcagcgatctgtctatttcgttcatccatagttgcctgactccccgtcgtgtaga<br>taactacgatacgggagggcttaccatctggccccagtgctgcaatgataccgcgagacccacgctcaccggct<br>ccagatttatcagcaataaaccagccagccggaagggccgagcgcagaagtggtcctgcaactttatccgcctc<br>catccagtctattaattgttgccgggaagctagagtaagtagttcgccagttaatagtttgcgcaacgttgttgccatt<br>gctacaggcatcgtggtgtcacgctcgtcgtttggtatggcttcattcagctccggttcccaacgatcaaggcgag<br>ttacatgatcccccatgttgtgcaaaaaagcggttagctccttcggtcctccgatcgttgtcagaagtaagttggcc<br>gcagtgttatcactcatggttatggcagcactgcataattctcttactgtcatgccatccgtaagatgcttttctgtgac<br>tggtgagtactcaaccaagtcattctgagaatagtgtatgcggcgaccgagttgctcttgcccggcgtcaatacgg<br>gataataccgcgccacatagcagaactttaaaagtgctcatcattggaaaacgacttcggggcgaaaactctcaa<br>ggatcttaccgctgagagatccagttcgatgtaacccactcgtgcacccaactgatcttcagcatcttttactacac<br>cagcgtttctgggtgagcaaaaacaggaaggcaaaatgccgcaaaaaagggaataagggcgacacggaaat<br>gttgaatactcatactctacctttttcaatattattgaagcatttatcagggttattgtctcatgagcggatacatatttga<br>atgtatttagaaaaataaacaaataggggttccgcgcacatttccccgaaaagtgccacctgacgtctaagaaac<br>cattattatcatgacattaacctataaaaataggcgtatcacgaggccctacgtctcgcgcgtacggtgatgacgg<br>tgaaaacctctgacacatgcagctcccggagacggtcacagcttgtctgtaagcggatgccgggagcagacaa<br>gcccgtcagggcgcgtcagcgggtgttggcgggtgtcggggctggcttaactatgcggcatcagagcagattg<br>tactgagagtgcaccaaatgcggtgtgaaataccgcacagatgcgtaaggagaaaataccgcatcaggcgcca<br>ttcgccattcaggctgcgcaactgttgggaagggcgatcggtgcgggcctcatcgctattacgccagctggcga<br>aaggggggatgtgctgcaaggcgattaagttgggtaacgccagggttttcccagtcacgacgttgtaaaacgacg<br>gccagtgcaacgcgatgacgatggatagcgattcatcgatgagctgacccgatcgccgccgccggagggttgc<br>gtttgagacgggcgacagatgaattccttctacaatgagctgcgtgtggctcccgaggagcaccccgtgctgctg | pActin-mmLvgag |

-continued

SEQUENCES

| # | SEQUENCE | ANNOTATION |
|---|---|---|
| | accgaggccccctgaaccccaaggccaaccgcgagaagatgacccagatcatgtttgagaccttcaacaccc<br>cagccatgtacgttgctatccaggctgtgctatccctgtacgcctctggccgtaccactggcatcgtgatggactc<br>cggtgacggggtcacccacactgtgcccatctg | |
| 31 | atgggagcacgggctagtgttctttctggaggtgagcttgacaggtgggagaagatcagactgcgccccggcg<br>gcaaaaagaagtacaagctgaagcacatcgtgtgggcctctcgcgaattggagaggtttgccgtgaaccccgg<br>gctcctggagacaagcgaggggtgccggcagatcctcggccaattgcagcccagtttgcaaaccggcagcga<br>ggagttgcggagcctgtacaacaccgtggccacattgtactgcgtccaccagcgcatcgaaatcaaggatacaa<br>aagaggccctggataaaatcgaagaggaacagaataagagcaaaaagaaggcccaacaagccgccgctgat<br>accggccattctaaccaagtgtctcagaactatcccatcgtccaaaatattcaaggccagatggtccaccaagcta<br>tcagcccccggaccctgaacgcctgggtgaaggtggtggaggaaaaagccttactcccgaggtcatccctatg<br>ttcagcgccctgagcgagggcgctacaccccaggacctgaatacaatgttgaataccgtcggcggccaccagg<br>ccgctatgcagatgctgaaggaaacaattaacgaagaggccgccgagtgggaccgggtccaccccgtccagg<br>ctggccccatcgcacccgggcaaatgcgggagccgagaggctccgatatcgccggcaccacctccacattgc<br>aagagcagatcggctggatgaccaacaatcccccaattcccgtgggcgagatctacaagcggtggatcattctc<br>ggcctgaacaagatcgtgcggatgtactctcccacatctatcctcgatatccggcagggccccaaagagcctttc<br>cgggattacgtggatagattttacaagaccttgcgggctgaacaggccagccaagaagtgaagaactggatgac<br>ggagacactcctcgtgcagaacgccaatcccgactgcaaaaccatcctgaaggccttgggcccagccgccac<br>cttggaggagatgatgaccgcctgccaaggcgtgggaggccctgggcacaaagcccgggtgctcgccgagg<br>ccatgtctcaggtgaccaacagcgccacaatcatgatgcaacgggggaacttccgcaatcagcggaaaatcgt<br>gaaatgctttaactgtggcaaagaagggcacacagcccgcaactgcagggcccctaggaaaaagggctgttg<br>gaaatgtggaaaggaaggacaccaaatgaaagattgtactgagagacaggctaattattagggaagatctggc<br>cttcccacaagggaaggccagggaattttcttcagagcagaccagagccaacagccccaccagaagagagctt<br>caggtttggggaagagacaacaactccctctcagaagcaggagccgatagacaaggaactgtatcctttagctt<br>ccctcagatcactctttggcagcgacccctcgtcacaataa | HIV Gag |
| 32 | atgtcactccctggtcggtggaagcctaagatgattggtggtataggggggcttcattaaggtgcggcaatacgac<br>caaatcttgatcgagatttgcggccacaaggccatcggcaccgtgctggtgggccccaccccccgtgaatatcat<br>cggccggaacctcctcacccaaatcggctgtaccctgaacttccctatctctcccatcgaaaccgtgcccgtgaa<br>gctgaaacccggcatggacgggcccaaggtgaagcagtggcccctcaccgaggagaagatcaaggccctgg<br>tggagatctgcaccgaaatggagaaagagggcaagatcagcaagatcggccccgagaacccctataacaccc<br>ccgtgttcgctatcaaaaagaaggattccaccaagtggcggaagctggtggactttcgggagttgaacaaacgg<br>acccaggatttagggaggtgcagctgggcatcccccaccctgccggcctgaagaaaaagaagagcgtgacc<br>gtgctcgacgtcggcgacgcctacttcagcgtgcctctggacgaggattttcgcaaatacaccgccttcacaatc<br>ccctccatcaataacgaaaccccggcatccggtaccaatataacgtcttgccccaaggctggaagggcagcc<br>ccgccatctttcagtcctctatgaccaagattctggaacccttccggaagcagaaccccgatatcgtgatttaccag<br>tatatggacgacctctacgtgggcagcgatctggagatcggccaacaccggaccaagatcgaagaactccggc<br>agcacctcctccgctggggcttgacaaccccgataagaagcaccaaaaggagcctccctattgtggatgggc<br>tacgagttgcaccccgacaagtggaccgtgcaacccatcgtcctccccgagaaggattcttggaccgtgaacga<br>tatccaaaaactggtcggcaagctcaactgggcctcccaaatctatcccggcatcaaggtgcgccagctgtgca<br>agttgttgcggggcacaaaggcgttgaccgaggtgatccccttgaccgaggaggccgaattggagctcgccga<br>gaatcgggaaatcttgaaggagcccgtgcacggcgtctactacgatcccagcaaggatctgatcgccgagatc<br>caaaaacaaggccaggggcagtggacctaccagatctaccaggaacccttcaagaacctcaagaccggcaag<br>tacgcccggatgagaggcgcccataccaacgacgtgaagcagctgaccgaagccgtccagaagatcacaac<br>cgagtctatcgtgatctggggcaaaacccccaagttcaagctccctatccagaaggaaacgtgggaaacctggt<br>ggaccgaatactggcaggctacatggattcccgaatgggagttcgtgaacacacccctctggtcaagctgtgg<br>tatcaactggaaaaggagcctatcgtgggcgccgagacattttacgtggacggcgctgccaatcgcgaaacca<br>agctgggcaaggccggctacgtgaccaatcggggccgccagaaggtggtgacattgaccgataccaccaacc<br>agaaaaccgaactgcaggccatctacttggccctccaagacagcggcctggaggtgaatatcgtgaccgatag<br>ccagtacgccctgggcattatccaggcccagcccgaccagtccgagagcgaactggtgaaccagatcatcgaa<br>caactgatcaagaaagagaaagtgtacctcgcctgggtgcccgcccataaggggatcggcggcaacgagcag<br>gtggacaagctggtgtccgccggcattcgcaaggtgttgttcctggacggcatcgacaaagctcaggacgagc<br>acgaaaagtaccattccaactggcgggccatggcctccgacttcaatttgccacccgtggtggccaaggagatc<br>gtggcttcttgcgacaagtgccaattgaagggcgaggctatgcacggccaggtggattgctcccccggcatctg<br>gcagttggactgcacccacctggagggcaaggtgattctcgtggccgtgcacgtggcttccggctacatcgagg<br>ctgaggtgatcccggccgaaaccggccaagagactgcctacttcttgctgaagctggccggcaggtggcccgt<br>aaagaccatccacaccgataacgggtctaactttacatccgccaccgtgaaagctgcttgctggtgggcaggcat<br>taaacaagagttcggcatcccttataaccctcagtcccagggcgtggtggagagcatgaacaaggagctgaaaa<br>agatcatcggccaagtgcgggaccaagccgagcacttgaaaaccgccgtgcagatggccgtgtttattcataac<br>ttcaagcggaagggcggcatcggcggctattccgccggtgagcggatcgtggatatcatcgccaccgatatcc<br>agaccaaggagctgcagaagcagatcaccaagatccagaacttcagagtgtactatcgcgattctcggaacccc<br>ttgtggaaggggccagccaaattgttgtggaagggggagggcgccgtggtgatccaggacaactccgatatca<br>aggtggtcccgcggaggaaggccaaaattatccgcgactacggcaagcaaatggccggcgacgactgcgtc<br>gcctcccggcaagacgaggactga | HIV Pol |
| 33 | gtcgagGGatCTCCATAagagAAGAGGGACAGCTATGACTGGGAGTAGTC<br>AGGAGAgGAgGAAAAATCTGGCTAGTAAAACATGTAAGGAAAATTT<br>TAGGGATGTTAAAGAAAAAAATAACACAAAACAAAATATAAAAAA<br>AATCTAACCTCAAGTCAAGGCTTTTCTATGGAATAAGGAATGGACA<br>GCAGGGGGCTGTTTCATATACTGATGACCTCTTTATAGCCAACCTTT<br>GTTCATGGCAGCCAGCATATGGGCATATGTTGCCAAACTCTAAACC<br>AAATACTCATTCTGATGTTTTAAATGATTTGCCCTCCCATATGTCCT<br>TCCGAGTGAGAGACACAAAAAATTCCAACACACTATTGCAATGAAA<br>ATAAATTTCCTTTATTAGCCAGAAGTCAGATGCTCAAGGGGCTTCAT<br>GATGTCCCCATAATTTTTGGCAGAGGGAAAAAGATCTGCTAGCTAT | HIV Rev |

-continued

SEQUENCES

| # | SEQUENCE | ANNOTATION |
|---|---|---|
| | AGTTCTAGAGGTACCGGTTGTTTCGAGCTTATAGCAAAATCCTTTCC<br>AAGCCCTGTCTTATTCTTCTAGGTATGTGGCGAATAGCTCTACAAGC<br>TCCTTGTACTACTTCTATAACCCTATCTGTCCCCTCAGCTACTGCTAT<br>GGCTGTGGCATTGAGCAAGCTAACAGCACTATTCTTTAGCTCCTGA<br>CTCCAATATTGTAGGAGATTCCACCAATATTTGAGGGCTTCCCACCC<br>CCTGCGTCCCAGAAGTTCCACAATCCTCGTTACAATCAAGAGTAAG<br>TCTCTCAAGCGGTGGTAGCTGAAGAGGCACAGGCTCCGCAgATCGT<br>CCCAGATAAGTGCCAAGGATCCGTTCACTAATCGAATGGATCTGTC<br>TCTGTCTCTCTCTCCACcTTCTTCTTCTATtCCTTCGGgCCTGTcGGGTC<br>CCCTCGGGGTTGGGAGGTGGGTCTGAAACGATAATGgTGAATATCC<br>CTGCCTAAcTCtATTCACTATAGAAAGTACAgcAAAaACTATTCTTAA<br>ACCTAccaAGcCTCCtACTATCATTATGAataattttatataccacagccaatttgttatgtta<br>aaccaattccacaaacttgcccatttatctaattccaataattcttgt | |
| 34 | tcgcgcgtttcggtgatgacggtgaaaacctctgacacatgcagctcccggagacggtcacagcttgtctgtaag<br>cggatgccgggagcagacaagcccgtcagggcgcgtcagcgggtgttggcgggtgtcggggctggcttaact<br>atgcggcatcagagcagattgtactgagagtgcaccaaatgcggtgtgaaataccgcacagatgcgtaaggag<br>aaaataccgcatcaggcgccattcgccattcaggctgcgcaactgttgggaagggcgatcggtgcgggcctcat<br>cgctattacgccagctggcgaaagggggatgtgctgcaaggcgattaagttgggtaacgccagggttttcccag<br>tcacgacgttgtaaaacgacggccagtgcaacgcgatgacgatggatagcgattcatcgatgagctgacccgat<br>cgccgccgccggagggttgcgtttgagacgggcgacagatgaattccttctacaatgagctgcgtgtggctccc<br>gaggagcaccccgtgctgctgaccgaggcccccctgaaccccaaggccaaccgcgagaagatgacccagat<br>catgtttgagaccttcaacaccccagccatgtacgttgctatccaggctgtgctatccctgtacgcctctggccgta<br>ccactggcatcgtgatggactccggtgacggggtcacccacactgtgcccatctgtcgacgcggccgcatggta<br>ttgctgcctgggtccatgcttctcacctcaaacctgcaccaccttcggcaccagatgagtcctgggagctggaaa<br>agactgatcatcctcttaagctgcgtattcggcggcggcgggacgagtctgcaaaataagaacccccaccagcc<br>catgaccctcacttggcaggtactgtcccaaactggagacgttgtctgggatacaaaggcagtccagccccccttg<br>gacttggtggcccacacttaaacctgatgtatgtgccttggcggctagtcttgagtcctgggatatcccgggaacc<br>gatgtctcgtcctctaaacgagtcagacctccggactcagactatactgccgcttataagcaaatcacctgggga<br>gccatagggtgcagctaccctcgggctaggactagaatggcaagctctaccttctacgtatgtccccgggatgg<br>ccggaccctacagaagctagaaggtgcggggggctagaatccctatactgtaaagaatgggattgtgagacca<br>cggggaccggttattggctatctaaatcctcaaaagacctcataactgtaaaatgggaccaaaatagcgaatgga<br>ctcaaaaatttcaacagtgtcaccagaccggctggtgtaaccccccttaaaatagatttcacagacaaaggaaaatt<br>atccaaggactggataacgggaaaaacctggggattaagattctatgtgtctggacatccaggcgtacagttcac<br>cattcgcttaaaaatcaccaacatgccagctgtggcagtaggtcctgacctcgtccttgtggaacaaggacctcct<br>agaacgtccctcgctctcccacctcctcttcccccaagggaagcgccaccgccatctctccccgactctaactcc<br>acagccctggcgactagtgcacaaactcccacggtgagaaaaacaattgttaccctaaacactccgcctcccac<br>cacaggcgacagactttttgatcttgtgcagggggccttcctaaccttaaatgctaccaacccaggggccactga<br>gtcttgctggctagtaggccatgggcccccttattatgaagcaatagcctcatcaggagaggtcgcctactcca<br>ccgaccttgaccggtgccgctgggggacccaaggaaagctcaccctcactgaggtctcaggacacgggttgtg<br>cataggaaaggtgccctttacccatcagcatctctgcaatcagaccctatccatcaattcctccggagaccatcag<br>tatctgctcccctccaaccatagctggtgggcttgcagcactggcctcaccccttgcctctccacctcagtttttaat<br>cagactagagatttctgtatccaggtccagctgattcctcgcatctattactatcctgaagaagttttgttacaggcct<br>atgacaattctcaccccaggactaaaagagaggctgtctcacttaccctagctgttttactggggttgggaatcac<br>ggcgggaataggtactggttcaactgccttaattaaaggacctatagacctccagcaaggcctgacaagcctcca<br>gatcgccatagatgctgacctccgggccctccaagactcagtcagcaagttagaggactcactgacttccctgtc<br>cgaggtagtgctccaaaataggagaggccttgacttgctgtttctaaaagaaggtggcctctgtgcggccctaaa<br>ggaagagtgctgtttttacatagaccactcaggtgcagtacgggactccatgaaaaaactcaaagaaaaactgga<br>taaaagacagttagagcgccagaaaagccaaaactggtatgaaggatggttcaataactccccttggttcactac<br>cctgctatcaaccatcgctgggcccctattactcctccttctgttgctcatcctcgggccatgcatcatcaataagtta<br>gttcaattcatcaatgataggataagtgcagttaaaattctggtccttagacagaaatatcaggccctagagaacga<br>aggtaacctttaaaagcttatcagttctggaccagcgagctgtgctgcgactcgtggcgtaatcatggtcatagct<br>gtttcctgtgtgaaattgttatccgctcacaattccacacaacatacgagccggaagcataaagtgtaaagcctgg<br>ggtgcctaatgagtgagctaactcacattaattgcgttgcgctcactgcccgctttccagtcgggaaacctgtcgtg<br>ccagctgcattaatgaatcggccaacgcgcggggagaggcggtttgcgtattgggcgctcttccgcttcctcgct<br>cactgactcgctgcgctcggtcgttcggctgcggcgagcggtatcagctcactcaaaggcggtaatacggttatc<br>cacagaatcaggggataacgcaggaaagaacatgtgagcaaaaggccagcaaaaggccaggaaccgtaaaa<br>aggccgcgttgctggcgtttttccataggctccgcccccctgacgagcatcacaaaaatcgacgctcaagtcaga<br>ggtggcgaaacccgacaggactataaagataccaggcgtttccccctggaagctccctcgtgcgctctcctgttc<br>cgaccctgtcgcttaccggatacctgtccgcctttctcccttcgggaagcgtggcgctttctcatagctcacgctgt<br>aggtatctcagttcggtgtaggtcgttcgctccaagctgggctgtgtgcacgaaccccccgttcagcccgaccgc<br>tgcgccttatccggtaactatcgtcttgagtccaacccggtaagacacgacttatcgccactggcagcagccact<br>ggtaacaggattagcagagcgaggtatgtaggcggtgctacagagttcttgaagtggtggcctaactacggcta<br>cactagaagaacagtatttggtatctgcgctctgctgaagccagttaccttcggaaaaagagttggtagctcttgat<br>ccggcaaacaaaccaccgctggtagcggtggtttttttgtttgcaagcagcagattacgcgcagaaaaaaaggat<br>ctcaagaagatcctttgatcttttctacggggtctgacgctcagtggaacgaaaactcacgttaagggattttggtc<br>atgagattatcaaaaaggatcttcacctagatccttttaaattaaaaatgaagttttaaatcaatctaaagtatatatga<br>gtaaacttggtctgacagttaccaatgcttaatcagtgaggcacctatctcagcgatctgtctatttcgttcatccata<br>gttgcctgactccccgtcgtgtagataactacgatacgggagggcttaccatctggccccagtgctgcaatgata<br>ccgcgagacccacgctcaccggctccagatttatcagcaataaaccagccagccggaagggccgagcgcag<br>aagtggtcctgcaactttatccgcctccatccagtctattaattgttgccgggaagctagagtaagtagttcgccagt<br>taatagtagcgcaacgagttgccattgctacaggcatcgtggtgtcacgctcgtcgtaggtatggcttcattcagc<br>tccggttcccaacgatcaaggcgagttacatgatcccccatgttgtgcaaaaaagcggttagctccttcggtcctc<br>cgatcgttgtcagaagtaagttggccgcagtgttatcactcatggttatggcagcactgcataattctcttactgtcat<br>gccatccgtaagatgcttttctgtgactggtgagtactcaaccaagtcattctgagaatagtgtatgcggcgaccga | pActin-GaLV |

-continued

SEQUENCES

| # | SEQUENCE | ANNOTATION |
|---|---|---|
| | gttgctcttgcccggcgtcaatacgggataataccgcgccacatagcagaactttaaaagtgctcatcattggaaa acgttcttcggggcgaaaactctcaaggatcttaccgctgttgagatccagttcgatgtaacccactcgtgcaccc aactgatcttcagcatatttactacaccagcgtactgggtgagcaaaaacaggaaggcaaaatgccgcaaaaa agggaataagggcgacacggaaatgagaatactcatactctacctattcaatattattgaagcatttatcagggtta ttgtctcatgagcggatacatatttgaatgtatttagaaaaataaacaaataggggttccgcgcacatttccccgaaa agtgccacctgacgtctaagaaaccattattatcatgacattaacctataaaaataggcgtatcacgaggccctttc gtc | |
| 35 | ATTGCCCGTCAAGCTCAGAT | VSV-G Forward Primer |
| 36 | GTGACTCTTGGGCATTTTGACTT | VSV-G Reverse Primer |
| 37 | TGGCATAATGACTTAATAGGCACAGCCTTA | VSV-G Probe |
| 38 | AGCGACGAAGACCTCCTCAAG | rev Forward Primer |
| 39 | CTCTCCACCTTCTTCTTCTATTCCTTC | rev Reverse Primer |
| 40 | CAAGTTTCTCTATCAAAGCAACCCACCTCC | rev Probe |
| 41 | GCGAGAAGATGACCCAGATCA | ACTB Forward Primer |

The invention claimed is:

1. A method comprising:

a) carrying out reverse transcriptase quantitative PCR (RT-qPCR) on RNA from a test sample using one or more oligonucleotide primers and a hydrolysis probe specific for a sequence of a viral RNA to determine a cycle threshold (Ct) value of the viral RNA in the test sample, wherein the test sample is a biological sample comprising a plurality of cells that have been transduced with a replication incompetent retroviral vector, wherein the replication incompetent retroviral vector comprises a heterologous nucleic acid encoding a heterologous protein, wherein:

the Ct value inversely correlates with the amount or concentration of the viral RNA in the biological sample;

the amount or concentration of the viral RNA in the biological sample indicates a presence or absence of, or risk of, a replication competent retrovirus in the biological sample;

the method excludes a step of amplification of potentially present replication competent retrovirus by cell culture in cells different from the transduced cells of the biological sample; and the viral RNA is required for, or encodes a gene product or specifically identifiable portion thereof that is required for, replication competency of a replication competent retrovirus, wherein the viral RNA is from the env, gag, pol, or rev genes.

2. The method of claim 1, wherein the viral RNA is determined to be present in the biological sample, if the Ct value for the test sample is below a first reference value, which is a reference Ct score.

3. A method comprising:

a) carrying out reverse transcriptase quantitative PCR (RT-qPCR) RNA from a test sample using one or more oligonucleotide primers and a hydrolysis probe specific for a sequence of a viral RNA to determine a cycle threshold (Ct) value of the viral RNA in the test sample, wherein:

the test sample is a biological sample comprising a plurality of cells that have been transduced with a replication incompetent retroviral vector, wherein the replication incompetent retroviral vector comprises a heterologous nucleic acid encoding a heterologous protein; and the Ct value inversely correlates with the amount or concentration of the first viral RNA in the biological sample;

b) carrying out RT-qPCR on RNA from the test sample using one or more oligonucleotide primers and a hydrolysis probe specific for a sequence of a second viral RNA to determine a Ct value of the second viral RNA in the test sample, wherein the Ct value inversely correlates with the amount or concentration of the second viral RNA in the biological sample;

wherein:

the amount or concentration of the first viral RNA or the second viral RNA, or the amount or concentration of both the first and the second viral RNA, in the biological sample indicates a presence or absence of, or risk of, a replication competent retrovirus in the biological sample;

the method excludes a step of amplification of potentially present replication competent retrovirus by cell culture in cells different from the transduced cells of the biological sample; and the first viral RNA, the second viral RNA, or both the first and the second viral RNA, is required for, or encodes a gene product or specifically identifiable portion thereof that is required for, replication competency of a replication competent retrovirus, wherein the first viral RNA and second viral RNA is from the env, gag, pol, or rev genes.

4. The method of claim 3, wherein at least one of the first viral RNA or the second viral RNA is an env viral gene and the env gene is GaLV env or VSVg env.

5. A method comprising:

a) carrying out reverse transcriptase quantitative PCR (RT-qPCR) on RNA from a test sample using one or more oligonucleotide primers and a hydrolysis probe specific for a sequence of a first viral RNA to determine a cycle threshold (Ct) value of the first viral RNA in the test sample, Wherein:

the test sample is a biological sample comprising a plurality of cells that have been transduced with a replication incompetent retroviral vector, wherein the replication incompetent retroviral vector comprises a heterologous nucleic acid encoding a heterologous protein;

the Ct value inversely correlates with the amount or concentration of the first viral RNA in the biological sample; and the first viral RNA is from a first viral gene that is an env gene, and b) carrying out RT-qPCR on RNA from the test sample using one or more oligonucleotide primers and a hydrolysis probe specific for a sequence of a second viral RNA to determine a Ct value of the second viral RNA in the test sample, wherein:

the Ct value inversely correlates with the amount or concentration of the second viral RNA in the biological sample; and the second viral RNA is from a gag, pol, or rev gene, wherein:

the amount or concentration of the first viral RNA or the second viral RNA, or the amount or concentration of both the first and the second viral RNA, in the biological sample indicates a presence or absence of, or risk of, a replication competent retrovirus the biological sample;

the method excludes a step of amplification of potentially present replication competent retrovirus by cell culture in cells different from the transduced cells of the biological sample; and the first viral RNA, the second viral RNA, or both the first and the second viral RNA, is required for, or encodes a gene product or specifically identifiable portion thereof that is required for, replication competency of a replication competent retrovirus.

6. The method of claim 2, wherein the reference value is or corresponds to a threshold level or a minimum detectable level.

7. The method of claim 3, wherein the biological sample is deemed replication competent virus negative if the amount or concentration of the first viral and the second viral RNA is not determined to be present above a threshold level in the biological sample.

8. The method of claim 1, wherein the replication incompetent retrovirus retroviral vector is a gammaretroviral vector or a lentiviral vector.

9. The method of claim 3, wherein the replication incompetent retrovirus retroviral vector is a gammaretroviral vector or a lentiviral vector.

10. The method of claim 5, wherein the replication incompetent retroviral vector is a gammaretroviral vector or a lentiviral vector.

11. The method of claim 1, wherein the biological sample is from a human and the plurality of cells are primary human cells.

12. The method of claim 1, wherein the heterologous nucleic acid encodes a recombinant receptor.

13. The method of claim 1, wherein:

the viral gene is GaLV env and the one or more oligonucleotide primers comprises a forward and reverse primer, respectively, comprising the sequences set forth in SEQ ID NOs: 4-5; or the viral gene is MMLV gag and the one or more oligonucleotide primers comprises a forward and reverse primer, respectively, comprising the sequences set forth in SEQ ID NOs. 16-17, SEQ ID Nos: 19-20 or SEQ ID Nos: 22-23.

14. The method of claim 13, wherein the viral gene is a GalV env viral gene and the hydrolysis probe comprises a sequence set forth in SEQ ID NO: 6.

15. The method of claim 13, wherein the viral gene is a MMLV gag viral gene and the hydrolysis probe comprises a sequence set forth in SEQ ID NO: 18, 21, or 24.

16. The method of claim 3, wherein:

the first viral RNA is determined to be present in the biological sample if the Ct value for the test sample is below a first reference value, which is a first reference Ct score; and the second viral RNA is determined to be present in the biological sample if the CT value for the test sample is below a second reference value, with is a second reference Ct score.

17. The method of claim 5, wherein:

the first viral RNA is determined to be present in the biological sample, if the CT value for the test sample is below a first reference value, which is a first reference Ct score; and the second viral RNA is determined to be present in the biological sample, if the CT value for the test sample is below a second reference value, with is a second reference Ct score.

18. The method of claim 1, wherein the plurality of cells are a plurality of T cells.

19. The method of claim 18, wherein said plurality of cells comprises unfractionated T cells, isolated CD8+T cells, or isolated CD4+T cells.

20. The method of claim 1, wherein the biological sample is collected from a process in which transduced cells have been cultured under conditions to expand the cells, at or about 37° C. and in the presence of one or more stimulating agents.

21. The method of claim 20, wherein the transduced cells have been cultured for from or from about 2 to 14 days.

22. The method of claim 5, wherein the biological sample is deemed replication competent virus negative if the amount or concentration of the first viral RNA and the second viral RNA is not determined to be present above a threshold level in the biological sample.

23. The method of claim 12, wherein the recombinant receptor is a chimeric receptor or a transgenic T cell receptor.

24. The method of claim 3, wherein the first or second viral gene is GaLV env and the one or more oligonucleotide primers comprises a forward and reverse primer, respectively, comprising the sequences set forth in SEQ ID NOs:4-5; and the other of the first or second viral gene is MMLV gag and the one or more oligonucleotide primers comprises a forward and reverse primer, respectively, comprising the sequences set forth in SEQ ID NOs. 16-17, SEQ ID Nos: 19-20 or SEQ ID Nos: 22-23.

25. The method of claim 5, wherein the first or second viral gene is GaLV env and the one or more oligonucleotide primers comprises a forward and reverse primer, respectively, comprising the sequences set forth in SEQ ID NOs:4-5; and the other of the first or second viral gene is MMLV gag and the one or more oligonucleotide primers comprises a forward and reverse primer, respectively, comprising the sequences set forth in SEQ ID NOs. 16-17, SEQ ID Nos: 19-20 or SEQ ID Nos: 22-23.

26. The method of claim 1, further comprising carrying out RT-qPCR on cDNA synthesized from RNA from the test sample to determine a Ct value of a control gene using one or more oligonucleotide primers and a hydrolysis probe specific to a sequence of the control gene.

27. The method of claim 26, wherein the control gene is or comprises β-actin.

28. The method of claim 27, wherein the one or more oligonucleotide primers individually comprises a forward primer and reverse primer, respectively comprising the sequences set forth in any one of SEQ ID NOs: 1 and 2, 1 and 8, 13 and 14, 10 and 11, or 41 and 2.

29. The method of claim 26, wherein the hydrolysis probe comprises a sequence set forth in SEQ ID NO: 3, 9, 7, 12, or 15.

30. The method of claim 3, further comprising carrying out RT-qPCR on cDNA synthesized from RNA from the test sample to determine a Ct value of a control gene using one or more oligonucleotide primers and a hydrolysis probe specific to a sequence of the control gene.

31. The method of claim 30, wherein the control gene is β-actin.

32. The method of claim 5, further comprising carrying out RT-qPCR on cDNA synthesized from RNA from the test sample to determine a Ct value of a control gene using one or more oligonucleotide primers and a hydrolysis probe specific to a sequence of the control gene.

33. The method of claim 32, wherein the control gene is β-actin.

34. The method of claim 3, wherein the plurality of cells are a plurality of T cells.

35. The method of claim 5, wherein the plurality of cells are a plurality of T cells.

* * * * *